United States Patent
Tsukahara et al.

(10) Patent No.: US 7,928,209 B2
(45) Date of Patent: *Apr. 19, 2011

(54) FUNGAL CELL WALL SYNTHESIS GENE

(75) Inventors: Kappei Tsukahara, Tsukuba (JP); Katsura Hata, Tsukuba (JP); Koji Sagane, Tsukuba (JP); Kazutaka Nakamoto, Tsukuba (JP); Mamiko Tsuchiya, Ushiku (JP); Naoaki Watanabe, Tsukuba (JP); Fuminori Ohba, Iruma-gun (JP); Itaru Tsukada, Ushiku (JP); Norihiro Ueda, Tsukuba (JP); Keigo Tanaka, Tsukuba (JP); Junko Kai, Niihari-gun (JP)

(73) Assignee: Eisai R & D Management Co. Ltd., Tokyo (JP)

( * ) Notice: Subject to any disclaimer, the term of this patent is extended or adjusted under 35 U.S.C. 154(b) by 197 days.

This patent is subject to a terminal disclaimer.

(21) Appl. No.: 11/958,310

(22) Filed: Dec. 17, 2007

(65) Prior Publication Data

US 2008/0166765 A1   Jul. 10, 2008

Related U.S. Application Data

(60) Continuation of application No. 11/409,530, filed on Apr. 21, 2006, now Pat. No. 7,375,204, which is a division of application No. 10/332,340, filed as application No. PCT/JP01/05899 on Jul. 6, 2001, now abandoned.

(30) Foreign Application Priority Data

Jul. 7, 2000   (JP) .................................. 2000-206968
Oct. 17, 2000  (JP) .................................. 2000-316027

(51) Int. Cl.
*C12N 15/80* (2006.01)
*A61K 36/06* (2006.01)
*A61K 38/00* (2006.01)

(52) U.S. Cl. ................... 536/23.1; 435/254.1; 435/7.31; 435/320; 435/69.1; 514/2

(58) Field of Classification Search .................... None
See application file for complete search history.

(56) References Cited

U.S. PATENT DOCUMENTS

| 4,013,666 | A  | 3/1977  | Lenz |
| 5,525,716 | A  | 6/1996  | Olsen et al. |
| 5,641,627 | A  | 6/1997  | Moehle |
| 5,648,465 | A  | 7/1997  | Margolis et al. |
| 5,962,252 | A  | 10/1999 | McFarland et al. |
| 5,969,102 | A  | 10/1999 | Bram et al. |
| 6,747,137 | B1 | 6/2004  | Weinstock et al. |
| 6,833,447 | B1 | 12/2004 | Goldman |
| 2002/0072051 | A1 | 6/2002 | Bulawa et al. |
| 2004/0029129 | A1 | 2/2004 | Wang et al. |
| 2006/0172404 | A1 | 8/2006 | Hata et al. |
| 2006/0234283 | A1 | 10/2006 | Tsukahara et al. |
| 2006/0240429 | A1 | 10/2006 | Tsukahara et al. |
| 2006/0280725 | A1 | 12/2006 | Bode |
| 2007/0287151 | A1 | 12/2007 | Linnarsson |
| 2008/0166765 | A1 | 7/2008 | Tsukahara et al. |

FOREIGN PATENT DOCUMENTS

| WO | WO 94/01567 A1 | 7/1993 |
| WO | WO 99/39197 A1 | 6/1999 |
| WO | WO 00/01387 A1 | 1/2000 |

OTHER PUBLICATIONS

Zhnag et al. (1996) An analysis of base frequencies in the anti-sense strands corresponding to the 180 human protein coding sequences, Amino acids, vol. 10, pp. 253-262.*
Anderson et al. (2005) DNA Quality control for oligonucleotide array CGH (aCGH) with the agilent 2100 bioanalyer, pp. 1-10.*
Miosga, et al.; GenBank Accession No. CAA89384 //www.ncbi.nlm.nih.gov/protein/1008262, (1997).
Wiktionary (2007, updated) "transformant" http://en.wiktionary.org/wiki/transformant, p. 1 Accessed Jan. 22, 2008, //en.wikitionary.org/w/index.php?title=transformant&pritable=yes.
Davila, J.C. et al.; "Cytotoxicity induced by papaverine hydrochloride in fungal cell systems"; 1990, *Toxicology Letter*, vol. 54, pp. 23-31.
Hamada, K., et al., "Screening for Glycosylphoshpatidylinositol (GPI)-Dependent Cell Wall Proteins in *Saccharomyces cerevisiae*," *Molecular and General Genetics*, Apr. 1998, pp. 53-59, vol. 258, No. 1-2, Springer-Verlag.
Ikezawa, H., et al., "Glycosylphosphatidylinositol (GPI)-anchored proteins," 2002, *Biol. Pharm. Bull.*, vol. 25,(4), pp. 409-417.
Mamyrbekova, Z.A. et al; "Synthesis, structure, and biological activity of paracyclophane derivatives"; 1995, *Chemical Abstracts*, vol. 123, p. 592.
Mamyrbekova, Z.A. et al.; 1994, *Khim Pharm.*, vol. 28, No. 3, pp. 48-51.
Miosga, T. et al.; "*S. cerevisiae* chromosome X reading frame ORF YJL091c"; *GenBank Database*; Aug. 11, 1997; Accession Number Z49366.
Miosga, T., et al., "Sequence analysis of a 33.1 kb fragment from the left arm of *Saccharomyces cerevisiae* chromosome X, including putative proteins with leucine zippers, a fungal ZN (II) 2-Cys6 binuclear cluster domain and putative alpha 2-SCB-alpha 2 binding site," NCBI; Accession Number P47026 (Feb. 1, 1996).

(Continued)

*Primary Examiner* — Anand U Desai
*Assistant Examiner* — Samuel Liu
(74) *Attorney, Agent, or Firm* — Kilpatrick Townsend and Stockton LLP

(57) ABSTRACT

A reporter system reflecting the transport process that transports GPI-anchored proteins to the cell wall was constructed and compounds inhibiting this process were discovered. Further, fungal genes conferring resistance to the above compounds were identified and methods of screening for compounds that inhibit the activity of the proteins encoded by these genes were developed. These genes encode proteins participating in fungal cell wall synthesis. Therefore, through the novel compounds, the present invention showed that antifungal agents having a novel mechanism, i.e. inhibiting the process that transports GPI-anchored proteins to the cell wall, could be achieved.

5 Claims, 7 Drawing Sheets

OTHER PUBLICATIONS

Miosga, et al., "Sequence Analysis Of A 33-1 kb Fragment From The Left Arm Of *Saccharomyces cerevisiae* Chromosomes X, Including Putative Proteins With Leucine Zippers, A Fungal $Zn(II)_2$-$Cys_6$ Binuclear Cluster Domain And A Putative α2-SCB-α2 Binding Site", *Yeast*, vol. 11: 681-689 (1995).

Mohuczy, et al., "Delivery of antisense DNA by vectors for prolonged effects in vitro and in vivo," *Methods Enzymol*, vol. 314, pp. 32-51 (1999).

Prostakov, N.S. et al.; 1980, *Chemical Abstracts* vol. 93, No. 17, p. 660.

Prostakov, N.S. et al.; 1980, *Khim Geterotsikl Soedin*, vol. 5, pp. 673-676.

Seow, W.K. et al.; 1993, *Chemical Abstracts*, vol. 119, No. 23, p. 32.

Seow, W.K. et al.; "Inhibitory effects of bisbenzylisoquinolines on synthesis of the inflammatory cytokines interleukin-1 and tumor necrosis factor-alpha"; 1993, *Mediators of Inflammation*, vol. 2, pp. 199-203.

Shiotani, Shunsaku et al.; "Wittig-Horner Reaction of a Phosphonate of Reissert Analogues of Furo"; 1997, *J. Heterocyclic Chemistry*, vol. 34, No. 1, pp. 129-141.

Skrzypek, M., et al., "Suppressor gene analysis reveals an essential role for sphingolipids in transport of glycosylphosphatidylinositol-anchored proteins in *Saccharomyces cerevisiae*," *J. Bacteriol.*, vol. 179(5), pp. 1513-1520 (1997).

Smirnov, L.D. et al.; 1975, *Chemical Abstracts*, vol. 82, No. 3, p. 484.

Smirnov, L.D. et al.; 1974, *Khim Geterotsikl*, vol. 8, pp. 1094-1095.

Sütterlin, C., et al., "*Saccharomyces cerevisiae* CGI10, the functional homologue of human PIG-B, is required for glycosylphosphatidylinositol-anchor synthesis," *Biochem. J.*, vol. 332, pp. 153-159 (1998).

Tsai, I.L. et al.; 1989, *Chemical Abstracts*, vol. 111, No. 5, p. 342.

Tsai, I.L. et al.; "Screening of Isoquinoline Alkaloids and their Derivatives for Antibacterial and Antifungal Activities"; 1989, *Kalhsiung J. Med. Sci.*, vol. 5, pp. 132-145.

Tsukahara, K., et al., "Medicinal Genetics Approach Towards Identifying the Molecular Target of a Novel Inhibitor of Fungal Cell Wall Assembly," *Molecular Microbiology*, May 2003, pp. 1029-1042, vol. 48, No. 4, Blackwell Publishing Ltd.

Umemura, M., et al., "*GWT1* Gene Is Required for Inositol Acylation of Glycosylphosphatidylinositol Anchors in Yeast," *Journal of Biological Chemistry*, Jun. 2003, pp. 23639-23647, vol. 278, No. 26, The American Society for Biochemistry and Molecular Biology, Inc., U.S.A.

Van Der Vaart, J. M., et al., "Identification of Three Mannoproteins in the Cell Wall of *Saccharomyces cerevisiae*," *Journal of Bacteriology*, Jun. 1995, pp. 3104-3110, vol. 117, No. 11, American Society of Microbiology.

White, et al., "Clinical, cellular, and molecular factors that contribute to antifungal drug resistance," *Clin. Microbiol. Rev.*, vol. 11(2), pp. 382-402, Review.

Database EMBL Online; Accession No. AL132675; Created on Oct. 27, 1999; Description: S.pombe Chromosome I Cosmid c144, 9 pages.

Attachment 1 (2005) Sequence alignment between nucleotide sequences of instant SEQ ID No. 3 and SEQ ID No. 998 of US Pat. No. 6,747,137, pp. 1-4.

GenBank Accession No. CAB59690; Oct. 1999 McDougall, R.C., et al. Wood, V., et al., "The genome sequence of Schizosaccharomyces pombe," 2002, Nature, vol. 415, pp. 871-880.

Wikipedia (2007, updated), "Homology (biology)" //en.wikipedia.org/wiki/Homology_(biology), p. 1.

Futerman, A., "Inhibition of sphingolipid synthesis: effects on glycosphingolipid-GPI-anchored protein microdomains," *Trends Cell Biol.*, vol. 5(10), pp. 377-380 (Oct. 1995).

Zhang, C.-T., et al., "An analysis of base frequencies in the anti-sense strands corresponding to the 180 human protein coding sequences," *Amino Acids*, vol, 10, pp. 253-262 (1996).

\* cited by examiner

Fig. 7

⟨F-domain⟩

| | | | | |
|---|---|---|---|---|
| S. cerevisiae | ILAVDF PI | FP  RR F | AKVETWG TS L | MDLGVGS F |
| C. albicans | ILAVDF PI | FP  RR F | AKVETWG TS M | MDLGVGS F |
| S. pombe | ILAVDF TL | FP  RR Y | AKVETWG TS L | MDLGVGS F |

⟨R-domain⟩

| | | | | |
|---|---|---|---|---|
| S. cerevisiae | YQEH VT | EYG V | HWNFF I | T |
| C. albicans | YQEH ET | EYG I | HWNFF F | T |
| S. pombe | YQEH VS | EYG M | HWNFF F | T |

FUNGAL CELL WALL SYNTHESIS GENE

CROSS-REFERENCES TO RELATED APPLICATIONS

This application is a continuation application claiming priority to U.S. application Ser. No. 11/409,530, filed Apr. 21, 2006, issued as U.S. Pat. No. 7,375,204, which is a divisional application claiming priority to U.S. application Ser. No. 10/332,340, filed May 14, 2003, now abandoned, which is a U.S. National Phase Application, filed under 35 U.S.C. §371 of Patent Cooperation Treaty Application Number PCT/JP01/05899, filed Jul. 6, 2001, and claims priority to Japanese Patent Application Number 2000-206968, filed Jul. 7, 2000 and Japanese Patent Application Number 2000-316027, filed Oct. 17, 2000. Each of the aforementioned applications are hereby incorporated by reference in their entirety and for all purposes.

BACKGROUND OF THE INVENTION

1. Technical Field

The present invention relates to DNAs encoding proteins participating in fungal cell wall synthesis, proteins encoded by the DNAs, methods for examining whether or not a certain compound has an influence on the transport process involved in the transport of glycosylphosphatidylinositol (GPI)-anchored proteins to the cell wall, and antifungal agents having an influence on the transport process involved in the transport of GPI-anchored proteins to the cell wall.

2. Background Art

In recent years, management of opportunistic infections are gaining importance more than ever due to an increase in the number of elderly people and immunocompromised patients as a result of advanced chemotherapies, etc. Deep-seated mycosis due to Candida, Aspergillus, Cryptococcus, and such, account for a portion of such opportunistic infections, and the proportion is increasing year after year. The fact that opportunistic infections by many avirulent bacteria occur one after another, shows that the problem of infectious diseases will not end as long as there are underlying diseases that diminish the immune functions of patients. Although new strategies for infectious diseases control, including the problem of resistant bacteria, will be one of the crucial issues in the soon-to-come aged society, extremely few effective therapeutic agents exist at present.

Up to now, therapeutic agents for fungal infections were developed based mainly on the strategy of creating novel compounds by chemically modifying known structure. However, due to problems such as the emergence of resistant bacteria, the development of new drugs based on new mechanisms is eagerly anticipated.

Considering such circumstances, the inventors focused on a novel approach in the area of antifungal agents in which the variety of therapeutic agents is still insufficient. Namely, the present inventors concentrated on influencing the onset, progress, and persistence of infections by preventing pathogens from showing pathogenicity. In order to avoid the establishment and progress of infection, the inventors thought that the most effective way would be to inhibit the adhesion onto the host, which is the first step in the establishment of infection, and the subsequent progression of colonization. In addition, a new unprecedented approach, namely, the inhibition of the expression of adhesion factors themselves, was also carried out.

In order to inhibit the expression of adhesion factors, the present inventors directed their attention to the hypothesis that cell wall glycoproteins such as adhesion factors are first GPI (Glycosylphosphatidylinositol)-anchored to the cell membrane, and then transported to the cell wall (FIG. 1). To date, 30 or more cell wall glycoproteins including adhesion ligands have been found to be transported via GPI-anchoring (referred to as GPI-anchored proteins). Hence, it was thought that if this transport step is inhibited, it may be quite possible to inhibit the expression of adhesion factors and major cell wall-constituting proteins at the cell wall (Hamada K et al, Mol. Gen. Genet., 258: 53-59, 1998). GPI-anchored proteins have been reported to be present in Candida, which is a pathogenic fungi (Kapteyn J C et al, Eur. J. Cell Biol., 65:402-407, 1994).

The inventors initiated their research believing that novel antifungal agents that inhibit cell wall synthesis can be produced by inhibiting the process that transports GPI-anchored proteins existing in the cell membrane of a fungus to the cell wall.

BRIEF SUMMARY OF THE INVENTION

Disclosure of the Invention

An objective of this invention is to develop antifungal agents showing effects against the onset, progress, and persistence of infections by inhibiting the expression of cell wall glycoproteins, inhibiting the cell wall assembly and also adhesion onto cells, and preventing pathogens from showing pathogenicity.

In order to screen for compounds that inhibit the process that transports GPI-anchored proteins to the cell wall, the present inventors produced a reporter system that uses a fusion protein comprising a reporter enzyme and a transport signal existing in the C-terminus of one of the GPI-anchored proteins, CWP2 (Van Der Vaat J M et al, J. Bacteriol., 177: 3104-3110, 1995).

When a DNA comprising a secretion signal gene+reporter enzyme gene+CWP2 C-terminus gene (present or absent) was constructed, and the fusion protein was expressed in Saccharomyces cerevisiae (hereinafter, referred to as S. cerevisiae), it was demonstrated that activity of the reporter enzyme is detected in the cell wall when the CWP2 C-terminus is present, and in the culture supernatant when the CWP2 C-terminus is absent. Accordingly, it was predicted that if the process that transports GPI-anchored proteins to the cell wall is inhibited by a test sample, the activity of the reporter enzyme in the cell wall will be diminished, or the activity of the reporter enzyme will be found in the culture supernatant. Thus was initiated the screening for compounds that inhibit the process that transports GPI-anchored proteins to the cell wall using this reporter system.

From the screening using this reporter system, several compounds that inhibit the process that transports GPI-anchored proteins to the cell wall were discovered. A representative example is the compound shown in formula (Ia).

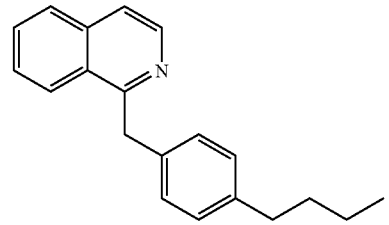

(Ia)

The compound shown in the aforementioned formula (Ia) (hereinafter abbreviated as "compound (Ia)") inhibits the growth of S. cerevisiae and Candida albicans (hereinafter, referred to as C. albicans), and C. albicans cultured in the presence of the aforementioned compound (Ia) shows a weak ability to adhere onto cells. Thus, the aforementioned compound (Ia) was confirmed to suit the initial objectives of the invention, which was to find a compound that inhibits the adhesion of fungi, due to suppressing the expression of the fungal adhesins, based on the inhibition of transport system of GPI-anchored proteins to the cell wall. Furthermore, observations using a transmission electron microscope confirmed that C. albicans cultured in the presence of the aforementioned compound (Ia) has an abnormality in its cell wall synthesis.

Using the aforementioned compound (Ia), the present inventors proved that antifungal agents based on the mechanism that inhibits the process that transports GPI-anchored proteins to the cell wall, could be achieved.

Furthermore, to specify the target protein on which the aforementioned compound (Ia) acts, the present inventors searched for genes that confer resistance to the aforementioned compound (Ia).

A plasmid library of the S. cerevisiae gene was introduced into S. cerevisiae, and by overexpression, plasmids were collected that showed resistance to the above-mentioned compound (Ia). The resistant gene was then cloned, the nucleotide sequence was determined, and the gene was named GWT1 (SEQ ID NO: 1). In S. cerevisiae overexpressing the GWT1 gene product, the aforementioned reporter enzyme that has the C-terminus of a GPI-anchored protein was transported to the cell wall, even in the presence of the aforementioned compound (Ia). Furthermore, observations under a transmission electron microscope confirmed that the cell wall is normal even in the presence of the aforementioned compound (Ia).

Moreover, when point mutations were randomly introduced to the genomic DNA of S. cerevisiae, and mutant strains R1 and R5 showing specific resistance to the aforementioned compound (Ia) were isolated, point mutations involving changes of the 405th codon of the GWT1 gene from GTC to ATC in the R1 mutant strain, and the 140th codon from GGG to AGG in the R5 mutant strain were discovered. Since resistance to the aforementioned compound (Ia) was seen when these mutant GWT1 genes were introduced to a GWT1 gene-disrupted strain, resistance to this compound was found to be explainable by the GWT1 gene alone. Therefore, this suggested that the aforementioned compound (Ia) directly acts on the GWT1 gene product to inhibit the function of the GWT1 protein.

By similar methods, the resistant genes of C. albicans (SEQ ID NOs: 3 and 5) were cloned, the nucleotide sequences were determined, and the genes were named CaGWT1.

Furthermore, a database homology search using GWT1, revealed a homologue (SEQ ID NO:27) of Schizosaccharomyces pombe (hereinafter, referred to as S. pombe). Furthermore, PCR with primers based on the sequence of the highly conserved region in the proteins encoded by the GWT1 genes of S. cerevisiae, S. pombe, and C. albicans, yielded homologues (SEQ ID NOs: 39 and 41) of Aspergillus fumigatus (hereinafter, referred to as A. fumigatus). Furthermore, by performing PCR based on the sequence discovered from a database homology search with GWT1, revealed homologues (SEQ ID NOs: 54 and 58) of Cryptococcus neoformans (hereinafter, referred to as C. neoformans).

More specifically, this invention relates to the following.

1. A DNA that encodes a protein having an activity to confer resistance to the compound shown in formula (Ia) on a fungus when the DNA is overexpressed in the fungus, wherein the DNA is selected from the group consisting of:
   (a) A DNA encoding a protein comprising the amino acid sequence of SEQ ID NOs: 2, 4, 6, 28, 40, or 59;
   (b) A DNA comprising the nucleotide sequence of SEQ ID NOs: 1, 3, 5, 27, 39, 41, 54, or 58;
   (c) A DNA that hybridizes under stringent conditions to a DNA comprising the nucleotide sequence of SEQ ID NOs: 1, 3, 5, 27, 39, 41, 54, or 58;
   (d) A DNA encoding a protein comprising the amino acid sequence of SEQ ID NOs: 2, 4, 6, 28, 40, or 59, wherein one or more amino acids have been added, deleted, substituted, and/or inserted;
   (e) A DNA that is amplified using SEQ ID NOs: 29 and 31 or SEQ ID NOs: 29 and as primers.

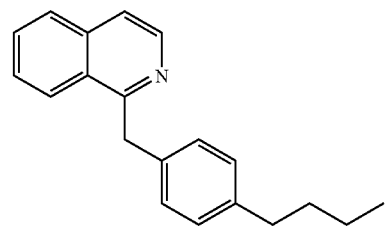

(Ia)

2. A DNA that encodes a protein having an activity to decrease the amount of a GPI-anchored protein in the cell wall of a fungus due to a defect in the function of the DNA, wherein the DNA is selected from the group consisting of:
   (a) A DNA encoding a protein comprising the amino acid sequence of SEQ ID NOs: 2, 4, 6, 28, 40, or 59;
   (b) A DNA comprising the nucleotide sequence of SEQ ID NOs: 1, 3, 5, 27, 39, 41, 54, or 58;
   (c) A DNA that hybridizes under stringent conditions to a DNA comprising the nucleotide sequence of SEQ ID NOs: 1, 3, 5, 27, 39, 41, 54, or 58;
   (d) A DNA encoding a protein comprising the amino acid sequence of SEQ ID NOs: 2, 4, 6, 28, 40, or 59, wherein one or more amino acids have been added, deleted, substituted, and/or inserted; and
   (e) A DNA that is amplified using SEQ ID NOs: 29 and 31 or SEQ ID NOs: 29 and 30 as primers;
   and wherein, "stringent conditions" refer to: for example, hybridization in 4×SSC at 65° C., then washing in 0.1× SSC for 1 hour at 65° C.; or in a different method, "stringent conditions" are 4×SSC at 42° C. in 50% formamide; or, hybridization in PERFECTHYB™ (TOYOBO) solution for 2.5 hours at 65° C., then washing in (i) 2×SSC, 0.05% SDS solution at 25° C. for 5 minutes, (ii) 2×SSC, 0.05% SDS solution at 25° C. for 15 minutes, and (iii) 0.1×SSC, 0.1% SDS solution at 50° C. for 20 minutes;
   a "defect in the DNA function" can occur, when the functional gene product of the DNA is not expressed or when the expression is diminished, for example by inserting a DNA that is irrelevant to the coding region of the DNA, for example a selection marker, using the homologous recombination technique;
   and a decrease in the protein derived from the GPI-anchored protein in the fungal cell wall is quantified by using any one of the following methods alone or in combination: (i) a reporter system reflecting the process that transports GPI-anchored proteins to the cell wall, (ii) an enzyme linked immunosorbant assay (ELISA) that quantifies a GPI-anchored protein in the cell wall, (iii) measuring the activity of a GPI-anchored protein, such as adhesion onto animal cells, or (4) observing the flocculent, fibrous structure of the outermost layer of the fungal cell by a transmission electron microscope.

3. A protein encoded by the DNA of 1 or 2.
4. A vector into which the DNA of 1 or 2 has been inserted.
5. A transformant harboring the DNA of 1 or 2, or the vector of 4.

6. The transformant of 5 which is a fungus that overexpresses the protein of 3.

7. A fungus, wherein the function of the protein of 3 is defective.

8. A method for producing the protein of 3, which comprises the steps of culturing the transformant of 5, and collecting the expressed protein from the transformant, or from the culture supernatant thereof.

9. An antibody that binds to the protein of 3.

10. A method of screening for a compound having an antifungal action, wherein the method comprises the steps of:
    (a) contacting a test sample with the protein of 3;
    (b) detecting the binding activity between the protein and the test sample; and
    (c) selecting a compound having an activity to bind to the protein.

11. A method of screening for a compound that has an antifungal action, which comprises the steps of:
    (a) contacting a test sample with a fungus that is overexpressing the protein of 3;
    (b) detecting the amount of transport of a GPI-anchored protein to the cell wall in the fungus; and
    (c) selecting a compound that diminishes the amount of transport of the GPI-anchored protein to the cell wall detected in step (b) as compared to the amount of transport detected when the test sample was contacted with a fungus that is not overexpressing the protein of 3,
    wherein, a decrease in the amount of GPI-anchored protein transported to the cell wall that results due to the test sample can be detected, for example, by detecting a decrease in growth rate, swelling, or temperature sensitivity of the cell, or by detecting a decrease of the protein derived from the GPI-anchored protein in the cell wall, but preferably, by detecting a decrease in the protein derived from the GPI-anchored protein at the cell wall;
    and wherein a decrease of the protein derived from the GPI-anchored protein is quantified by using any one of the following methods alone or in combination:
    (i) a reporter system reflecting the process that transports GPI-anchored proteins to the cell wall, (ii) an ELISA that quantifies one type of the GPI-anchored protein in the cell wall, (iii) measuring the activity of a GPI-anchored protein such as adhesion to animal cells, and (iv) observing the flocculent, fibrous structure of the outermost layer of a fungal cell by a transmission electron microscope.

12. A compound having an antifungal action that is isolated by the screening of 10 or 11.

13. An antifungal agent, comprising as an active ingredient a compound that inhibits the transport of GPI-anchored proteins to the cell wall of a fungus.

14. An antifungal agent, comprising as an active ingredient the antibody of 9 or the compound of 12.

15. The antifungal agent of 13, comprising as an active ingredient the compound represented by the general formula (I), a salt thereof, or a hydrate thereof, wherein in formula (I):

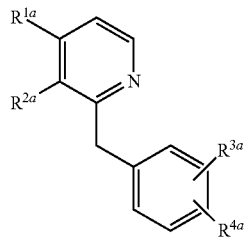

(I)

[$R^{1a}$ and $R^{2a}$ are identical to or different from each other and denote individually a hydrogen atom, halogen atom, hydroxyl group, nitro group, cyano group, trifluoromethyl group, trifluoromethoxy group, a substituted or unsubstituted $C_{1-6}$ alkyl group, $C_{2-6}$ alkenyl group, $C_{2-6}$ alkynyl group, a substituted or unsubstituted $C_{1-6}$ alkoxy group, or a group represented by the formula:

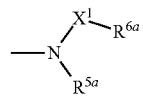

(wherein $X^1$ stands for a single bond, carbonyl group, or a group represented by the formula —S(O)$_2$—;
$R^{5a}$ and $R^{6a}$ are identical to or different from each other and denote a hydrogen atom or a substituted or unsubstituted $C_{1-6}$ alkyl group). Furthermore, $R^{1a}$ and $R^{2a}$ may together form a condensed ring selected from the group consisting of a substituted or unsubstituted benzene ring, a substituted or unsubstituted pyridine ring, a substituted or unsubstituted pyrrole ring, a substituted or unsubstituted thiophene ring, a substituted or unsubstituted furan ring, a substituted or unsubstituted pyridazine ring, a substituted or unsubstituted pyrimidine ring, a substituted or unsubstituted pyrazine ring, a substituted or unsubstituted imidazole ring, a substituted or unsubstituted oxazole ring, a substituted or unsubstituted thiazole ring, a substituted or unsubstituted pyrazole ring, a substituted or unsubstituted isoxazole ring, a substituted or unsubstituted isothiazole ring, a substituted or unsubstituted cyclohexane ring, and a substituted or unsubstituted cyclopentane ring;
$R^{3a}$ and $R^{4a}$ are identical to or different from each other and denote individually a hydrogen atom, halogen atom, hydroxyl group, nitro group, cyano group, carboxyl group, formyl group, hydroxyimino group, trifluoromethyl group, trifluoromethoxy group, $C_{1-6}$ alkyl group, $C_{1-6}$ alkoxy group, $C_{2-6}$ alkenyl group, $C_{2-6}$ alkynyl group, a group represented by the formula —C(O)NR$^{7a}$R$^{7b}$ (wherein R$^{7a}$ and R$^{7b}$ are identical to or different from each other and denote individually a hydrogen atom, or a $C_{1-6}$ alkyl group), the formula —CO$_2$R$^{7a}$ (wherein R$^{7a}$ has the same meaning as defined above), the formula —S(O)$_n$R$^{7a}$, (wherein n stands for an integer of 0 to 2 and R$^{7a}$ has the same meaning as defined above), the formula —S(O)$_2$NR$^{7a}$R$^{7b}$ (wherein R$^{7a}$ and R$^{7b}$ have the same meaning as defined above), a group of the formula

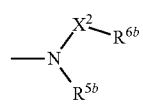

(wherein $X^2$ denotes a single bond, carbonyl group, or a group of the formula —S(O)$_2$—;
$R^{5b}$ and $R^{6b}$ are identical to or different from each other, and denote a hydrogen atom, a substituted or unsubstituted $C_{1-6}$ alkyl group, or a substituted or unsubstituted $C_{6-14}$ aryl group), or a group of the formula

—Z$^1$—Z$^2$ (wherein $Z^1$ denotes a single bond, oxygen atom, vinylene group, or ethynylene group;
$Z^2$ denotes a single bond, or a $C_{1-6}$ alkyl group substituted or unsubstituted with 0 to 4 substituents). $R^{3a}$ and $R^{4a}$ may together stand for a methylenedioxy group or 1,2-ethylenedioxy group, alternatively, R³ᵃ and R⁴ᵃ may together stand for the formation of a condensed ring selected from a group consisting of a substituted or unsubstituted benzene ring, substituted or unsubstituted pyridine ring, substituted or unsubstituted pyrrole ring, substituted or unsubstituted thiophene ring, substituted or unsubstituted furan ring, substituted or unsubstituted pyridazine ring, substituted or unsubstituted pyrimidine ring, substituted or unsubstituted pyrazine ring, substituted or unsubstituted imidazole ring, substituted or unsubstituted oxazole ring, substituted or unsubstituted thiazole ring, substituted or unsubstituted pyrazole ring, substituted or unsubstituted isoxazole ring, substituted or unsubstituted isothiazole ring, substituted or unsubstituted cyclohexane ring, and substituted or unsubstituted cyclopentane ring, except in cases where both $R^{1a}$ and $R^{2a}$ stand for hydrogen atoms.]

16. The aforementioned antifungal agent of 13, comprising as the active ingredient compound (Ia) of the formula:

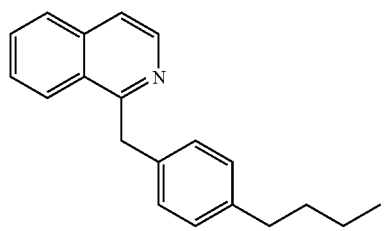

(Ia)

17. A compound represented by the general formula (II), a salt or a hydrate thereof, wherein in formula (II),

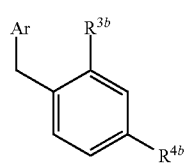

(II)

[Ar stands for a substituent selected from a group consisting of the formulae (IIIa) to (IIIf):

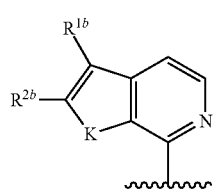

(IIIa)

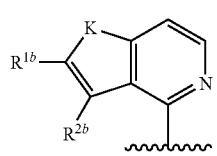

(IIIb)

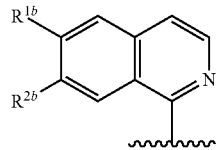

(IIIc)

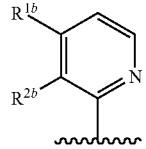

(IIId)

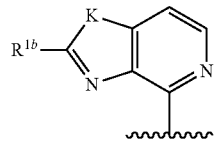

(IIIe)

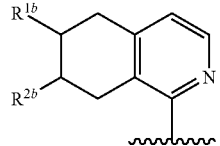

(IIIf)

(wherein K denotes a sulfur atom, oxygen atom, or a group represented by the formula —NH—;
$R^{1b}$ and $R^{2b}$ are identical to or different from each other and denote individually a hydrogen atom, halogen atom, hydroxyl group, nitro group, cyano group, trifluoromethyl group, trifluoromethoxy group, a group represented by the formula

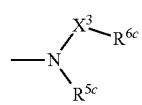

(wherein $X^3$ denotes a single bond, carbonyl group, or a group represented by the formula —S(O)₂—;
$R^{5c}$ and $R^{6c}$ are identical to or different from each other and denote a hydrogen atom, or a substituted or unsubstituted $C_{1-6}$ alkyl group), or a group represented by the formula —$X^4$—$R^{8a}$ (wherein $X^4$ denotes a single bond, oxygen atom, or sulfur atom; $R^{8a}$ denotes a $C_{1-6}$ alkyl group, $C_{2-6}$ alkenyl group, $C_{2-6}$ alkynyl group, $C_{3-8}$ cycloalkyl group, or $C_{3-8}$ cycloalkenyl group). Alternatively, $R^{1b}$ and $R^{2b}$ may together form a methylenedioxy group, or a 1,2-ethylenedioxy group.);
$R^{3b}$ and $R^{4b}$ are identical to or different from each other and denote individually a hydrogen atom, halogen atom, hydroxyl group, nitro group, cyano group, carboxyl group, formyl group, hydroxyimino group, trifluoromethyl group, trifluoromethoxy group, $C_{1-6}$ alkyl group, $C_{1-6}$ alkoxy group, $C_{2-6}$ alkenyl group, $C_{2-6}$ alkynyl group, or a group represented by the formula —$Z^{1b}$—$Z^{2b}$ (wherein $Z^{1b}$ denotes a single bond, vinylene group, or ethynylene group;
$Z^{2b}$ denotes a single bond, or a $C_{1-6}$ alkyl group that is substituted or unsubstituted with 0 to 4 substituents);

except in cases where (1) Ar stands for the aforementioned formula (IIId) wherein $R^{1b}$ and $R^{2b}$ are both hydrogen atoms, (2) at least one of $R^{3b}$ or $R^{4b}$ denotes a hydrogen atom and the other is a hydrogen atom, methoxy group, hydroxyl group, methyl group, benzyloxy group, or a halogen atom, and Ar stands for the aforementioned formula (IIIc) wherein $R^{1b}$ and $R^{2b}$ both denote hydrogen atoms or methoxy groups, (3) at least one of $R^{3b}$ or $R^{4b}$ denotes a hydrogen atom and the other is a hydrogen atom, hydroxyl group, methoxy group, or benzyloxy group, and Ar stands for the aforementioned formula (IIIc) wherein $R^{1b}$ and $R^{2b}$ both denote hydroxyl groups or benzyloxy groups, or (4) Ar stands for the aforementioned formula (IIId) wherein $R^{1b}$ is a hydrogen atom and $R^{2b}$ is a formyl group, hydroxymethyl group, or methoxycarbonyl group.]

18. The compound of 17, or a salt or hydrate thereof, wherein Ar stands for the formula:

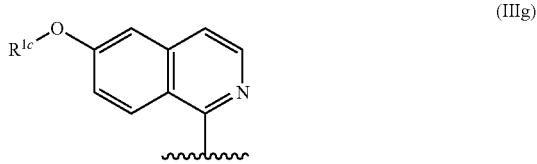

(IIIg)

(wherein $R^{1c}$ denotes a hydrogen atom, a substituted or unsubstituted $C_{1-6}$ alkyl group, or a benzyl group), and excluding the case when $R^{3b}$ denotes a hydrogen atom.

19. A compound represented by the general formula (IIIc2), or a salt or hydrate thereof, wherein in formula (IIIc2),

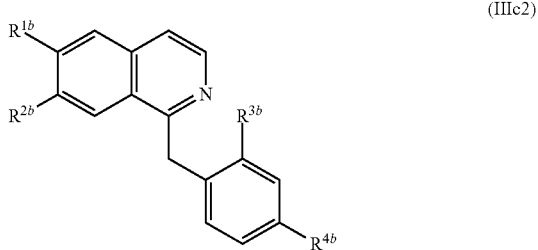

(IIIc2)

[$R^{1b}$ and $R^{2b}$ have the same meaning as defined above, except in cases wherein (1) $R^{1b}$ denotes a group represented by the formula $R^{1c}$—O— (wherein $R^{1c}$ has the same meaning as defined above), $R^{2b}$ is a hydrogen atom, and $R^{3b}$ denotes a hydrogen atom, (2) at least one of $R^{3b}$ or $R^{4b}$ denotes a hydrogen atom, and the other is a hydrogen atom, methoxy group, hydroxyl group, methyl group, benzyloxy group, or a halogen atom, and $R^{1b}$ and $R^{2b}$ both denote hydrogen atoms or methoxy groups, or (3) at least one of $R^{3b}$ or $R^{4b}$ denotes a hydrogen atom, and the other is a hydrogen atom, hydroxyl group, methoxy group, or benzyloxy group, and $R^{1b}$ and $R^{2b}$ both denote hydroxyl groups or benzyloxy groups]

20. The antifungal agent of 17, having an antifungal action.

21. The antifungal agent of 15, wherein at least one of $R^{3a}$ and $R^{4a}$ denotes a group represented by the formula —C(O)NR$^{7a}$R$^{7b}$ (wherein $R^{7a}$ and $R^{7b}$ have the same meaning as defined above), the formula —CO$_2$R$^{7a}$ (wherein $R^{7a}$ has the same meaning as defined above), the formula —S(O)$_n$R$^{7a}$ (wherein n denotes an integer of 0 to 2 and $R^{7a}$ has the same meaning as defined above.), the formula —S(O)$_2$NR$^{7a}$R$^{7b}$ (wherein $R^{7a}$ and $R^{7b}$ have the same meaning as defined above), the formula

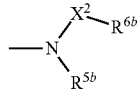

(wherein $X^2$, $R^{5b}$, and $R^{6b}$ have the same meaning as defined above), or a $C_{1-6}$ alkoxy group substituted or unsubstituted with 0 to 4 substituents, or $R^{3a}$ and $R^{4a}$ together denote a methylenedioxy group, or a 1,2-ethylenedioxy group.

22. The aforementioned antifungal agent of 15, wherein the compound having an antifungal action is (1) 1-benzylisoquinoline, (2) 1-(4-bromobenzyl)isoquinoline, (3) 1-(4-chlorobenzyl)isoquinoline, (4) 1-(4-fluorobenzyl)isoquinoline, (5) 1-(4-iodobenzyl)isoquinoline, (6) 1-(3-methylbenzyl)isoquinoline, (7) 1-(4-methylbenzyl)isoquinoline, (8) 1-(3,4-dimethylbenzyl)isoquinoline, (9) 1-(3-methoxybenzyl)isoquinoline, (10) 1-(4-methoxybenzyl)isoquinoline, (11) 1-(3,4-methylenedioxybenzyl)isoquinoline, (12) 1-(4-benzyloxybenzyl)isoquinoline, (13) 1-(4-cyanobenzyl)isoquinoline, (14) 1-(4-nitrobenzyl)isoquinoline, (15) 1-(4-aminobenzyl)isoquinoline, (16) 1-(4-methoxybenzyl)-6,7-dichloro-isoquinoline, (17) 1-(4-methoxy-2-nitro-benzyl)-isoquinoline, (18) 1-(4-methoxybenzyl)-6,7-methylenedioxy-isoquinoline, (19) 1-(2-amino-4-methoxybenzyl)isoquinoline, (20) 1-(4-methoxybenzyl)-7-hydroxy-6-methoxy-isoquinoline, (21) 1-(4-benzyloxybenzyl)-6,7-dimethoxy-isoquinoline, (22) 1-(4-methoxybenzyl)6,7-dimethoxy-isoquinoline, (23) 1 (4-methoxy-2-nitro-benzyl)-isoquinoline, (24) 3-[4-(1-isoquinolylmethyl)phenoxy]propylcyanide, (25) 1-[4-(2,2,3,3-tetrafluoropropoxy)benzyl]isoquinoline, (26) 1-[4-(2-piperidinoethoxy)benzyl]isoquinoline, (27) 4-(1-isoquinolylmethyl)phenyl(2-morpholinoethyl)ether, (28) 1-[4-(2-methoxyethoxy)benzyl]isoquinoline, (29) N-{2-[4-(1-isoquinolylmethyl)phenoxy]ethyl}-N,N-dimethylamine, (30) 1-[4-(phenethyloxy)benzyl]isoquinoline, (31) 1-{4-[(2-methylallyl)oxy]benzyl}isoquinoline, (32) 1-(4-isobutoxybenzyl)isoquinoline, (33) 1-[4-(2-phenoxyethoxy)benzyl]isoquinoline, (34) methyl 2-[4-(1-isoquinolylmethyl)phenoxy]acetate, (35) 2-[4-(1-isoquinolylmethyl)phenoxy]-1-ethanol, (36) t-butyl N-{2-[4-(1-isoquinolylmethyl)phenoxy]ethyl}carbamate, (37) 1-{4-[3-(tetrahydro-2H-2-pyranyloxy)propoxy]benzyl} isoquinoline, (38) 2-[4-(1-isoquinolylmethyl)phenoxy]-1-ethaneamine, (39) 1-[4-(3-piperidinopropoxy)benzyl]isoquinoline, (40) 3-[4-(1-isoquinolylmethyl)phenoxy]-1-propanol, (41) 1-[4-(2-ethylbutoxy)benzyl]isoquinoline, (42) 4-[4-(1-isoquinolylmethyl)phenoxy]butanoic acid, (43) 1-(4-{3-[(4-benzylpiperazino)sulfonyl]propoxy}benzyl)isoquinoline, (44) 1-(4-{3-[4-(4-chlorophenyl)piperazino]propoxy}benzyl)isoquinoline, (45) 4-(1-isoquinolylmethyl)aniline, (46) N-[4-(1-isoquinolylmethyl)phenyl]butaneamide, (47) N-[4-(1-isoquinolylmethyl)phenyl]propaneamide, (48) N-[4-(1-isoquinolylmethyl)phenyl]-1-ethanesulfonamide, (49) N-[4-(1-isoquinolylmethyl)phenyl]-N-methylethanesulfonamide, (50) N-[4-(1-isoquinolylmethyl)phenyl]-N-methylamine, (51) N-[4-(1-isoquinolylmethyl)phenyl]-N-propylamine, or (52) N-[4-(1-isoquinolylmethyl)phenyl]-N-methyl-N-propylamine.

23. A method for treating a mycotic infection comprising administering a therapeutically effective dose of any one of the antifungal agents of 13 to 22 to a mammal.

BRIEF DESCRIPTION OF THE DRAWINGS

FIG. 7 is a diagram in which the highly conserved regions in the proteins encoded by the GWT1 genes of *S. cerevisiae* (SEQ ID NO:64 (F-domain) and SEQ ID NO:67 (R-domain)), *S. pombe* (SEQ ID NO:65 (F-domain) and SEQ ID NO:68 (R-domain)), and *C. albicans* (SEQ ID NO:66 (F-domain) and SEQ ID NO:69 (R-domain)) are aligned.

DETAILED DESCRIPTION OF THE INVENTION

Figure 1:
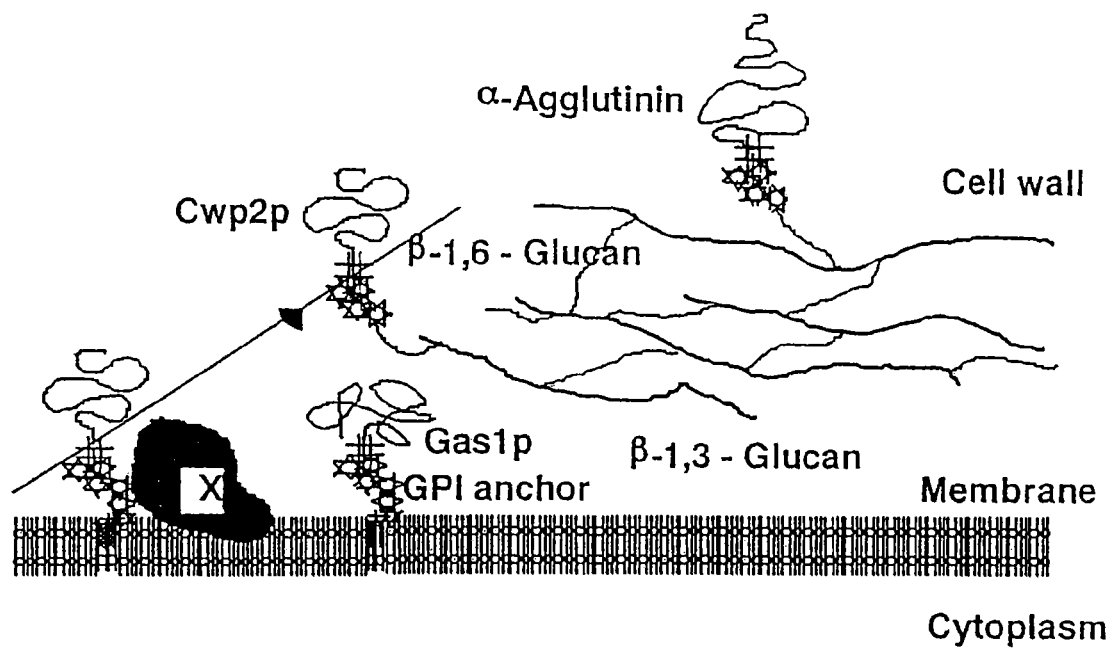
FIG. 1 is a schematic diagram of the process that transports GPI-anchored proteins to the cell wall. A GPI (Glycosylphosphatidylinositol)-anchored protein is first anchored to the plasma membrane, and then transported to the cell wall. In the formula, X is a leaving group such as a halogen group and acyl group.

The present invention will be described in detail below by explaining the meaning of the terms, symbols, and such mentioned in the present description.

In the present description, the structural formula of the compounds may represent a certain isomer for convenience, however, the present invention includes all geometrical isomers, optical isomers based on asymmetric carbon, stereoisomers, and tautomers that structurally arise from compounds, and mixtures of isomers, and it is not to be construed as being limited to the representation in the formula made for convenience, and may be any one or a mixture of isomers. Therefore, an optically active substance and a racemic substance having an asymmetric carbon atom in the molecule may exist, but in this invention there are no particular limitations and any one of them are included. Furthermore, crystal polymorphism may exist, but similarly there are no limitations, and the crystal form may be any one form or may be a mixture, and may be either an anhydride or a hydrate.

Furthermore, the compounds of the present invention include compounds exhibiting antifungal action after being metabolized, such as after being oxidized, reduced, hydrolyzed, or conjugated in vivo. Furthermore, the present invention includes compounds that produce the compounds of this invention after being metabolized, such as after being oxidized, reduced, and hydrolyzed in vivo.

The "$C_{1-6}$ alkyl group" in the present description means a straight chain or branched chain alkyl group, wherein the number of carbon ranges from 1 to 6, and specific examples include a methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 2-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, 3-methylpentyl group, and so on.

The "$C_{2-6}$ alkenyl group" in the present description means a straight chain or branched chain alkenyl group, wherein the number of carbon ranges from 2 to 6, and specific examples include a vinyl group, allyl group, 1-propenyl group, isopropenyl group, 1-butene-1-yl group, 1-butene-2-yl group, 1-butene-3-yl group, 2-butene-1-yl group, 2-butene-2-yl group, and so on.

The "$C_{2-6}$ alkynyl group" in the present description means a straight chain or branched chain alkynyl group, wherein the number of carbon ranges from 2 to 6, and specific examples include an ethynyl group, 1-propynyl group, 2-propynyl group, butynyl group, pentynyl group, hexynyl group, and so on.

The "$C_{1-6}$ alkoxy group" in the present description means an oxy group to which "$C_{1-6}$ alkyl group" defined above is bound, and specific examples include a methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group, 1-ethyl-2-methylpropoxy group, and so on.

The "$C_{6-14}$ aryl group" in the present description refers to an aromatic ring group, wherein the number of carbon ranges from 6 to 14, and specific examples include a phenyl group, 1-naphthyl group, 2-naphthyl group, as-indacenyl group, s-indacenyl group, acenaphthylenyl group, and so on.

The "halogen atom" of the present description means a fluorine atom, chlorine atom, bromine atom, and iodine atom.

"Substituted or unsubstituted" in the present description means "the substitutable site may have an arbitrary combination of one or more substituents" and specifically the substituents are, for example, a hydrogen atom, halogen, nitro group, cyano group, hydroxyl group, mercapto group, hydroxyalkyl group, carboxyl group, $C_{1-6}$ alkoxycarbonyl group, $C_{2-7}$ acylamino group, $C_{1-6}$ alkylamino group, pyridyl group, $C_{1-6}$ alkylsulfinyl group, $C_{1-6}$ alkylsulfonyl group, $C_{1-6}$ alkylsulfamoyl group, $C_{1-6}$ alkylsulfinamoyl group, $C_{1-6}$ alkylsulfenamoyl group, tetrahydropyranyl group, $C_{1-6}$ alkylcarbamoyl group, or the formula —$X^4$—$R^{8a}$ (wherein $X^4$ denotes a single bond, oxygen atom, or sulfur atom; $R^{8a}$ denotes a $C_{1-6}$ alkyl group, $C_{2-6}$ alkenyl group, $C_{2-6}$ alkynyl group, $C_{6-14}$ aryl group, $C_{3-8}$ cycloalkyl group, or $C_{3-8}$ cycloalkenyl group), and so on.

"May be substituted with 0 to 4 substituents" has the same meaning as "the substitutable site may have an arbitrary combination of 1 to 4 substituents" and the substituents have the same meaning as defined above.

"Salt" in the present invention refers to a pharmaceutically acceptable salt, and there are no particular limitations as long as the salt has formed an addition salt with a compound of this invention, and a preferred example is a haloid acid salt such as hydrofluoride, hydrochloride, hydrobromide, and hydroiodide; an inorganic acid salt such as a sulfate, nitrate, perchlorate, phosphate, carbonate, and bicarbonate; an organic carboxylate such as an acetate, oxalate, maleate, tartrate, and fumarate; an organic sulfonate such as a methanesulfonate, trifluoromethanesulfonate, ethanesulfonate, benzenesulfonate, toluenesulfonate, and camphorsulfonate; an amino acid salt such as an aspartate, and glutamate; salts with an amine such as a trimethylamin, triethylamine, procaine, pyridine, and phenethylbenzylamine; alkali metal salts such as sodium, and potassium; alkaline earth metal salts such as magnesium and calcium; and so on.

Herein below, the following will be disclosed: 1. A method for obtaining DNAs encoding proteins participating in cell wall synthesis, 2. a method for examining whether or not a test sample influences the process that transports GPI-anchored proteins to the cell wall, and 3. a method for obtaining the aforementioned compound (Ia) of the present invention.

1. A Method for Obtaining DNAs Encoding Proteins Participating in Fungal Cell Wall Synthesis Hereinafter, (1) a method for obtaining a DNA encoding a protein for acquiring resistance to the aforementioned compound (Ia) by overexpression in fungi; (2) a method for obtaining a DNA that hybridizes under stringent conditions with the DNA of SEQ ID NO:1, SEQ ID NO:3, or SEQ ID NO:5; (3) a method for obtaining a DNA that encodes a protein that participates in fungal cell wall synthesis, based on a homology search; and (4) a method for obtaining a fungus that overexpressed or lacked the protein for acquiring resistance to the aforementioned compound (Ia), will be described.

(1). A Method for Obtaining a DNA Encoding a Protein for Acquiring Resistance to the Aforementioned Compound (Ia) by Overexpression of the DNA in a Fungus Herein, "fungus" means a fungus belonging to Division Zygomycota, Ascomycota, Basidiomycota, and Deuteromycota. Preferable is a pathogenic fungus, *Mucor, Saccharomyces, Candida, Cryptococcus, Trichosporon, Malassezia, Aspergillus, Trichophyton, Microsporum, Sporothrix, Blastmyces, Coccidioides, Paracoccidioides, Penicillinium,* or *Fusarium*, and more preferable is *C. albicans, C. glabrata, C. neoformans*, or *A. fumigatus. S. cerevisiae* and *S. pombe*, for which genetic analyses are easy, are also preferred strains.

A plasmid library of a fungal gene is introduced into a fungus. The plasmid library of *S. cerevisiae* and *S. pombe* can be obtained from ATCC (Information for ATCC Number: 37323), and the plasmid library of *C. albicans* can be produced by the method according to Navaro-Garcia, F. et al, Mol. Cell. Biol., 15: 2197-2206, 1995. The obtained plasmid library is introduced to the fungi by the method according to Gietz, D. et al, Nucl. Acids Res. 20: 1425, 1992. Alternatively, a kit such as YEASTMAKER™ Yeast Transformation System (Clontech) may be used.

The Fungus to which the plasmid library is introduced is cultured in the presence of the aforementioned compound (Ia). Specifically, an agar medium containing the aforementioned compound (Ia) at a concentration of 1.56 to 25 µg/ml, preferably 1.56 to 6.25 µg/ml, and more preferably 3.125 µg/ml is inoculated with the fungus into which a plasmid library has been introduced, is cultured for an appropriate length of time, at 30° C. to 42° C. for 2 to 5 days, or preferably at 37° C. for 3 days. The colony formed upon proliferation is further cultured in a medium containing the aforementioned compound (Ia), and the plasmid is purified from the proliferated fungal cells. Purification of the plasmid can be performed by the method according to METHODS IN ENZYMOLOGY, Vol. 194: 169-182 (1991), for example.

Preferably, the nucleotide sequence of the obtained plasmid is determined directly, but if necessary, cloning into an appropriate vector, for example pBluescript II, and pUC19 suitable for nucleotide sequence determination, is done to determine the nucleotide sequence. A nucleotide sequence can be determined for example by the method accompanying the ABI377 System (PE applied Biosystems) manual.

In the Examples of the present invention, all 27 of the independently obtained colonies of *S. cerevisiae*, and 28 colonies out of 30 colonies of *C. albicans* contained the DNAs of this invention. Only one gene that confers resistance to the aforementioned compound (Ia) exists in these fungi and this can be obtained by the abovementioned method.

(2). A Method for Obtaining a DNA that Hybridizes Under Stringent Conditions to the DNA of SEQ ID NO:1 SEQ ID NO:3 or SEQ ID NO:5

An example of a method for obtaining a DNA encoding a protein participating in fungal cell wall synthesis according to the present invention comprises designing a primer from the information of the nucleotide sequence of SEQ ID NO:1 using the genomic DNA of *S. cerevisiae* as a template, or designing a primer from the information of the nucleotide sequence of SEQ ID NO:3 or SEQ ID NO:5 using the genomic DNA of *C. albicans* as the template, then performing PCR, and cloning the amplified DNA into an appropriate vector, such as pBlueScript. The primer is designed as necessary according to the region to be amplified, and the length is preferably 15 bp or more, more preferably 20 bp or more, and in some cases sequences necessary for subsequent DNA construction, such as restriction enzyme sites, may be added. The conditions for PCR can be determined appropriately according to factors such as the length of primer, the length of the region to be amplified, and the amount of template DNA to be used. For example, a DNA encoding a protein participating in cell wall synthesis in a fungus can be obtained using 200 ng of the genomic DNA of *C. albicans* as a template, and SEQ ID NO:21 and SEQ ID NO:22 as primers under conditions of 94° C. for 4 minutes→(94° C. for 30 seconds→68° C. for 5 minutes)×35 cycles→72° C. for 4 minutes.

The DNA obtained by PCR may be used as a probe for obtaining other types of fungal DNA showing homology to the DNA encoding the protein participating in cell wall synthesis. Specifically, for example, to obtain a homologous gene of *C. albicans* encoding the protein participating in *S. cerevisiae* cell wall synthesis, DNA that hybridizes under stringent conditions can be cloned from the genomic library or cDNA library of *C. albicans*, using the genomic DNA of *S. cerevisiae* as a template, and using DNA that is obtained by PCR as a probe. Herein, stringent conditions refer to hybridization in 4×SSC at 65° C., then washing in 0.1×SSC at 65° C. for 1 hour, for example. Furthermore, in another the stringent conditions are 4×SSC at 42° C. in 50% formamide. Alternatively, conditions such as hybridization in the PerfectHyb™ (TOYOBO) solution at 65° C. for 2.5 hours, then washing in 1). 2×SSC, 0.05% SDS solution at 25° C. for 5 minutes, 2). 2×SSC, 0.05% SDS solution at 25° C. for 15 minutes, and 3). 0.1×SSC, 0.1% SDS solution at 50° C. for 20 minutes, are also allowed.

The Examples of this invention demonstrate from Southern Blot analysis that there is only one gene in *C. albicans* that hybridizes with the DNA of SEQ ID NO:1, and shows the cloning of this gene. From the above-mentioned method, DNA that hybridizes with SEQ ID NO:1 or SEQ ID NO:3 can be obtained.

(3). A Method for Obtaining a DNA that Encodes a Protein that Participates in Fungal Cell Wall Synthesis Based on a Homology Search The present invention revealed the GWT1 homologues of *S. cerevisiae*, *C. albicans*, *S. pombe*, *A. fumigatus*, and *C. neoformans*. The region conserved among these genes is considered to be important for GWT1 gene products to exhibit their function, and may very well be conserved in other fungi.

Therefore, a DNA encoding a protein participating in fungal cell wall synthesis can be obtained by either carrying out hybridization upon constructing a probe based on the amino acid sequence of the conserved region, or by performing PCR by designing primers based on the sequence. The PCR primer may be of any sequence as long as it is designed to encode the conserved region, but is preferably SEQ ID NOs: 29 and 31 or preferably SEQ ID NOs: 29 and 30.

Furthermore, as another method, a DNA encoding a protein participating in fungal cell wall synthesis can be obtained by carrying out PCR with cDNA or genomic DNA upon finding a nucleotide sequence showing homology to GWT1 from gene fragments registered in databases, and then designing primers based on that nucleotide sequence.

Examples of PCR methods for obtaining a full-length gene based on the obtained sequence are techniques such as 3'-RACE, 5'-RACE, and inverse PCR, and it is also possible to select by hybridization a clone containing neighboring sequences. A full-length gene can be obtained by combining these techniques.

(4). A Method for Obtaining a Fungus that Overexpresses or Lacks a Protein for Acquiring Resistance to the Aforementioned Compound (Ia)

A Fungus, preferably *S. cerevisiae*, that overexpresses a protein for acquiring resistance to the aforementioned compound (Ia) of this invention can be obtained by the method of inserting an expression vector expressing the protein into a particular position on the fungal chromosome, for example an expression vector in which the DNA of SEQ ID NO:1 is connected downstream of a promoter, which can forcibly express the protein in fungi, preferably the promoter of budding yeast enolase gene (ENO1). The insertion method can be performed, for example, by the steps of, inserting a desired sequence into the multicloning site of pRS304 (Sikorski R S et al, Genetics. 122 (1): 19-27, 1989), constructing a vector for integration, and introducing the vector into the fungus. One can refer to METHODS IN ENZYMOLOGY Vol. 194: 281-301 (1991) for details.

Furthermore, an overexpressed strain of *C. albicans* can be obtained by incorporating the gene of SEQ ID NO:3 or SEQ ID NO:5 into an expression vector for *C. albicans*, such as pCARS1 and pRM1(Pla J et al, Yeast 12: 1677-1702, 1996), and then transforming *C. albicans* (Sanglard D et al, Antimicrobiol. Agents Chemother. 40: 2300-2305, 1996).

Fungi of this invention lacking a gene for acquiring resistance against the aforementioned compound (Ia), preferably *S. cerevisiae*, can be obtained by the following methods, but is not to be construed as being limited thereto.

PCR amplification is carried out using a marker gene, preferably his5 gene of *S. pombe*, as a template, and using primers that are designed so that PCR products that contain the gene to be deleted (30 bp or more, or preferably 40 bp or more). In the case of *S. cerevisiae*, the genetic sequence of SEQ ID NO:1, positioned on both ends can be obtained. The PCR products can be purified and introduced into fungi, then cultured in a selection medium corresponding to the marker gene, for example, his⁻ for his5, to obtain the deletion strain.

Furthermore, the deletion strain of *C. albicans* is obtained by the usual method using a hisG-URA3-hisG cassette (Fonzi W A et al, Genetics 134: 717-728,1993) based on the nucleotide sequence information of SEQ ID NO:3 or SEQ ID NO:5.

2. A Method for Examining Whether or not the Test Sample Influences the Process that Transports GPI-Anchored Proteins to the Cell Wall Whether or not the test sample inhibits the process that transports GPI-anchored proteins to the cell wall, or whether or not the test sample inhibits the expression of the GPI-anchored protein in the fungal surface can be examined by (1) a method using a reporter enzyme, (2) a method using an antibody that reacts with the surface glycoprotein of the fungal cell wall, (3) a method for examining the adhesion ability towards animal cells, and (4) a method for observing fungi using an optical microscope or an electron microscope.

By using the methods of (1) to (4) described below, preferably the methods of (1) to (4) in combination, the test sample is judged to inhibit the process that transports GPI-anchored proteins to the cell wall, or the expression of the GPI-anchored proteins at the fungal surface. Furthermore, it is judged that the test sample influences the process that transports GPI-anchored proteins to the cell wall when the degree of inhibition diminishes or the inhibition is no longer seen when the protein encoded by the DNA of the present invention is overexpressed in fungi.

Hereinafter, the methods of (1) to (4) will be described.

(1). A Method Using a Reporter Enzyme

The process that transports GPI-anchored proteins to the cell wall can be quantified by a tracer experiment such as labeling a GPI-anchored protein with a radioactive isotope, then upon fractionation of the fungal cell wall fraction, immunoprecipitating with an antibody against a GPI-anchored protein. Alternatively, the quantification can be more readily done by expressing the C-terminal sequence considered to function as a transport signal, which is commonly observed among GPI-anchored proteins, as a fusion protein with an easily measurable enzyme (reporter enzyme), fractionating the fungal cell wall fraction, and then using a reporter system that measures the enzyme activity of each fraction (Van Berkel M A A et al, FEBS Letters, 349: 135-138, 1994). Hereinafter, a method using the reporter enzyme will be explained, but the present invention is not to be construed as being limited thereto.

First, the reporter gene is constructed and is introduced into a fungus. The reporter gene is constructed by linking a promoter sequence that functions in fungi, followed by DNAs that respectively encode a signal sequence, a reporter enzyme, and a GPI-anchored protein C-terminal sequence so that the reading frames match. Examples of the promoter sequences are those of promoters such as GAL10, and ENO1. Examples of signal sequences are those of α-factor, invertase, lysozyme, and such. Examples of reporter enzymes are β-lactamase, lysozyme, alkaline phosphatase, β-galactosidase, and such. Green Fluorescence Protein (GFP), which can be detected easily, can be used, even though it does not have enzyme activity. Examples of GPI-anchored protein C-terminal sequences are α-agglutinin C-terminal sequence, CWP2 C-terminal sequence, and such. Furthermore, it is preferable to insert an appropriate selection marker such as LEU2, and URA3 into the vector containing the constructed reporter gene.

The constructed reporter gene is inserted into a fungus by an appropriate method, such as the lithium acetate method (Gietz D et al, Nucl. Acids Res. 20: 1425, 1992), and cultured, if necessary by a method suitable for the selection marker, such as Leu⁻ medium for LEU2, and Ura⁻ medium for URA3, and then fungi into which the DNA has been introduced are selected.

Whether or not a test sample influences the process that transports GPI-anchored proteins to the cell wall is examined by the following method.

The reporter gene-introduced fungi are cultured under appropriate conditions, for example at 30° C. for 48 hours, in the presence of a test sample. After culturing, the culture supernatant is centrifuged, and the reporter enzyme activity of the culture supernatant fraction is measured. The remaining cell fraction is washed, then the cell wall components are separated by an appropriate method, such as degrading the cell wall glucan with glucanase, and then measuring the reporter enzyme activity of the cell wall fraction and the cytoplasmic fraction. The assay can be simply carried out by determining the amount of reporter enzyme in the cell fraction by centrifuging, then without washing the cells, determining the amount of reporter enzyme derived from the culture supernatant fraction that remains in the cell fraction by proportional calculation, and subtracting this from the amount of reporter enzyme of the cell fraction.

If an activity to increase the reporter enzyme activity within the culture supernatant fraction (activity per cell), or an activity to decrease the reporter enzyme activity in the cell wall fraction (activity per cell) is confirmed in the test sample, the test sample is judged to have influenced the process that transports GPI-anchored proteins to the cell wall.

(2). A Method Using an Antibody that Reacts with the Surface Glycoprotein of a Fungal Cell Wall Whether or not the test sample influences the expression of the GPI-anchored protein at the fungal surface layer can be detected by quantifying a GPI-anchored protein in the fungal cell wall using an antibody that reacts with the protein.

For example, as the antibody, the antigenic determinant is predicted from the amino acid sequence of a GPI-anchored protein, for example, α-agglutinin, Cwp2p, and Als1p (Chen M H et al, J. Biol. Chem., 270:26168-26177, 1995; Van Der Vaat J M et al, J. Bacteriol., 177:3104-3110, 1995; Hoyer L L et al, Mol. Microbiol., 15:39-54, 1995), the peptide of that region is synthesized, this is bound to an antigenic substance, such as a carrier protein, and then polyclonal antibodies can be obtained by immunizing a rabbit and such, or a monoclonal antibody can be obtained by immunizing a mouse and such. Furthermore, a house rabbit polyclonal antibody against the Als1p peptide is preferable.

In an alternative method, a monoclonal antibody against a GPI-anchored protein may be obtained by immunizing a mouse and such with a fungus, preferably a fungus overexpressing the GPI-anchored protein, such as α-agglutinin, Cwp2p, and Als1p, and in some cases, by immunizing with the partially purified GPI-anchored protein, and selecting the clone yielded as a result of the fusion by ELISA, Western blot analysis, and such.

Whether or not the test sample influences the process that transports GPI-anchored proteins to the cell wall, and diminishes the amount of the protein derived from the GPI-anchored protein in the cell wall can be examined by the following method.

A fungus is cultured in the presence of a test sample under appropriate conditions, such as 30° C., for 48 hours. The cultured fungus is collected by centrifugation and the cells are disrupted, preferably using glass beads. The washed, disrupted cells are preferably subjected to centrifugal extraction with SDS, then the precipitate is washed. After the extraction, the disrupted cells are treated with an enzyme that degrades glucan, preferably glucanase, and the centrifuged supernatant thereof is the GPI-anchored protein sample.

The anti-Als1p peptide antibody is coated onto a 96-well plate by incubating at 4° C. overnight. After washing with a washing solution, preferably PBS containing 0.05% Tween 20 (PBST), blocking is carried out with a reagent that blocks the non-specific adsorption sites of the 96-well plate, preferably a protein such as BSA, and gelatin, more preferably BlockAce. After washing again with a washing solution, preferably PBST, in some cases, after adding an appropriately diluted GPI-anchored protein sample, the reaction is carried out for an appropriate length of time, such as 2 hours at room temperature. After washing with a washing solution, preferably with PBST, an antibody against the enzyme-labeled *C. albicans*, preferably HRP-labeled anti-Candida antibody, is reacted for an appropriate length of time, such as 2 hours at room temperature. The method for labeling may be enzyme labeling or radioactive isotope labeling. After washing with a washing solution, preferably PBST, the amount of Als1p in the GPI-anchored protein sample is calculated by a method appropriate for the type of label, i.e. for an enzyme label, adding a substrate solution, and then upon stopping the reaction, measuring the absorbance at 490 nm.

(3). A Method for Examining the Adhesion Ability Towards Animal Cells

Whether or not the test sample influences expression of a GPI-anchored protein on the fungal surface can be examined by measuring the activity of the GPI-anchored protein in the fungal cell wall, preferably by measuring the adhesion ability of fungi to animal cells, and such. Besides Als1p, Hwp1p, and such participating in adhesion to animal cells, α-agglutinin participating in mating, Flo1p participating in yeast aggregation, and such are known as GPI-anchored proteins. Hereinafter, examination methods that use the adhesion ability of fungi to animal cells will be explained in detail, but this invention is not to be construed as being limited thereto.

As the fungus, a fungus having an adhesion ability towards cells is used, and preferably, the fungus is *C. albicans*. For mammalian cells, cells that adhere to the fungus are used, and preferably, are intestinal epithelial cells. The mammalian cells are cultured and are immobilized by an appropriate method such as ethanol immobilization. The test sample and the fungi, which have been incubated for an appropriate length of time, such as 48 hours at 30° C., are inoculated, then after culturing for a certain length of time, for example 1 hour at 30° C., the culture supernatant is removed, washed with a buffer, and is superposed onto an agar media, such as Sabouraud Dextrose Agar Medium (Difco). After culturing at 30° C. overnight, the number of colonies is counted, and the adhesion rate is calculated.

If activity to lower the number of colonies formed by adhesion of fungi to cells is observed in a test sample compared to that of fungi that are not treated with the compound, the test sample is judged to have influenced the process that transports GPI-anchored proteins to the cell wall.

(4). A Method for Observing Fungi Using an Electron Microscope or an Optical Microscope Whether or not a test sample influences the expression of the GPI-anchored proteins in the fungal surface can be examined by observing the structure of the fungal cell wall using an electron microscope.

In the presence of a test sample, a fungus such as *C. albicans* is cultured for a certain length of time, for example, 48 hours at 30° C., and the ultrafine morphological structure is observed with a transmission electron microscope. Herein, observation with a transmission electron microscope can be carried out, for example by the method according to the Electron Microscope Chart Manual (Medical Publishing Center). The flocculent fibrous structure of the outermost layer of the fungal cell that has a high electron density and is observable by transmission electron microscope image, is considered to be a surface glycoprotein layer having GPI-anchored proteins as its constituents, and is not influenced by other existing antifungal agents. When this flocculent fibrous structure of the outermost layer of a fungal cell, which has a high electron density, disappears leaving a slight layer with a high electron density, compared to that in the untreated cells, the test sample is judged to have influenced the process that transports GPI-anchored proteins to the cell wall.

When images, in which fungal cells are largely swollen and budding (division) is inhibited, are observed under a transmission electron microscope in addition to an optical microscope, the test sample is judged to have an influence on the cell wall.

The compounds of the present invention represented by the formula (I)

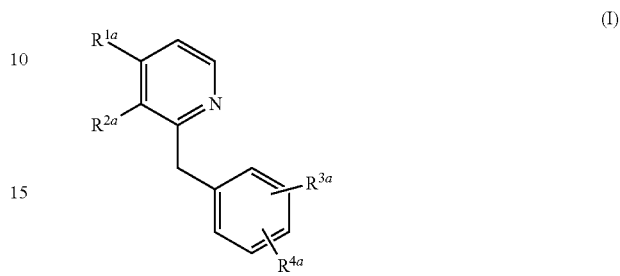

(wherein the symbols have the same meaning as defined above) can be synthesized by utilizing conventional organic chemical reactions and such that have been known to date. For example, it can be synthesized by the following methods.

Production Method (1)

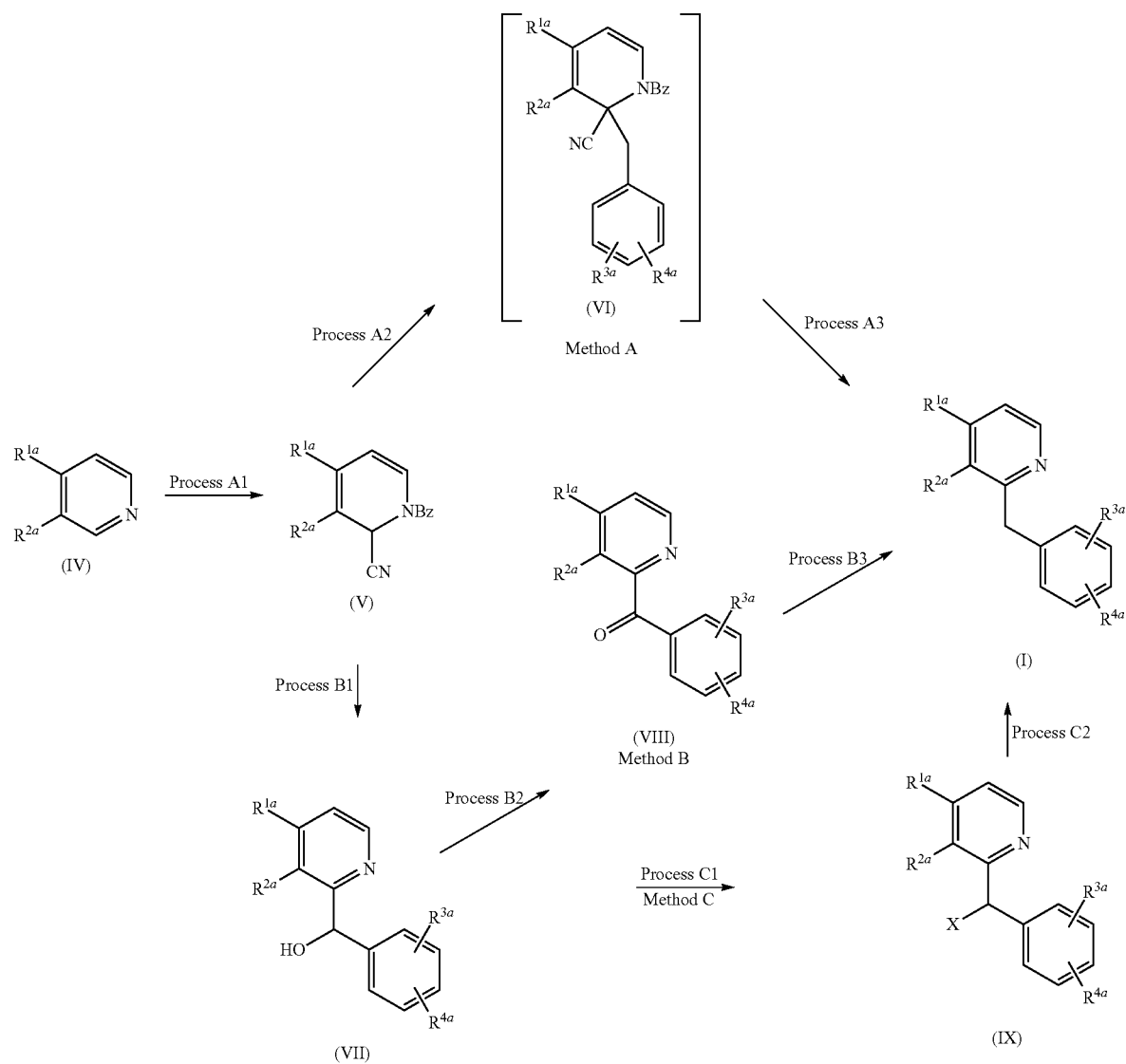

In the above formulae, X is a leaving group such as a halogen group and acyl group. Other symbols in the formulae have the same meaning as defined above.

Process A1

A reaction for producing the Reissert compound (V). The compound can be produced based on the reaction conditions according to the literature, such as Org. Synth., VI, 115 (1988); Heterocycles, 36 (11), 2489 (1993); J. Chem. Soc. (C), 666 (1969); or J. Heterocycl. Chem., 29(5), 1165 (1992). Specifically, the reagents used are, for example, a combination of benzoyl chloride and potassium cyanide.

Process A2

A process for alkylation. The compound (VI) can be produced by reacting the compound (V) with a substituted benzyl halide derivative, a substituted benzylmethanesulfonate derivative, or such in the presence of a base. Specific examples of the base include sodium hydride, sodium hydroxide.

Process A3

A process for hydrolysis reaction. The compound (I) can be produced by hydrolysis of the compound (VI) in the presence of a base.

Method A is a method for producing the compound (I) via Process A1, Process A2, and Process A3.

Process B1

A process for conversion of the compound (V) to the compound (VII). The compound (VII) can be produced by reacting the compound (V) with a substituted benzaldehyde in the presence of a base and a phase-transfer catalyst. Examples of the base include sodium hydroxide and potassium hydroxide. Examples of the phase-transfer catalyst include triethylbenzylammonium chloride.

Process B2

A process for oxidation of the alcohol to the ketone. The ketone derivative (VIII) can be produced by using an oxidizing agent and a condition conventionally used for the oxidation reaction of an alcohol to a ketone. Specifically, the oxidizing agent is, for example, manganese dioxide, chromium dioxide, or benzoquinone.

Process B3

A process for reduction of the ketone to the methylene. The methylene derivative (I) can be produced by using a conventionally used combination of reducing agents for the reduction reaction of the ketone derivative (VIII) to the methylene derivative (I). Examples of the combination of the reducing agents include hydrazine hydrate and sodium hydroxide or potassium hydroxide, and triethylsilane and boron trifluoride, or trifluoromethanesulfonic acid.

Method B is a method for producing the compound (I) via Process A1, Process B1, Process B2, and Process B3.

Process C1

A process for halogenation or acylation of the hydroxyl group. The compound (IX) can be produced by reacting a halogenating agent or an acylating agent with the compound (VII). Examples of the halogenating agent include thionyl chloride, concentrated hydrochloric acid, and phosphorus tribromide. Furthermore, examples of the acylating agent include acid halides such as acetyl chloride and acid anhydrides such as acetic anhydride.

Process C2

A process for reductive elimination reaction of the halogen group or the acyl group. The compound (I) can be produced by hydroelimination of the compound (IX), for example, by using a catalyst.

Examples of the catalyst include palladium-carbon.

Method C is a method for producing the compound (I) via Process A1, Process B1, Process C1, and Process C2.

Production Method (2)

The compound of the present invention represented by the formula (I) can also be synthesized by the following method.

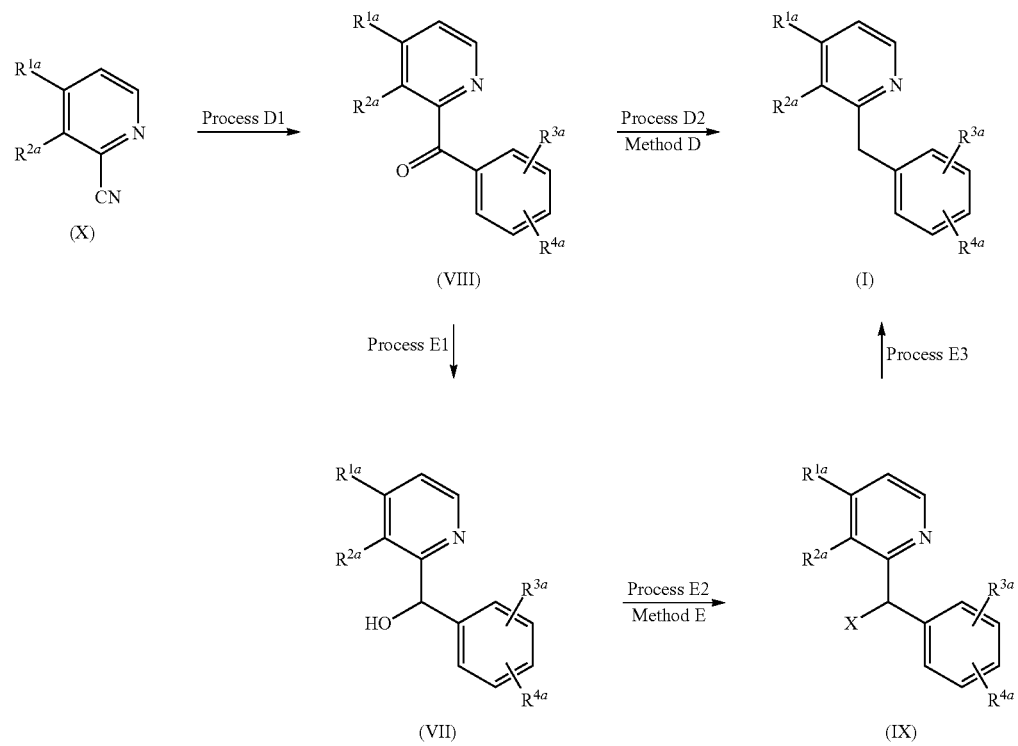

In the formula, X is a leaving group such as a halogen group and acyl group. Other symbols in the formulae have the same meaning as defined above.

Process D1

A process for a Grignard reaction and a subsequent acid hydrolysis reaction. The compound (VIII) can be produced by reacting the compound (X) with a substituted or unsubstituted phenyl Grignard reagent, followed by hydrolysis in the presence of an acid.

Process D2

The methylene derivative (I) can be produced from the ketone derivative (VIII) by conditions similar to that of Process B3.

Method D is a method for producing the compound (I) via Process D1 and Process D2.

Process E1

A process for the reduction reaction from the ketone to the alcohol. The compound (VII) can be produced from the compound (VIII) using a reducing agent and conditions conventionally used for the reduction reaction of a ketone to an alcohol. Specific examples of the reducing agent include sodium borohydride and lithium aluminum hydride.

Process E2

Under conditions similar to that of Process C1, the halogenated or acylated derivative (IX) can be produced from the alcohol derivative (VII).

Process E3

Under conditions for reductive elimination reaction similar to that of Process C2, the compound (I) can be produced from the compound (IX).

Method E is a method for producing the compound (I) via Process D1, Process E1, Process E2, and Process E3.

Production Method (3)

The compound of the present invention represented by the formula (I) can also be synthesized by the following method.

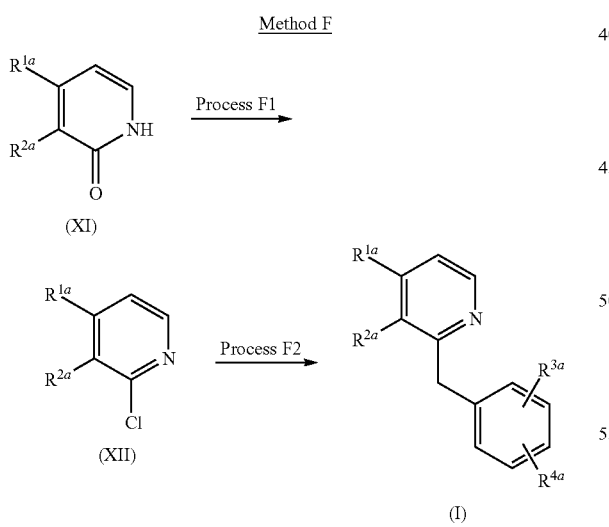

Method F

The symbols in the formulae have the same meaning as defined above.

Process F1

A process for the chlorination reaction. The compound (XIX) can be produced by reacting the compound (XI) with a chlorinating agent. Examples of the chlorinating agent include phosphorus oxychloride and thionyl chloride.

Process F2

A process for the coupling reaction with a Grignard reagent. The compound (I) can be produced by reacting the compound (XII) with a substituted or unsubstituted benzyl Grignard reagent in the presence of a catalyst, based on the reaction conditions according to the literature, such as Arch. Pharm, 314, 156 (1981). Examples of the catalyst include [1,1'-bis(diphenylphosphino)ferrocene]dichloro nickel(II).

Method F is a method for producing the compound (I) via Process F1 and Process F2.

Production Method (4)

The compound of the present invention of the formula (I), wherein $R^{1a}$ and $R^{2a}$ together form a condensed ring such as a benzene ring, pyridine ring, pyrrole ring, thiophene ring, furan ring, cyclohexane ring, or cyclopentane ring, can be synthesized by the following method.

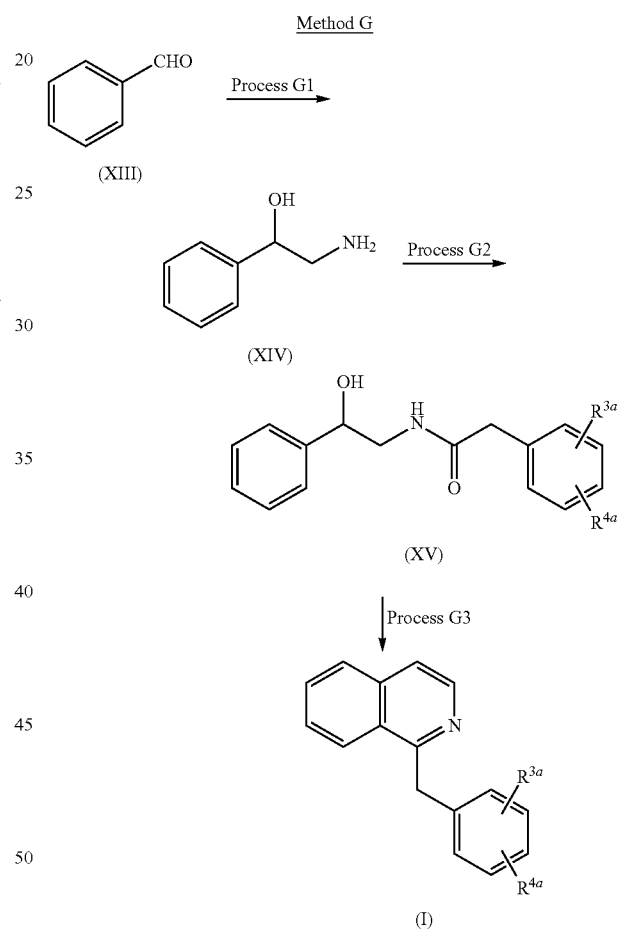

The symbols in the formulae have the same meaning as defined above.

The production method in which the isoquinoline ring is formed is shown below as an example.

Process G1

A process for the condensation reaction and the subsequent reduction reaction. The compound (XIV) can be produced by a condensation reaction between the substituted or unsubstituted benzaldehyde derivative (XIII) and nitromethane, followed by reduction of the nitro group. Examples of the reagent used for the reduction of the nitro group include a combination of palladium-carbon and ammonium formate, and lithium aluminum hydride.

Process G2

An amide bond formation reaction. The compound (XV) can be produced by reacting the compound (XIV) and a substituted or unsubstituted phenylacetyl chloride with a coupling reagent for an amide bond formation reaction. Examples of the coupling reagent include a combination of N,N'-dicyclohexylcarbodiimide and N-hydroxysuccinimide, a combination of N,N'-dicyclohexylcarbodiimide and N-hydroxybenzotriazole, and 1,1'-carbonyldiimidazole.

Process G3

A process for the cyclization reaction. The compound (XV) can be produced based on the reaction conditions according to the literature, such as Organic Reaction, 6, 74 (1951); J. Hetetocyclic Chem., 30, 1581 (1993). Examples of the reagent for this reaction include phosphorus oxychloride and polyphosphoric acid.

Method G is a method for producing the compound (I) via Process G1, Process G2, and Process G3.

Production Method (5-1)

Replacement of the substituent $R^{3a}$ or $R^{4a}$ of the compound (I) synthesized by the aforementioned production method (5-1) Replacement of the substituent with an amino group, amide group, sulfonamide group, etc.

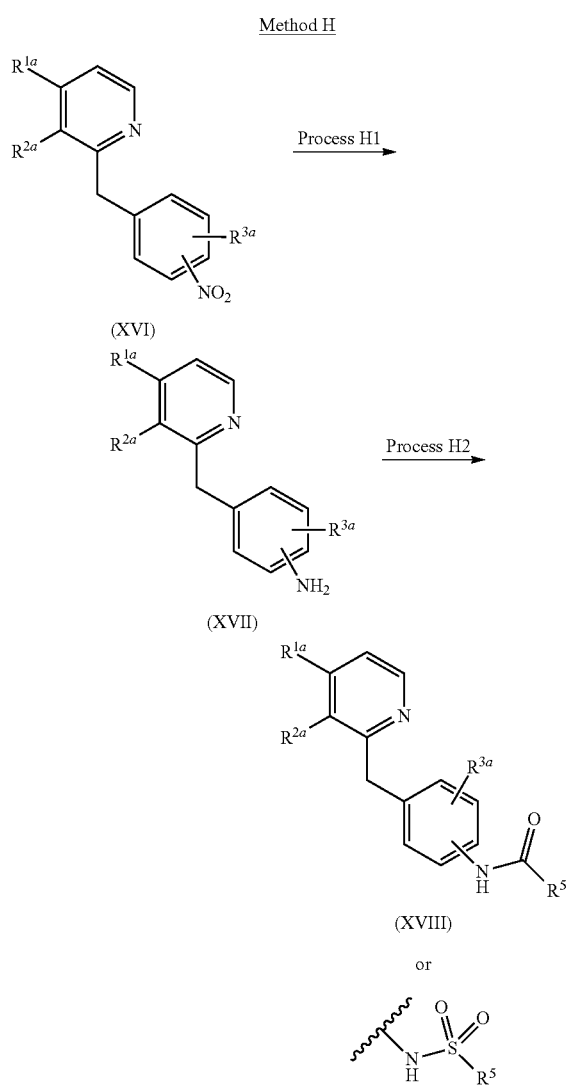

Process H1

A reduction reaction of the nitro group. The compound (XVII) can be produced by reducing the compound (XVI) with a conventionally used method for reduction of a nitro group. Examples of the reduction method are catalytic hydrogenation reduction by palladium-carbon, or palladium hydroxide, and reduction by iron-ammonium chloride, iron-hydrochloric acid, iron-acetic acid, etc.

Process H2

A process for the acylation or sulfonylation reaction. The compound (XVIII) can be produced by treating the compound (XVII) with an acid chloride or acid anhydride.

Method H is a method for producing the compound (XVIII) via Process H1 and Process H2.

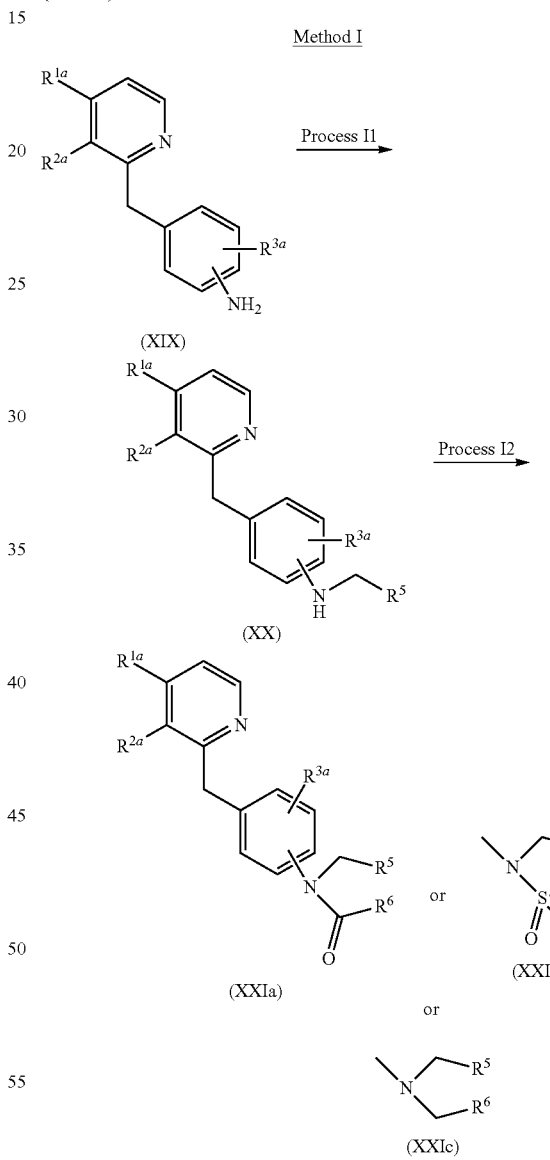

The symbols in the formulae have the same meaning as defined above.

Process I1

A process for the reductive amination reaction. The compound (XX) can be produced from the compound (XIX) and a substituted or unsubstituted aldehyde based on the reaction conditions according to the literature, such as J. Am. Chem. Soc., 93, 2897 (1971); Comprehensive Organic Synthese, 8, 25 (1991); Tetrahedron, 40, 1783 (1984); and Tetrahedron, 41, 5307 (1985). Examples of the reductive amination reagent include sodium triacetoxyhydroborate, sodium cyanotrihydroborate, borane-pyridine complex, and palladium-carbon/hydrogen.

Process I2

A process for the acylation, sulfonylation, or reductive amination reaction. The compound (XXIa) or the compound (XXIb) can be produced from the compound (XX) using an acid chloride or an acid anhydride. The compound (XXIc) can be produced by carrying out a reductive amination reaction similarly to that of Process I1.

Method I is a method for producing the compound (XXIa), the compound (XXIb), or the compound (XXIc) via Process I1 and Process I2.

Production Method (5-2)

Replacement of the substituent $R^{3a}$ or $R^{4a}$ of the compound (I) synthesized by the aforementioned production method (5-2) Replacement of the substituent with a hydroxyl group, alkoxy group, etc.

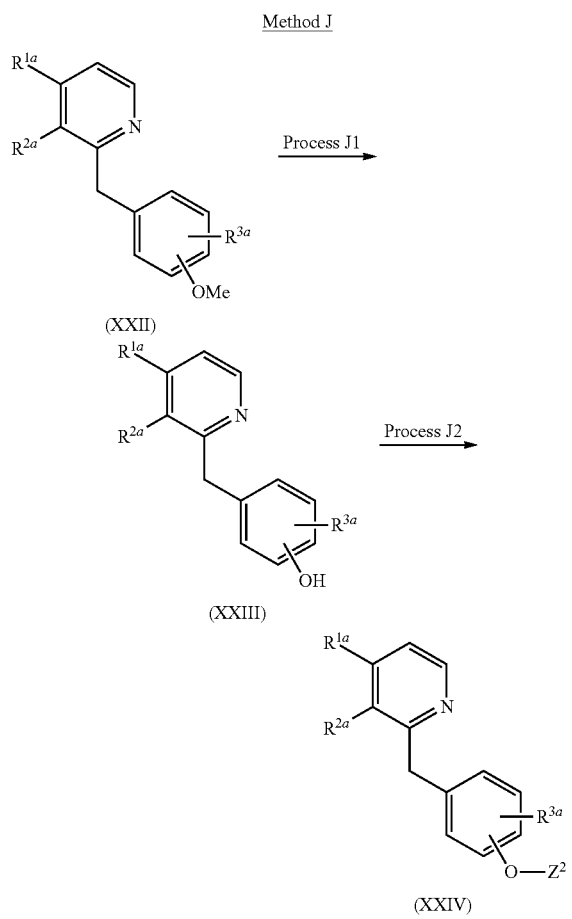

Process J1

The compound (XXIII) can be produced from the compound (XXII) by a demethylation reaction based on the reaction conditions according to the literature, such as Bull. Chem. Soc. Jpn., 44, 1986 (1971); Org. Synth., Collect. Vol. V, 412 (1073); J. Am. Chem. Soc., 78, 1380 (1956); or J. Org. Chem., 42, 2761 (1977). Examples of the reagent used for the demethylation reaction include 47% aqueous hydrobromic acid solution, boron tribromide, pyridine hydrochloride, and iodotrimethylsilane.

Process J2

A process for the alkylation reaction. The compound (XXIV) can be produced by reacting the compound (XXIII) with a substituted or unsubstituted alkyl halide, a substituted or unsubstituted alkylmethane sulfonate, or such in the presence of a base.

Method J is a method for producing the compound (XXIV) via Process J1 and Process J2.

Production Method (5-3)

Replacement of the substituent $R^{3a}$ or $R^{4a}$ of the compound (I) synthesized by the aforementioned production method (5-3) Replacement of the substituent with a vinylene group, an ethynylene group, alkyl group, etc.

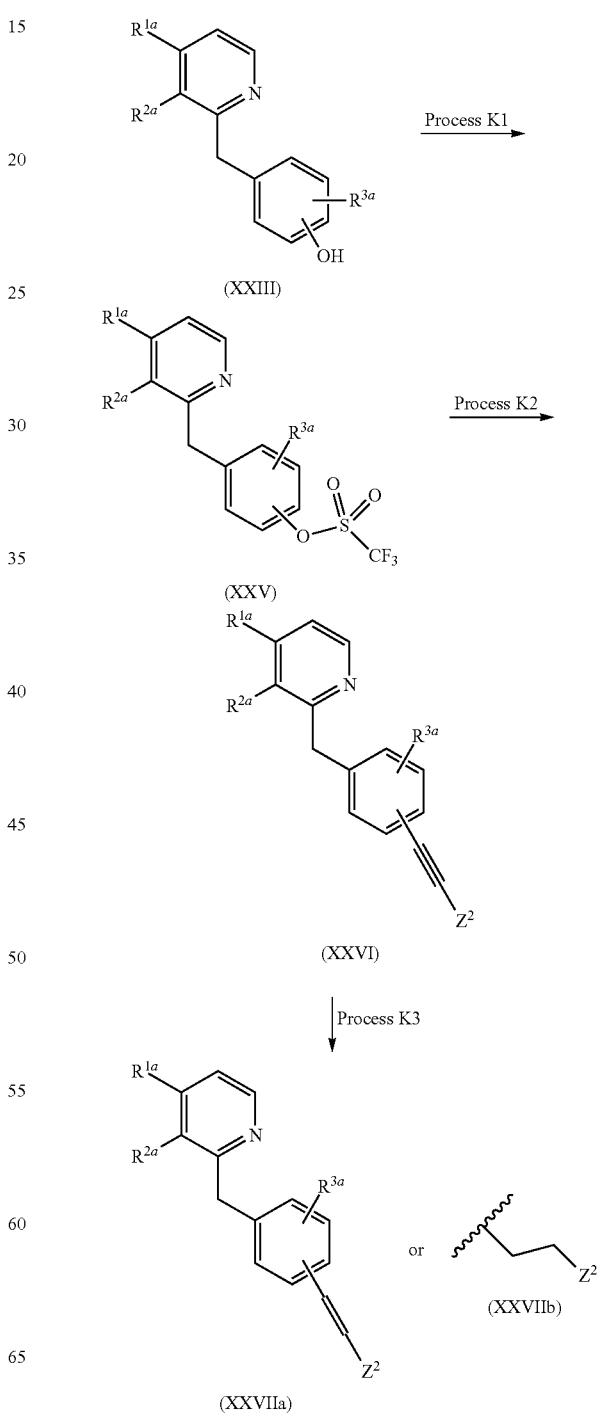

The symbols in the formulae have the same meaning as defined above.

Process K1

A process for the triflation reaction. The compound (XXV) can be produced by reacting the compound (XXIII) with trifluoromethane sulfonic acid anhydride in the presence of a base.

Process K2

A process for the coupling reaction with an alkyne. The compound (XXVI) can be produced by coupling the compound (XXV) with an alkyne derivative in the presence of a palladium phosphine complex, copper iodide, and a base. Examples of reagents that produce the palladium phosphine complex in the reaction system include a combination of palladium-carbon and triphenylphosphine, tetrakistriphenylphosphine palladium (0) and triphenylphosphine, dichlorobistriphenylphosphine palladium (II), palladium (II) acetate and tri(o-tolyl)phosphine, and palladium(II) acetate and 1,1'-bis(diphenylphosphino)ferrocene. Examples of the base include triethylamine, piperidine, pyridine, and potassium carbonate. Depending on the reaction, lithium chloride may be used.

Process K3

A process for the reduction reaction of the unsaturated hydrocarbon. The compound (XXVIIa) or the compound (XXVIIb) can be produced from the compound (XXVI), for example, by catalytic hydrogenation using a catalyst. Examples of the catalyst include palladium-carbon, palladium hydroxide, platinum oxide, and palladium-carbon-calcium carbonate.

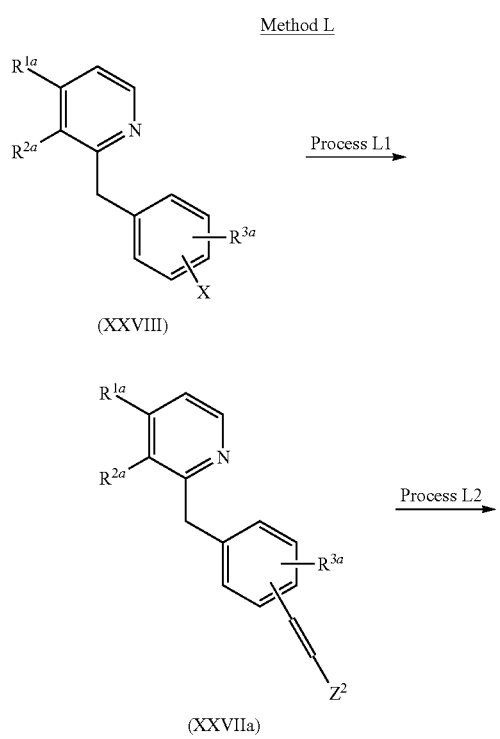

Method L (XXVIII)

Process L1 →

(XXVIIa)

Process L2 →

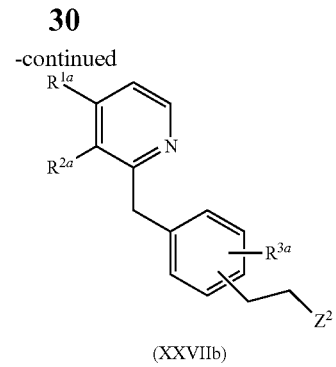

(XXVIIb)

X denotes a leaving group, such as a halogen group and trifluorosulfonate.

The symbols in the formulae have the same meaning as defined above.

Process L1

A process of the coupling reaction (Heck Reaction) with the alkene. The compound (XXVIIa) can be produced from the compound (XXVIII) using a catalyst (e.g. palladium complex and its ligand), based on the reaction conditions according to the literature, such as J. Org. Chem., 37, 2320 (1972); Org. Reactions., 27, 345 (1982); Comprehensive Organic Synthesis, Vol. 4, 833 (1991); Palladium Reagents and Catalysts, 125 (1995); Chem. Commun., 1287 (1984); Tetrahedron Lett, 26, 2667 (1985); and Tetrahedron Lett, 31, 2463 (1990). Examples of the combination of the catalysts used for this reaction (palladium complex and its ligand) include palladium (II) acetate and 1,1'-bis(diphenylphosphino)ferrocene, and palladium (II) acetate and tri(o-tolyl)phosphine. Examples of the tertiary base include triethylamine, diisopropylethylamine, and 1,8-diazabicyclo[5.4.0]-7-undecene. X of the compound (XXVIII) denotes a leaving group, such as a halogen group and trifluoromethanesulfonyloxy group.

Process L2

The compound (XXVIIb) can be produced from the compound (XXVIIa) according to the conditions for a reduction reaction of an unsaturated hydrocarbon, similar to that of process K3.

Method L is a method for producing the compound (XXVIIa) by Process L1, followed by producing the compound (XXVIIb) by Process L2.

Various isomers of the compounds represented by the formula (I) of the present invention can be purified and isolated using ordinary separation techniques (for example, recrystallization, chromatography, and so on).

Compounds of the present invention or salts thereof, or hydrates thereof can be administered as they are to mammals (preferably humans). They can also be formulated by a conventional method into tablets, powders, fine granules, granules, coated tablets, capsules, syrups, troches, inhalants, suppositories, injections, ointments, eye ointments, eye drops, nasal drops, ear drops, cataplasms, lotions, and such, then administered. For the pharmaceutical formulation, ordinarily used auxiliary agents for pharmaceutical formulation (for example, fillers, binders, lubricants, coloring agents, flavoring agents, and as necessary, stabilizers, emulsifiers, absorbefacient, surfactants, pH regulators, antiseptics, antioxidants, etc.) can be used. The pharmaceutical formulation can be prepared by an ordinary method by combining components that are generally used as ingredients for pharmaceutical preparations. For example, oral preparations can be produced by combining the compounds of the present invention or a pharmaceutically acceptable salt thereof with fillers, and as necessary, binders, disintegrators, lubricants, coloring agents, flavoring agents, and such, and formulating the mixture into powders, fine granules, granules, tablets, coated tablets, capsules, and such by usual methods. Examples of these components include animal fat and vegetable oil such as soybean oil, beef tallow, and synthetic glyceride; hydrocarbons such as liquid paraffin, squalene, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hardened castor oil, and polyoxyethylene polyoxypropylene block copolymer; water-soluble macromolecules such as hydroxyethyl cellulose, polyacrylic acid, carboxyvinyl polymer, polyethylene glycol, polyvinyl pyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as silicic acid anhydride, magnesium aluminum silicate, and aluminum silicate; purified water, etc. Examples of fillers include lactose, corn starch, refined white sugar, glucose, mannitol, sorbitol, crystalline cellulose, and silicon dioxide. Examples of binders include polyvinyl alcohol, polyvinyl ether, methyl cellulose, ethyl cellulose, gum arabic, tragacanth, gelatin, shellac, hydroxypropylmethyl cellulose, hydroxypropyl cellulose, polyvinyl pyrrolidone, polypropyleneglycol polyoxyethylene block polymer, and meglumine. Examples of disintegrators include starch, agar, powdered gelatin, crystalline cellulose, calcium carbonate, sodium hydrogencarbonate, calcium citrate, dextrin, pectin, and calcium carboxymethylcellulose. Examples of lubricants include magnesium stearate, talc, polyethyleneglycol, silica, and hardened vegetable oil. Examples of coloring agents are those accepted for addition to medicaments. Examples of flavoring agents include cocoa powder, l-menthol, aromatic dispersant, mint oil, borneol, and cinnamon powder. The use of sugar coating and other appropriate coating as necessary is of course permissible for these tablets and granules. Furthermore, liquid preparations such as syrups and injections can be prepared using conventional methods by adding pH regulators, solubilizers, isotonizing agents, and such, and as necessary, solubilizing adjuvants, stabilizers, and such to the compounds of this invention or pharmaceutically acceptable salts thereof. The method for producing external preparations is not limited and can be produced by a conventional method. That is, base materials used for formulation can be selected from various materials ordinarily used for medicaments, quasi-drugs, cosmetics, and such. Specifically, the base materials to be used are, for example, animal fat and vegetable oil, mineral oil, ester oil, waxes, higher alcohols, fatty acids, silicone oil, surfactants, phospholipids, alcohols, polyhydric alcohols, water soluble macromolecules, clay minerals, and purified water. As necessary, pH regulators, antioxidants, chelating agents, antiseptic and antifungal agents, coloring matters, fragrances, and such may be added, but the base materials of the external preparations of the present invention are not to be construed as being limited thereto. Furthermore, as necessary, components such as those that have a differentiation induction effect, blood flow accelerants, fungicides, antiphlogistic agents, cell activators, vitamins, amino acids, humectants, and keratolytic agents can be combined. The abovementioned base materials is added to an amount that leads to the concentration usually used for external preparations.

When the compounds of this invention or salts thereof, or hydrates thereof, is administered, there are no particular limitations on their form, and they can be administered orally or parenterally by a conventionally used method. They can be formulated into as dosage forms such as tablets, powder, fine granules, capsules, syrups, troches, inhalants, suppositories, injections, ointments, eye ointments, eye drops, nasal drops, ear drops, cataplasms, and lotions. The dose of the pharmaceutical compositions of this invention can be selected appropriately depending on the degree of the symptom, age, sex, weight, the dosage form, the type of salt, the specific type of disease, and such.

A curative dose of the antifungal agent of this invention is administered to a patient. Herein, "curative dose" refers to the amount of the pharmaceutical agent that yields the desired pharmacological result and is effective for recovery or relief from the symptoms of a patient to be treated. The dose differs markedly depending on the weight of the patient, type of disease, degree of symptom, age of the patient, sex, sensitivity towards the agent, and such. Usually, the daily dose for an adult is approximately 0.03 to 1000 mg, preferably 0.1 to 500 mg, more preferably 0.1 to 100 mg, and is administered once to several times per day, or once to several times per several days. The dose for injections is normally, approximately 1 to 3000 µg/kg, and is preferably approximately 3 to 1000 µg/kg.

BEST MODE FOR CARRYING OUT THE INVENTION

EXAMPLE A

The present invention is specifically illustrated below with reference to Examples, but it is not to be construed as being limited thereto.

EXAMPLE A1

Construction of the Reporter Gene and Introduction Thereof into *S. cerevisiae*

(1). Construction of the Reporter Gene where Lysozyme is the Reporter Enzyme

A lysozyme gene comprising a promoter sequence was amplified by PCR using pESH plasmid comprising the ENO1 promoter+secretion signal+the lysozyme gene (Ichikawa K et al, Biosci. Biotech. Biochem., 57 (10), 1686-1690, 1993) as template, and the oligonucleotides of SEQ ID NO:8 and SEQ ID NO:9 as primers, and this was subcloned into the SalI-EcoRI site of pCR-Script SK(+) (a). Furthermore, a CWP2 gene was amplified by PCR using *S. cerevisiae* chromosomal DNA as template, and the oligonucleotides of SEQ ID NO:10 and SEQ ID NO:11 as primers, and this was subcloned into the EcoRI-HindIII site of pUC19 (b). Similarly, CYC1 terminator was amplified by PCR using pYES2 (INVITROGEN) as a template, and the oligonucleotides of SEQ ID NO:12 and SEQ ID NO:13 as primers, and this was subcloned into the newly introduced NotI-KpnI site of pUC19 (c).

Next, the lysozyme gene excised with SalI-EcoRI (a), and the CWP2 gene excised with EcoRI-HindIII (b) were inserted into the SalI-HindIII cleavage site of pESH. Finally, pRLW63T was produced by excising a gene comprising the ENO1 promoter+secretion signal+lysozyme gene+CWP2 gene using BamHI-HindIII, inserting this into a pRS306 integration vector (Sikorski R S et al, Genetics. 122 (1):19-27, 1989), and then inserting the CYC1 terminator excised with HindIII-KpnI (c) into the HindIII-KpnI cleavage site.

(2). Construction of the Reporter Gene where Cephalosporinase is the Reporter Enzyme DNA comprising a promoter sequence and secretion signal portion was amplified by PCR using the abovementioned pESH as template, and the oligonucleotides of SEQ ID NO:14 and SEQ ID NO:15 as primers, and this was subcloned into the BamHI-NotI site newly introduced into pUC19 (d). Furthermore, a cephalosporinase gene was amplified by PCR using *Citrobacter freundii* chromosomal DNA as template, and the oligonucleotides of SEQ ID NO:16 and SEQ ID NO:17 as primers, and this was subcloned into the NspV-XbaI site newly introduced into pUC19 (e). Similarly, the CWP2 gene was amplified by PCR using the *S. cerevisiae* chromosomal DNA as template, and the oligonucleotides of SEQ ID NO:18 and SEQ ID NO:19 as primers, and this was subcloned into the XbaI-HindIII site of pUC19 (f).

After producing the full length ENO1 promoter+secretion signal portion by inserting the BamHI-SalI fragment of pESH into the BamHI-SalI cleavage site of a plasmid into which (d) has been inserted, the cephalosporinase gene excised with NspV-XbaI, and the CWP2 gene excised with XbaI-HindIII were inserted into the NspV-HindIII cleavage site. Next, pRCW63T was produced by excising with EcoRI-HindIII, inserting this fragment into the abovementioned pRS306, and then inserting the CYC1 terminator into the HindIII-KpnI cleavage site.

(3). Introduction of the Reporter Gene into *S. cerevisiae*

*S. cerevisiae* G2-10 strain was cultured by shaking in 10 ml of YPD medium at 30° C., then the cells were collected at the late logarithmic growth phase ($2-5 \times 10^7$ cells/ml). After washing with sterilized water, the above mentioned pRLW63T and pRCW63T were introduced by lithium acetate method that uses YEASTMAKER™ Yeast Transformation System (Clontech) (according to the YEAST-MAKER™ Yeast Transformation System User Manual). pRLW63T and pRCW63T in which the URA3 gene was cleaved with EcoRV and ApaI, respectively, were used. After culturing in SD(Ura$^-$) medium at 30° C. for 3 days, the grown colonies were cultured in YPD medium.

When the localizations of lysozyme and cephalosporinase activities were confirmed, both activities were mainly localized in the cell wall, and the C-terminal sequence of CWP2 was confirmed to function as a transport signal to the cell wall.

EXAMPLE A2

Screening of Pharmaceutical Agents by the *S. cerevisiae* Reporter System

Since sensitivity of the enzyme reaction is better with cephalosporinase compared to lysozyme, *S. cerevisiae* introduced with pRCW63T (*S. cerevisiae* CW63 strain) was used for the screening of compounds.

After stationary cultivation in YPD liquid medium at 30° C. for 48 hours, the yeast cell culture was diluted 100 times with YPD liquid medium ($3-5 \times 10^5$ cells/ml) and 75 µl/well aliquots thereof were inoculated into a V-bottomed 96-well plate containing 25 µl/well of a diluted test sample, and this was subjected to stationary cultivation at 30° C. for 48 hours. After centrifuging the plate, 25 µl of the supernatant was sampled and placed in a flat-bottomed 96-well plate, and this was used as the culture supernatant fraction.

The precipitated cells were suspended, and 75 µl/well aliquots of Zymolyase (Seikagaku Corporation) solution prepared with 2.4 M sorbitol were added and were allowed to react at 30° C. for 1 hour. After centrifuging the plate, 10 µl of the supernatant was sampled and placed in a flat-bottomed 96-well plate, 15 µl of phosphate buffer was added, and this was used as the cell wall fraction.

The cephalosporinase activities in the medium and in the cell wall fraction were measured by adding 200 µM of nitrocefin solution to a pooled sample, and after a certain period of time, stopping the reaction with citric acid buffer, and then measuring the absorbance at 490 nm.

Furthermore, fungal growth in the presence of the test sample was determined by visual observation.

Figure 2:
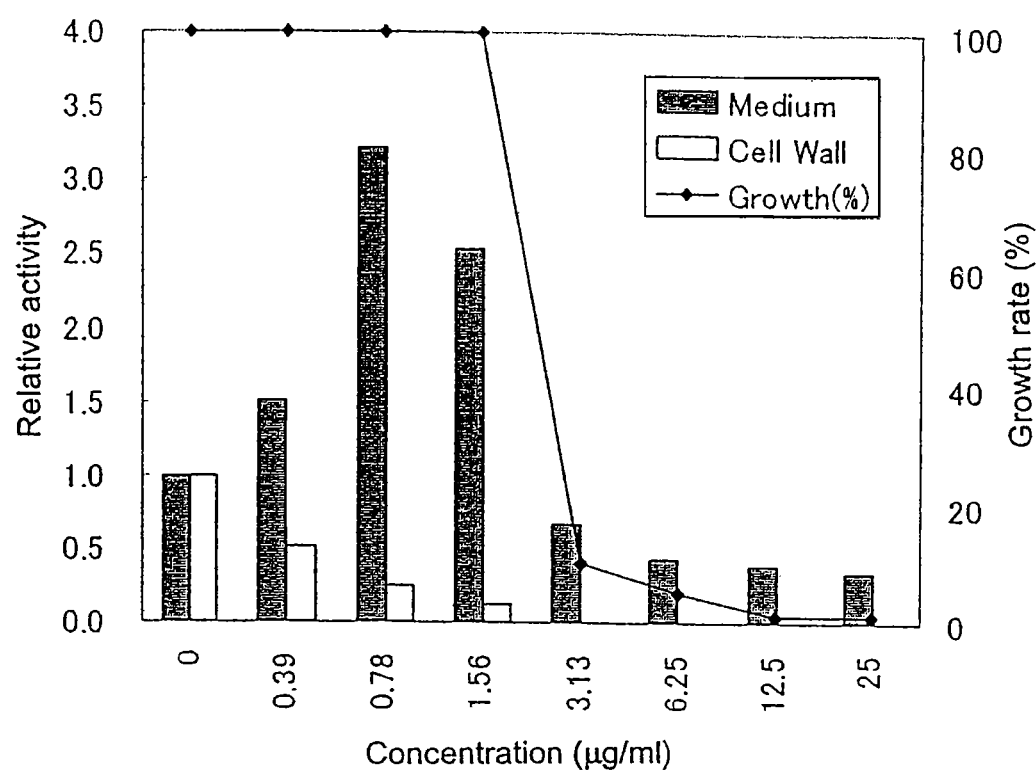
FIG. 2 is a graph showing the activity of the aforementioned compound (Ia) in the *S. cerevisiae* reporter system. In the presence of the aforementioned compound (Ia) at a concentration of 0.39 to 1.56 μg/ml, cephalosporinase activity increased in the culture supernatant fraction and decreased in the cell wall fraction, and at a concentration of 3.13 μg/ml or more, growth inhibition was observed.

FIG. 2 showed that in the presence of the aforementioned compound (Ia) at a concentration of 0.39 to 1.56 µg/ml, cephalosporinase activity increases in the culture supernatant fraction, and the activity decreases in the cell wall fraction. In this manner, a compound that increases the cephalosporinase activity in the culture supernatant fraction, and in addition decreases the cephalosporinase activity in the cell wall fraction was considered to be a compound that inhibits the process that transports GPI-anchored proteins to the cell wall.

EXAMPLE A3

Screening of Pharmaceutical Agents Using the Adhesion of *Candida* to Animal Cells Three-milliliter aliquots of IEC-18 cells ($1 \times 10^5$ cells/ml in D-MEM medium (Nissui Pharmaceutical) containing 10% fetal calf serum and 2 mM glutamine) were placed in each well of a 6-well multi-well plate. The plate was incubated in a carbon dioxide gas incubator at 37° C. for 3 days, the culture supernatant was removed, and ethanol immobilization was carried out.

*C. albicans* cultured in Sabouraud Dextrose Liquid Medium containing various concentrations of the test sample at 30° C. for 48 hours was adjusted to $4 \times 10^2$ cells/ml, and 1 ml was inoculated into each well of the plate in which the immobilized IEC-18 cells were cultured. After cultivation at 30° C. for 1 hour, the culture supernatant was removed, washed with PBS, and then 2 ml of Sabouraud Dextrose Agar Medium (Difco) was superposed. After cultivation at 30° C. overnight, the number of colonies (CFU) that had grown was counted and the adhesion rate was calculated.

Figure 3:
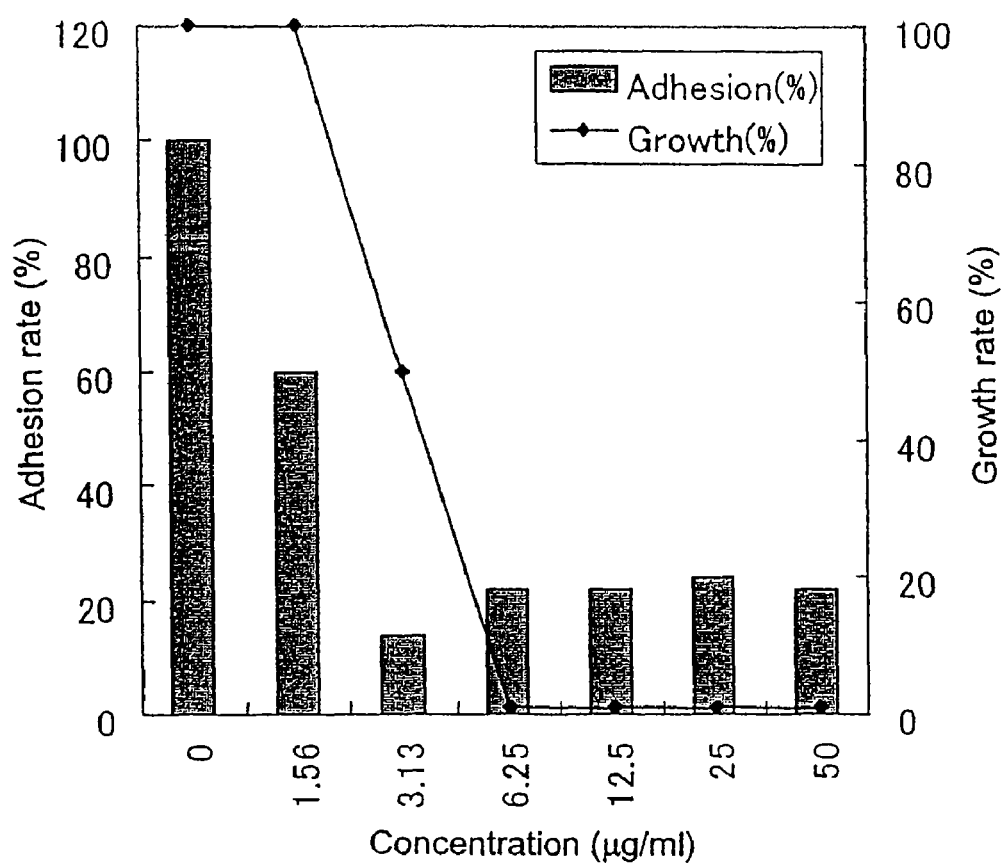
FIG. 3 is a graph showing the effect of the aforementioned compound (Ia) on the adhesion of *C. albicans* to animal cells. Even at a concentration of 1.56 μg/ml in which growth inhibition cannot be observed, adhesion of *C. albicans* to animal cells was inhibited to about a half.

FIG. 3 shows that even at a concentration of 1.56 µg/ml of the aforementioned compound (Ia), in which growth inhibition cannot be observed, adhesion of *C. albicans* to animal cells was inhibited to about a half. Compared to untreated *C. albicans*, a test sample that diminished CFU that adhered to cells was considered as a compound that inhibits the adhesion of *C. albicans* to animal cells.

EXAMPLE A4

Screening of Pharmaceutical Agents Using the Amount of the GPI-Anchored Protein Quantified by ELISA (1). Production of Anti-Als1p Peptide Antibody A house rabbit was immunized with the synthetic peptide of SEQ ID NO:20 which was conjugated with KLH. The obtained antisera was affinity-purified, and the IgG fraction was used as the anti-Als1p peptide antibody.

(2). Screening of Pharmaceutical Agents by ELISA Using Anti-Als1p Peptide Antibody

*C. albicans* was cultured in Sabouraud Dextrose Liquid Medium (5 ml) containing various concentrations of the test sample at 30° C. for 48 hours, and the cells were collected by centrifugation, washed, and then suspended in 300 µl of Tris-HCl buffer. The suspended cells were transferred to a microtube containing glass beads, and were disrupted by repeating 10 cycles of stirring for 1 minute and cooling on ice for 1 minute. The disrupted cells that were washed were extracted with 2% SDS at 95° C. for 10 minutes, centrifuged, and then the precipitate was washed 5 times with phosphate buffer. To this precipitate, 0.5 ml of 5 μg/ml Zymolyase solution was added, reacted at 37° C. for 1 hour, and the centrifuged supernatant was used as the GPI-anchored protein sample.

A 96-well plate was coated with 50 μof anti-Als1p peptide antibody (40 μg/ml) at 4° C. overnight. After washing 5 times with PBS containing 0.05% Tween 20 (PBST), blocking was carried out with 25% BlockAce at room temperature for 2 hours. After washing 3 times with PBST, 50 μl of the 2-fold serially diluted GPI-anchored protein sample was reacted at room temperature for 2 hours. After washing 5 times with PBST, 100 μl of 1000-fold diluted HRP-labeled anti-Candida antibody (ViroStat) was reacted at room temperature for 2 hours, then upon washing 5 times with PBST, 75 μl of substrate solution was added. After the reaction was stopped, absorbance at 490 nm was measured.

Figure 4:
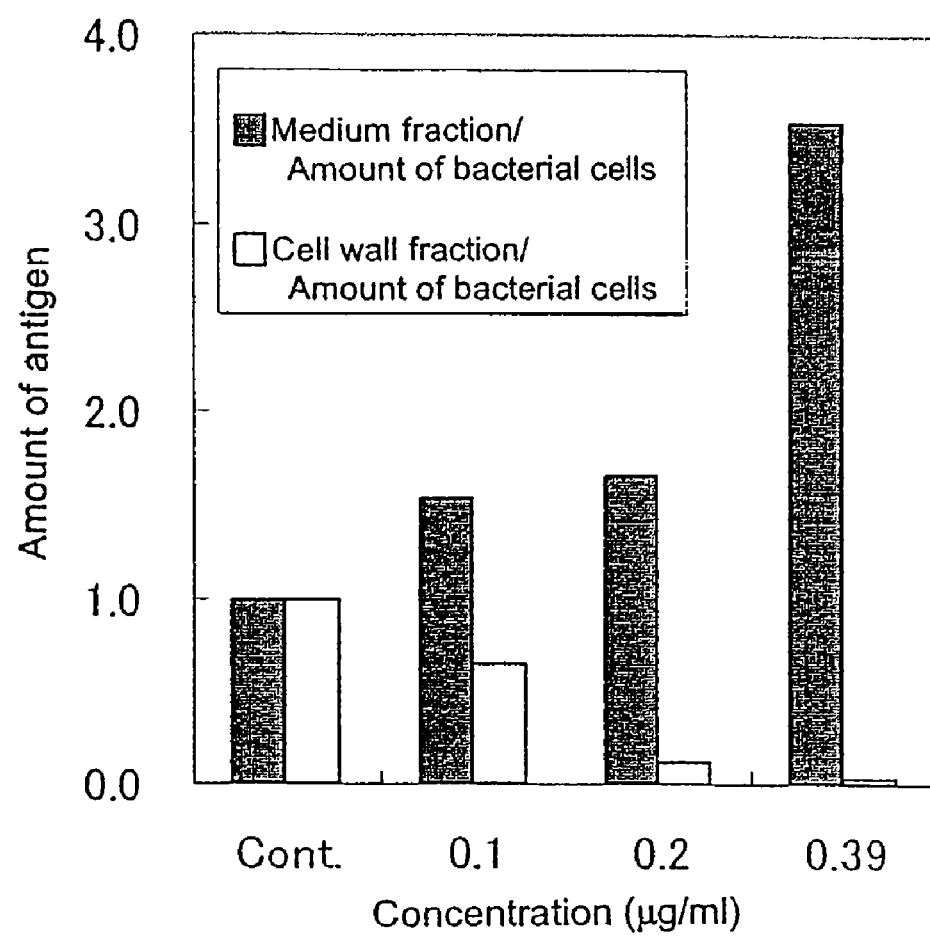
FIG. 4 is a graph showing the effect of the aforementioned compound (Ia) on the amount of the Als1p antigen of *C. albicans*. In the presence of the aforementioned compound (Ia) at a concentration of 0.1 to 0.39 μg/ml, the amount of the Als1p antigen increased in the culture supernatant fraction and the amount of the antigen decreased in the cell wall fraction.

FIG. 4 shows that in the presence of the aforementioned compound (Ia) at a concentration of 0.1 to 0.39 μg/ml, the amount of Als1p antigen increases in the culture supernatant fraction, and the amount of antigen decreases in the cell wall fraction. In this manner, a compound that increased the amount of Als1p in the culture supernatant, or decreased the amount of Als1p in the cell wall fraction, as quantified by ELISA, compared to the amount of Als1p in *C. albicans* untreated with the compound, was considered to be a compound that inhibits the process that transports GPI-anchored proteins to the cell wall in *C. albicans*.

EXAMPLE A5

Observation of the Cell Wall of *C. albicans* Cultured in the Presence of a Test Sample by an Electron Microscope

*C. albicans* which was cultured in Sabouraud Dextrose Liquid Medium (5 ml) containing various concentrations of the test agent at 30° C. for 48 hours, then centrifuged, and collected, was immobilized by potassium permanganate immobilization method, and the transmission electron microscope image thereof was observed.

The flocculent fibrous structure with high electron density was observed in the outermost layer of the cell, and was considered to be the surface layer glycoprotein layer having the GPI-anchored protein as its constituent. This flocculent fibrous structure was not influenced by other existing antifungal agents.

In *C. albicans* cultured in the presence of the aforementioned compound (Ia), the flocculent fibrous structure of the outermost layer of the cell having high electron density disappeared leaving a small amount of the layer with high electron density, compared to that in untreated cells. In this manner, when the flocculent fibrous structure of the outermost layer of the fungal cell having high electron density disappeared, the test sample was considered to be the compound influencing the process that transports GPI-anchored proteins to the cell wall.

EXAMPLE A6

Screening of the Resistant Gene to the Aforementioned Compound (Ia) of *S. cerevisiae*

The plasmid library of the *S. cerevisiae* gene was obtained from ATCC (Information for ATCC Number: 37323).

*S. cerevisiae* G2-10 strain was cultured while shaking in 10 ml of YPD medium at 30° C., and cells were collected at the late logarithmic growth phase ($1-2\times10^7$ cells/ml). After washing the cells with sterilized water, the plasmid library of the *S. cerevisiae* gene was introduced by the lithium acetate method that uses YEASTMAKER™ Yeast Transformation System (Clontech) (according to YEASTMAKER™ Yeast Transformation System User Manual), and this was spread onto a SD(Leu⁻) plate, and approximately 80,000 colonies were obtained. The colonies were collected and diluted, and were spread onto a SD(Leu⁻) plate containing the aforementioned compound (Ia) at a concentration of 1.56 μg/ml and 3.125 μg/ml so that there were 570,000 colonies per plate. Subsequently, the resistant clone was obtained by incubation at 37° C. for 72 hours.

When 27 clones were picked and plasmids were collected by the method according to METHODS IN ENZYMOLOGY, Vol. 194: 169-182 (1991), and the inserts were analyzed, all 27 contained the same fragment.

As a result of determining the nucleotide sequence using the ABI377 system (PE Applied Biosystems), the DNA of SEQ ID NO:1 was found to be the DNA that confers resistance to the aforementioned compound (Ia), and was named GWT1.

EXAMPLE A7

Southern Blot Analysis of a *C. albicans* Homologue of the *S. cerevisiae* GWT1 Gene A sample was prepared by treating 25 μg of the *C. albicans* genomic DNA with EcoRI (TaKaRa), HindIII (TaKaRa), BamHI (TOYOBO), or PstI (New England Biolabs) (including a combination of 2 types of enzymes) for 16 hours, then concentrating by ethanol precipitation, and dissolving in 25 μl of sterilized water. Twenty-five micrograms of genomic DNA digested with restriction enzymes was separated by 0.75% agarose gel electrophoresis method, and was transferred to a nylon membrane (GeneScreen PLUS/NEN).

A probe was produced by labeling 20 ng of the approximately 1.5 kb DNA fragment of SEQ ID NO:1 with alpha33P-dCTP by the random primer method, and was purified using a GeneQuant column (Amersham-Pharmacia).

Hybridization was carried out by soaking the membrane in 10 ml of PerfectHyb™ (TOYOBO) solution, preincubating at 65° C. for 1 hour, then adding the labeled probe mentioned above, and incubating at 65° C. for 2.5 hours. Washing was carried out with 1). 2×SSC, 0.05% SDS solution at 25° C. for 5 minutes, 2). 2×SSC, 0.05% SDS solution at 25° C. for 15 minutes, and 3). 0.1×SSC, 0.1% SDS solution at 50° C. for 20 minutes. The washed membrane was wrapped with Saran Wrap, and contacted with an Imaging Plate (FUJI) for 12 hours at room temperature, the image that was transferred to the Imaging Plate was captured using BAS2000 (FUJI), and the image was analyzed.

Figure 5:
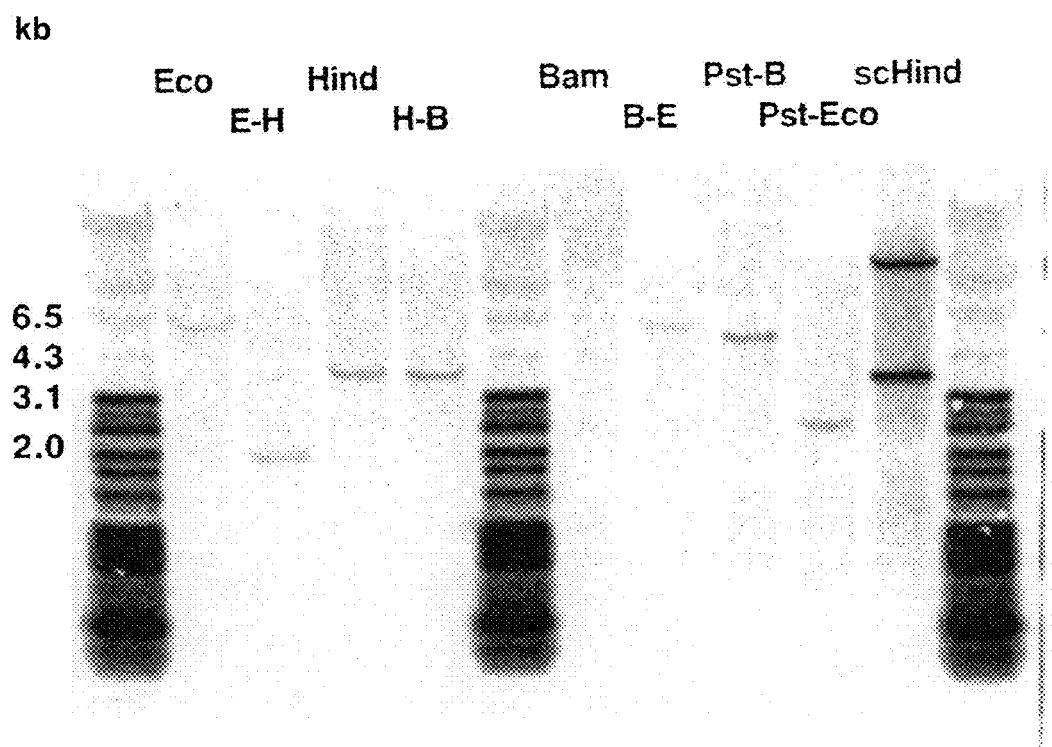
FIG. 5 is a photograph showing the Southern Blot of *C. albicans* genomic DNA analysis using the *S. cerevisiae* GWT1 gene as a probe. A single band was observed at 6.5 kb with EcoRI, at 4.0 kb with HindIII, at 2.0 kb with EcoRI-HindIII, and at 2.5 kb with EcoRI-PstI, and the homologue of the resistant gene to the aforementioned compound (Ia) in *C. albicans* was expected to exist as a single gene.

As a result, single bands were observed at 6.5 kb with EcoRI, 4.0 kb with HindIII, 2.0 kb with EcoRI-HindIII, and 2.5 kb with EcoRI-PstI (FIG. 5), and the homologue of the resistant gene to the aforementioned compound (Ia) of *C. albicans* was expected to exist as a single gene.

EXAMPLE A8

Screening of the Resistant Gene to the Aforementioned Compound (Ia) of *C. albicans*

The genomic library of *C. albicans* was produced by the method according to Navaro-Garcia F et al, Mol. Cell. Biol., 15: 2197-2206, 1995. Specifically, the genomic DNA of *C. albicans* was partially digested with Sau3AI, then DNA fragments around 3 to 5 were collected, and these were inserted into the BamHI site of YEp352 shuttle vector.

S. cerevisiae G2-10 strain was cultured by shaking in 10 ml of YPD medium at 30° C., and cells were collected at the late logarithmic growth phase (2–5×10$^7$ cells/ml). After washing the cells with sterilized water, a genomic library of the C. albicans was introduced by the lithium acetate method that uses YEASTMAKER™ Yeast Transformation System (Clontech) (according to YEASTMAKER™ Yeast Transformation System User Manual), and this was spread onto a SD(Ura$^-$) plate, and approximately 25,000 colonies were obtained. The colonies were collected and diluted, and were spread onto a SD plate containing the aforementioned compound (Ia) at a concentration of 1.56 μg/ml so that there were 500,000 colonies per plate. Subsequently, the resistant clones were obtained by incubation at 30° C. for 6 hours, and then transferred to 37° C. and incubated for 66 hours.

When 30 clones were picked and plasmids were collected by the method according to METHODS IN ENZYMOLOGY, Vol. 194: 169-182 (1991), and the inserts were analyzed, 28 out of 30 contained the same fragment.

As a result of determining the nucleotide sequence using the ABI377 system (PE Applied Biosystems), the DNA of SEQ ID NO:3 was found to be the DNA that confers resistance to the aforementioned compound (Ia).

EXAMPLE A9

Cloning of a Homologue of the Resistant Gene to the Aforementioned Compound (Ia) from the Clinical Isolate of C. albicans.

PCR amplification was carried out using as template a genomic DNA that was purified from a clinical isolate of C. albicans that is stored by the inventors, and SEQ ID NO:21 and SEQ ID NO:22 as primers. A DNA fragment of approximately 1.6 kb was amplified from all three of the independent PCR samples, the amplified fragments were purified, subcloned into a pT7-Blue vector (Novagen), and the nucleotide sequence was determined, and thereby, the DNA sequence of SEQ ID NO:5 was discovered. The sequence was different at three positions as compared to the DNA of Example A7 (SEQ ID NO:3).

Furthermore, in the nucleotide sequence of the C. albicans gene determined at Stanford University Sequence Center (on the worldwide web at sequence-www.stanford.edu/), a homologue of the DNA of Example A7 was found (SEQ ID NO:7), and the sequence was different at four positions as compared to the DNA of Example A7 (SEQ ID NO:3).

EXAMPLE A10

Construction of S. cerevisiae Overexpressing the GWT1 Gene Product

PCR amplification was carried out using a plasmid purified from the resistant clone to the aforementioned compound (Ia) obtained in Example A6 as a template, and SEQ ID NO:23 and SEQ ID NO:24 as primers. A PCR product cleaved with PvuII was inserted into the SalI-HinIII cleavage site of pRLW63T produced in Example A1. The entire insert was excised with BamHI-KpnI, and was inserted into the MCS (multi-cloning site) of pRS304 (Sikorski R S et al, Genetics. 122 (1): 19-27, 1989) to produce a vector for integration.

S. cerevisiae CW63 strain having a cephalosporinase gene as the reporter gene was cultured by the method according to Example A1, TRP1 of the integration vector was cleaved with EcoRV, and then transformation was carried out by the method of Example A1. GWT1-overexpressed strain (S. cerevisiae CW63/GWT1 strain) was obtained by culturing in SD(Trp$^-$) medium at 30° C. for 3 days.

Other than showing resistance to the aforementioned compound (Ia), GWT1-overexpressed strain is not different from the wild type strain, and was sensitive towards other antifungal agents, cycloheximide, benomyl, and amphotericin B.

EXAMPLE A11

Construction of S. cerevisiae Mutant Lacking the GWT1 Gene

His5 cassette containing the GWT1 sequence on both ends was amplified by PCR using the his5 gene of S. pombe (Longtine M S et al, Yeast, 14: 953-961, 1998) as template and SEQ ID NO:25 and SEQ ID NO:26 as primers.

S. cerevisiae G2-10 was cultured and the cells were collected by the method according to Example A1, and the abovementioned PCR product was transformed by the method according to Example A1. A GWT1-deficient strain was obtained by cultivation in SD(His$^-$) medium at 30° C. for 5 to 7 days.

Although the GWT1-deficient strain shows very slow growth, it was suggested that the growth is not influenced by the aforementioned compound (Ia), and the GWT1 gene product is the target of the compound. Furthermore, the GWT1-deficient strain indicated the following characteristics: it cannot grow at high temperatures; the cells are swollen; and in the observation by a transmission electron microscope, the flocculent fibrous structure of the outermost layer of the fungal cell having high electron density had disappeared.

EXAMPLE A12

Activity of the Aforementioned Compound (Ia) in S. cerevisiae Overexpressing the GWT1 Gene Product Using S. cerevisiae CW63 strain and GWT1 gene introduced S. cerevisiae CW63/GWT1, activity of the aforementioned compound (Ia) was examined by a method according to the method described in Example A2.

Figure 6A:
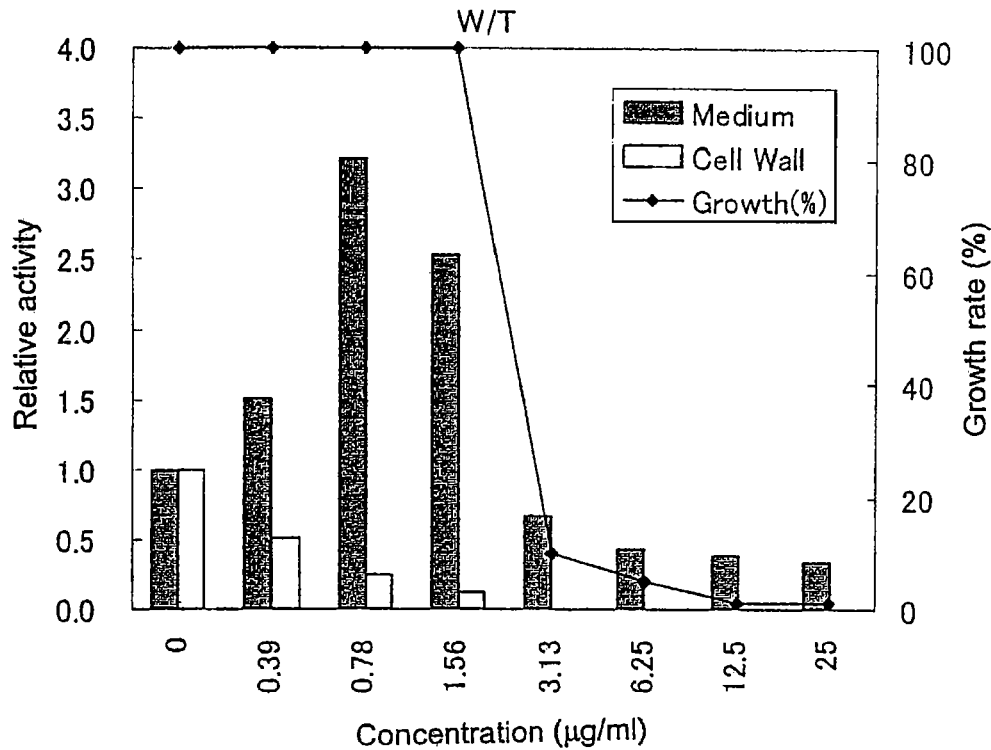
FIGS. 6A and 6B are graphs showing the activity of the aforementioned compound (Ia) in *S. cerevisiae* that overexpressed the GWT1 gene product. In *S. cerevisiae* CW63 strain (FIG. 6A), even at the concentration of the aforementioned compound (Ia) (0.39 to 1.56 μg/ml) in which cephalosporinase activity in the culture supernatant fraction is increased, and activity in the cell wall fraction is decreased, such an effect was not observed in *S. cerevisiae* CW63/GWT1 strain, and in *S. cerevisiae* CW63 strain, even at the concentration of the aforementioned (>3.13 μg/ml) in which growth is inhibited, growth inhibition was not observed in *S. cerevisiae* CW63/GWT1 strain (FIG. 6B).
Figure 6B:
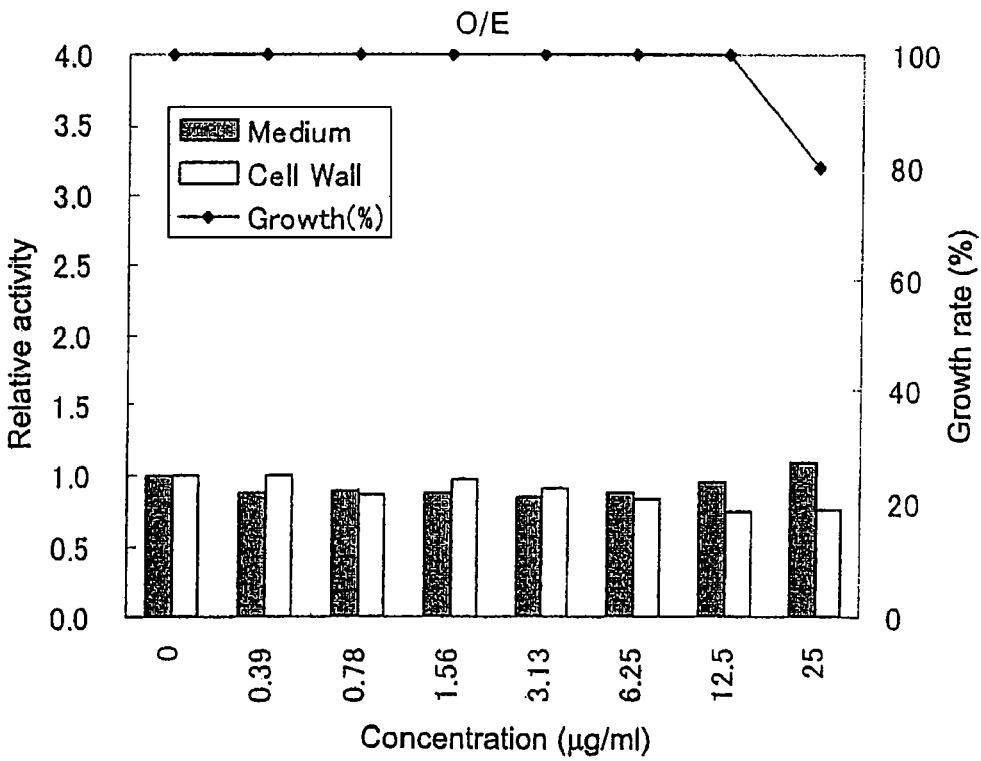

As a result, even at a concentration (0.39 to 1.56 μg/ml) of the aforementioned compound (Ia) at which cephalosporinase activity in the culture supernatant fraction is increased, and the activity in the cell wall fraction is decreased in S. cerevisiae CW63 strain, no influence was observed in the S. cerevisiae CW63/GWT1 strain, and even at a concentration (>3.13 μg/ml) of the aforementioned compound (Ia) at which growth is inhibited in S. cerevisiae CW63 strain, growth inhibition was not observed in the S. cerevisiae CW63/GWT1 strain (FIG. 6).

EXAMPLE A13

Synthesis Of (4n-butylphenyl)(1-isoquinolyl)ketone

Under a nitrogen atmosphere, 1-bromo-4-butylbenzene (2.29 ml, 13.0 mmol) was added to a mixed solution of magnesium (338 mg, 13.9 mmol) and tetrahydrofuran (6.5 ml), and as an initiator, catalytic amount of 1,2-dibromoethane was added, and this was stirred under reflux for 10 minutes. The solution was cooled to 0° C., a tetrahydrofuran solution of 1-isoquinolinecarbonitrile (1.0 g, 6.49 mmol) was added, and was stirred for another 1 hour at room temperature, and at 70° C. for 3 hours. Subsequently, the solution was cooled again to 0° C., concentrated hydrochloric acid (2.56 ml) and methanol (11 ml) were added, and then refluxed for 2 hours. The concentrated residue was dissolved in 5 N sodium hydroxide and toluene, and was filtered through celite. The toluene layer of the filtrate was divided, washed with water, dried over magnesium sulfate, and concentrated. The residue was purified by silica gel column chromatography to give 1.72 g of the title compound.

$^1$H-NMR (CDCl$_3$) δ(ppm): 0.93 (3H, t), 1.32-1.43 (2H, m), 1.58-1.66 (2H, m), 2.68 (2H, t), 7.28 (2H, d), 7.61 (1H, td), 7.74 (1H, td), 7.80 (1H, d), 7.87 (2H, d), 7.92 (1H, d), 8.20 (1H, d), 8.60 (1H, d)

EXAMPLE A14

Synthesis of {1-(4-butylbenzyl)isoquinoline}, the aforementioned compound of the formula (Ia)

The compound of Example A13 (1.72 g, 5.95 mmol), hydrazine monohydrate (836 mg, 16.7 mmol), and potassium hydroxide (769 mg, 13.7 mmol) were added to diethylene glycol (8.5 ml), and were stirred at 80° C. for 1 hour, at 160° C. for 3 and a half hours, and at 200° C. for 1 hour. Upon cooling to room temperature, ice water was added and extracted with ethyl acetate. This was washed with water, then dried over magnesium sulfate, and concentrated. The residue was purified by silica gel column chromatography to give 914 mg of the aforementioned compound of the formula (Ia).

$^1$H-NMR (CDCl$_3$) δ(ppm): 0.89 (3H, t), 1.26-1.36 (2H, m), 1.50-1.59 (2H, m), 2.53 (2H, t), 4.64 (2H, s), 7.06 (2H, d), 7.19 (2H, d), 7.53 (1H, td), 7.56 (1H, d), 7.64 (1H, td), 7.81 (1H, d), 8.18 (1H, dd,), 8.50 (1H, d)

EXAMPLE A15

Another method for producing {1-(4-butylbenzyl)isoquinoline}, the aforementioned Compound of the Formula (Ia)

To a dimethylformamide (1.8 ml) solution of 60% sodium hydride (16 mg, 0.40 mmol), a dimethylformamide (3.6 ml) solution of 1-cyano-2-benzoyl-1,2-dihydroisoquinoline (100 mg, 0.38 mmol) synthesized according to the literature of Org. Synth., VI, 115 (1988), and 4-n-butylbenzylchloride (70 mg, 0.38 mmol) was added dropwise under nitrogen atmosphere at −16° C., and was further stirred at room temperature for 30 minutes. Water was added, this was concentrated, and toluene and water were added to this residue. The toluene layer was washed with water, dried over potassium carbonate, and concentrated. To an ethanol (1.6 ml) solution of the residue, 50% aqueous sodium hydroxide solution (0.63 ml) was added, and this was refluxed for 2 hours. After concentration, toluene and water were added. The toluene layer was washed with water, then dried over calcium carbonate, and then concentrated. The residue was purified by silica gel column chromatography to give 18 mg of the aforementioned compound of the formula (Ia).

EXAMPLE A16

Cloning of the C. albicans Homologue of the S. Cerevisiae GWT1 Gene

The C. albicans genomic DNA (25 μg) treated with HindIII (TaKaRa) for 16 hours was separated by 0.75% agarose gel electrophoresis method, and the DNA fragments ranging in size from approximately 3.5 to 4.5 kb were recovered from the gel. The recovered DNA fragments were inserted into the HindIII site of the pKF3 vector (TaKaRa), and a Candida genomic library was produced.

Using the produced library, approximately 10,000 colonies were displayed on an LB/Ampicillin plate, colony lifting was performed using a Colony/Plaque Screen (NEN) membrane, and then this was subjected to hybridization. A probe was produced by labeling 20 ng of the approximately 1.5 kb DNA fragment of SEQ ID NO:1 with alpha $^{33}$P-dCTP by the random primer method, and purifying using a GeneQuant column (Amersham-Pharmacia).

Hybridization was carried out by pre-incubating the membrane in a PerfectHyb™ (TOYOBO) solution at 65° C. for 1 hour, then adding the labeled probe mentioned above, and incubating further at 65° C. for 2.5 hours. Washing was carried out with (i) 2×SSC, 0.05% SDS solution at 25° C. for 5 minutes, (ii) 2×SSC, 0.05% SDS solution at 25° C. for 15 minutes, and (iii) 0.1×SSC, 0.1% SDS solution at 50° C. for 20 minutes. The washed membrane was wrapped with Saran Wrap, contacted with an X-RAY FILM (KONICA) for 24 hours at room temperature, and then developed. The E. coli colonies corresponding to the exposed spots were isolated, and were subjected to secondary screening. Approximately 200 of the isolated colonies were displayed on each LB/Ampicillin plate, colony lifting was performed in a similar manner to primary screening, which was followed by hybridization. The conditions for hybridization were the same as the conditions for primary screening.

As a result, a single colony of E. coli that reacts strongly with the probe was isolated. Plasmids were collected from this colony, and when the contained sequence was determined, a novel sequence having the same sequence as that revealed in Example A9 (SEQ ID NO:5) was found (the sequence of Candida GWT1), and was presumed to be a C. albicans homologue.

EXAMPLE A17

The S. Pombe Homologue of the S. cerevisiae GWT1 Gene

S. Pombe genes that show homology to the S. cerevisiae GWT1 gene (SEQ ID NO:27, and the amino acid sequence of the gene product thereof: SEQ ID NO:28) were found from a database search, and were considered to be the S. Pombe homologues of GWT1.

EXAMPLE A18

Cloning of the Aspergillus Fumigatus Homologue Of The S. cerevisiae GWT1 Gene

By genetic sequence analysis, the inventors discovered two highly conserved regions in the protein encoded by the GWT1 genes of S. cerevisiae, S. pombe, and C. albicans (FIG. 7; SEQ ID NOs:64-69). Based on the presumed DNA that encodes the amino acid sequence of this conserved region, primers of SEQ ID NO:29, SEQ ID NO:30, and SEQ ID NO:31 were designed. PCR amplification was carried out using 1 μl of the library purchased from STRATAGENE (Aspergillus fumigatus cDNA library: #937053) as a template, and using primers of SEQ ID NO:29 and SEQ ID NO:31. Furthermore, as a result of carrying out nested-PCR using 1 μg of this amplified sample as a template, and using primers of SEQ ID NO:29 and SEQ ID NO:30, amplification of a single fragment of approximately 250 bp was confirmed. When the sequence of this fragment was determined, a novel sequence having homology to the GWT1 gene of *S. cerevisiae*, shown in SEQ ID NO:32, was obtained, and this was presumed to be the homologue of *A. fumigatus*.

To obtain a full length cDNA, primers of SEQ ID NO:33 and SEQ ID NO:34 were designed based on the sequence of the amplified fragment. Furthermore, primers outside the gene insertion site of the library, SEQ ID NO:35 and SEQ ID NO:36, were designed. As a result of performing PCR using the *A. fumigatus* cDNA library as a template, and the primer set of SEQ ID NO:33 and SEQ ID NO:35, or the primer set of SEQ ID NO:34 and SEQ ID NO:36, amplification of a DNA fragment of approximately 1 kb was confirmed (by both primer sets). As a result of determining the nucleotide sequences of these fragments, a novel sequence that is highly homologous to the GWT1 genes of *S. cerevisiae* shown in SEQ ID NO:1 was obtained. Since the sequence is highly homologous to the GWT1 genes of *S. cerevisiae*, *S. pombe*, and *C. albicans* throughout the entire gene, this sequence was strongly suggested to be a homologue of *A. fumigatus*.

To clone the entire homologue of *A. fumigatus*, the primer shown in SEQ ID NO:37 that corresponds to the sequence upstream of the initiation codon, and the primer of SEQ ID NO:38 that corresponds to the sequence downstream of the stop codon were newly designed based on the obtained sequence. As a result of performing 35 cycles of PCR using the *A. fumigatus* cDNA library (STRATAGENE) and the *A. fumigatus* genomic library (STRATAGENE) as templates, and primers of SEQ ID NO:37 and SEQ ID NO:38, a single amplified fragment of approximately 1.6 kb was detected from both templates. As a result of determining the nucleotide sequence of this fragment by Direct-Sequencing, the nucleotide sequence shown in SEQ ID NO:39 was found from the cDNA library, and was suggested to encode a protein comprising 501 amino acids shown in SEQ ID NO:40. Furthermore, the nucleotide sequence of SEQ ID NO:41 was found from the genomic library, and was found to have an intron comprising 77 base pairs in one position.

EXAMPLE A19

Cloning of the *Cryptococcus* Homologue of the *S. cerevisiae* GWT1 Gene

1). Database Search

As a result of database searching for genes showing homology to the *S. cerevisiae* GWT1 gene, the sequence of 502042C05.x1 was found from the server of the Genome Center at Stanford University (on the worldwide web at baggage.stanford.edu/cgi-misc/cneoformans/). Furthermore, the sequence of b6e06cn.f1 was found from the server at Oklahoma University, U.S.A (on the worldwide web at genome.o-u.edu/cneo_blast.html).

2). PCR Using Genomic DNA as Template

The primer of SEQ ID NO:42 was constructed based on the sequence of 502042C05.x1, and the primer of SEQ ID NO:43 was constructed based on the sequence of b6e06cn.f1. When PCR amplification was carried out using the genomic DNA of *Cryptococcus* (*Cryptococcus neoformans*) as a template, and using the primer of SEQ ID NO:42, and the primer of SEQ ID NO:43, an amplified fragment of approximately 2 kb was detected. When the nucleotide sequence of this fragment was determined, a novel sequence showing homology to the GWT1 gene of *S. cerevisiae*, shown in SEQ ID NO:44, was obtained.

In order to obtain the sequence upstream of the initiation codon of the *Cryptococcus* GWT1 gene, the primer of SEQ ID NO:45 was designed based on the sequence of 502042C05.x1, and the primer of SEQ ID NO:46 was designed based on the sequence of SEQ ID NO:44. When PCR amplification was carried out using the genomic DNA of *Cryptococcus* as a template, and using the primer of SEQ ID NO:45, and the primer of SEQ ID NO:46, an amplified fragment of approximately 500 bp was detected. When the nucleotide sequence of this fragment was determined, the sequence of SEQ ID NO:47 was obtained, and this was found to overlap with SEQ ID NO:44.

3). 3'-Race

To obtain the 3'-terminal sequence of the *Cryptococcus* GWT1 gene, 3'-RACE was carried out. Reverse transcription was carried out by priming with the adaptor-primer of SEQ ID NO:48, which is based on 16 μg of total RNA extracted from *Cryptococcus*, and by using SuperScript II Reverse Transcriptase (GIBCO/BRL), and a single stranded cDNA, which is to become the template for the RT-PCR that follows, was produced. As a result of performing 35 cycles of PCR using the single stranded cDNA as a template, and the primers of SEQ ID NO:49 and SEQ ID NO:50, an amplified fragment of approximately 1.2 kb was detected. When the nucleotide sequence of this fragment was analyzed by the Direct-Sequencing method, the novel sequence shown in SEQ ID NO:51 showing homology to the *S. cerevisiae* GWT1 gene was obtained.

4). PCR of a Full Length Genomic DNA

Using the primer of SEQ ID NO:52 that was designed based on SEQ ID NO:47, and the primer of SEQ ID NO:53 that was designed based on SEQ ID NO:51, 35 cycles of PCR was carried out on three independent preparations with the genomic DNA of *Cryptococcus* as template. As a result, an amplified fragment of approximately 2 kb was detected from all three of the independent tubes, and therefore, each of them were individually subjected to Direct-Sequencing, and their entire nucleotide sequences were determined. As a result, the three independent sequences completely matched, and a sequence comprising the full length GWT1 gene homologue of *Cryptococcus* shown in SEQ ID NO:54 was obtained.

5). Determination of the cDNA Sequence

Comparison of the sequence of the *Cryptococcus* GWT1 gene derived from the genome shown in SEQ ID NO:54 with the cDNA sequence (SEQ ID NO:51) obtained by 3'-RACE suggested the presence introns at two positions. Furthermore, since the open reading frame following the ATG initiation codon is not continuous, the presence of another intron was suggested. Therefore, the cDNA structure was predicted from the presumed amino acid sequence and the splicing donor/acceptor sequence, and the primers of SEQ ID NO:55 and SEQ ID NO:56 were designed at the position predicted to be the junction between exons. As a result of performing 35 cycles of PCR using the single stranded cDNA derived from *Cryptococcus* as template with the above-mentioned primers, an amplified fragment of approximately 1.4 kb was confirmed. As a result of determining the nucleotide sequence by subjecting the fragment to Direct-Sequencing, the sequence of SEQ ID NO:57 was obtained, and by comparing with SEQ ID NO:54, the cDNA sequence of the GWT1 gene of *Cryptococcus* was suggested to have the structure of SEQ ID NO:58 and encode the protein shown in SEQ ID NO:59. Since the sequence shows high homology at certain regions with the GWT1 genes of *S. cerevisiae*, *S. pombe*, *C. albicans*, and *A. fumigatus*, this sequence was strongly suggested to be a homologue of *Cryptococcus*.

EXAMPLE A20

Genetic Mutation that Confers Resistance to the Aforementioned Compound of the Formula (Ia)

*S. cerevisiae* LW63 strain having a lysozyme gene as the reporter gene due to introduction of pRLW63T was treated with ethyl methanesulfonate, then by culturing in a SD medium containing the aforementioned compound of the formula (Ia) at concentrations of 1.56, 3.13, and 6.25 μg/ml at 37° C. for 3 days, five resistant mutant strains (R1 to R5) were obtained. Among them, the R1 mutant strain and the R5 mutant strain were found to have acquired a specific resistant characteristic to the aforementioned compound of the formula (Ia) due to a mutation of a single gene. To confirm whether or not these two mutant strains have mutations on the GWT1 gene, genomic DNAs were extracted from both mutant strains, and the nucleotide sequence of the GWT1 gene portion was determined. As a result, in the R1 mutant strain, guanine at position 1213 had been mutated to adenine. Furthermore, in the R5 mutant strain, guanine at position 418 had been mutated to adenine. Therefore, it was elucidated that in the R1 mutant strain, the 405th amino acid, isoleucine, had been changed to valine, and in the R5 mutant strain, the 140th amino acid, glycine, had been changed to arginine.

Next, to confirm whether or not these mutations are the cause of the acquisition of the specific resistant characteristic to the aforementioned compound of the formula (Ia), the mutant GWT1 gene (R1 or R5) was isolated using the genomic DNAs derived from both mutant strains as templates and the primers of SEQ ID NOs: 60 and 61. Simultaneously, the GWT1 promoter region (SEQ ID NO:62) and the terminator region (SEQ ID NO:63) were isolated, the GWT1 gene promoter, mutant GWT1 gene ORF, and the GWT1 gene terminator were inserted into the pRS316 vector, and plasmids that express a single copy of the mutant GWT1 gene were constructed (pRS316GWT1-R1, pRS316GWT1-R5). This was introduced to a diploid strain (WDG1) in which only a single copy of the GWT1 gene is disrupted. Spores were formed by culturing the colonies on a sporulation medium, and a clone in which the GWT1 gene on the chromosome is disrupted and also harbors the abovementioned plasmid was obtained by performing a tetrad analysis. When this was cultured in a medium containing the aforementioned compound of the formula (Ia), resistance to the aforementioned compound of the formula (Ia) was seen, similarly to the original R1 mutant strain and R5 mutant strain. From the above, it was elucidated that the specific resistant characteristic to the aforementioned compound of the formula (Ia) is conferred by a point mutation accompanying an amino acid mutation, that occurred on the GWT1 gene, and this compound was strongly suggested to inhibit the function of the GWT1 protein by directly binding to the protein.

EXAMPLE B

The compounds of this invention can be produced, for example, by the method of the Examples below. However, the Examples are for illustration purpose only and the compounds of this invention are not to be construed as being limited to those prepared in the following specific examples under any circumstances.

EXAMPLE B1

1-(Chloromethyl)-4-n-butylbenzene

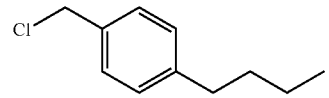

Thionyl chloride (2.5 ml, 34 mmol) was added to a solution of 4-n-butylbenzyl alcohol (2.0 g, 12 mmol) in ether (25 ml), and this mixture was stirred at room temperature for 3 hours. After concentration of the mixture, excess thionyl chloride was removed by azeotropic distillation with benzene to give the title compound (2.3 g). This compound was used in the following reaction without purification.

EXAMPLE B2

1-(4-Butylbenzyl)isoquinoline

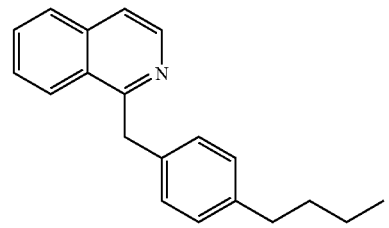

A solution of 1-cyano-2-benzoyl-1,2-dihydroisoquinoline (100 mg, 0.38 mmol), which was synthesized according to Org. Synth., VI, 115 (1988), and 4-n-butylbenzyl chloride (70 mg, 0.38 mmol) in dimethylformamide (3.6 ml) was added dropwise to a solution of 60% sodium hydride (16 mg, 0.40 mmol) in dimethylformamide (1.8 ml) under nitrogen atmosphere at −16° C., and this mixture was stirred at room temperature for 30 minutes. Water was added, the mixture was concentrated under reduced pressure, and toluene and water were added to the residue. The toluene layer was washed with water, dried over potassium carbonate, then concentrated under reduced pressure. A 50% aqueous sodium hydroxide solution (0.63 ml) was added to a solution of the residue in ethanol (1.6 ml). This mixture was heated under reflux for 2 hours and concentrated, and then toluene and water were added. The toluene layer was washed with water, dried over calcium carbonate, and then concentrated under reduced pressure. The residue was purified by silica gel column chromatography to give the title compound (18 mg).

$^1$H-NMR (CDCl$_3$) δ(ppm): 0.89 (3H, t), 1.26-1.36 (2H, m), 1.50-1.59 (2H, m), 2.53 (2H, t), 4.64 (2H, s), 7.06 (2H, d), 7.19 (2H, d), 7.53 (1H, td), 7.56 (1H, d), 7.64 (1H, td), 7.81 (1H, d), 8.18 (1H, dd), 8.50 (1H, d)

EXAMPLE B3

(4-Butylphenyl)(1-isoquinolyl)ketone

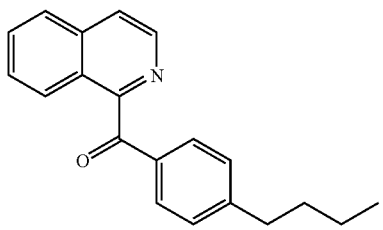

1-Bromo-4-butylbenzene (2.29 ml, 13 mmol) and a catalytic amount of 1,2-dibromoethane as an initiator were added to a mixed solution of magnesium (338 mg, 14 mmol) and tetrahydrofuran (6.5 ml) under nitrogen atmosphere, and this mixture was stirred under reflux for 10 minutes. The mixture was cooled to 0° C., a solution of 1-isoquinolinecarbonitrile (1.0 g, 6.5 mmol) in tetrahydrofuran was added, and this mixture was stirred at room temperature for 1 hour, then at 70° C. for 3 hours. Thereafter, the mixture was cooled again to 0° C., concentrated hydrochloric acid (2.6 ml) and methanol (11 ml) were added, and this mixture was heated under reflux for 2 hours. After the mixture was concentrated, the residue was dissolved in 5 N sodium hydroxide and toluene, and was filtered through celite. The toluene layer of the filtrate was separated, washed with water, dried over anhydrous magnesium sulfate, and then concentrated under reduced pressure. The residue was purified by silica gel column chromatography to give the title compound (1.7 g).

$^1$H-NMR (CDCl$_3$) δ(ppm): 0.93 (3H, t), 1.32-1.43 (2H, m), 1.58-1.66 (2H, m), 2.68 (2H, t), 7.28 (2H, d), 7.61 (1H, td), 7.74 (1H, td), 7.80 (1H, d), 7.87 (2H, d), 7.92 (1H, d), 8.20 (1H, d), 8.60 (1H, d)

EXAMPLE B4

Alternative method for the production of 1-(4-butylbenzyl)isoquinoline

The compound of Example B3 (1.7 g, 6.0 mmol), hydrazine monohydrate (836 mg, 17 mmol), and potassium hydroxide (769 mg, 14 mmol) were added to diethylene glycol (8.5 ml), and this mixture was stirred at 80° C. for 1 hour, at 160° C. for 3.5 hours, then at 200° C. for 1 hour. The mixture was cooled to room temperature, ice water was added, and this was extracted with ethyl acetate. The extract was washed with water, dried over anhydrous magnesium sulfate, and concentrated under reduced pressure. The residue was purified by silica gel column chromatography to give the title compound (914 mg).

$^1$H-NMR (CDCl$_3$) δ(ppm): 0.89 (3H, t), 1.26-1.36 (2H, m), 1.50-1.59 (2H, m), 2.53 (2H, t), 4.64 (2H, s), 7.06 (2H, d), 7.19 (2H, d), 7.53 (1H, td), 7.56 (1H, d), 7.64 (1H, td), 7.81 (1H, d), 8.18 (1H, dd), 8.50 (1H, d)

EXAMPLE B5

1-(4-Ethylbenzyl)isoquinoline

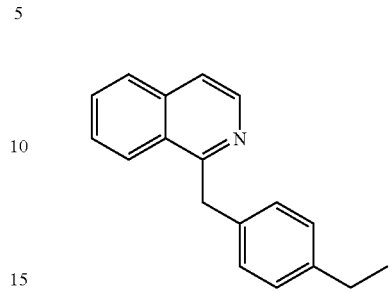

Using p-ethylbenzyl chloride, the title compound was obtained in the same manner as in Example B2.

$^1$H-NMR (CDCl$_3$) δ(ppm): 1.18 (3H, t), 2.57 (2H, q), 4.64 (2H, s), 7.08 (2H, d), 7.20 (2H, d), 7.50-7.55 (2H, m), 7.61-7.65 (1H, m), 7.80 (1H, d), 8.16-8.18 (1H, m), 8.49 (1H, d)

EXAMPLE B6

(4-Propylphenyl)methanol

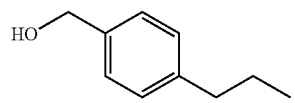

A solution of sodium borohydride (2.9 g, 76 mmol) and concentrated sulfuric acid in ether (prepared by adding 2.0 ml of concentrated sulfuric acid to 4.0 ml of ether) was added dropwise to a solution of p-n-propylbenzoic acid (5.0 g, 32 mmol) in tetrahydrofuran (20 ml) cooled to 0° C. keeping the temperature of the reaction system below 20° C., and then this mixture was stirred at room temperature for 3 hours. After the mixture was cooled on ice, methanol and 1 N sodium hydroxide were added, and this mixture was extracted with ethyl acetate. The ethyl acetate layer was washed with saturated brine, dried over anhydrous magnesium sulfate, and then concentrated under reduced pressure to give the title compound (4.33 g). This compound was used in the following reaction without purification.

EXAMPLE B7

1-(Chloromethyl)-4-propylbenzene

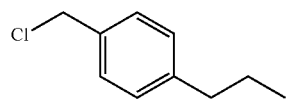

The title compound was obtained by treating the compound of Example B6 in the same manner as in Example B1. This compound was used in the following reaction without further purification.

EXAMPLE B8

1-(4-Propylbenzyl)isoquinoline

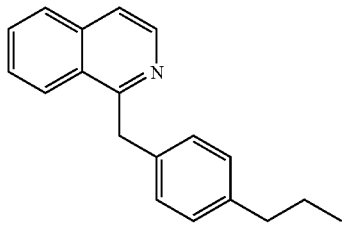

The title compound was obtained by treating the compound of Example B7 in the same manner as in Example B2.

$^1$H-NMR (CDCl$_3$) δ(ppm): 0.90 (3H, t), 1.55-1.61 (2H, m), 2.51 (2H, t), 4.64 (2H, s), 7.06 (2H, d), 7.19 (2H, d), 7.51-7.55 (2H, m), 7.61-7.65 (1H, m), 7.81 (1H, d), 8.17 (1H, dd), 8.49 (1H, d)

EXAMPLE B9

(4-Pentylphenyl)methanol

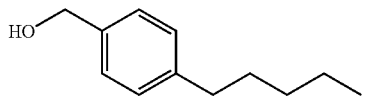

The title compound was obtained by reducing 4-n-amyl-benzoic acid in the same manner as in Example B6.

EXAMPLE B10

1-(Chloromethyl)-4-pentylbenzene

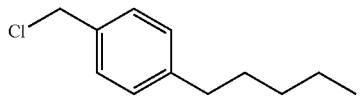

The title compound was obtained by treating the compound of Example B9 in the same manner as in Example B1. This compound was used in the following reaction without further purification.

EXAMPLE B11

1-(4-Pentylbenzyl)isoquinoline

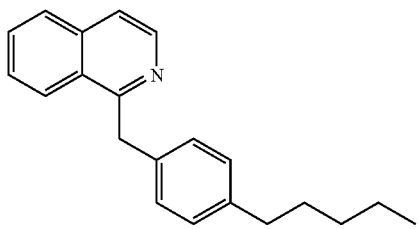

The title compound was obtained by treating the compound of Example B10 in the same manner as in Example B2.

$^1$H-NMR (CDCl$_3$) δ(ppm): 0.86 (3H, t), 1.26-1.33 (4H, m), 1.52-1.59 (2H, m), 2.52 (2H, t), 4.64 (2H, s), 7.06 (2H, d), 7.18 (2H, d), 7.50-7.55 (2H, m), 7.61-7.65 (1H, m), 7.80 (1H, d), 8.17 (1H, dd), 8.49 (1H, d)

EXAMPLE B12

(4-Hexylphenyl)methanol

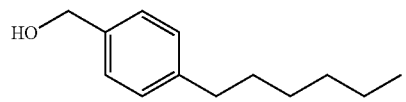

The title compound was obtained by reducing 4-n-hexyl-benzoic acid in the same manner as in Example B6. This compound was used in the following reaction without further purification.

EXAMPLE B13

1-(Chloromethyl)-4-hexylbenzene

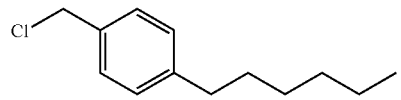

The title compound was obtained by treating the compound of Example B12 in the same manner as in Example B1. This compound was used in the following reaction without further purification.

EXAMPLE B14

1-(4-Hexylbenzyl)isoquinoline

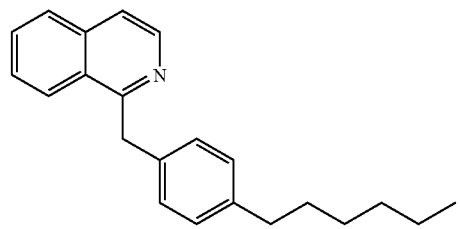

The title compound was obtained by treating the compound of Example B13 in the same manner as in Example B2.

$^1$H-NMR (CDCl$_3$) δ(ppm): 0.86 (3H, t), 1.26-1.31 (6H, m), 1.51-1.58 (2H, m), 2.52 (2H, t), 4.63 (2H, s), 7.06 (2H, d), 7.18 (2H, d), 7.50-7.55 (2H, m), 7.61-7.65 (1H, m), 7.80 (1H, d), 8.17 (1H, dd), 8.49 (1H, d)

EXAMPLE B15

1-(4-Isopropylbenzyl)isoquinoline

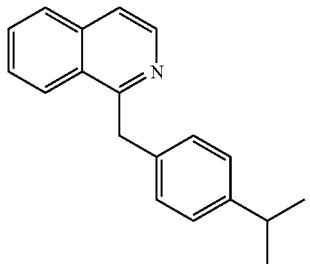

The title compound was obtained by treating p-isopropylbenzyl chloride in the same manner as in Example B2.

$^1$H-NMR (CDCl$_3$) δ(ppm): 1.19 (6H, d), 2.80-2.87 (1H, m), 4.64 (2H, s), 7.11 (2H, d), 7.21 (2H, d), 7.51-7.56 (2H, m), 7.61-7.65 (1H, m), 7.81 (1H, d), 8.19 (1H, dd), 8.50 (1H, d)

EXAMPLE B16

1-[4-(tert-Butyl)benzyl]isoquinoline

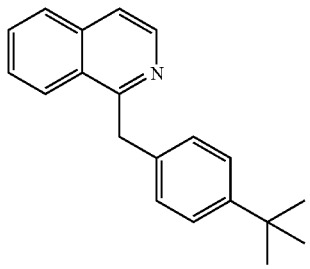

The title compound was obtained by treating 4-tert-butylbenzyl chloride in the same manner as in Example B2.

$^1$H-NMR (CDCl$_3$) δ(ppm): 1.26 (9H, s), 4.64 (2H, s), 7.22 (2H, d), 7.27 (2H, d), 7.52-7.56 (2H, m), 7.62-7.66 (1H, m), 7.81 (1H, d), 8.19 (1H, dd), 8.50 (1H, d)

EXAMPLE B17

(4-Isobutylphenyl)methanol

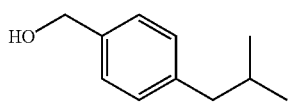

The title compound was obtained by reducing 4-isobutylbenzoic acid in the same manner as in Example B6. This was used in the following reaction without further purification.

EXAMPLE B18

1-(Chloromethyl)-4-isobutylbenzene

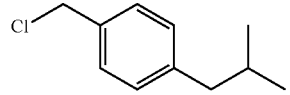

The title compound was obtained by treating the compound of Example B17 in the same manner as in Example B1. This was used in the following reaction without further purification.

EXAMPLE B19

1-(4-Isobutylbenzyl)isoquinoline

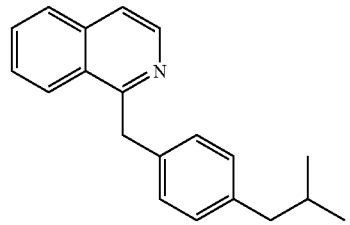

The title compound was obtained by treating the compound of Example B18 in the same manner as in Example B2.

$^1$H-NMR (CDCl$_3$) δ(ppm): 0.86 (6H, d), 1.75-1.83 (1H, m), 2.39 (2H, d), 4.66 (2H, s), 7.02 (2H, d), 7.18 (2H, d), 7.52-7.58 (2H, m), 7.63-7.67 (1H, m), 7.82 (1H, d), 8.18 (1H, d), 8.50 (1H, d)

EXAMPLE B20

1-(Chloromethyl)-4-(trifluoromethyl)benzene

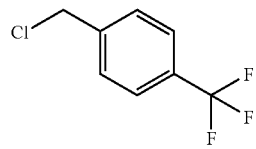

The title compound was obtained by treating 4-trifluoromethylbenzyl alcohol in the same manner as in Example B1. This was used in the following reaction without further purification.

EXAMPLE B21

1-[4-(Trifluoromethyl)benzyl]isoquinoline

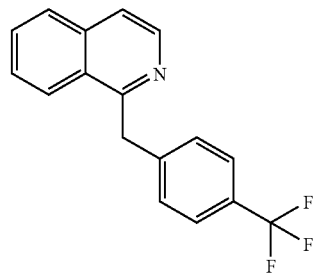

The title compound was obtained by treating the compound of Example B20 in the same manner as in Example B2.

¹H-NMR (CDCl₃) δ(ppm): 4.73 (2H, s), 7.39 (2H, d), 7.51 (2H, d), 7.54-7.60 (2H, m), 7.65-7.69 (1H, m), 7.84 (1H, d), 8.09-8.10 (1H, m), 8.51 (1H, d)

EXAMPLE B22

1-(Chloromethyl)-4-(trifluoromethoxy)benzene

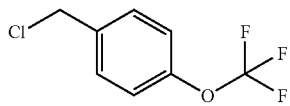

The title compound was obtained by treating 4-trifluoromethoxybenzoyl alcohol in the same manner as in Example B1. This was used in the following reaction without further purification.

EXAMPLE B23

1-[4-(Trifluoromethoxy)benzyl]isoquinoline

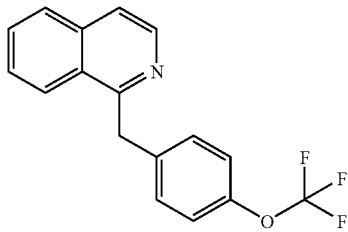

The title compound was obtained by treating the compound of Example B22 in the same manner as in Example B2.

¹H-NMR (CDCl₃) δ(ppm): 4.67 (2H, s), 7.10 (2H, d), 7.27 (2H, d), 7.54-7.59 (2H, m), 7.64-7.68 (1H, m), 7.84 (1H, d), 8.11 (1H, dd), 8.50 (1H, d)

EXAMPLE B24

1-(Chloromethyl)-2-iodobenzene

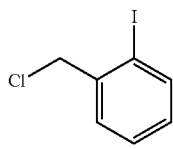

Methanesulfonyl chloride (2.0 ml, 29 mmol) and triethylamine (3.6 ml, 26 mmol) were added to a solution of o-iodobenzyl alcohol (5.0 g, 21 mmol) in methylene chloride (50 ml) cooled to 0° C., and the mixture was stirred at that temperature for 19 hours. A 5% aqueous sodium hydrogencarbonate solution was added, and the resulting mixture was extracted with methylene chloride. The methylene chloride layer was dried over anhydrous magnesium sulfate and concentrated under reduced pressure to give the title compound (5.34 g).

EXAMPLE B25

1-(2-Iodobenzyl)isoquinoline

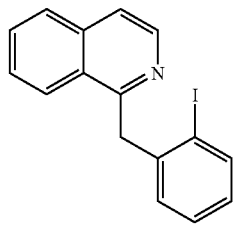

The title compound was obtained by treating the compound of Example B24 in the same manner as in Example B2.

¹H-NMR (CDCl₃) δ(ppm): 4.74 (2H, s), 6.81-6.84 (1H, m), 6.87-6.92 (1H, m), 7.11-7.15 (1H, m), 7.55-7.57 (1H, m), 7.60 (1H, d), 7.64-7.68 (1H, m), 7.83-7.86 (1H, m), 7.89-7.91 (1H, m), 8.00-8.02 (1H, m), 8.50 (1H, d)

EXAMPLE B26

1-[2-(2-Phenyl-1-ethynyl)benzyl]isoquinoline

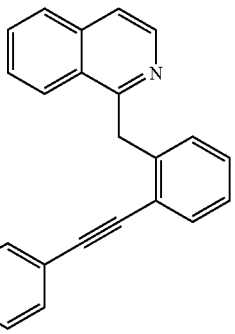

A solution of tetrakis(triphenylphosphine)palladium (58 mg, 0.05 mmol) and ethynylbenzene (204 mg, 2.0 mmol) in pyrrolidine (1.5 ml) was added to a solution of the compound of Example B25 (345 mg, 1.07 mmol) in pyrrolidine (1.5 ml) under nitrogen atmosphere, and the mixture was stirred at 80° C. for 3 hours. The mixture was cooled to room temperature, diluted with ethyl acetate, washed with a saturated aqueous ammonium chloride solution, dried over anhydrous magnesium sulfate, and then concentrated under reduced pressure. The residue was purified by silica gel chromatography to give the title compound (280 mg).

¹H-NMR (CDCl₃) δ(ppm): 4.95 (2H, s), 6.98-7.06 (2H, m), 7.10-7.21 (2H, m), 7.31-7.35 (3H, m), 7.48-7.51 (3H, m), 7.57-7.65 (2H, m), 7.82 (1H, d), 8.25 (1H, d), 8.52 (1H, d)

EXAMPLE B27

1-(2-Phenylethylbenzyl)isoquinoline

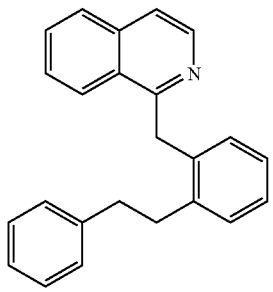

Palladium-carbon (10%, 230 mg) was added to a solution of the compound of Example B26 (280 mg, 0.88 mmol) in tetrahydrofuran (30 ml), and this mixture was stirred at room temperature under hydrogen atmosphere (1 atm) for 3 hours. The catalyst was removed by filtration and the obtained filtrate was concentrated under reduced pressure. The residue was purified by silica gel chromatography to give the title compound (162 mg).

$^1$H-NMR (CDCl$_3$) δ(ppm): 2.90-2.94 (2H, m), 3.07-3.10 (2H, m), 4.67 (2H, s), 6.80 (1H, d), 7.02-7.06 (1H, m), 7.15-7.30 (7H, m), 7.49-7.53 (1H, m), 7.58 (1H, d), 7.64-7.68 (1H, m), 7.84 (1H, d), 7.95 (1H, d), 8.50 (1H, d)

EXAMPLE B28

1-{2-[4-(Tetrahydro-2H-2-pyranyloxy)-1-butynyl]benzyl}-isoquinoline

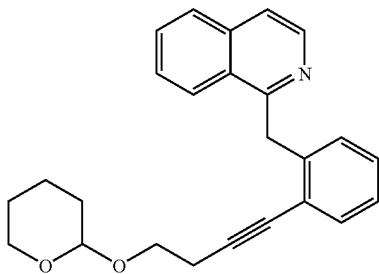

A solution of tetrakis(triphenylphosphine)palladium (58 mg, 0.05 mmol) and 2-(3-butynyloxy)-tetrahydro-2H-pyran (208 mg, 2.0 mmol) in pyrrolidine (1.5 ml) was added to a solution of the compound of Example B25 (345 mg, 1.07 mmol) in pyrrolidine (1.5 ml) under nitrogen atmosphere, and this mixture was stirred for four days at room temperature, and for another 30 minutes at 80° C. The mixture was cooled to room temperature, diluted with ethyl acetate, washed with a saturated aqueous ammonium chloride solution, dried over anhydrous magnesium sulfate, and then concentrated under reduced pressure. The residue was purified by silica gel chromatography to give the title compound (277 mg).

$^1$H-NMR (CDCl$_3$) δ(ppm): 1.42-1.60 (4H, m), 1.64-1.68 (1H, m), 1.75-1.81 (1H, m), 2.76-2.80 (2H, m), 3.46-3.51 (1H, m), 3.60-3.66 (1H, m), 3.85-3.95 (2H, m), 4.64-4.66 (1H, m), 4.85 (2H, s), 6.95-6.98 (1H, m), 7.05-7.13 (2H, m), 7.44-7.46 (1H, m), 7.49-7.53 (1H, m), 7.56 (1H, d), 7.60-7.65 (1H, m), 7.80-7.82 (1H, m), 8.15-8.18 (1H, m), 8.49-8.51 (1H, m)

EXAMPLE B29

4-[2-(1-Isoquinolylmethyl)phenyl]-3-butyn-1-ol

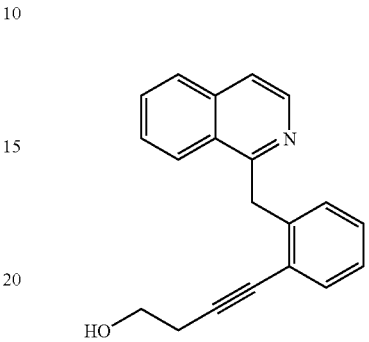

After the compound of Example B28 (200 mg, 0.54 mmol) was cooled to 0° C., a hydrochloric acid-methanol solution (10%, 5 ml) was added, and this mixture was stirred for 15 minutes. A saturated aqueous sodium hydrogencarbonate solution was added, and this mixture was extracted with ethyl acetate. The ethyl acetate layer was dried over anhydrous magnesium sulfate and concentrated under reduced pressure. The residue was purified by silica gel chromatography to give the title compound (86 mg).

$^1$H-NMR (CDCl$_3$) δ(ppm): 2.72 (2H, t), 3.53-3.60 (1H, brs), 3.85 (2H, t), 4.85 (2H, s), 7.12-7.15 (2H, m), 7.22-7.24 (1H, m), 7.42-7.44 (1H, m), 7.55-7.59 (2H, m), 7.63-7.67 (1H, m), 7.81 (1H, d), 8.30 (1H, m), 8.46 (1H, m)

EXAMPLE B30

4-[2-(1-Isoquinolylmethyl)phenyl]-1-butanol

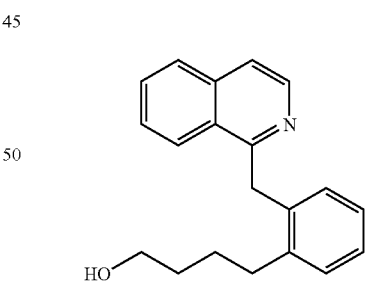

Palladium-carbon (10%, 10 mg) was added to a solution of the compound of Example B29 (44 mg, 0.15 mmol) in tetrahydrofuran (5 ml), and this mixture was stirred at room temperature under hydrogen atmosphere (1 atm) for 1 hour. After the catalyst was removed by filtration, the filtrate was concentrated under reduced pressure. The residue was purified by silica gel chromatography to give the title compound (18 mg).

$^1$H-NMR (CDCl$_3$) δ(ppm): 1.61-1.75 (4H, m), 2.33 (1H, brs), 2.77 (2H, t), 3.67 (2H, t), 4.70 (2H, s), 6.91 (1H, d), 7.02-7.06 (1H, m), 7.12-7.16 (1H, m), 7.19-7.21 (1H, m), 7.50-7.55 (1H, m), 7.57 (1H, d), 7.63-7.67 (1H, d), 7.83 (1H, d), 8.09 (1H, d), 8.47 (1H, d)

EXAMPLE B31

1-Bromo-2-(chloromethyl)benzene

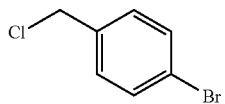

The title compound was obtained by treating p-bromobenzyl alcohol in the same manner as in Example B1.

EXAMPLE B32

1-(4-Bromobenzyl)isoquinoline

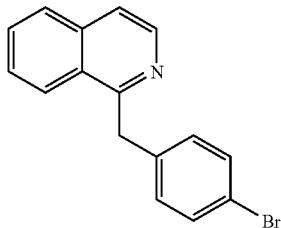

The title compound was obtained by treating the compound of Example B31 in the same manner as in Example B2.

$^1$H-NMR (CDCl$_3$) δ(ppm): 4.61 (2H, s), 7.14-7.16 (2H, m), 7.35-7.39 (2H, m), 7.52-7.58 (2H, m), 7.63-7.67 (1H, m), 7.82 (1H, d), 8.07-8.10 (1H, m), 8.49 (1H, d)

EXAMPLE B33

Ethyl(E)-3-[4-(isoquinolylmethyl)phenyl]-2-propanoate

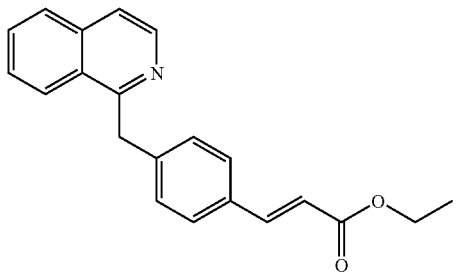

Tris(2-methylphenyl)phosphine (20 mg, 0.067 mmol), palladium(II) acetate (7.5 mg, 0.034 mmol), and triethylamine (70 μl, 0.50 mmol) were added to a solution of the compound of Example B32 (100 mg, 0.34 mmol) and vinyl propionate (73 μl, 0.67 mmol) in dimethylformamide (1.0 ml) under nitrogen atmosphere, and this mixture was stirred at 100° C. for 4 hours. After the mixture was cooled to room temperature, water was added, and this mixture was extracted with ethyl acetate. The organic layer was washed with water, dried over anhydrous magnesium sulfate, and then concentrated under reduced pressure. The residue was purified by silica gel column chromatography to give the title compound (74 mg).

$^1$H-NMR (CDCl$_3$) δ(ppm): 1.32 (3H, t), 4.24 (2H, q), 4.69 (2H, s), 6.36 (1H, d), 7.29 (2H, d), 7.42 (2H, d), 7.53-7.67 (4H, m), 7.83 (1H, d), 8.11-8.13 (1H, m), 8.50 (1H, d)

EXAMPLE B34

Ethyl 3-[4-(1-isoquinolylmethyl)phenyl]propanoate

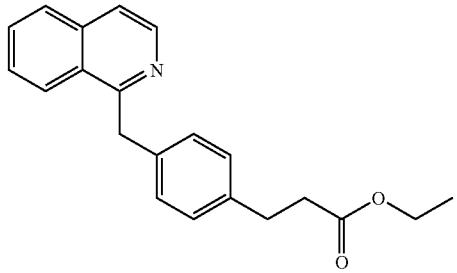

Palladium-carbon (10%, 20 mg) was added to a solution of the compound of Example B33 (71 mg, 0.22 mmol) in methanol (5.0 ml), and this reaction mixture was stirred at room temperature under hydrogen atmosphere at atmospheric pressure for 5.5 hours. After the catalyst was removed from the reaction mixture by filtration, the filtrate was concentrated under reduced pressure. The residue was purified by silica gel column chromatography to give the title compound (52 mg).

$^1$H-NMR (CDCl$_3$) δ(ppm): 1.20 (3H, t), 2.56 (2H, t), 2.88 (2H, t), 4.09 (2H, q), 4.64 (2H, s), 7.09 (2H, d), 7.20 (2H, d), 7.51-7.57 (2H, m), 7.62-7.66 (1H, m), 7.82 (1H, d), 8.15 (1H, dd), 8.50 (1H, d)

EXAMPLE B35

3-[4-(1-Isoquinolylmethyl)phenyl]-1-propanol

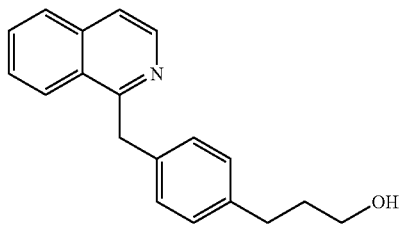

Lithium aluminum hydride (6 mg, 0.16 mmol) was added to tetrahydrofuran (1.0 ml) cooled to 0° C. under nitrogen atmosphere. A solution of the compound of Example B34 (46 mg, 0.14 mmol) in tetrahydrofuran (1.0 ml) was further added, and this reaction mixture was stirred at that temperature for 3 hours. A mixed solution of methanol and water (9:1, 1.0 ml) was added to the reaction mixture, a saturated aqueous ammonium chloride solution was further added, then this mixture was extracted with chloroform. The organic layer was dried over anhydrous magnesium sulfate and concentrated under reduced pressure. The residue was purified by silica gel column chromatography to give the title compound (22 mg).

¹H-NMR (CDCl₃) δ(ppm): 1.30-1.35 (1H, brs), 1.81-1.88 (2H, m), 2.64 (2H, t), 3.62-3.65 (2H, m), 4.64 (2H, s), 7.09 (2H, d), 7.20 (2H, d), 7.51-7.57 (2H, m), 7.62-7.66 (1H, m), 7.81 (1H, d), 8.16-8.18 (1H, m), 8.49 (1H, d)

EXAMPLE 36

1-Isoquinolyl(4-methoxyphenyl)ketone

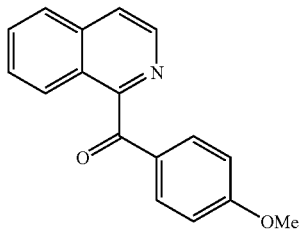

4-Bromoanisol (15.3 ml, 122 mmol) and a catalytic amount of 1,2-dibromoethane as an initiator were added to a mixed solution of magnesium (3059 mg, 125.8 mmol) and tetrahydrofuran (20 ml) under nitrogen atmosphere, and this reaction mixture was stirred while heating under reflux for 45 minutes. The mixture was cooled to 0° C., a solution of 1-isoquinolinecarbonitrile (10.78 g, 69.9 mmol) in tetrahydrofuran (30 ml) was added dropwise thereto, and this reaction mixture was stirred at room temperature for 2 hours. The reaction mixture was cooled on ice, concentrated hydrochloric acid (24 ml) and methanol (120 ml) were added, and this mixture was heated under reflux for 1.5 hours. After cooling on ice, the mixture was adjusted to pH 8 by adding aqueous sodium hydroxide, extracted with ether, washed with saturated brine, dried over anhydrous magnesium sulfate, and then concentrated under reduced pressure. The residue was purified by silica gel column chromatography to give the title compound (15.87 g).

¹H-NMR (CDCl₃) δ(ppm): 3.88 (3H, s), 6.95 (2H, d), 7.61 (1H, dd), 7.74 (1H, dd), 7.76 (1H, d), 7.85 (2H, d), 8.17 (1H, dd), 8.60 (1H, d).

EXAMPLE B37

1-Isoquinolyl(4-methoxyphenyl)methanol

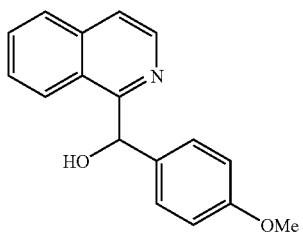

Sodium borohydride (1855 mg) was added to an ice-cooled solution of the compound of Example B36 (8608 mg) in ethanol (170 ml), and this mixture was stirred at room temperature for 35 minutes. Sodium borohydride (957 mg) was further added, and this reaction mixture was stirred at 40° C. for 40 minutes. The reaction mixture was concentrated under reduced pressure, water was added, and this mixture was extracted with ether. The organic layer was washed with water and saturated brine, dried over anhydrous magnesium sulfate, and then concentrated under reduced pressure. The obtained title compound (7881 mg) was used in the following reaction without further purification.

¹H-NMR (DMSO-d6) δ(ppm): 3.66 (3H, s), 6.30-6.32 (1H, brs), 6.81 (2H, d), 7.28 (2H, d), 7.54 (1H, dd), 7.68 (1H, dd), 7.76 (1H, d), 7.94 (1H, d), 8.37 (1H, d), 8.47 (1H, d).

The proton of the hydroxyl group was not observed in the NMR spectrum.

EXAMPLE B38

1-Isoquinolyl(4-methoxyphenyl)methyl acetate

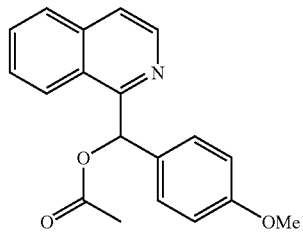

Acetic anhydride (20 ml) was added to a solution of the compound of Example B37 (7881 mg) in pyridine (100 ml), and this reaction mixture was stirred at 50° C. for 4 hours. The reaction mixture was concentrated under reduced pressure and subjected to azeotropic distillation with toluene. The residue was purified by silica gel column chromatography to give the title compound (8.79 g).

¹H-NMR (CDCl₃) δ(ppm): 2.22 (3H, s), 3.76 (3H, s), 6.84 (2H, d), 7.39 (2H, d), 7.54 (1H, dd), 7.56 (1H, s), 7.60 (1H, d), 7.64 (1H, dd), 7.82 (1H, d), 8.19 (1H, d), 8.57 (1H, d).

EXAMPLE B39

1-(4-Methoxybenzyl)isoquinoline

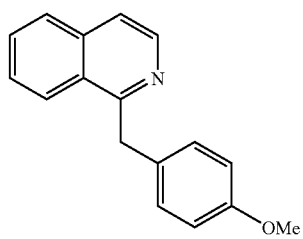

Palladium-carbon (10%, 4.0 g) was added to a solution of the compound of Example B38 (8.79 g) in methanol (150 ml), and this mixture was stirred at room temperature under hydrogen atmosphere at atmospheric pressure for 5.5 hours. The catalyst was removed by filtration through celite, and the filtrate was concentrated under reduced pressure. The residue was purified by silica gel column chromatography to give the title compound (4.48 g).

¹H-NMR (CDCl₃) δ(ppm): 3.74 (3H, s), 4.61 (2H, s), 6.79 (2H, d), 7.21 (2H, d), 7.53 (1H, dd), 7.56 (1H, d), 7.63 (1H, dd), 7.80 (1H, d), 8.16 (1H, d), 8.49 (1H, d).

EXAMPLE B40

4-(1-Isoquinolylmethyl)phenol

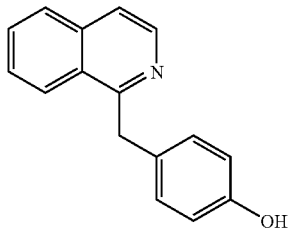

An aqueous hydrobromic acid solution (47%, 40 ml) was added to the compound of Example B39 (2185 mg), and this reaction mixture was heated under reflux for 14 hours. The reaction mixture was cooled to room temperature, further cooled on ice, neutralized with a 50% aqueous sodium hydroxide solution, and extracted with ethyl acetate. The ethyl acetate layer was washed with water, dried over anhydrous magnesium sulfate, and then concentrated under reduced pressure. The obtained powder was washed with petroleum ether to give the title compound (1822 mg).

¹H-NMR (DMSO-d6) δ(ppm): 4.48 (2H, s), 6.61 (2H, d), 7.07 (2H, d), 7.60 (1H, dd), 7.68 (1H, d), 7.71 (1H, dd), 7.92 (1H, d), 8.27 (1H, d), 8.41 (1H, d), 9.19 (1H, brs).

EXAMPLE B41

4-(1-Isoquinolylmethyl)phenyl trifluoromethanesulfonate

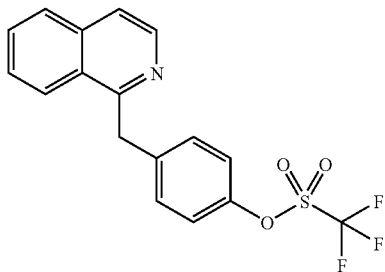

Trifluoromethanesulfonic anhydride (0.55 ml) was added dropwise to an ice-cold solution of the compound of Example B40 (513 mg) in pyridine (10 ml), and this reaction mixture was stirred at that temperature for 45 minutes. After ice was added, the reaction mixture was extracted with ether. The organic layer was washed with water and saturated brine, dried over anhydrous magnesium sulfate, and then concentrated under reduced pressure. The residue was purified by silica gel column chromatography to give the title compound (546 mg).

¹H-NMR (CDCl₃) δ(ppm): 4.69 (2H, s), 7.16 (2H, d), 7.35 (2H, d), 7.57 (1H, dd), 7.60 (1H, d), 7.68 (1H, dd), 7.85 (1H, d), 8.09 (1H, d), 8.50 (1H, d).

EXAMPLE B42

1-[4-(2-Phenyl-1-ethynyl)benzyl]isoquinoline

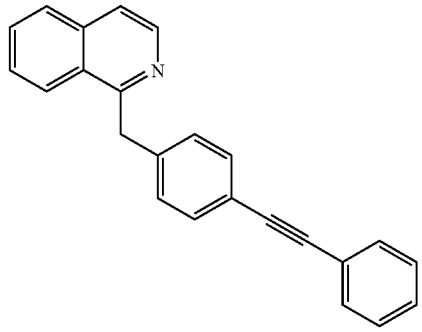

Phenylacetylene (53 μl), palladium acetate (9 mg), 1,1'-bis(diphenylphosphino)ferrocene (67 mg), copper(I) iodide (3 mg), lithium chloride (20 mg), and triethylamine (50 μl) were added to a solution of the compound of Example B41 (88 mg) in N,N-dimethylformamide (2.0 ml) that had been degassed and placed under nitrogen, and this mixture was stirred at 80° C. for 8 hours. After cooling the mixture to room temperature, water was added, and this mixture was extracted with ethyl acetate. The organic layer was washed with water and saturated brine, dried over anhydrous magnesium sulfate, and then concentrated under reduced pressure. The residue was purified by silica gel column chromatography to give the title compound (53 mg).

¹H-NMR (CDCl₃) δ(ppm): 4.69 (2H, s), 7.12-7.32 (3H, m), 7.25 (2H, d), 7.42 (2H, d), 7.43-7.52 (2H, m), 7.54 (1H, dd), 7.58 (1H, d), 7.65 (1H, dd), 7.83 (1H, d), 8.10 (1H, d), 8.51 (1H, d).

EXAMPLE B43

1-(4-Phenethylbenzyl)isoquinoline

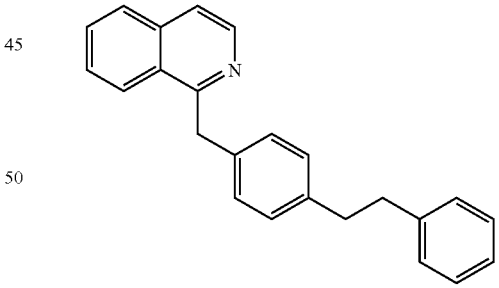

Palladium-carbon catalyst (10%, 20 mg) was added to a solution of the compound of Example B42 (45 mg) in tetrahydrofuran (2 ml), and this mixture was stirred at room temperature under hydrogen atmosphere at atmospheric pressure for 2 hours. The catalyst was removed by filtration through celite, and the filtrate was concentrated under reduced pressure. The residue was purified by silica gel column chromatography to give the title compound (23 mg).

¹H-NMR (CDCl₃) δ(ppm): 2.78-2.90 (4H, m), 4.64 (2H, s), 7.07 (2H, d), 7.10-7.20 (5H, m), 7.22 (2H, d), 7.53 (1H, dd), 7.55 (1H, d), 7.63 (1H, dd), 7.80 (1H, d), 8.15 (1H, d), 8.49 (1H, d).

EXAMPLE B44

1-[4-(4-Phenyl-1-butynyl)benzyl]isoquinoline

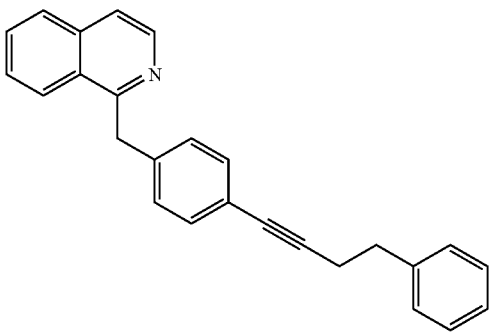

The title compound was obtained by treating the compound of Example B41 and 4-phenyl-1-butyne in the same manner as in Example B42.

$^1$H-NMR (CDCl$_3$) δ(ppm): 2.65 (2H, t), 2.88 (2H, t), 4.68 (2H, s), 7.12-7.40 (9H, m), 7.50-7.70 (3H, m), 7.80-7.88 (1H, m), 8.00-8.10 (1H, m), 8.48-8.51 (1H, m).

EXAMPLE B45

1-[4-(4-Phenyl-1-butyl)benzyl]isoquinoline

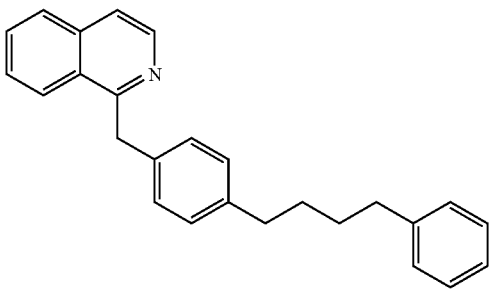

The title compound was obtained by treating the compound of Example B44 in the same manner as in Example B43.

$^1$H-NMR (CDCl$_3$) δ(ppm): 1.55-1.80 (4H, m), 2.50-2.65 (4H, m), 4.68 (2H, s), 7.00-7.30 (9H, m), 7.52 (1H, dd), 7.56 (1H, d), 7.63 (1H, dd), 7.81 (1H, d), 8.15 (1H, d), 8.50 (1H, d).

EXAMPLE B46

1-{4-[4-(tetrahydro-2H-2-pyranyloxy)-1-butynyl]benzyl}-isoquinoline

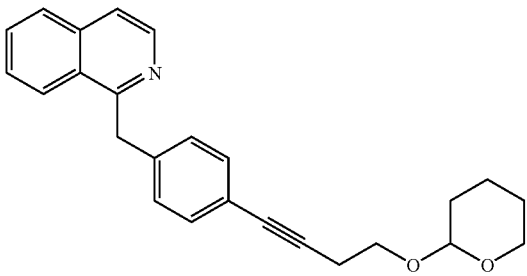

The title compound was obtained by treating the compound of Example B41 and 2-(3-butynyloxy)tetrahydro-2H-pyran in the same manner as in Example B42.

$^1$H-NMR (CDCl$_3$) δ(ppm): 1.48-1.90 (6H, m), 2.67 (2H, t), 3.49-3.55 (1H, m), 3.60 (1H, dd), 3.65-3.94 (2H, m), 4.66 (2H, s), 4.65-4.70 (1H, m), 7.14-7.20 (2H, m), 7.23-7.30 (2H, m), 7.53 (1H, dd), 7.58 (1H, d), 7.65 (1H, dd), 7.82 (1H, d), 8.10 (1H, d), 8.49 (1H, d).

EXAMPLE B47

4-[4-(1-Isoquinolylmethyl)phenyl]-3-butyn-1-ol

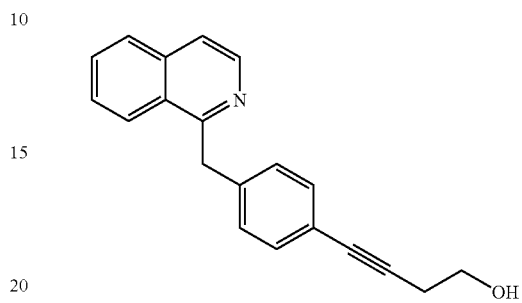

The compound of Example B46 (1048 mg) was dissolved in a 10% hydrochloric acid-methanol solution (50 ml), and this reaction mixture was stirred at room temperature for 1.5 hours. The reaction mixture was cooled on ice, a saturated aqueous sodium hydrogencarbonate solution was added, and the resulting mixture was extracted with ethyl acetate. The organic layer was washed with water and saturated brine, dried over anhydrous magnesium sulfate, and then concentrated under reduced pressure. The residue was purified by silica gel column chromatography to give the title compound (666 mg).

$^1$H-NMR (CDCl$_3$) δ(ppm): 2.65 (2H, t), 3.77 (2H, t), 4.65 (2H, s), 7.18 (2H, d), 7.29 (2H, d), 7.52 (1H, dd), 7.57 (1H, d), 7.64 (1H, dd), 7.81 (1H, d), 8.07 (1H, d), 8.49 (1H, d).

The proton of the hydroxyl group was not observed in the NMR spectrum.

EXAMPLE B48

4-[4-(1-Isoquinolylmethyl)phenyl]-1-butanol

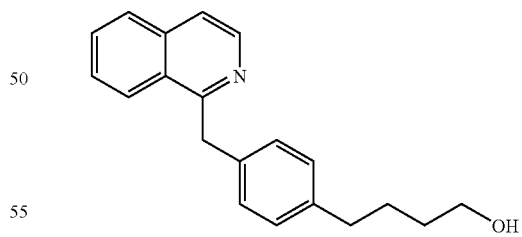

The title compound was obtained by treating the compound of Example B47 in the same manner as in Example B43.

$^1$H-NMR (CDCl$_3$) δ(ppm): 1.50-1.70 (4H, m), 2.57 (2H, t), 3.62 (2H, t), 4.64 (2H, s), 7.06 (2H, d), 7.18 (2H, d), 7.53 (1H, dd), 7.55 (1H, d), 7.63 (1H, dd), 7.80 (1H, d), 8.16 (1H, d), 8.49 (1H, d).

The proton of the hydroxyl group was not observed in the NMR spectrum.

EXAMPLE B49

1-[4-(3-Cyclopentyl-1-propynyl)benzyl]isoquinoline

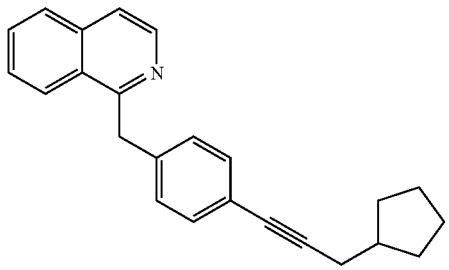

The title compound was obtained by treating the compound of Example B41 and 3-cyclopentyl-1-propyne in the same manner as in Example B42.

$^1$H-NMR (CDCl$_3$) δ(ppm): 1.25-1.35 (2H, m), 1.45-1.70 (6H, m), 1.75-1.85 (2H, m), 2.05-2.13 (1H, m), 4.65 (2H, s), 7.17 (2H, d), 7.27 (2H, d), 7.51 (1H, dd), 7.56 (1H, d), 7.64 (1H, dd),
7.81 (1H, d), 8.08 (1H, d), 8.49 (1H, d).

EXAMPLE B50

1-[4-(3-Cyclopentylpropyl)benzyl]isoquinoline

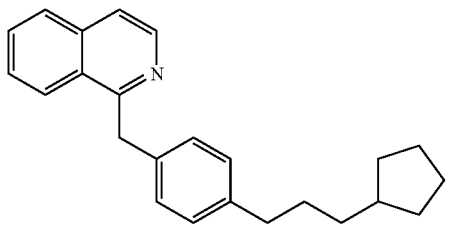

The title compound was obtained by treating the compound of Example B49 in the same manner as in Example B43.

$^1$H-NMR (CDCl$_3$) δ(ppm): 1.25-1.74 (13H, m), 2.49-2.54 (2H, m), 4.64 (2H, s), 7.06 (2H, d), 7.18 (2H, d), 7.53 (1H, dd), 7.55 (1H, d), 7.63 (1H, dd), 7.80 (1H, d), 8.17 (1H, d), 8.49 (1H, d).

EXAMPLE B51

4-[4-(1-Isoquinolylmethyl)phenyl]-2-methyl-3-butyn-2-ol

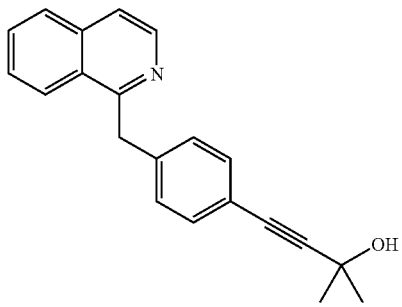

The title compound was obtained by treating the compound of Example B41 and 2-methyl-3-butyn-2-ol in the same manner as in Example B42.

$^1$H-NMR (DMSO-d6) δ(ppm): 1.35 (1H, s), 1.40 (6H, s), 4.62 (2H, s), 7.20-7.30 (4H, m), 7.61 (1H, dd), 7.71 (1H, d), 7.69-7.76 (1H, m), 7.95 (1H, d), 8.26 (1H, d), 8.42 (1H, d).

EXAMPLE B52

4-[4-(1-Isoquinolylmethyl)phenyl]-2-methyl-2-butanol

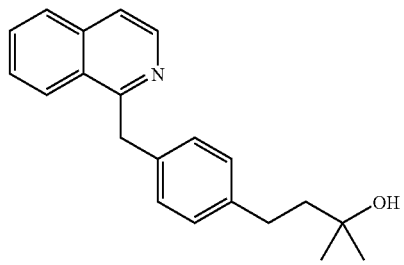

The title compound was obtained by treating the compound of Example B51 in the same manner as in Example B43.

$^1$H-NMR (CDCl$_3$) δ(ppm): 1.25 (6H, s), 1.70-1.77 (2H, m), 2.60-2.67 (2H, m), 4.64 (2H, s), 7.08 (2H, d), 7.19 (2H, d), 7.53 (1H, dd), 7.55 (1H, d), 7.63 (1H, dd), 7.80 (1H, d), 8.16 (1H, d), 8.49 (1H, d).

The proton of the hydroxyl group was not observed in the NMR spectrum.

EXAMPLE B53

1-[4-(3-Methoxy-1-propynyl)benzyl]isoquinoline

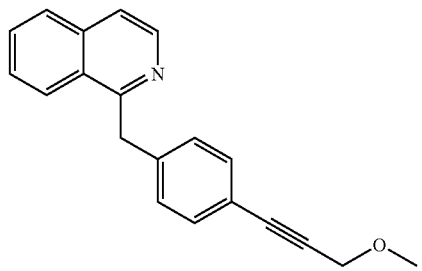

The title compound was obtained by treating the compound of Example B41 and methylpropargyl ether in the same manner as in Example B42.

$^1$H-NMR (CDCl$_3$) δ(ppm): 3.42 (3H, s), 4.29 (2H, s), 4.66 (2H, s), 7.21 (2H, d), 7.34 (2H, d), 7.54 (1H, dd), 7.58 (1H, d), 7.65 (1H, dd) 7.82 (1H, d), 8.10 (1H, d) 8.49 (1H, d).

EXAMPLE B54

1-[4-(3-Methoxypropyl)benzyl]isoquinoline

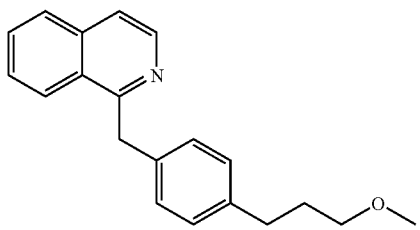

The title compound was obtained by treating the compound of Example B53 in the same manner as in Example B43.

$^1$H-NMR (CDCl$_3$) δ(ppm): 1.78-1.87 (2H, m), 2.06 (2H, t), 3.31 (3H, s), 3.35 (2H, t), 4.64 (2H, s), 7.07 (2H, d), 7.22 (2H, d), 7.53 (1H, dd), 7.55 (1H, d), 7.64 (1H, dd), 7.81 (1H, d), 8.17 (1H, d), 8.49 (1H, d).

EXAMPLE B55

1-{4-[2-(2-Pyridyl)-1-ethynyl]benzyl}isoquinoline

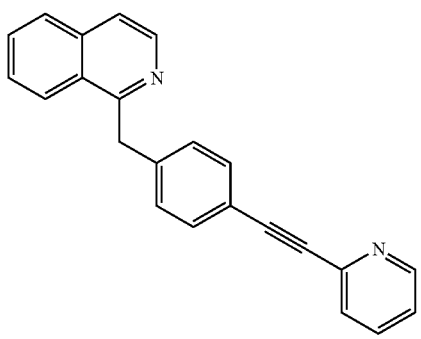

The title compound was obtained by treating the compound of Example B41 and 2-ethylnylpyridine in the same manner as in Example B42.

$^1$H-NMR (CDCl$_3$) δ(ppm): 4.71 (2H, s), 7.20-7.25 (2H, m), 7.29 (2H, d), 7.48-7.53 (1H, m), 7.51 (2H, d), 7.57 (1H, dd), 7.61 (1H, d), 7.67 (1H, dd), 7.85 (1H, d), 8.13 (1H, d), 8.53 (1H, d), 8.59-8.63 (1H, m).

EXAMPLE B56

1-{4-[2-(2-Pyridyl)ethyl]benzyl}isoquinoline

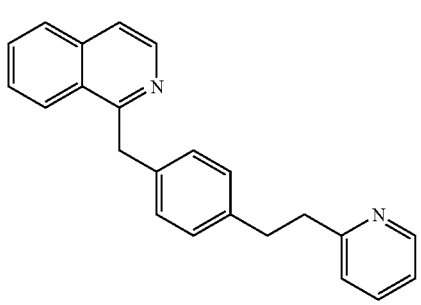

The title compound was obtained by treating the compound of Example B55 in the same manner as in Example B43.

$^1$H-NMR (CDCl$_3$) δ(ppm): 2.94-3.06 (4H, m), 4.64 (2H, s), 7.04 (1H, d), 7.09 (1H, dd), 7.09 (2H, d), 7.18 (2H, d), 7.53 (1H, ddd), 7.54 (1H, dd), 7.55 (1H, d), 7.64 (1H, dd), 7.81 (1H, d), 8.15 (1H, d), 8.49 (1H, d), 8.53 (1H, dd).

EXAMPLE B57

1-{4-[2-(3-pyridyl)-1-ethynyl]benzyl}isoquinoline

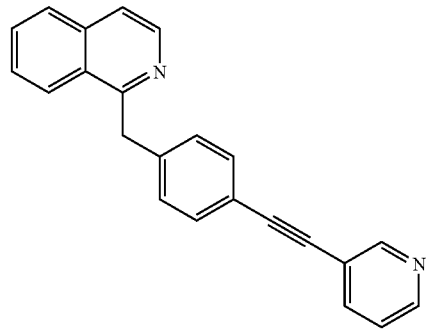

The title compound was obtained by treating the compound of Example B41 and 3-ethynylpyridine in the same manner as in Example B42.

$^1$H-NMR (CDCl$_3$) δ(ppm): 4.69 (2H, s), 7.27 (2H, d), 7.31 (1H, dd), 7.43 (2H, d), 7.55 (1H, dd), 7.59 (1H, d), 7.66 (1H, dd), 7.82 (1H, ddd), 7.83 (1H, d), 8.10 (1H, d), 8.51 (1H, d), 8.60 (1H, dd), 8.77 (1H, d).

EXAMPLE B58

1-{4-[2-(3-Pyridyl)ethyl]benzyl} isoquinoline

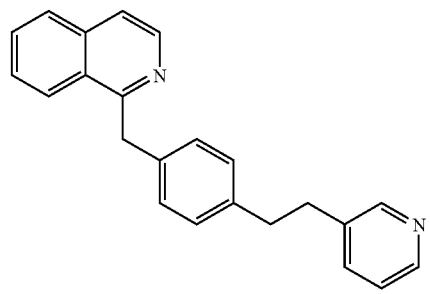

The title compound was obtained by treating the compound of Example B57 in the same manner as in Example B43.

$^1$H-NMR (CDCl$_3$) δ(ppm): 2.80-2.90 (4H, m), 4.65 (2H, s), 7.04 (2H, d), 7.15 (1H, dd), 7.19 (2H, d), 7.39 (1H, dd), 7.54 (1H, dd), 7.56 (1H, d), 7.64 (1H, dd), 7.81 (1H, d), 8.15 (1H, d), 8.40 (1H, d), 8.42 (1H, d), 8.49 (1H, d).

EXAMPLE B59

N-(2-propynyl)acetamide

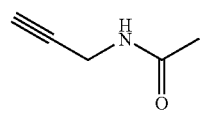

Pyridine (16.3 ml) and acetic anhydride (10.4 ml) were added to an ice-cooled solution of propargylamine (3023 mg) in methylene chloride (30 ml), and this reaction mixture was stirred at room temperature for 1 hour. The reaction mixture was poured on ice, extracted with ethyl acetate, washed successively with 1 N hydrochloric acid, a saturated aqueous sodium hydrogencarbonate solution, and saturated brine, dried over anhydrous magnesium sulfate, and then filtered through silica gel. The filtrate was concentrated under reduced pressure to give the title compound (743 mg). The obtained compound was used in the following reaction without further purification.

$^1$H-NMR (DMSO-d6) δ(ppm): 1.79 (3H, s), 3.07 (1H, t), 3.81 (2H, d), 8.25 (1H, brs).

EXAMPLE B60

N-{3-[4-(1-Isoquinolylmethyl)phenyl]-2-propynyl}acetamide

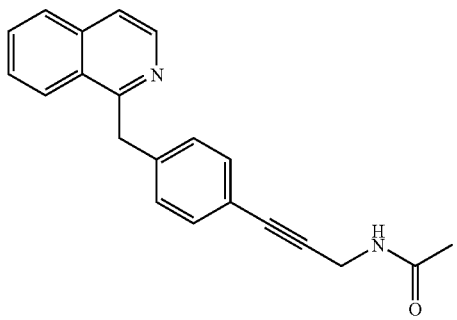

The title compound was obtained by treating the compound of Example B41 and the compound of Example B59 in the same manner as in Example B42.

$^1$H-NMR (DMSO-d6) δ(ppm): 1.79 (3H, s), 4.04 (2H, s), 4.61 (2H, s), 7.45-7.68 (4H, m), 7.68-7.75 (2H, m), 7.90-8.00 (1H, m), 8.25-8.38 (2H, m), 8.40-8.45 (1H, m).

EXAMPLE B61

N-{3-[4-(1-Isoquinolylmethyl)phenyl]propyl}acetamide

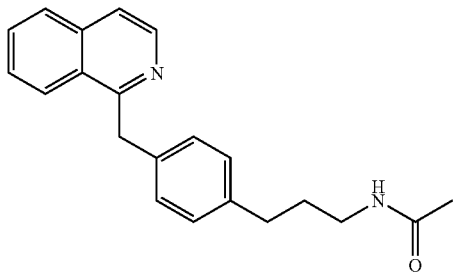

The title compound was obtained by treating the compound of Example B60 in the same manner as in Example B43.

$^1$H-NMR (CDCl$_3$) δ(ppm): 1.95 (3H, s), 1.74-1.84 (2H, m), 2.55 (2H, t), 3.25 (2H, dt), 4.68 (2H, s), 7.10 (2H, d), 7.18 (2H, d), 7.20-7.28 (1H, m), 7.50-7.58 (2H, m), 7.60-7.68 (1H, m), 7.75-7.85 (1H, m), 8.10-8.16 (1H, m), 8.45-8.50 (1H, m).

EXAMPLE B62

N-(2-Propynyl)methanesulfonamide

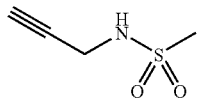

Triethylamine (9.77 ml) was added to an ice-cooled solution of propargylamine (3023 mg) in methylene chloride (30 ml). After dropwise addition of methanesulfonyl chloride (5.19 ml), the reaction mixture was stirred for 3 hours at that temperature, warmed to room temperature, and further stirred for 2 hours. Ice was added to the reaction mixture, the resulting mixture was extracted with ethyl acetate, washed with saturated brine, dried over anhydrous magnesium sulfate, and concentrated under reduced pressure. The residue was dissolved in methanol (120 ml), potassium carbonate (11.7 g) was added, and this reaction mixture was stirred at room temperature for 3 hours. The reaction mixture was concentrated under reduced pressure, neutralized with dilute hydrochloric acid while cooling on ice, and then extracted with ethyl acetate. The extract was washed with saturated brine, dried over anhydrous magnesium sulfate, and then concentrated under reduced pressure. The residue was purified by silica gel column chromatography to give the title compound (6.67 g).

$^1$H-NMR (CDCl$_3$) δ(ppm): 2.39 (1H, t), 3.10 (3H, s), 3.99 (2H, dd), 4.60 (1H, brs).

EXAMPLE B63

N-{3-[4-(1-isoquinolylmethyl)phenyl]-2-propynyl}-methanesulfonamide

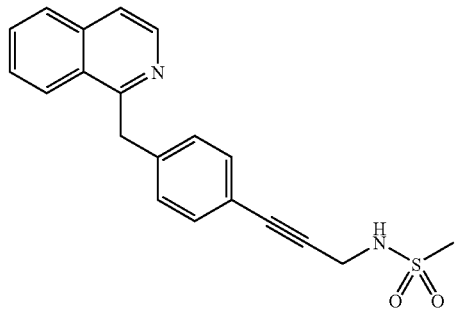

The title compound was obtained by treating the compound of Example B41 and the compound of Example B62 in the same manner as in Example B42.

$^1$H-NMR (DMSO-d6) δ(ppm): 2.97 (3H, s), 4.00 (2H, d), 4.63 (2H, s), 7.25-7.37 (4H, m), 7.57 (1H, t), 7.62 (1H, dd), 7.71 (1H, d), 7.73 (1H, dd), 7.94 (1H, d), 8.28 (1H, d), 8.42 (1H, d).

EXAMPLE B64

N-{3-[4-(1-isoquinolylmethyl)phenyl]propyl}methanesulfonamide

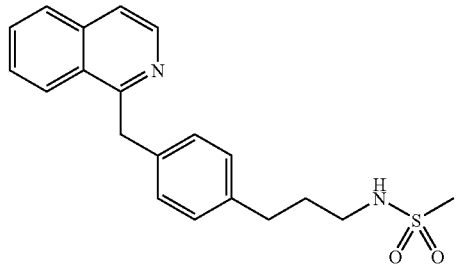

The title compound was obtained by treating the compound of Example B63 in the same manner as in Example B43.

$^1$H-NMR (CDCl$_3$) δ(ppm): 1.80-1.90 (2H, m), 2.62 (2H, t), 2.89 (3H, s), 3.11 (2H, dt), 4.25 (1H, brs), 4.64 (2H, s), 7.05 (2H, d), 7.20 (2H, d), 7.50 (1H, dd), 7.56 (1H, d), 7.63 (1H, dd), 7.81 (1H, d), 8.15 (1H, d), 8.49 (1H, d).

EXAMPLE B65

1-{4-[3-(Ethylsulfanyl)-1-propynyl]benzyl} isoquinoline

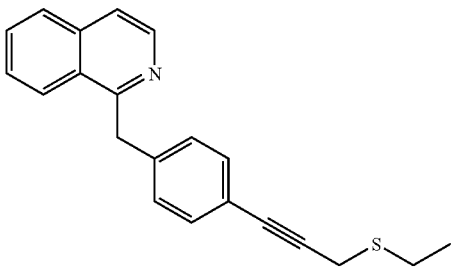

The title compound was obtained by treating the compound of Example B41 and propargyl ethyl sulfide in the same manner as in Example B42.

$^1$H-NMR (CDCl$_3$) δ(ppm): 1.30 (3H, t), 2.73 (2H, q), 3.47 (2H, s), 4.67 (2H, s), 7.20-7.32 (4H, m), 7.52 (1H, dd), 7.57 (1H, d), 7.64 (1H, dd), 7.81 (1H, d), 8.08 (1H, d), 8.49 (1H, d).

EXAMPLE B66 t-Butyl N-(2-propynyl)carbamate

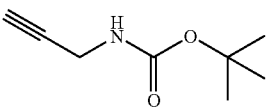

A solution of di-t-butyl-dicarbonate (10.84 g) in tetrahydrofuran (20 ml) was added dropwise to an ice-cooled solution of propargylamine (3040 mg) in tetrahydrofuran (20 ml), the temperature of the mixture was gradually raised to room temperature, and the reaction mixture was stirred for 20 hours. After water was added, the reaction mixture was extracted with ethyl acetate, washed with saturated brine, dried over anhydrous magnesium sulfate, and then concentrated under reduced pressure to give the title compound (9.34 g). The obtained compound was used in the following reaction without further purification.

$^1$H-NMR (DMSO-d6) δ(ppm): 1.36 (9H, s), 3.04 (1H, t), 3.62-3.70 (2H, m), 7.20-7.30 (1H, m)

EXAMPLE B67 tert-Butyl N-{3-[4-(1-isoquinolylmethyl)phenyl]-2-propynyl}-carbamate

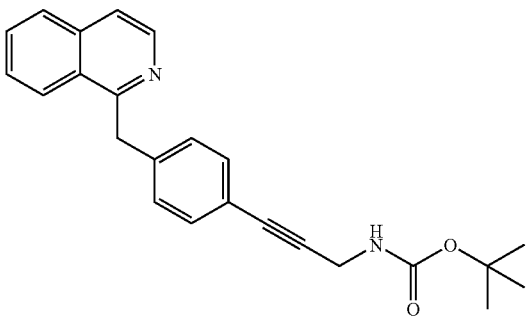

The title compound was obtained by treating the compound of Example B41 and the compound of Example B66 in the same manner as in Example B42.

$^1$H-NMR (CDCl$_3$) δ(ppm): 1.45 (9H, s), 4.06-4.13 (2H, m), 4.66 (2H, s), 7.19 (2H, d), 7.20-7.28 (1H, m), 7.29 (2H, d), 7.52 (1H, dd), 7.57 (1H, d), 7.65 (1H, dd), 7.82 (1H, d), 8.08 (1H, d), 8.49 (1H, d).

EXAMPLE B68 tert-Butyl N-{3-[4-(1-isoquinolylmethyl)phenyl]propyl}carbamate

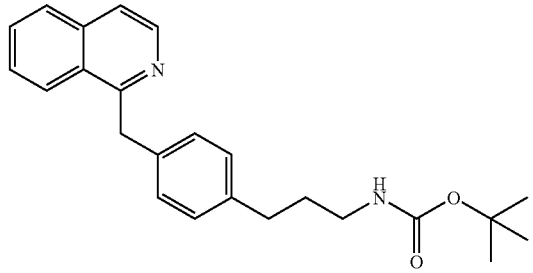

The title compound was obtained by treating the compound of Example B67 in the same manner as in Example B43.

$^1$H-NMR (CDCl$_3$) δ(ppm): 1.43 (9H, s), 1.70-1.81 (2H, m), 2.54-2.60 (2H, m), 3.01-3.20 (2H, m), 4.47-4.57 (1H, m), 4.65 (2H, s), 7.07 (2H, d), 7.21 (2H, d), 7.55 (1H, dd), 7.57 (1H, d), 7.65 (1H, dd), 7.83 (1H, d), 8.18 (1H, d), 8.51 (1H, d).

EXAMPLE B69

3-[4-(1-Isoquinolylmethyl)phenyl]-2-propyn-1-amine

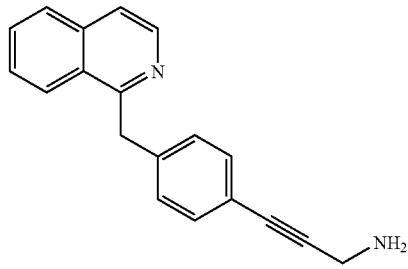

Trifluoroacetic acid (0.3 ml) was added to an ice-cooled solution of the compound of Example B67 (4 mg) in methylene chloride (0.6 ml), and the reaction mixture was stirred at that temperature for 1 hour. After a saturated aqueous sodium hydrogencarbonate solution was added, the reaction mixture was extracted with ethyl acetate, dried over anhydrous magnesium sulfate, and then concentrated under reduced pressure. The residue was purified by silica gel column chromatography to give the title compound (4 mg).

$^1$H-NMR (CDCl$_3$) δ(ppm): 3.60-3.68 (2H, m), 4.66 (2H, s), 7.19 (2H, d), 7.29 (2H, d), 7.53 (1H, dd), 7.56 (1H, d), 7.63 (1H, dd), 7.82 (1H, d), 8.10 (1H, d), 8.49 (1H, d).

The amine proton was not observed in the NMR spectrum.

EXAMPLE B70

3-[4-(1-Isoquinolylmethyl)phenyl]-1-propanamine

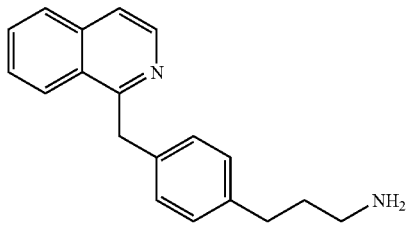

The title compound was obtained by treating the compound of Example B68 in the same manner as in Example B69.

$^1$H-NMR (CDCl$_3$) δ(ppm): 1.20-1.30 (2H, m), 1.78-1.88 (2H, m), 2.45-2.52 (2H, m), 2.73-2.81 (2H, m), 4.55 (2H, s), 6.94 (2H, d), 7.08 (2H, d), 7.50 (1H, dd), 7.51 (1H, d), 7.61 (1H, dd), 7.76 (1H, d), 8.10 (1H, d), 8.38 (1H, d).

EXAMPLE B71

N-methyl-N-(2-propynyl)acetamide

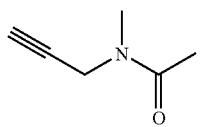

The title compound was obtained by treating N-methyl-N-(2-propynyl)amine in the same manner as in Example B59.

$^1$H-NMR (CDCl$_3$) δ(ppm): 2.11 (2.1H, s), 2.17 (0.9H, s), 2.21 (0.7H, t), 2.31 (0.3H, t), 3.00 (0.9H, s), 3.08 (2.1H, s), 4.04 (0.6H, d), 4.23 (1.4H, d).

The obtained compound contained a 7:3 mixture of geometrical isomers of the amide.

EXAMPLE B72

N-{3-[4-(1-isoquinolylmethyl)phenyl]-2-propynyl}-N-methyl-acetamide

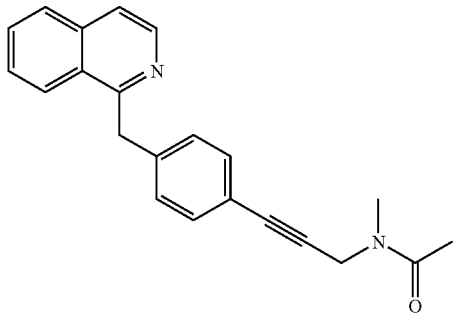

The title compound was obtained by treating the compound of Example B41 and the compound of Example B71 in the same manner as in Example B42.

$^1$H-NMR (CDCl$_3$) δ(ppm): 2.10 (1.8H, s), 2.11 (1.2H, s), 3.01 (1.2H, s), 3.10 (1.8H, s), 4.21 (1.2H, s), 4.41 (0.8H, s), 4.67 (2H, s), 7.18-7.23 (2H, m), 7.29-7.32 (2H, m), 7.53 (1H, dd), 7.58 (1H, d), 7.65 (1H, dd), 7.82 (1H, d), 8.09 (1H, d), 8.49 (1H, d).

The obtained compound contained a 3:2 mixture of geometrical isomers of the amide.

EXAMPLE B73

N-{3-[4-(1-isoquinolylmethyl)phenyl]propyl}-N1-ethylacetamide

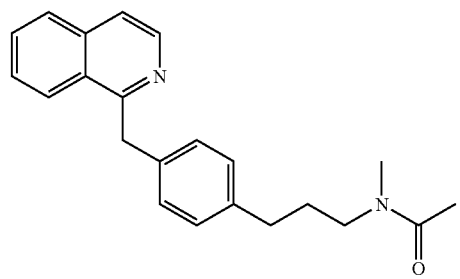

The title compound was obtained by treating the compound of Example B72 in the same manner as in Example B43.

$^1$H-NMR (CDCl$_3$) δ(ppm): 1.70-1.90 (2H, m), 1.89 (1.5H, s), 2.03 (1.5H, s), 2.50-2.59 (2H, m), 2.88 (1.5H, s), 2.91 (1.5H, s), 3.20-3.25 (1H, m), 3.36-3.40 (1H, m), 4.66 (2H, s), 7.03-7.10 (2H, m), 7.18-7.30 (2H, m), 7.53 (1H, dd), 7.58 (1H, d), 7.66 (1H, dd), 7.82 (1H, d), 8.17 (1H, d), 8.50 (1H, d).

The obtained compounds contained a 1:1 mixture of geometrical isomers of the amide.

EXAMPLE B74

N-methyl-N-(2-propynyl)methanesulfonamide

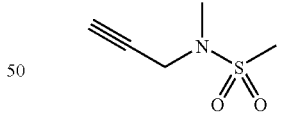

Triethylamine (6.55 ml) was added to an ice-cooled solution of N-methyl-N-(2-propynyl)amine (2603 mg) in methylene chloride (25 ml). Methanesulfonyl chloride (3.50 ml) was further added dropwise, the reaction mixture was stirred at that temperature for 1 hour, and then stirred further at room temperature for 2 hours. After ice was added, the reaction mixture was extracted with ethyl acetate, washed successively with 1 N hydrochloric acid, a saturated aqueous sodium hydrogencarbonate solution, and saturated brine, dried over anhydrous magnesium sulfate, and then filtered through silica gel. The filtrate was concentrated under reduced pressure to give the title compound (4522 mg). The obtained compound was used in the following reaction without further purification.

¹H-NMR (CDCl₃) δ(ppm): 2.41 (1H, t), 2.93 (3H, s), 2.96 (3H, s), 4.09 (2H, d).

EXAMPLE B75

N-{3-[4-(1-isoquinolylmethyl)phenyl]-2-propynyl}-N-methyl methanesulfonamide

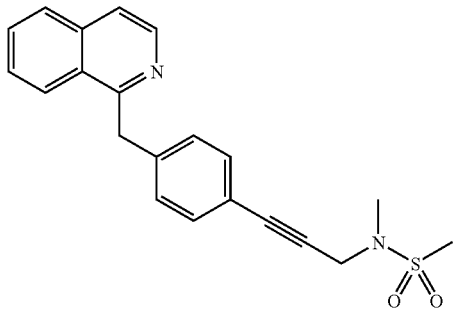

The title compound was obtained by treating the compound of Example B41 and the compound of Example B74 in the same manner as in Example B42.

¹H-NMR (CDCl₃) δ(ppm): 2.95 (3H, s), 2.97 (3H, s), 4.26 (2H, s), 4.68 (2H, s), 7.24 (2H, d), 7.31 (2H, d), 7.55 (1H, dd), 7.59 (1H, d), 7.66 (1H, dd), 7.83 (1H, d), 8.10 (1H, d), 8.49 (1H, d).

EXAMPLE B76

N-{3-[4-(1-isoquinolylmethyl)phenyl]propyl}-N-methyl methane-sulfonamide

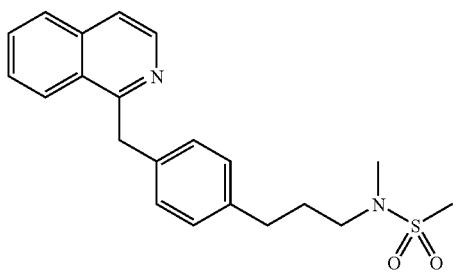

Treating the compound of Example B75 in the same manner as in Example B43, the obtained residue was separated and purified by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)] to give the title compound.

MS m/z(ESI:MH⁺):369.2

EXAMPLE B77

5-[4-(1-Isoquinolylmethyl)phenyl]-4-pentyn-2-ol

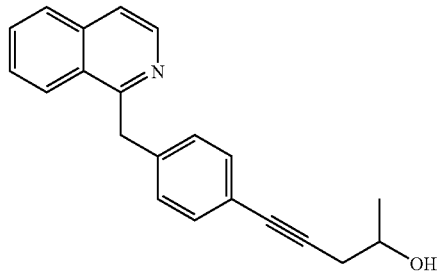

The title compound was obtained by treating the compound of Example B41 and 4-pentyn-2-ol in the same manner as in Example B42.

¹H-NMR (CDCl₃) δ(ppm): 1.27 (3H, t), 2.38-2.62 (2H, m), 3.95-4.03 (1H, m), 4.65 (2H, s), 7.19 (2H, d), 7.29 (2H, d), 7.52 (1H, dd), 7.57 (1H, d), 7.64 (1H, dd), 7.81 (1H, d), 8.08 (1H, d), 8.48 (1H, d).

The proton of the hydroxyl group was not observed in the NMR spectrum.

EXAMPLE B78

5-[4-(1-Isoquinolylmethyl)phenyl]-2-pentanol

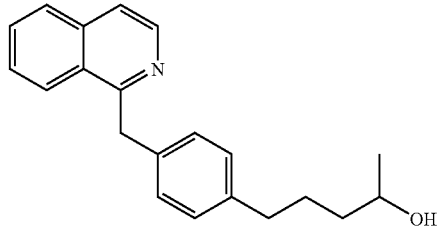

Treating the compound of Example B77 in the same manner as in Example B43, the obtained residue was separated and purified by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)] to give the title compound.

MS m/z(ESI:MH⁺):306.2

EXAMPLE B79

3-Butylphenol

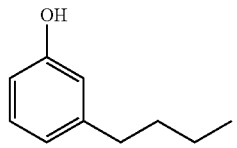

The title compound was obtained by treating 1-butyl-3-methoxybenzene in the same manner as in Example B40.

¹H-NMR (CDCl₃) δ(ppm): 0.94 (3H, t), 1.30-1.55 (2H, m), 1.55-1.62 (2H, m), 2.56 (2H, t), 4.76 (1H, brs), 6.63 (1H, dd), 6.66 (1H, d), 6.75 (1H, d), 7.12 (1H, dd).

EXAMPLE B80

1-Butyl-3-(methoxymethoxy)benzene

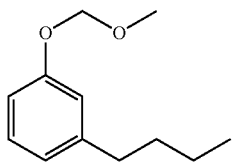

A 60% suspension of sodium hydride dispersed in mineral oil (102 mg) was added to an ice-cooled solution of the compound of Example B79 (318 mg) in dimethylformamide (5 ml), and the reaction mixture was stirred at room temperature for 30 minutes. The mixture was cooled again on ice, chloromethyl methyl ether (0.18 ml) was added, and this reaction mixture was stirred at room temperature for 12 hours. After water was added, the reaction mixture was extracted with ethyl acetate, washed with a saturated aqueous sodium hydrogencarbonate solution and saturated brine, dried over anhydrous magnesium sulfate, and then filtered through silica gel. The filtrate was concentrated under reduced pressure to give the title compound (341 mg). The obtained compound was used in the following reaction without further purification.

¹H-NMR (CDCl₃) δ(ppm): 0.94 (3H, t), 1.30-1.42 (2H, m), 1.55-2.04 (2H, m), 2.58 (2H, t), 3.49 (3H, s), 5.17 (2H, s), 6.80-6.87 (3H, m), 7.18 (1H, dd).

EXAMPLE B81

4-Butyl-2-(methoxymethoxy)benzaldehyde

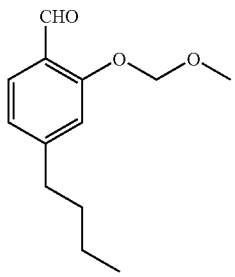

A solution of t-butyl lithium in pentane (1.51 M, 10.6 ml) was added dropwise to a solution of the compound of Example B80 (2396 mg) in petroleum ether cooled to −20° C., and this reaction mixture was stirred at a temperature in the range of −10° C. to 0° C. for 1.5 hours. The reaction mixture was cooled to −70° C., anhydrous ether (17 ml) and dimethylformamide (1.91 ml) were added, and the resulting mixture was stirred at that temperature for 3 hours, then stirred for another 1 hour at room temperature. The reaction mixture was cooled on ice, a saturated aqueous ammonium chloride solution was added, and the mixture was extracted with ethyl acetate. The extract was washed with saturated brine, dried over anhydrous magnesium sulfate, and then concentrated under reduced pressure. The residue was purified by silica gel column chromatography to give the title compound (1821 mg).

¹H-NMR (CDCl₃) δ(ppm): 0.94 (3H, t), 1.32-1.42 (2H, m), 1.57-1.65 (2H, m), 2.64 (2H, t), 3.54 (3H, s), 5.29 (2H, s), 6.91 (1H, d), 7.01 (1H, s), 7.76 (1H, d), 10.44 (1H, s).

EXAMPLE B82

[4-Butyl-2-(methoxymethoxy)phenyl](1-isoquinolyl)methanol

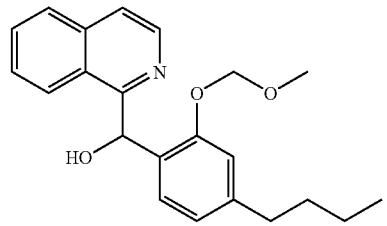

An aqueous sodium hydroxide solution (50%, 1.4 ml) was added to a solution of 1-cyano-benzoyl-1,2-dihydroisoquinoline (815 mg), which was synthesized according to Org. Synth., IV, 155 (1988), the compound of Example B81 (869 mg), and triethylbenzylammonium chloride (7 mg) in methylene chloride (1.6 ml), and the reaction mixture was subjected to ultrasonication in a water bath for 10 minutes. After methylene chloride (8.3 ml) and ethanol (4.4 ml) were added, the reaction mixture was further subjected to ultrasonication in a water bath for 85 minutes. Water was added and the resulting reaction mixture was extracted with methylene chloride. The extract was dried over anhydrous magnesium sulfate, then concentrated under reduced pressure. The residue was purified by silica gel column chromatography to give the title compound (1144 mg).

¹H-NMR (DMSO-d6) δ(ppm): 0.86 (3H, t), 1.22-1.31 (2H, m), 1.44-1.52 (2H, m), 2.44-2.51 (2H, m), 3.16 (3H, s), 5.10 (1H, d), 5.12 (1H, d), 6.72 (1H, s), 6.75 (1H, d), 6.84 (1H, s), 7.21 (1H, d), 7.61 (1H, dd), 7.72 (1H, dd), 7.74 (1H, d), 7.95 (1H, d), 8.31 (1H, d), 8.42 (1H, d).

The proton of the hydroxyl group was not observed in the NMR spectrum.

EXAMPLE B83

[4-Butyl-2-(methoxymethoxy)phenyl](1-isoquinolyl)methyl acetate

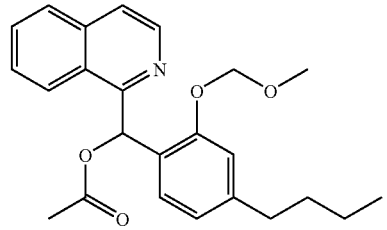

The title compound was obtained by treating the compound of Example B82 in the same manner as in Example B38.

¹H-NMR (CDCl₃) δ(ppm): 0.90 (3H, t), 1.28-1.40 (2H, m), 1.50-1.60 (2H, m), 2.22 (3H, s), 2.54 (2H, t), 3.41 (3H, s), 5.22 (1H, d), 5.26 (1H, d), 6.77 (1H, d), 6.94 (1H, s), 7.29 (1H, d), 7.55 (1H, dd), 7.58 (1H, d), 7.70 (1H, dd), 7.81 (1H, d), 8.05 (1H, s), 8.35 (1H, d), 8.55 (1H, d).

EXAMPLE B84

1-[4-Butyl-2-(methoxymethoxy)benzyl]isoquinoline

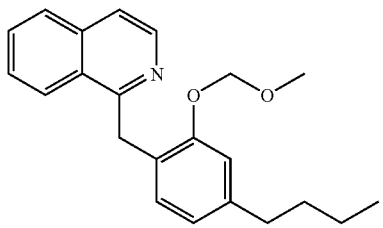

The title compound was obtained by treating the compound of Example B83 in the same manner as in Example B39.

¹H-NMR (CDCl₃) δ(ppm): 0.89 (3H, t), 1.28-1.37 (2H, m), 1.50-1.58 (2H, m), 2.53 (2H, t), 3.46 (3H, s), 4.65 (2H, s), 5.24 (2H, s), 6.66 (1H, dd), 6.89 (1H, d), 6.92 (1H, d), 7.51 (1H, dd), 7.53 (1H, d), 7.62 (1H, dd), 7.79 (1H, d), 8.23 (1H, d), 8.47 (1H, d).

EXAMPLE B85

5-Butyl-2-(1-isoquinolylmethyl)phenol

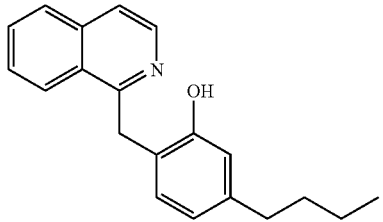

5 N hydrochloric acid (1.0 ml) was added to a solution of the compound of Example B84 (88 mg) in methanol (1.5 ml), and this reaction mixture was stirred at room temperature for 14 hours. The reaction mixture was neutralized with a 5 N aqueous sodium hydroxide solution, adjusted to pH 6.8 with phosphate buffer, and extracted with ethyl acetate. The extract was dried over anhydrous magnesium sulfate and concentrated under reduced pressure to give the title compound (44 mg).

¹H-NMR (CDCl₃) δ(ppm): 0.89 (3H, t), 1.23-1.37 (2H, m), 1.48-1.60 (2H, m), 2.51 (2H, t), 4.56 (2H, s), 6.65 (1H, dd), 6.82 (1H, d), 7.21 (1H, d), 7.55 (1H, d), 7.68 (1H, dd), 7.72 (1H, dd), 7.82 (1H, d), 8.35 (1H, d), 8.44 (1H, d).

The proton of the hydroxyl group was not observed in the NMR spectrum.

EXAMPLE B86

N-{3-[4-(1-isoquinolylmethyl)phenyl]-2-propynyl}-N,N-dimethyl-amine

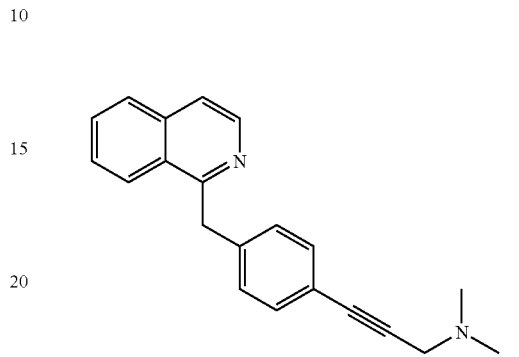

The title compound was obtained by treating the compound of Example B41 and 1-dimethylamino-2-propyne in the same manner as in Example B42.

¹H-NMR (CDCl₃) δ(ppm): 2.04 (3H, s), 2.34 (3H, s), 3.47 (2H, s), 4.66 (2H, s), 7.20 (2H, d), 7.32 (2H, d), 7.53 (1H, dd), 7.56 (1H, d), 7.65 (1H, dd), 7.82 (1H, d), 8.10 (1H, d), 8.50 (1H, d).

EXAMPLE B87

1-{4-[3-(Tetrahydro-2H-2-pyranyloxy)-1-propynyl]benzyl}iso-quinoline

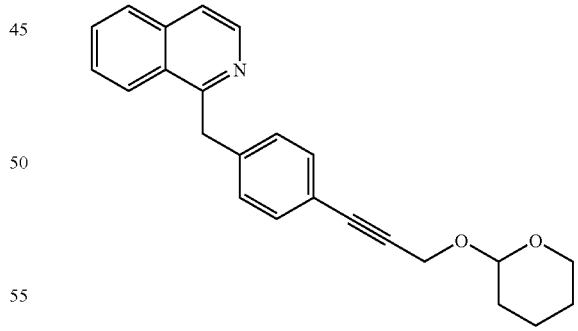

The title compound was obtained by treating the compound of Example B41 and tetrahydro-2-(2-propynyloxy)-2H-pyran in the same manner as in Example B42.

¹H-NMR (CDCl₃) δ(ppm): 1.45-1.85 (6H, m), 3.50-3.60 (1H, m), 3.84-3.90 (1H, m), 4.42 (1H, d), 4.48 (1H, d), 4.66 (2H, 8), 4.87 (1H, dd), 7.15-7.21 (2H, m), 7.33-7.36 (2H, m), 7.50-7.70 (3H, m), 7.81-7.86 (1H, m), 8.07-8.10 (1H, m), 8.48-8.51 (1H, m).

EXAMPLE B88

3-[4-(1-Isoquinolylmethyl)phenyl]-2-propyn-1-ol

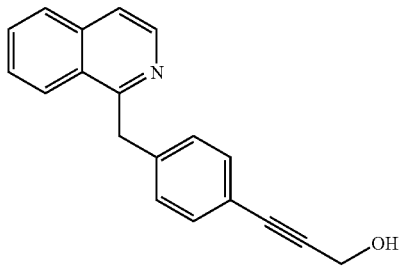

The title compound was obtained by treating the compound of Example B87 in the same manner as in Example B47.

¹H-NMR (CDCl₃) δ(ppm): 1.20-1.30 (1H, m), 4.46 (2H, s), 4.67 (2H, s), 7.23 (2H, d), 7.31 (2H, d), 7.53 (1H, dd), 7.58 (1H, d), 7.65 (1H, dd), 7.83 (1H, d), 8.09 (1H, d), 8.49 (1H, d).

EXAMPLE B89

N,N-dimethyl-4-pentanamide

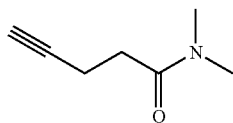

Dimethylamine (2 M solution in tetrahydrofuran, 8.53 ml), triethylamine (2.59 ml), and 1-(3-dimethylaminopropyl)-3-ethylcarbodiimide (3221 mg), were added to a solution of 4-pentatonic acid (552 mg) in methylene chloride (150 ml) and this reaction mixture was stirred at room temperature for 24 hours. The reaction mixture was washed successively with 1 N hydrochloric acid, a saturated aqueous sodium hydrogencarbonate solution, water, and saturated brine, dried over anhydrous magnesium sulfate, then concentrated under reduced pressure to give the title compound (129 mg). The obtained compound was used in the following reaction without further purification.

¹H-NMR (CDCl₃) δ(ppm): 1.96-1.99 (1H, m), 2.50-2.60 (4H, m), 2.96 (3H, s), 3.02 (3H, s).

EXAMPLE B90

N,N-dimethyl-5-[4-(1-isoquinolylmethyl)phenyl]-4-pentanamide

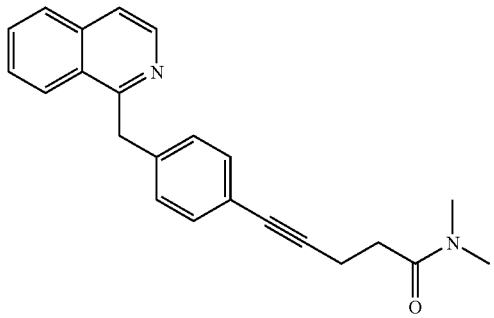

The title compound was obtained by treating the compound of Example B41 and the compound of Example B89 in the same manner as in Example B42.

¹H-NMR (CDCl₃) δ(ppm): 2.59-2.64 (2H, m), 2.71-2.75 (2H, m), 2.96 (3H, s), 3.03 (3H, s), 4.66 (2H, s), 7.18 (2H, d), 7.28 (2H, d), 7.43-7.70 (3H, m), 7.90 (1H, d), 8.09 (1H, d), 8.50 (1H, d).

EXAMPLE B91

1-Methyl-2-propynyltetrahydro-2H-2-pyranyl ether

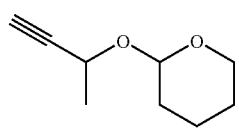

3,4-Dihydro-2H-pyran (7.15 ml) and pyridinium p-toluenesulfonate (2187 mg) were added to a solution of 3-butyn-2-ol (3051 mg) in dichloromethane (150 ml), and this reaction mixture was stirred at room temperature for 29 hours.

The reaction mixture was washed successively with a saturated aqueous sodium hydrogencarbonate solution, water, and saturated brine, dried over anhydrous magnesium sulfate, and then concentrated under reduced pressure. The residue was purified by silica gel column chromatography to give the title compound (4698 mg).

¹H-NMR (CDCl₃) δ(ppm): 1.45 (1.05H, d), 1.48 (1.95H, d), 1.50-1.90 (6H, m), 2.37 (0.65H, d), 2.43 (0.35H, d), 3.50-3.60 (1.3H, m), 3.80-3.86 (0.7H, m), 4.4-3-4.50 (0.35H, m), 4.52-4.60 (0.65H, m), 4.77 (0.35H, t), 4.94 (0.65H, t).

EXAMPLE B92

1-{4-[3-(Tetrahydro-2H-2-pyranyloxy)-1-butynyl]benzyl}iso-quinoline

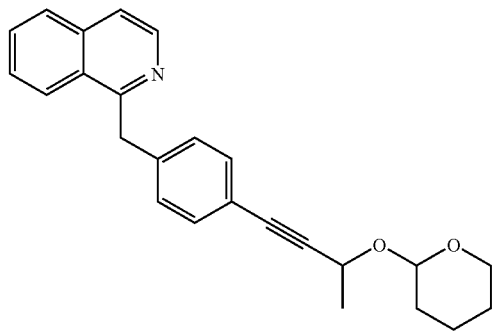

The title compound was obtained by treating the compound of Example B41 and the compound of Example B91 in the same manner as in Example B42.

¹H-NMR (CDCl₃) δ(ppm): 1.40-1.80 (6H, m), 1.49 (1.05H, d), 1.52 (1.95H, d), 3.49-3.60 (1H, m), 3.80-3.88 (0.65H, m), 3.99-4.06 (0.35H, m), 4.65 (2H, s), 4.74 (1H, q), 4.83 (0.35H, t), 4.97 (0.65H, t), 7.18-7.22 (2H, m), 7.32 (2H, d), 7.54 (1H, dd), 7.57 (1H, d), 7.64 (1H, dd), 7.82 (1H, d), 8.08 (1H, d), 8.49 (1H, d).

EXAMPLE B93

4-[4-(1-Isoquinolylmethyl)phenyl]-3-butyn-2-ol

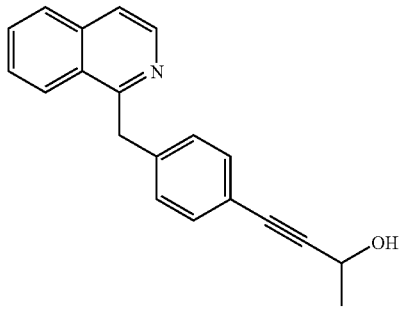

The title compound was obtained by treating the compound of Example B92 in the same manner as in Example B47.

$^1$H-NMR (CDCl$_3$) δ(ppm): 1.53 (3H, d), 2.15 (1H, brs), 4.68 (2H, s), 4.72 (1H, q), 7.21 (2H, d), 7.31 (2H, d), 7.54 (1H, dd), 7.59 (1H, d), 7.66 (1H, dd), 7.84 (1H, d), 8.10 (1H, d), 8.51 (1H, d).

EXAMPLE B94

4-[4-(1-Isoquinolylmethyl)phenyl]-2-butanol

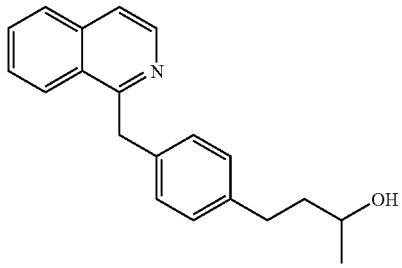

Treating the compound of Example B93 in the same manner as in Example B43, the obtained residue was separated and purified by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ$_x$ 50 mm (long)] to give the title compound.

MS m/z(ESI:MH$^+$):292.2

EXAMPLE B95

2-Methyl-4-pentyn-2-ol

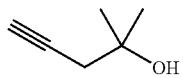

Lithium acetylide-ethylenediamine complex was added gradually to a mixed solution of isobutylene oxide (1889 mg) in tetrahydrofuran (13 ml) and dimethyl sulfoxide (20 ml) cooled to 0° C., and this reaction mixture was stirred at 0° C. for 5 hours. After water was added, the reaction mixture was extracted with ethyl acetate, washed with saturated brine, dried over anhydrous magnesium sulfate, and then filtered through silica gel. The filtrate was concentrated under reduced pressure to give the title compound (3316 mg). This was used in the following reaction without further purification.

$^1$H-NMR (CDCl$_3$) δ(ppm): 1.33 (6H, s), 2.09 (1H, t), 2.38 (2H, t).

The proton of the hydroxyl group was not observed in the NMR spectrum.

EXAMPLE B96

5-[4-(1-Isoquinolylmethyl)phenyl]-2-methyl-4-pentyn-2-ol

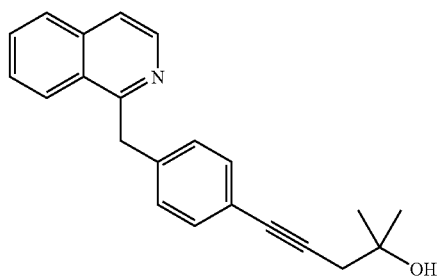

The title compound was obtained by treating the compound of Example B41 and the compound of Example B95 in the same manner as in Example B42.

$^1$H-NMR (DMSO-d6) δ(ppm): 1.18 (6H, s), 2.28 (1H, s), 2.42 (2H, s), 4.62 (2H, s), 7.10-7.30 (4H, m), 7.62 (1H, dd), 7.71 (1H, d), 7.72 (1H, dd), 7.94 (1H, d), 8.27 (1H, d), 8.42 (1H, d).

EXAMPLE B97

5-[4-(1-Isoquinolylmethyl)phenyl]-2-methyl-2-pentanol

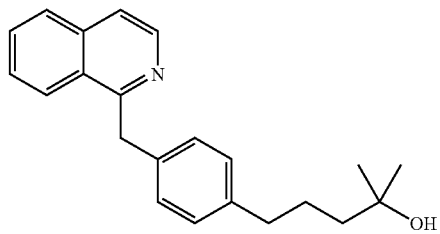

Treating the compound of Example B96 in the same manner as in Example B43, the obtained residue was separated and purified by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)] to give the title compound.

MS m/z(ESI:MH$^+$):320.2

EXAMPLE B98

4-Benzyloxy-2-(methoxymethoxy)benzaldehyde

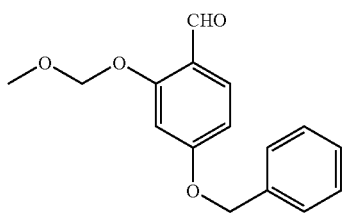

N,N-diisopropylethylamine (1.98 ml) and chloromethyl methyl ether (0.76 ml) were added to a solution of 4-benzyloxy-2-hydroxybenzaldehyde (2071 mg) in tetrahydrofuran (30 ml), and this reaction mixture was stirred and heated under reflux for 19 hours. N,N-diisopropylethylamine (2.7 ml) and chloromethyl methyl ether (1.04 ml) were further added, and the resulting mixture was stirred and heated under reflux for another 10 hours. After water was added, the reaction mixture was extracted with ethyl acetate, washed with a saturated aqueous ammonium chloride solution and saturated brine, dried over anhydrous magnesium sulfate, then filtered through silica gel and alumina. The filtrate was concentrated under reduced pressure to give the title compound (2470 mg). This compound was used in the following reaction without further purification.

$^1$H-NMR (CDCl$_3$) δ(ppm): 3.52 (3H, s), 5.12 (2H, s), 5.27 (2H, s), 6.68 (1H, dd), 6.80 (1H, d), 7.33-7.45 (5H, m), 7.82 (1H, d), 10.33 (1H, s).

EXAMPLE B99

[4-(Benzyloxy)-2-(methoxymethoxy)phenyl](1-isoquinolyl)methanol

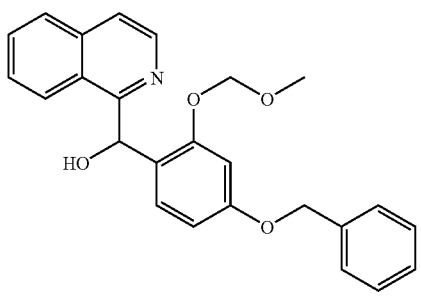

The title compound was obtained by treating the compound of Example B98 in the same manner as in Example B82.

$^1$H-NMR (DMSO-d6) δ(ppm): 3.16 (3H, s), 5.01 (2H, s), 5.11 (1H, d), 5.14 (1H, d), 6.59 (1H, dd), 6.66-6.70 (2H, m), 7.18 (1H, d), 7.31 (1H, d), 7.34-7.42 (4H, m), 7.61 (1H, dd), 7.71 (1H, d), 7.75 (1H, d), 7.95 (1H, d), 8.28 (1H, d), 8.43 (1H, d).

The proton of the hydroxyl group was not observed in the NMR spectrum.

EXAMPLE B100

[4-(Benzyloxy)-2-(methoxymethoxy)phenyl](1-isoquinolyl)methyl acetate

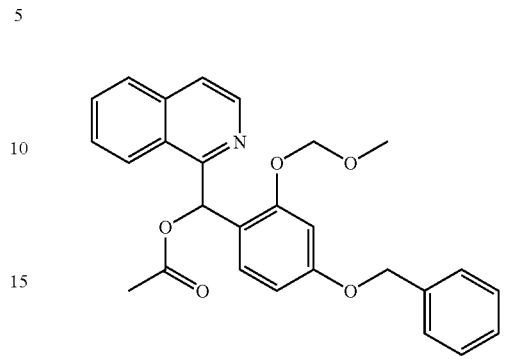

The title compound was obtained by treating the compound of Example B99 in the same manner as in Example B38.

$^1$H-NMR (CDCl$_3$) δ(ppm): 2.21 (3H, s), 3.42 (3H, s), 4.98 (1H, d), 5.00 (1H, d), 5.21-5.27 (2H, m), 6.54 (1H, dd), 6.81 (1H, d), 7.25 (1H, d), 7.30-7.41 (5H, m), 7.53 (1H, dd), 7.57 (1H, d), 7.63 (1H, dd), 7.80 (1H, d), 8.00 (1H, s), 8.29 (1H, d), 8.55 (1H, d).

EXAMPLE B101

4-(1-Isoquinolylmethyl)-3-(methoxymethoxy)phenol

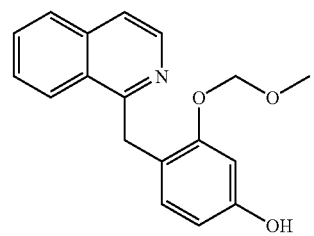

The title compound was obtained by treating the compound of Example B100 in the same manner as in Example B39.

$^1$H-NMR (DMSO-d6) δ(ppm): 3.36 (3H, s), 4.44 (2H, s), 5.17 (2H, s), 6.22 (1H, d), 6.52 (1H, s), 6.67 (1H, d), 7.57-7.76 (3H, m), 7.92 (1H, d), 8.22 (1H, d), 8.37 (1H, d), 9.24 (1H, brs).

EXAMPLE B102

4-(1-Isoquinolylmethyl)-3-(methoxymethoxy)phenyl trifluoro-methanesulfonate

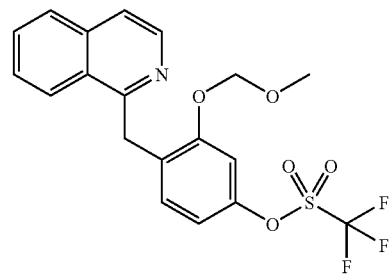

The title compound was obtained by treating the compound of Example B101 in the same manner as in Example B41.

$^1$H-NMR (CDCl$_3$) δ(ppm): 3.43 (3H, s), 4.65 (2H, s), 5.24 (2H, s), 6.77 (1H, dd), 7.04 (1H, d), 7.07 (1H, d), 7.54-7.61 (2H, m), 7.67 (1H, dd), 7.84 (1H, d), 8.16 (1H, d), 8.47 (1H, d).

EXAMPLE B103

1-{2-(Methoxymethoxy)-[4-(tetrahydro-2H-2-pyranyloxy)-1-butynyl]benzyl} isoquinoline

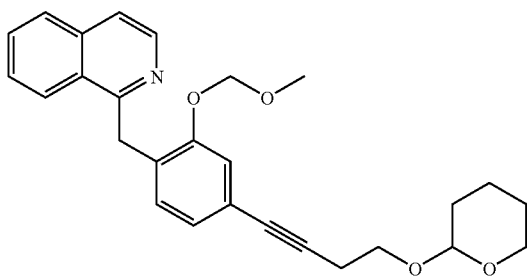

The title compound was obtained by treating the compound of Example B102 and 2-(3-butynyloxy)tetrahydro-2H-pyran in the same manner as in Example B42.

$^1$H-NMR (CDCl$_3$) δ(ppm): 1.51-1.90 (6H, m), 2.68 (2H, t), 3.50 (3H, s), 3.49-3.55 (1H, m), 3.58-3.65 (1H, m), 3.84-3.94 (2H, m), 4.63-4.68 (1H, m), 4.65 (2H, s), 5.23 (2H, s), 6.76 (1H, dd), 7.04 (1H, d), 7.07 (1H, d), 7.49-7.69 (3H, m), 7.81 (1H, d), 8.14 (1H, d), 8.47 (1H, d).

EXAMPLE B104

5-(4-Hydroxy-1-butynyl)-2-(1-isoquinolylmethyl)phenol

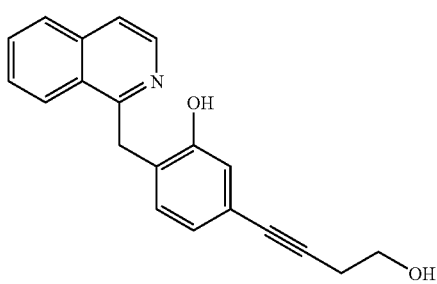

The title compound was obtained by treating the compound of Example B103 in the same manner as in Example B85.

$^1$H-NMR (CDCl$_3$) δ(ppm): 1.80 (1H, brs), 2.66 (2H, t), 3.73-3.82 (2H, m), 4.58 (2H, s), 6.87 (1H, d), 7.04 (1H, s), 7.23 (1H, d), 7.60 (1H, d), 7.69-7.78 (2H, m), 7.86 (1H, d), 8.37 (1H, d), 8.42 (1H, d).

The proton of the phenolic hydroxyl group was not observed in the NMR spectrum.

EXAMPLE B105

1-(t-Butyl)-1,1-dimethylsilyl {4-[4-(1-isoquinolylmethyl)-phenyl]-2-methyl-3-butynyl}ether

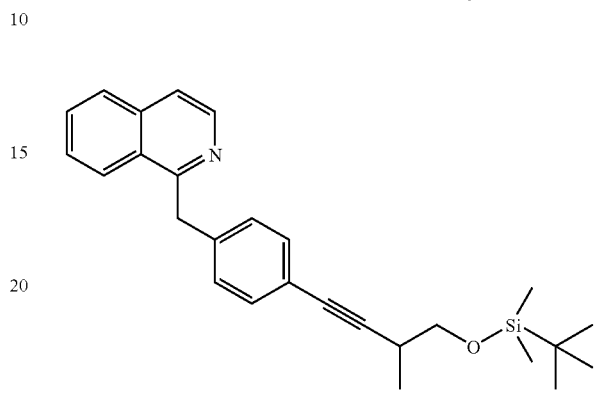

Triphenylphosphine (18.37 g) was added to an ice-cooled solution of carbon tetrabromide (11.19 g) in methylene chloride (60 ml), and this reaction mixture was stirred at that temperature for 1 hour. A solution of 3-{[1-(t-butyl)-1,1-dimethylsilyl]oxy}-2-methylpropanal, which was synthesized according to Tetrahedron Lett., 4347 (1979), in methylene chloride (14 ml) was added dropwise, and the resulting reaction mixture was further stirred for 1 hour. The reaction mixture was diluted with methylene chloride, washed successively with saturated aqueous sodium hydrogencarbonate solution, saturated an aqueous ammonium chloride solution and saturated brine, dried over magnesium sulfate, and then concentrated under reduced pressure. Ether was added to this residue, insoluble material was separated by filtration, and the filtrate was concentrated under reduced pressure. The residue was purified by silica gel column chromatography to give t-butyl[(4,4-dibromo-2-methyl-3-butenyl)oxy]-dimethylsilane (2385 mg).

Next, a 2.47 M n-butyl lithium solution in hexane (3.15 ml) was added dropwise to a solution of t-butyl[(4,4-dibromo-2-methyl-3-butenyl)oxy]dimethylsilane (1326 mg) in tetrahydrofuran (10 ml) cooled to −70° C., and this mixture was stirred at that temperature for 1 hour. A saturated aqueous ammonium chloride solution was further added, and the resulting mixture was warmed to room temperature. After water was added, the reaction mixture was extracted with ether. The ether layer was washed with saturated brine, dried over anhydrous magnesium sulfate, then filtered through silica gel. The filtrate was concentrated under reduced pressure. The obtained residue and the compound of Example B41 were treated in the same manner as in Example B42 to obtain the title compound.

$^1$H-NMR (CDCl$_3$) δ(ppm): 0.07 (6H, s), 0.90 (9H, s), 1.18 (3H, d), 2.70-2.80 (1H, m), 3.47 (1H, dd), 3.70 (1H, dd), 4.65 (2H, s), 7.16 (2H, d), 7.27 (2H, d), 7.51 (1H, dd), 7.56 (1H, d), 7.64 (1H, dd), 7.81 (1H, d), 8.07 (1H, d), 8.49 (1H, d).

EXAMPLE B106

4-[4-(1-Isoquinolylmethyl)phenyl]-2-methyl-3-butyn-1-ol

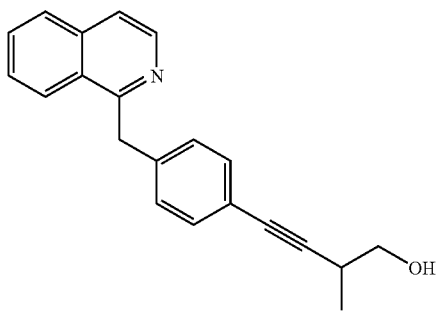

The title compound was obtained by treating the compound of Example B105 in the same manner as in Example B47.

$^1$H-NMR(DMSO-d6)δ(ppm): 1.11(3H, d), 2.60-2.70(1H, m), 3.28(1H, d), 3.44(1H, d), 4.58(2H, s), 4.85-4.90(1H, m), 7.23(4H, s), 7.61(1H, dd), 7.70(1H, d), 7.71(1H, dd), 7.93(1H, d), 8.25(1H, d), 8.42(1H, d).

EXAMPLE B107

1-{[1-(t-Butyl)-1,1-dimethylsilyl]oxy}-3-butyn-2-ol

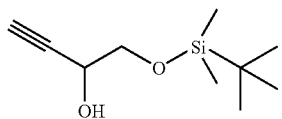

Ethynyl magnesium bromide in tetrahydrofuran (0.5 M, 90 ml) was added to anhydrous tetrahydrofuran (20 ml) cooled to −78° C. under nitrogen atmosphere. A solution of t-butyldimethylsiloxyacetaldehyde (6000 mg) in tetrahydrofuran (30 ml) was added dropwise, and the resulting mixture was stirred at −78° C. for 45 minutes, warmed to room temperature, stirred for 1 hour 40 minutes, then cooled on ice. After a saturated aqueous ammonium chloride solution was added, the reaction mixture was extracted with ether, washed with water and saturated brine, dried over anhydrous magnesium sulfate, and then filtered through silica gel. The filtrate was concentrated under reduced pressure to give the title compound (8.55 g). This compound was used in the following reaction without further purification.

$^1$H-NMR(CDCl$_3$)δ(ppm): 0.08(6H, s), 0.91(9H, s), 2.43(1H, d), 2.60-2.66(1H, m), 3.65-3.70(1H, m), 3.73-3.81(1H, m), 4.38-4.42(1H, m).

EXAMPLE B108

1-{[1-(t-Butyl)-1,1-dimethylsilyl]oxy}methyl)-2-propynyl acetate

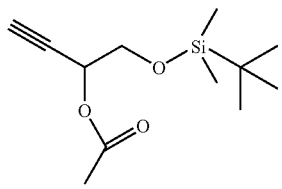

The title compound was obtained by treating the compound of Example B107 in the same manner as in Example B38.

$^1$H-NMR(CDCl$_3$)δ(ppm): 0.08(6H, s), 0.90(9H, s), 2.11(3H, s), 2.44(1H, d), 3.80-3.88(2H, m), 5.41-5.55(1H, m).

EXAMPLE B109

4-[4-(1-Isoquinolylmethyl)phenyl]-3-butyn-1,2-diol

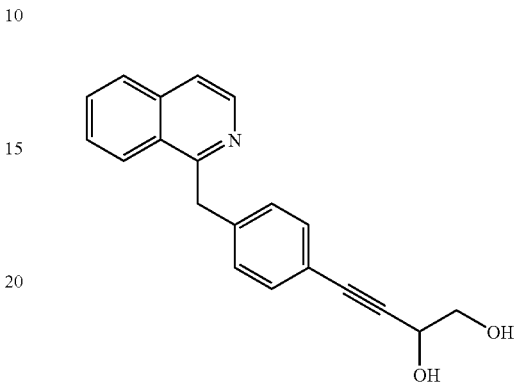

The compound of Example B41 and the compound of Example B108 were treated in the same manner as in Example B42 to give the coupling product. The title compound was obtained by deprotecting the hydroxyl protecting group of the coupling product in the same manner as in Example B47.

$^1$H-NMR(DMSO-d6)δ(ppm): 3.40-3.45(1H, m), 3.70-3.82(1H, m), 4.30-4.35(1H, m), 4.63(2H, s), 4.90(1H, t), 5.46(1H, d), 7.25-7.30(4H, m), 7.62(1H, dd), 7.71(1H, d), 7.73(1H, dd), 7.94(1H, d), 8.28(1H, d), 8.43(1H, d).

EXAMPLE B110

1-{4-[2-(2,2-Dimethyl-1,3-dioxolan-4-yl)-1-ethynyl]benzyl}-isoquinoline

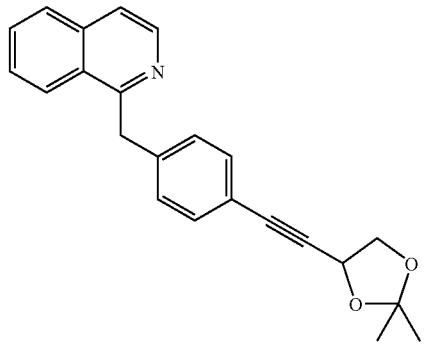

2,2-Dimethoxypropane (0.36 ml), 10-camphorsulfonic acid (43 mg), and molecular sieves (4 Å) were added to a solution of the compound of Example B109 (34 mg) in dimethylformamide (2 ml), and this reaction mixture was stirred at 75° C. for 9 hours. After an saturated aqueous sodium carbonate solution was added, the reaction mixture was extracted with ethyl acetate, washed with water, dried over anhydrous magnesium sulfate, and then concentrated under reduced pressure. The residue was purified by silica gel column chromatography to give the title compound (14 mg).

¹H-NMR(CDCl₃)δ(ppm): 1.40(3H, s), 1.50(3H, s), 3.97 (1H, dd), 4.21(1H, dd), 4.66(2H, s), 4.91(1H, dd), 7.19(2H, d), 7.32(2H, d), 7.52(1H, dd), 7.65-7.78(2H, m), 8.08(1H, d), 8.09(1H, d), 8.49(1H, d).

EXAMPLE B111 t-Butyl {[2-(1-ethoxyethoxy)-3-butynyl]oxy}dimethylsilane

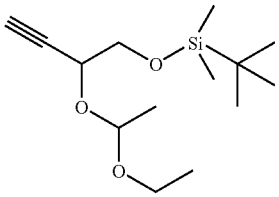

Ethyl vinyl ether (1.21 ml) and pyridinium p-toluenesulfonate (317 mg) were added to a solution of 1-{[1-(t-butyl)-1,1-dimethylsilyl]oxy}-3-butyn-2-ol (1687 mg) in methylene chloride (90 ml), and this mixture was stirred at room temperature for 1 hour. The methylene chloride layer was washed with a saturated aqueous sodium hydrogencarbonate solution and saturated brine, dried over anhydrous magnesium sulfate, then concentrated under reduced pressure to give the title compound (1962 mg). This compound was used in the following reaction without further purification.

¹H-NMR(DMSO-d6)δ(ppm): 0.00(6H, s), 0.81(9H, s), 1.01-1.07(3H, m), 1.10-1.20(1H, m), 1.18(3H, d), 3.35-3.63 (4H, m), 4.18-4.27(1H, m), 4.74(0.5H, q), 4.81(0.5H, q).

EXAMPLE B112

1-{4-[4-{[1-(t-Butyl)-1,1-dimethylsilyl]oxy}-3-(1-ethoxyethoxy)-1-butynyl]benzyl}isoquinoline

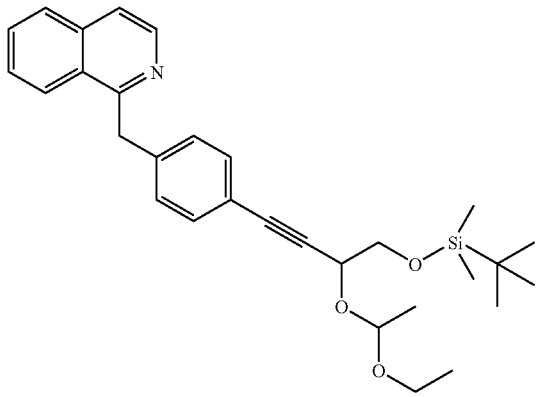

The title compound was obtained by treating the compound of Example B41 and the compound of Example B111 in the same manner as in Example B42.

¹H-NMR(DMSO-d6)δ(ppm): 0.00(6H, s), 0.80(9H, s), 1.01-1.05(3H, m), 1.19(3H, d), 3.39-3.70(4H, m), 4.41(0.5H, t), 4.48(0.5H, t), 4.59(2H, s), 4.79(0.5H, q), 4.87(0.5H, q), 7.20-7.30(4H, m), 7.58(1H, dd), 7.68(1H, d), 7.69(1H, dd), 7.91(1H, d), 8.24(1H, d), 8.38(1H, d).

EXAMPLE B113

1-{[1-(t-Butyl)-1,1-dimethylsilyl]oxy}4-[4-(1-isoquinolyl-methyl)phenyl]-3-butyn-2-ol

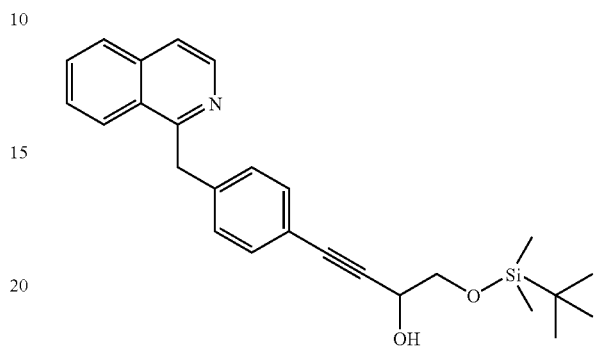

Pyridinium p-toluenesulfonate (486 mg) was added to a solution of the compound of Example B112 (474 mg) in methanol (15 ml), and this reaction mixture was stirred at room temperature for 24 hours. After ethyl acetate was added, the reaction mixture was washed with a saturated aqueous sodium hydrogencarbonate solution and saturated brine, dried over anhydrous magnesium sulfate, and then concentrated under reduced pressure. The residue was purified by silica gel column chromatography to give the title compound (265 mg).

¹H-NMR(DMSO-d6)δ(ppm): 0.01(6H, s), 0.82(9H, s), 3.55-3.62(2H, m), 4.30-4.39(1H, m), 4.61(2H, s), 5.51(1H, d), 7.20-7.27(4H, m), 7.50-7.63(1H, m), 7.67-7.74(2H, m), 7.92(1H, d), 8.27(1H, d), 8.41(1H, d).

EXAMPLE B114

1-(t-Butyl)-1,1-dimethylsilyl {2-fluoro-4-[4-(1-isoquinolyl-methyl)phenyl]-3-butynyl}ether

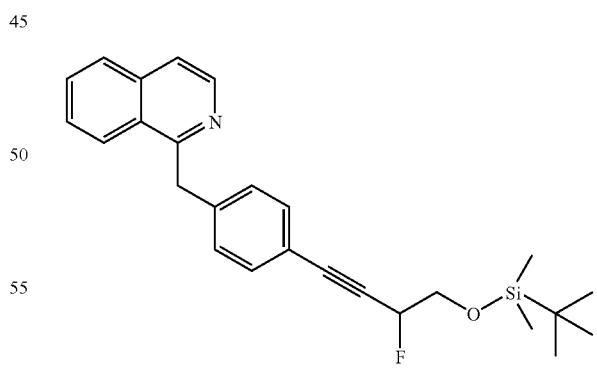

A solution of the compound of Example B113 (116 mg) in methylene chloride (2 ml) was added dropwise to a solution of (diethylamino)sulfur trifluoride (44 μl) in methylene chloride (2 ml) cooled to −78° C. under nitrogen atmosphere. Upon stirring for 15 minutes, the reaction mixture was stirred at room temperature for another 8 hours. A saturated aqueous sodium hydrogencarbonate solution was added, the resulting reaction mixture was extracted with methylene chloride. The methylene chloride layer was washed with water, dried over anhydrous magnesium sulfate, and then concentrated under reduced pressure. The residue was purified by silica gel column chromatography to give the title compound (42 mg).

$^1$H-NMR(CDCl$_3$)δ(ppm): 0.10(6H, s), 0.91(9H, s), 3.83-4.00(2H, m), 4.67(2H, s), 5.17(1H, ddd), 7.22(2H, d), 7.34(2H, d), 7.53(1H, dd), 7.58(1H, d), 7.65(1H, dd), 7.83(1H, d), 8.08(1H, d), 8.50(1H, d).

EXAMPLE B115

2-Fluoro-4-[4-(1-isoquinolylmethyl)phenyl]-3-butyn-1-ol

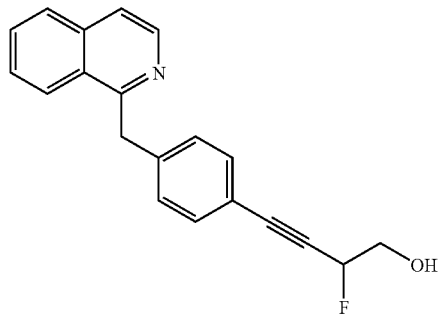

The title compound was obtained by treating the compound of Example B114 in the same manner as in Example B47.

$^1$H-NMR(CDCl$_3$)δ(ppm): 1.31(1H, brs), 3.77-3.95(2H, m), 4.67(2H, s), 5.35(1H, ddd), 7.22(2H, d), 7.35(2H, d), 7.53(1H, dd), 7.58(1H, d), 7.65(1H, dd), 7.83(1H, d), 8.07(1H, d), 8.50(1H, d).

EXAMPLE B116

1-(t-Butyl)-1,1-dimethylsilyl {6-[4-(1-isoquinolylmethyl)-phenyl]-5-hexynyl}ether

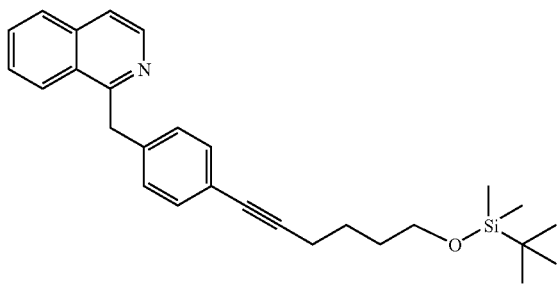

The title compound was obtained by treating the compound of Example B41 and t-butyl (5-hexynyloxy)dimethylsilane in the same manner as in Example B42.

$^1$H-NMR(CDCl$_3$)δ(ppm): 0.04(6H, s), 0.88(9H, s), 1.55-1.70(4H, m), 2.39(2H, t), 3.64(2H, t), 4.65(2H, s), 7.17(2H, d), 7.27(2H, d), 7.51(1H, dd), 7.55(1H, d), 7.64(1H, dd), 7.82(1H, d), 8.08(1H, d), 8.49(1H, d).

EXAMPLE B117

6-[4-(1-Isoquinolylmethyl)phenyl]-5-hexyn-1-ol

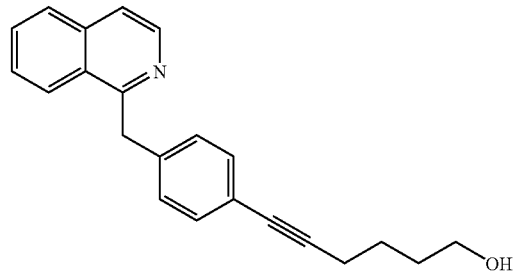

The title compound was obtained by treating the compound of Example B116 in the same manner as in Example B47.

$^1$H-NMR(CDCl$_3$)δ(ppm): 1.60-1.80(4H, m), 2.42(2H, t), 3.69(2H, t), 4.65(2H, s), 7.17(2H, d), 7.27(2H, d), 7.52(1H, dd), 7.57(1H, d), 7.64(1H, dd), 7.81(1H, d), 8.08(1H, d), 8.49(1H, d).

The proton of the hydroxyl group was not observed in the NMR spectrum.

EXAMPLE B118

6-[4-(1-Isoquinolylmethyl)phenyl]-1-hexanol

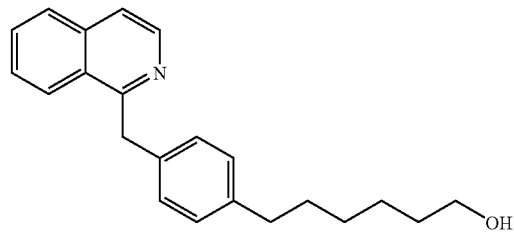

Treating the compound of Example B117 in the same manner as in Example B43, the obtained residue was separated and purified by LC-MS [eluent: an acetonitrile solution containing 0.1% trifluoroacetic acid: an aqueous solution containing 0.1% trifluoroacetic acid =1:99 to 100:0/20-minute cycle, flow rate: 20 ml/minute, column: YMC Combiprep ODS-AM, 20 mm Φ×50 mm (long)] to give the title compound.

MS m/z(ESI:MH$^+$):320.2

EXAMPLE B119

2-(4-Pentynyloxy)tetrahydro-2H-pyran

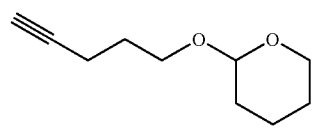

The title compound was obtained by treating 4-pentyn-1-ol in the same manner as in Example B91.

$^1$H-NMR(CDCl$_3$)δ(ppm): 1.50-1.90(8H, m), 1.95(1H, t), 2.30-2.35(2H, m), 3.46-3.54(2H, m), 3.80-3.90(2H, m), 4.60 (1H, dd).

EXAMPLE B120

1-{4-[5-(Tetrahydro-2H-2-pyranyloxy)-1-pentynyl]benzyl}-isoquinoline

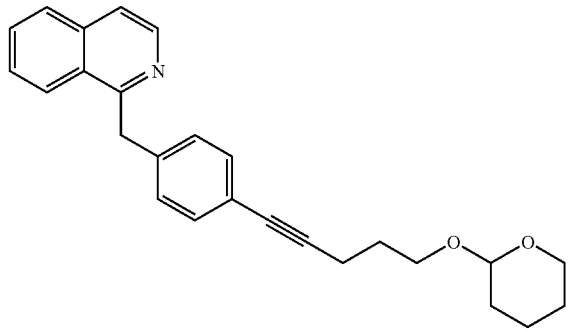

The title compound was obtained by treating the compound of Example B41 and the compound of Example B119 in the same manner as in Example B42.

$^1$H-NMR(CDCl$_3$)δ(ppm): 1.49-1.90(8H, m), 2.49(2H, t), 3.47-3.54(2H, m), 3.82-3.90(2H, m), 4.60(1H, dd), 4.65(2H, s), 7.17(2H, d), 7.27(2H, d), 7.52(1H, dd), 7.58(1H, d), 7.64(1H, dd), 7.82(1H, d), 8.09(1H, d), 8.49(1H, d).

EXAMPLE B121

5-[4-(1-Isoquinolylmethyl)phenyl]-4-pentyn-1-ol

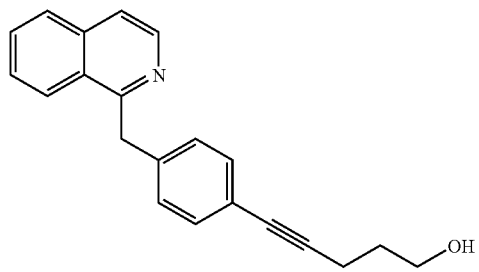

The title compound was obtained by treating the compound of Example B120 in the same manner as in Example B47.

$^1$H-NMR(CDCl$_3$)δ(ppm): 1.80-1.88(2H, m), 2.51(2H, t), 3.80(2H, t), 4.65(2H, s), 7.18(2H, d), 7.29(2H, d), 7.52(1H, dd), 7.58(1H, d), 7.65(1H, dd), 7.82(1H, d), 8.09(1H, d), 8.49(1H, d).

The proton of the hydroxyl group was not observed in the NMR spectrum.

EXAMPLE B122

5-[4-(1-Isoquinolylmethyl)phenyl]-4-pentynylcyanide

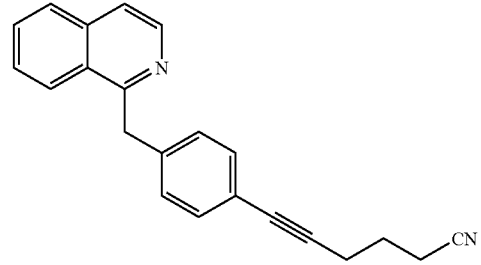

The title compound was obtained by treating the compound of Example B41 and 5-cyano-1-pentyne in the same manner as in Example B42.

$^1$H-NMR(CDCl$_3$)δ(ppm): 1.85-1.98(2H, m), 2.40-2.60(4H, m), 4.66(2H, s), 7.20(2H, d), 7.28(2H, d), 7.53(1H, dd), 7.58(1H, d), 7.65(1H, dd), 7.83(1H, d), 8.09(1H, d), 8.50(1H, d).

EXAMPLE B123

1-[4-(3-Methyl-1-butynyl)benzyl]isoquinoline

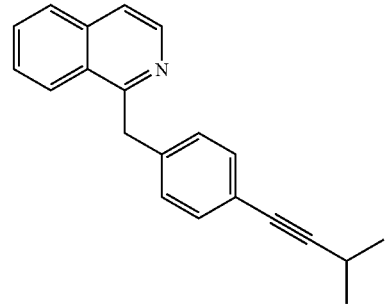

The title compound was obtained by treating the compound of Example B41 and 3-methyl-1-butyne in the same manner as in Example B42.

$^1$H-NMR(CDCl$_3$)δ(ppm): 1.23(6H, d), 2.70-2.78(1H, m), 4.65(2H, s), 7.18(2H, d), 7.28(2H, d), 7.51(1H, dd), 7.58(1H, d), 7.64(1H, dd), 7.82(1H, d), 8.08(1H, d), 8.50(1H, d).

EXAMPLE B124

1-[4-(5-Methyl-1-hexynyl)benzyl]isoquinoline

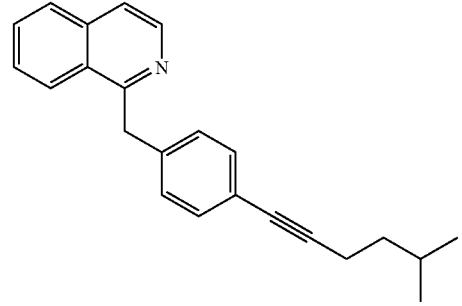

The title compound was obtained by treating the compound of Example B41 and 5-methyl-1-hexyne in the same manner as in Example B42.

$^1$H-NMR(CDCl$_3$)δ(ppm): 0.91(6H, d), 1.47(2H, dt), 1.68-1.77(1H, m), 2.37(2H, t), 4.65(2H, s), 7.17(2H, d), 7.28(2H, d), 7.52(1H, dd), 7.57(1H, d), 7.64(1H, dd), 7.81(1H, d), 8.09(1H, d), 8.49(1H, d).

EXAMPLE B125

4-Pentynamide

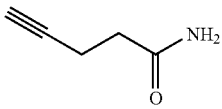

1-Ethoxycarbonyl-2-ethoxy-1,2-dihydroquinoline (6775 mg) and ammonium hydrogencarbonate (5905 mg) were added to a solution of 4-pentynoic acid (2446 mg) in chloroform (75 ml), and this reaction mixture was stirred at room temperature for 17.5 hours. The reaction mixture was filtered through celite and concentrated under reduced pressure. The residue was purified by silica gel column chromatography to give the title compound (249 mg).

$^1$H-NMR(DMSO-d6)δ(ppm): 2.21(2H, t), 2.29-2.33(2H, m), 2.73(1H, t), 6.78-6.88(1H, m), 7.28-7.38(1H, m).

EXAMPLE B126

5-[4-(1-Isoquinolylmethyl)phenyl]-4-pentynamide

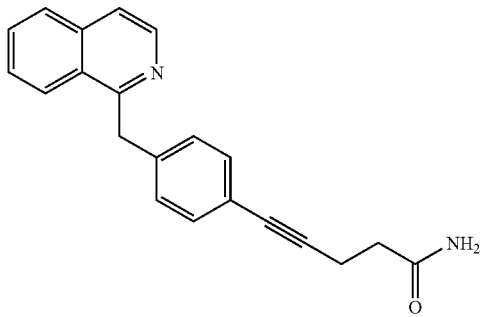

The title compound was obtained by treating the compound of Example B41 and the compound of Example B125 in the same manner as in Example B42.

$^1$H-NMR(DMSO-d6)δ(ppm): 2.51(2H, t), 2.85(2H, t), 3.70(2H, brs), 4.59(2H, s), 7.05(2H, d), 7.23(2H, d), 7.61(1H, dd), 7.70(1H, d), 7.72(1H, dd), 7.94(1H, d), 8.30(1H, d), 8.43(1H, d).

EXAMPLE B127 t-Butyl 4-pentynoate

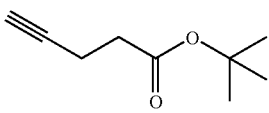

Benzyltriethylammonium chloride (5.92 g), potassium carbonate (93.4 g), and t-butyl bromide (143 ml) were added to a solution of 4-pentynoic acid (2550 mg) in N,N-dimethylacetamide (230 ml), and this reaction mixture was stirred at 55° C. for 24 hours. After water was added, the reaction mixture was extracted with ethyl acetate, washed with water, dried over anhydrous magnesium chloride, and then filtered through silica gel. The filtrate was concentrated under reduced pressure to give the title compound (2.10 g). This compound was used in the following reaction without further purification.

$^1$H-NMR(CDCl$_3$)δ(ppm): 1.46(9H, s), 1.96-1.97(1H, m), 2.45-2.47(4H, m).

EXAMPLE B128 t-Butyl 5-[4-(1-isoquinolylmethyl)phenyl]-4-pentynoate

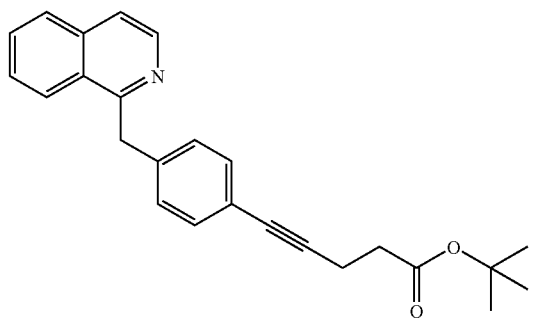

The title compound was obtained by treating the compound of Example B41 and the compound of Example B127 in the same manner as in Example B42.

$^1$H-NMR(CDCl$_3$)δ(ppm): 1.45(9H, s), 2.49(2H, t), 2.64 (2H, t), 4.64(2H, s), 7.21(2H, d), 7.26(2H, d), 7.52(1H, dd), 7.57(1H, d), 7.64(1H, dd), 7.82(1H, d), 8.09(1H, d), 8.49(1H, d).

EXAMPLE B129

5-[4-(1-Isoquinolylmethyl)phenyl]-4-pentynoic acid

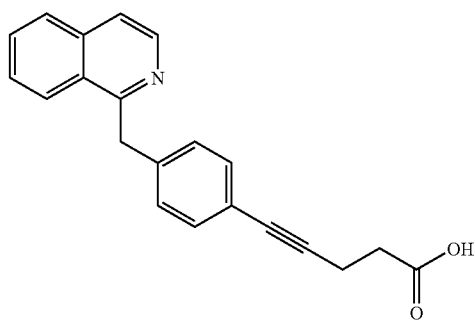

Treating the compound of Example B128 in the same manner as in Example B69, the obtained residue was separated and purified by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)] to give the title compound.

MS m/z(ESI:MH$^+$):316.1

The following compounds were synthesized as follows. That is, the title compound was obtained by reacting the compound of Example B41 with various reactants described below, according to Example B33. The various reactants are acrylamide, N,N-dimethylacrylamide, t-butyl acrylate, and methyl vinyl sulfone. Furthermore, the coupling product obtained in this manner was subjected to either the reduction according to Example B39 or the deprotection of t-butyl ester according to Example B40, or both. The resulting product was purified by silica gel column chromatography or by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)].

EXAMPLE B130

(E)-3-[4-(1-isoquinolylmethyl)phenyl]-2-propenamide

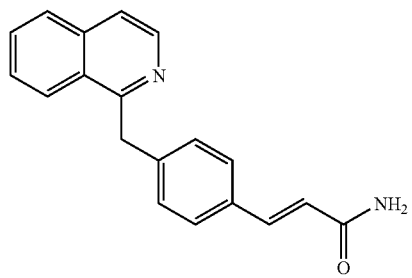

MS m/z(ESI:MH$^+$):289.3

EXAMPLE B131

3-[4-(1-Isoquinolylmethyl)phenyl]-2-propanamide

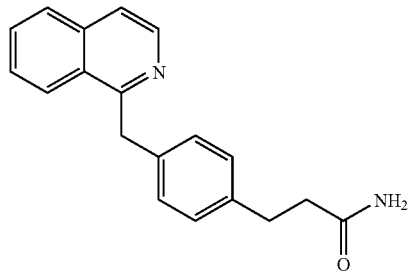

MS m/z(ESI:MH$^+$):291.2

EXAMPLE B132

N,N-dimethyl-(E)-3-[4-(1-isoquinolylmethyl)phenyl]-2-propenamide

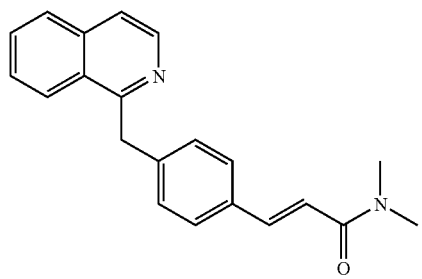

MS m/z(ESI:MH$^+$):317.3

EXAMPLE B133

N,N-dimethyl-3-[4-(1-isoquinolylmethyl)phenyl]propanamide

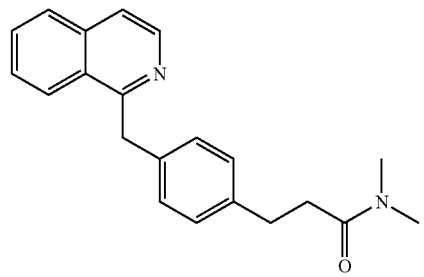

MS m/z(ESI:MH$^+$):319.1

EXAMPLE B134 t-Butyl(E)-3-[4-(1-isoquinolylmethyl)phenyl]-2-propenoate

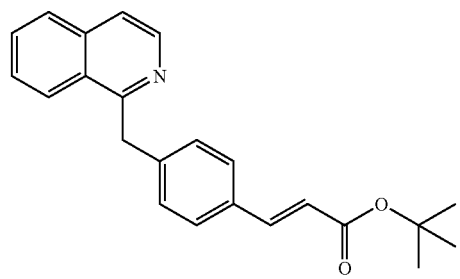

$^1$H-NMR(CDCl$_3$)δ(ppm): 1.51(9H, s), 4.68(2H, s), 6.28 (1H, d), 7.27(2H, d), 7.39(2H, d), 7.49-7.60(3H, m), 7.65(1H, dd), 7.82(1H, d), 8.11(1H, d), 8.50(1H, d).

EXAMPLE B135

(E)-3-[4-(1-isoquinolylmethyl)phenyl]-2-propenoic acid

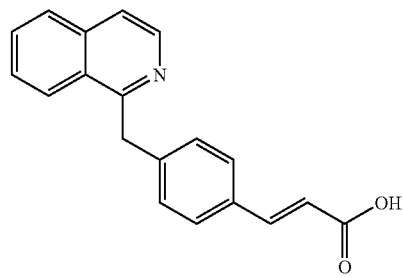

MS m/z(ESI:MH$^+$):290.2

EXAMPLE B136 t-Butyl 3-[4-(1-isoquinolylmethyl)phenyl]propanoate

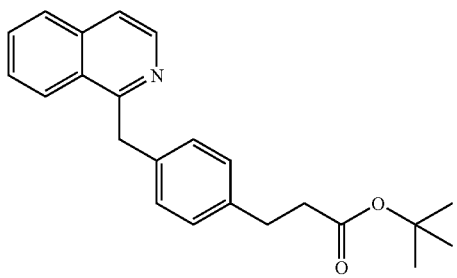

$^1$H-NMR(CDCl$_3$)δ(ppm): 1.37(9H, s), 2.47(2H, t), 2.83 (2H, t), 4.64(2H, s), 7.07(2H, d), 7.19(2H, d), 7.52(1H, dd), 7.56(1H, d), 7.63(1H, dd), 7.81(1H, d), 8.14(1H, d), 8.49(1H, d).

EXAMPLE B137

3-[4-(1-Isoquinolylmethyl)phenyl]propanoic acid

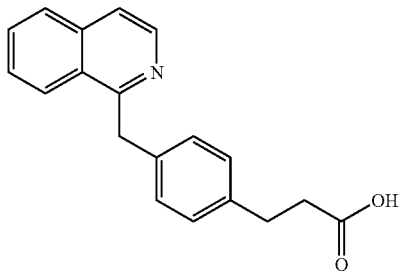

MS m/z(ESI:MH$^+$):292.1

EXAMPLE B138

(E)-2-[4-(1-isoquinolylmethyl)phenyl]-1-ethenyl methylsulfone

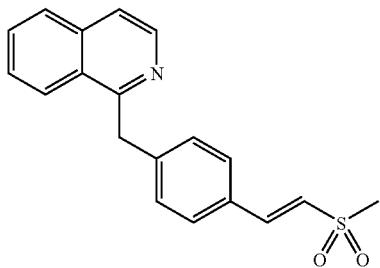

MS m/z(ESI:MH$^+$):324.1

EXAMPLE B139

1-{4-[2-(Methylsulfonyl)ethyl]benzyl} isoquinoline

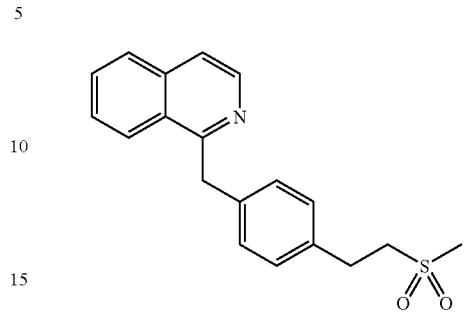

MS m/z(ESI:MH$^+$):326.1

EXAMPLE B140

2-Benzoyl-6,7-dimethoxy-1,2-dihydro-1-isoquinolinecarbonitrile

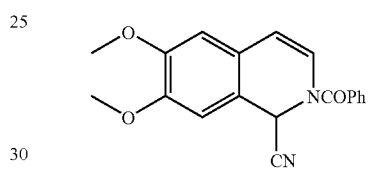

An aqueous potassium cyanide (1.0 g, 16 mmol) solution (2.3 ml) and benzoyl chloride (1.1 ml, 9.5 mmol) were added to a solution of 6,7-dimethoxyisoquinoline (1.0 g, 5.3 mmol), which was synthesized according to Tetrahedron, 37 (23), 3977 (1981), in methylene chloride (6.0 ml), and this reaction mixture was stirred while heating under reflux for 2 hours. The reaction mixture was cooled to room temperature, filtered through celite, and washed with methylene chloride and water. After the obtained filtrate was separated, the methylene chloride layer was washed successively with water, 2 N hydrochloric acid, water, and 2 N sodium hydroxide, dried over anhydrous magnesium sulfate, and then concentrated under reduced pressure. The residue was purified by silica gel column chromatography to give the title compound (573 mg).

$^1$H-NMR(CDCl$_3$)δ(ppm): 3.92(3H, s), 3.94(3H, s), 5.99 (1H, d), 6.51-6.55(2H, m), 6.73(1H, s), 6.85(1H, s), 7.45-7.49 (2H, m), 7.53-7.56(1H, m), 7.58-7.61(2H, m)

EXAMPLE B141

1-(4-Butylbenzyl)-6,7-dimethoxyisoquinoline

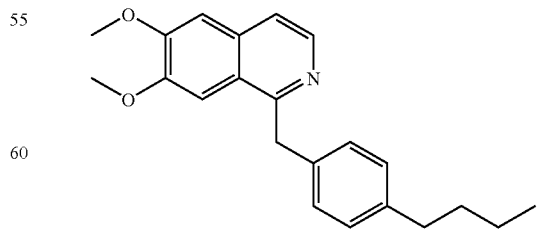

The title compound was obtained by treating the compound of Example B140 and the compound of Example B1 in the same manner as in Example B2.

$^1$H-NMR(CDCl$_3$)δ(ppm): 0.90(3H, t), 1.27-1.36(2H, m), 1.51-1.58(2H, m), 2.54(2H, t), 3.88(3H, s), 4.01(3H, s), 4.57 (2H, s), 7.05(1H, s), 7.07(2H, d), 7.19(2H, d), 7.32(1H, s), 7.43(1H, d), 8.37(1H, d)

EXAMPLE B142

1-(3-Methoxyphenyl)-2-nitro-1-ethanol

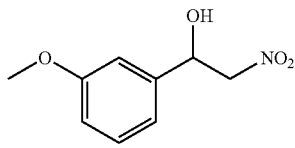

An aqueous sodium hydroxide solution (1.5 g of sodium hydroxide (37 mmol) was dissolved in 15 ml of water) was added dropwise to a solution of m-anisaldehyde (5.0 g, 37 mmol) and nitromethane (4.0 ml, 73 mmol) in methanol (50 ml) keeping the temperature of the solution at not higher than 30° C. The reaction mixture was then stirred at room temperature for 4 hours. Upon cooling on ice, an aqueous acetic acid solution (glacial acetic acid (37 mmol) was dissolved in 250 ml of water) was added, the resulting reaction mixture was extracted with ethyl acetate. The ethyl acetate layer was washed successively with water and a 5% aqueous sodium hydrogencarbonate solution, dried over anhydrous magnesium sulfate, then concentrated under reduced pressure. The residue was purified by silica gel column chromatography to give the title compound (6.09 g).

$^1$H-NMR(CDCl$_3$)δ(ppm): 3.83(3H, s), 4.52(1H, dd), 4.61 (1H, dd), 4.76-4.78(1H, m), 5.44-5.48(1H, m), 6.90(1H, dd), 6.96-6.98(2H, m), 7.25-7.34(1H, m)

EXAMPLE B143

2-Amino-1-(3-methoxyphenyl)-1-ethanol

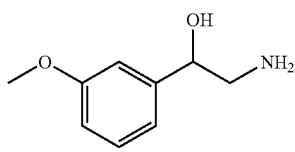

Palladium-carbon (10%, 0.64 g) and ammonium formate (4.8 g) were added to a mixed solution of the compound of Example B142 (3.0 g, 15 mmol) in tetrahydrofuran (43 ml) and methanol (43 ml), and this mixture was stirred at room temperature for 18 hours. The catalyst was removed by filtration, the filtrate was diluted with ether, precipitates were removed by filtration, and the obtained filtrate was concentrated to give the title compound (1.82 g). This compound was used in the following reaction without further purification.

EXAMPLE B144

2-(4-Butylphenyl)acetic acid

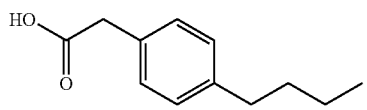

Thionyl chloride (4.7 ml, 66 mmol) was added dropwise to a solution of 4-n-butylbenzyl alcohol (9.6 g, 59 mmol) in ether (120 ml), and this mixture was stirred at room temperature for 2 hours. The solvent was removed under reduced pressure, and excess thionyl chloride was removed by azeotropic distillation with benzene. The residue was dissolved in dimethyl sulfoxide (50 ml), sodium cyanide (86 g, 1.8 mol) and n-tetrabutylammonium iodide (2.2 g, 5.9 mmol) were added to this solution, and the resulting mixture was stirred at room temperature for 16 hours. Water was added, and this mixture was extracted with ethyl acetate. The ethyl acetate layer was washed successively with water and saturated brine, dried over anhydrous magnesium sulfate, and then concentrated under reduced pressure. The residue was purified by silica gel column chromatography to give n-butylphenylacetonitrile (8.2 g) as a yellow oil. Next, concentrated sulfuric acid (48 ml) was added dropwise to water (58 ml), this solution was cooled to 50° C., and n-Butylphenylacetonitrile (8.2 g) obtained above was added dropwise to the solution. The resulting mixture was stirred while heating under reflux for 16 hours. Upon cooling to room temperature, the precipitated crystals were collected by filtration, washed with water, and dissolved in a 0.1 N aqueous sodium hydroxide solution (200 ml). Norit (5 g) was added, and this mixture was stirred and refluxed for 2 hours. After Norit was removed by filtration through celite, the filtrate was cooled to room temperature and acidified with 1 N hydrochloric acid to precipitate crystals. The precipitated crystals were collected by filtration, washed with water, and dried to give the title compound (3.5 g).

$^1$H-NMR(CDCl$_3$)δ(ppm): 0.93(3H, t), 1.30-1.40(2H, m), 1.53-1.62(2H, m), 2.59(2H, t), 3.62(2H, s), 7.15(2H, d), 7.20 (2H, d)

The OH of the carboxyl group was not observed in the NMR spectrum.

EXAMPLE B145

N-[2-Hydroxy-2-(3-methoxyphenyl)ethyl]-2-(4-butylphenyl)-acetamide

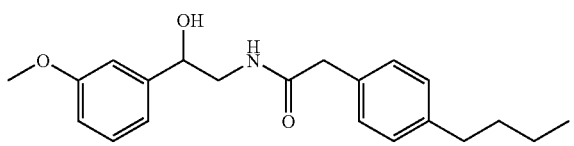

Thionyl chloride (0.76 ml, 10 mmol) was added to a solution of the compound of Example B144 (1.0 g, 5.2 mmol) in benzene (10 ml), and the mixture was stirred under reflux for 2 hours. Upon concentration, excess thionyl chloride was removed by azeotropic distillation with benzene. The obtained residue and the compound of Example B 143 (0.87 g, 5.2 mmol) were dissolved in ether (5 ml), an aqueous sodium hydroxide solution (0.21 g of sodium hydroxide was dissolved in 4.2 ml of water) was added thereto, and the mixture was stirred vigorously at room temperature for 30 minutes. The ether layer was separated and concentrated under reduced pressure to give the title compound (600 mg).

¹H-NMR(CDCl₃)δ(ppm): 0.94(3H, t), 1.31-1.40(2H, m), 1.57-1.63(2H, m), 2.60(2H, m), 3.30-3.37(1H, m), 3.56(2H, s), 3.60-3.66(1H, m), 3.80(3H, s), 3.81(1H, d), 4.79-4.81(1H, m), 6.80-6.89(3H, m), 7.10(2H, d), 7.16(2H, d), 7.20-7.25 (1H, m)

EXAMPLE B146

1-(4-Butylbenzyl)-6-methoxyisoquinoline

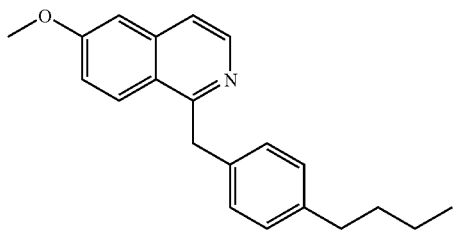

Phosphorus oxychloride (1.6 ml) was added to a solution of the compound of Example B145 (600 mg, 1.7 mmol) in acetonitrile (15 ml), and the mixture was stirred under reflux for 1 hour 30 minutes. The mixture was cooled on ice, made alkaline with a 5% aqueous sodium hydrogencarbonate solution, extracted with ethyl acetate, dried over anhydrous magnesium sulfate, and then concentrated under reduced pressure. The residue was purified by silica gel column chromatography to give the title compound (82 mg).

¹H-NMR(CDCl₃)δ(ppm): 0.89(3H, t), 1.27-1.36(2H, m), 1.50-1.58(2H, m), 2.53(2H, t), 3.92(3H, s), 4.57(2H, s), 7.05-7.07(3H, m), 7.13-7.18(3H, m), 7.45(1H, d), 8.06(1H, d), 8.41(1H, d)

EXAMPLE 147

1-(4-Butylbenzyl)-6-isoquinolinyl

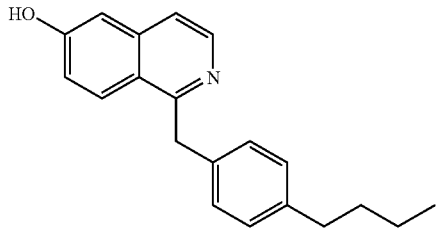

A 47% hydrobromic acid solution was added to the compound of Example B146 (82 mg), and the mixture was stirred under reflux for 19 hours. The mixture was concentrated under reduced pressure, water was added, and the resulting mixture was neutralized with sodium carbonate to precipitate crystals. The obtained crystals were collected by filtration, washed with water, and then dried to give the title compound (74 mg).

¹H-NMR(CD₃OD)δ(ppm): 0.89(3H, t), 1.25-1.34(2H, m), 1.49-1.57(2H, m), 2.52(2H, t), 4.63(2H, s), 7.03-7.13(6H, m), 7.49(1H, d), 8.10(1H, d), 8.18(1H, d)

EXAMPLE B148

1-(4-Butylbenzyl)-6-propoxyisoquinoline

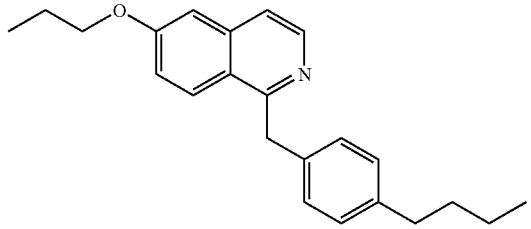

Silver carbonate (40 mg, 0.14 mmol) was added to a solution of the compound of Example B147 (20 mg, 0.069 mmol) and 1-iodopropane (0.4 ml, 4.1 mmol) in toluene (1.0 ml), and the mixture was stirred in the dark at 50° C. for 4 hours. Upon cooling to room temperature, the mixture was filtered through celite and washed with a mixed solution of toluene and methanol (9:1). The obtained filtrate was concentrated under reduced pressure, and the resulting residue was purified by silica gel column chromatography to give the title compound (13 mg).

¹H-NMR(CDCl₃)δ(ppm): 0.90(3H, t), 1.08(3H, t), 1.30-1.33(2H, m), 1.51-1.57(2H, m), 1.86-1.91(2H, m), 2.54(2H, t), 4.05(2H, t), 4.58(2H, s), 7.05-7.07(3H, m), 7.14-7.18(3H, m), 7.43-7.44(1H, m), 8.05-8.07(1H, m), 8.40-8.41(1H, m)

EXAMPLE B149

1-(4-Butylbenzyl)-6-(2-piperidinoethoxy)isoquinoline

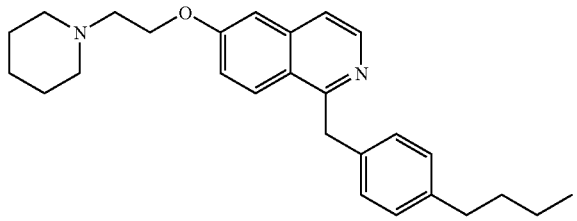

The title compound was obtained in the same manner as in Example 148.

¹H-NMR(CDCl₃)δ(ppm): 0.89(3H, t), 1.26-1.36(2H, m), 1.46-1.57(8H, m), 2.50-2.54(6H, m), 2.83-2.86(2H, m), 4.23 (2H, t), 4.56(2H, s), 7.04-7.06(3H, m), 7.13-7.17(3H, m), 7.43(1H, d), 8.04(1H, d), 8.40(1H, d)

EXAMPLE B150

N-({[1-(4-butylbenzyl)-6-isoquinolyl]oxy}ethyl)-N,N-dimethyl-amine

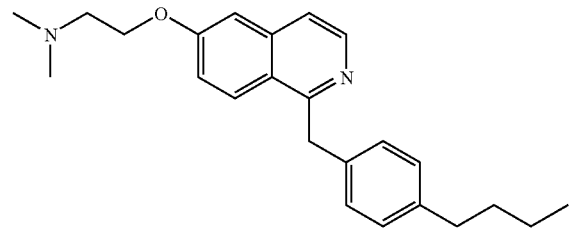

The title compound was obtained in the same manner as in Example 148.

¹H-NMR(CDCl₃)δ(ppm): 0.89(3H, t), 1.26-1.36(2H, m), 1.49-1.57(2H, m), 2.37(6H, s), 2.52(2H, t), 2.80(2H, t), 4.19 (2H, t), 4.57(2H, s), 7.04-7.06(3H, m), 7.15-7.19(3H, m), 7.43(1H, d), 8.05(1H, d), 8.40(1H, d)

EXAMPLE B 151

2-Benzoyl-7-methoxy-1,2-dihydro-1-isoquinolinecarbonitrile

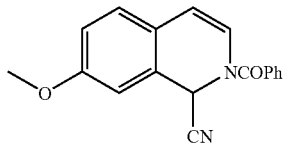

The title compound was obtained by treating 7-methoxyisoquinoline, which was synthesized according to Tetrahedron, 27, 1253 (1971), in the same manner as in Example B140.

¹H-NMR(CDCl₃)δ(ppm): 3.87(3H, s), 6.03(1H, brd), 6.56-6.54(2H, m), 6.90(1H, s), 6.95(1H, dd), 7.17(1H, d), 7.46-7.50(2H, m), 7.54-7.62(3H, m)

EXAMPLE B 152

1-(4-Butylbenzyl)-7-methoxyisoquinoline

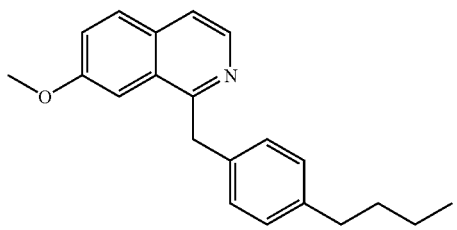

The title compound was obtained by treating the compound of Example B1 and the compound of Example B 151 in the same manner as in Example B2.

¹H-NMR(CDCl₃)δ(ppm): 0.89(3H, t), 1.27-1.36(2H, m), 1.56-1.58(2H, m), 2.55(2H, t), 3.82(3H, s), 4.59(2H, s), 7.07 (2H, d), 7.20(2H, d), 7.26-7.29(1H, m), 7.35(1H, d), 7.49(1H, d), 7.70(1H, d), 8.38-8.40(1H, m)

EXAMPLE B153

1-(4-Bromobenzyl)-7-methoxyisoquinoline

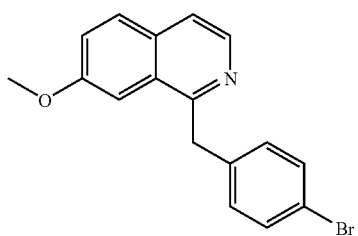

The title compound was obtained by treating the compound of Example B31 and the compound of Example B 151 in the same manner as in Example B2.

¹H-NMR(CDCl₃)δ(ppm): 3.84(3H, s), 4.57(2H, s), 7.14-7.16(2H, m), 7.26(1H, s), 7.29-7.32(1H, m), 7.37-7.39(2H, m), 7.51(1H, d), 7.73(1H, d), 8.39(1H, d)

EXAMPLE B 154

1-(4-Butylbenzyl)-7-isoquinolinyl

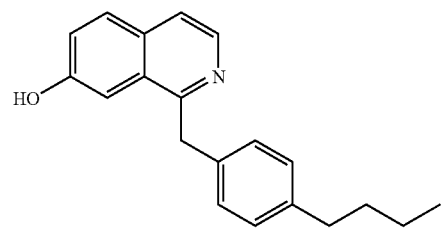

The title compound was obtained by treating the compound of Example B152 in the same manner as in Example B147.

¹H-NMR(DMSO-d₆)δ(ppm): 0.83(3H, t), 1.21-1.26(2H, m), 1.44-1.48(2H, m), 4.68(2H, s), 7.11(2H, d), 7.18(2H, d), 7.59-7.62(2H, m), 8.10-8.17(2H, m), 8.38(1H, d), 10.9(1H, brs)

(The two methylene protons of the butyl group overlapped with the DMSO signal and could not be observed.)

EXAMPLE B155

1-(4-Butylbenzyl)-7-isoquinolyl trifluoromethanesulfonate

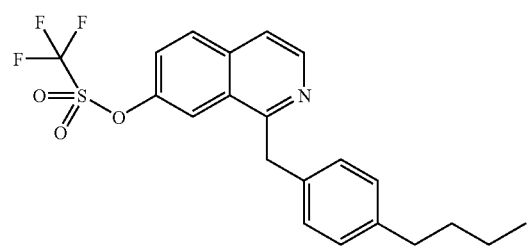

4-Nitrophenol triflate (0.72 g, 2.7 mmol), which was synthesized according to J. Org. Chem., 64, 7638 (1999), and potassium carbonate (1.1 g, 8.1 mmol) were added to a solution of the compound of Example B154 (1.0 g, 2.7 mmol) in dimethylformamide (30 ml), and the mixture was stirred at room temperature for 2 hours. After water was added, the resulting mixture was extracted with ethyl acetate. The ethyl acetate layer was washed with 1 N sodium hydroxide and saturated brine, dried over magnesium sulfate, and then concentrated under reduced pressure. The residue was purified by silica gel column chromatography to give the title compound (1.0 g).

¹H-NMR(CDCl₃)δ(ppm): 0.90(3H, t), 1.27-1.37(2H, m), 1.51-1.59(2H, m), 2.54(2H, t), 5.10(2H, s), 6.38(1H, s), 6.95 (2H, d), 7.04(2H, d), 7.44(1H, d), 7.55(1H, d), 7.75(1H, d), 8.45(1H, d)

EXAMPLE B156

1-(4-Butylbenzyl)-7-isoquinolinecarbonitrile

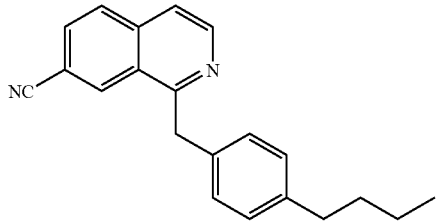

Zinc cyanide (215 mg, 1.8 mmol), tetrakis(triphenylphosphine)palladium (41 mg, 0.035 mmol), and lithium chloride (120 mg, 2.8 mmol) were added to a solution of the compound of Example B155 (400 mg, 0.95 mmol) in dimethylformamide (2 ml) under nitrogen atmosphere, and the mixture was stirred at 120° C. for 2 hours. After cooling to room temperature, saturated sodium hydrogencarbonate was added, and the resulting mixture was extracted with ethyl acetate. The ethyl acetate layer was washed with saturated brine, dried over anhydrous magnesium sulfate, and then concentrated under reduced pressure. The residue was purified by silica gel column chromatography to give the title compound (71 mg).

¹H-NMR(CDCl₃)δ(ppm): 0.89(3H, t), 1.26-1.35(2H, m), 1.47-1.55(2H, m), 2.50(2H, t), 4.91(2H, s), 6.97(2H, d), 7.07 (2H, d), 7.28-7.31(1H, m), 7.42(1H, d), 7.51(1H, d), 7.74(1H, d), 8.34(1H, d)

EXAMPLE B157

1-(4-Butylbenzyl)-7-[2-(1,1,1-trimethylsilyl)-1-ethynyl]-isoquinoline

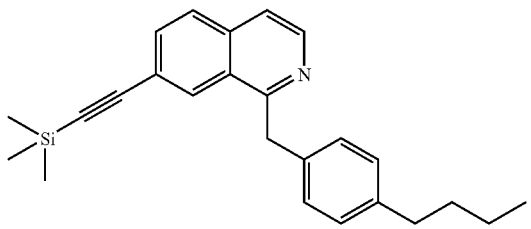

Palladium acetate (11 mg, 0.047 mmol), 1,1'-bis(diphenylphosphino)ferrocene (72 mg, 0.13 mmol), and lithium chloride (25 mg, 0.59 mmol) were added to a solution of the compound of Example B155 (100 mg, 0.24 mmol) and trimethylsilylacetylene (65 μl, 0.47 mmol) in dimethylformamide (3.0 ml), and the reaction system was purged with nitrogen. Triethylamine (59 μl, 0.43 mmol) and copper iodide (2 mg, 0.018 mmol) were added, and the resulting mixture was stirred at 80° C. for 21 hours, then cooled to room temperature. After water and ethyl acetate were added for partition, the ethyl acetate layer was washed with water, dried over anhydrous magnesium sulfate, and then concentrated under reduced pressure. The residue was purified by silica gel column chromatography to give the title compound (7.0 mg).

¹H-NMR(CDCl₃)δ(ppm): 0.28-0.32(9H, m), 0.92(3H, t), 1.32-1.38(2H, m), 1.54-1.57(2H, m), 2.57(2H, t), 4.63(2H, s), 7.10(2H, d), 7.20(2H, d), 7.52(1H, d), 7.67-7.69(1H, m), 7.75(1H, d), 8.34(1H, d), 8.51(1H, d)

EXAMPLE B158

1-(4-Butylbenzyl)-7-(1-ethynyl)isoquinoline

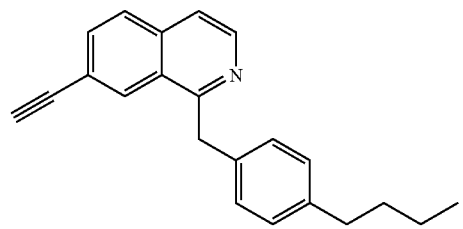

Potassium carbonate (13 mg, 0.094 mmol) was added to a solution of the compound of Example B157 (6 mg, 0.016 mmol) in methanol (1.0 ml), and the mixture was stirred at room temperature for 1 hour. Upon concentration under reduced pressure, the obtained residue was purified by silica gel column chromatography to give the title compound (3.0 mg).

¹H-NMR(CDCl₃)δ(ppm): 0.91(3H, t), 1.29-1.38(2H, m), 1.52-1.57(2H, m), 2.55(2H, t), 3.19(1H, s), 4.62(2H, s), 7.09 (2H, d), 7.20(2H, d), 7.53(1H, d), 7.67-7.69(1H, m), 7.77(1H, d), 8.36(1H, s), 8.52(1H, d)

EXAMPLE B159

1-(4-Butylbenzyl)-7-ethylisoquinoline

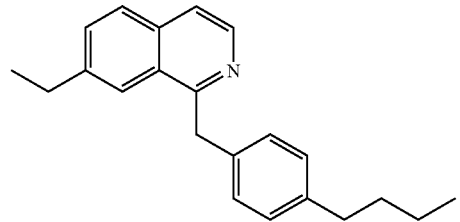

Palladium-carbon (10%, 5.0 mg) was added to a solution of the compound of Example B158 (2.0 mg) in tetrahydrofuran (2.0 ml), and the mixture was stirred at room temperature under nitrogen atmosphere (1 atm) for 1 hour. The catalyst was removed by filtration, and the filtrate was concentrated. The residue was purified by silica gel column chromatography to give the title compound (0.21 mg).

¹H-NMR(CDCl₃)δ(ppm): 0.89(6H, t), 1.25-1.32(2H, m), 1.48-1.57(2H, m), 2.53(2H, t), 2.80(2H, q), 4.62(2H, s), 7.06 (2H, d), 7.20(2H, d), 7.49-7.52(2H, m), 7.73(1H, d), 7.95(1H, s), 8.43(1H, d)

EXAMPLE B 160

1-(4-Butylbenzyl)-7-[4-(tetrahydro-2H-2-pyranyloxy)-1-butynyl]-isoquinoline

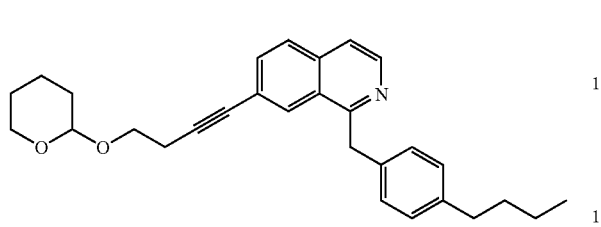

Palladium acetate (11 mg, 0.047 mmol), 1,1'-bis(diphenylphosphino)ferrocene (72 mg, 0.13 mmol), and lithium chloride (25 mg, 0.59 mmol) were added to a solution of the compound of Example B155 (100 mg, 0.24 mmol) and 2-(3-butynyloxy)tetrahydro-2H-pyran (73 mg, 0.47 mmol) in dimethylformamide (3.0 ml), and the system was purged with nitrogen. Furthermore, triethylamine (59 μl, 0.43 mmol) and copper iodide (2 mg, 0.018 mmol) were added, and the resulting mixture was stirred at 80° C. for 24 hours. The mixture was cooled to room temperature, water was added, and the resulting mixture was extracted with ethyl acetate. The ethyl acetate layer was washed with water, dried over anhydrous magnesium sulfate, and then concentrated under reduced pressure. The residue was purified by silica gel column chromatography to give the title compound (25 mg).

$^1$H-NMR(CDCl$_3$)δ(ppm): 0.90(3H, t), 1.28-1.38(2H, m), 1.52-1.67(6H, m), 1.72-1.79(1H, m), 1.79-1.88(1H, m), 2.54 (2H, t), 2.78(2H, t), 3.53-3.56(1H, m), 3.66-3.72(1H, m), 3.91-3.99(2H, m), 4.60(2H, s), 4.71-4.73(1H, m), 7.08(2H, d), 7.19(2H, d), 7.50(1H, d), 7.59-7.62(1H, m), 7.72(1H, d), 8.24(1H, s), 8.48(1H, d)

EXAMPLE B161

4-[1-(4-Butylbenzyl)-7-isoquinolyl]-3-butyn-1-ol

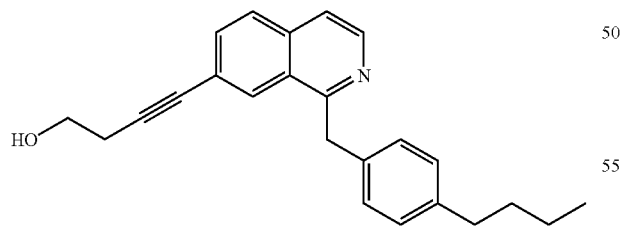

The title compound was obtained by treating the compound of Example B160 in the same manner as in Example B29.

$^1$H-NMR(CDCl$_3$)δ(ppm): 0.89(3H, t), 1.27-1.39(2H, m), 1.51-1.57(2H, m), 1.83(1H, brs), 2.55(2H, t), 2.75(2H, t), 3.84-3.89(2H, m), 4.60(2H, s), 7.08(2H, d), 7.18(2H, d), 7.50 (1H, d), 7.60-7.62(1H, m), 7.73(1H, d), 8.25(1H, s), 8.48(1H, d)

EXAMPLE B 162

4-[1-(4-Butylbenzyl)-7-isoquinolyl]-1-butanol

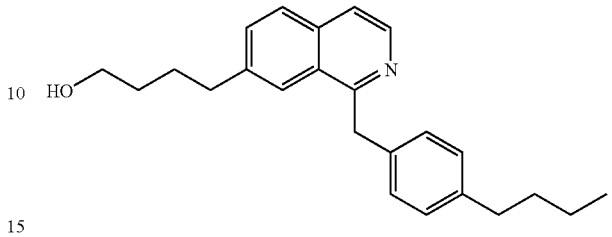

The title compound was obtained by treating the compound of Example B 161 in the same manner as in Example B30.

$^1$H-NMR(CDCl$_3$)δ(ppm): 0.89(3H, t), 1.28-1.36(2H, m), 1.50-1.59(4H, m), 1.67-1.77(3H, m), 2.53(2H, t), 2.79(2H, t), 3.63(2H, t), 4.62(2H, s), 7.06(2H, d), 7.18(2H, d), 7.47-7.52 (2H, m), 7.73(1H, d), 7.92(1H, s), 8.43(1H, d)

EXAMPLE B 163

1-(4-Butylbenzyl)-7-propoxyisoquinoline

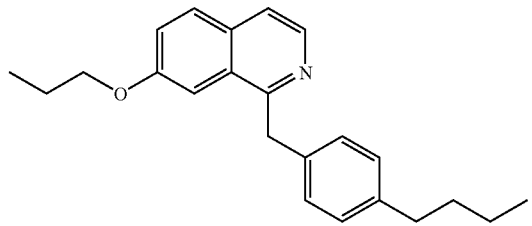

The title compound was obtained by treating the compound of Example B154 in the same manner as in Example B148.

$^1$H-NMR(CDCl$_3$)δ(ppm): 0.90(3H, t), 1.05(3H, t), 1.27-1.36(2H, m), 1.50-1.56(2H, m), 1.76-1.84(2H, m), 2.53(2H, t), 3.92(2H, t), 4.58(2H, s), 7.06(2H, d), 7.19(2H, d), 7.26-7.29(1H, m), 7.34(1H, d), 7.48(1H, d), 7.70(1H, d), 8.38(1H, d)

EXAMPLE B 164

1-(4-Butylbenzyl)-7-(2-piperidinoethoxy)isoquinoline

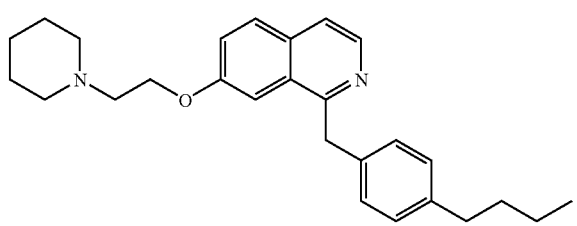

The title compound was obtained in the same manner as in Example B148.

¹H-NMR(CDCl₃)δ(ppm): 0.89(3H, t), 1.27-1.36(2H, m), 1.43-1.58(4H, m), 1.61-1.69(4H, m), 2.51-2.55(6H, m), 2.79(2H, t), 4.11(2H, t), 4.57(2H, s), 7.06(2H, d), 7.18(2H, d), 7.28-7.30(1H, m), 7.36(1H, d), 7.48(1H, d), 7.70(1H, d), 8.38(1H, d)

EXAMPLE B 165

N-(2-{[1-(4-butylbenzyl)-7-isoquinolyl]oxy}ethyl)-N,N-dimethyl-amine

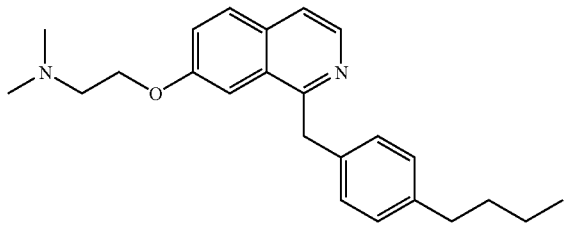

The title compound was obtained in the same manner as in Example B148.
¹H-NMR(CDCl₃)δ(ppm): 0.89(3H, t), 1.27-1.36(2H, m), 1.50-1.57(2H, m), 2.35(6H, s), 2.53(2H, t), 2.75(2H, t), 4.06(2H, t), 4.58(2H, s), 7.06(2H, d), 7.18(2H, d), 7.30-7.33(1H, m), 7.36(1H, d), 7.48(1H, d), 7.70(1H, d), 8.39(1H, d)

EXAMPLE B166

1-(4-Butylbenzyl)-7-isoquinolyl-(2-morpholinoethyl)ether

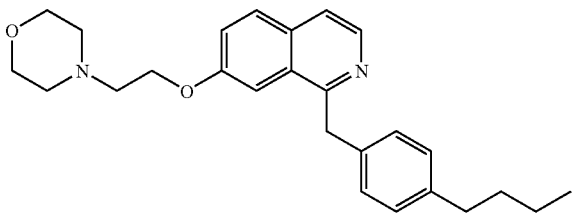

The title compound was obtained in the same manner as in Example B148.
¹H-NMR(CDCl₃)δ(ppm): 0.89(3H, t), 1.27-1.36(2H, m), 1.50-1.58(2H, m), 2.51-2.58(6H, m), 2.81(2H, t), 3.75(4H, t), 4.11(2H, t), 4.58(2H, s), 7.06(2H, d), 7.17(2H, d), 7.28-7.31(1H, m), 7.35(1H, d), 7.49(1H, d), 7.71(1H, d), 8.39(1H, d)

EXAMPLE B167

7-(Benzyloxy)-1-(4-butylbenzyl)isoquinoline

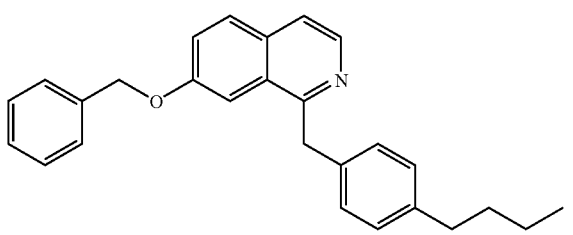

The title compound was obtained in the same manner as in Example B148.
¹H-NMR(CDCl₃)δ(ppm): 0.89(3H, t), 1.27-1.36(2H, m), 1.50-1.54(2H, m), 2.54(2H, t), 4.54(2H, s), 5.06(2H, s), 7.05(2H, d), 7.14(2H, d), 7.34-7.43(7H, m), 7.49(1H, d), 7.72(1H, d), 8.39(1H, d)

EXAMPLE B168

1-(4-Butylbenzyl)-7-(2-pyridylmethoxy)isoquinoline

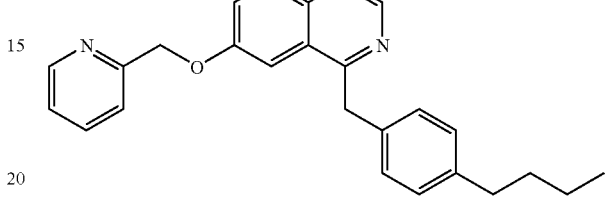

The title compound was obtained in the same manner as in Example B148.
¹H-NMR(CDCl₃)δ(ppm): 0.89(3H, t), 1.27-1.36(2H, m), 1.49-1.57(2H, m), 2.52(2H, t), 4.51(2H, s), 5.25(2H, s), 7.02(2H, d), 7.14(2H, d), 7.24-7.27(1H, m), 7.40(1H, dd), 7.47-7.50(3H, m), 7.68-7.72(1H, d), 7.74(1H, d), 8.39(1H, d), 8.64-8.66(1H, m)

EXAMPLE B169

1-(4-Butylbenzyl)-7-(3-pyridylmethoxy)isoquinoline

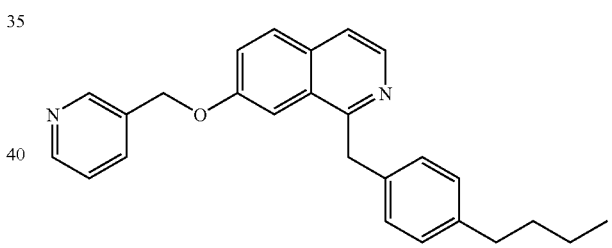

The title compound was obtained in the same manner as in Example B148.
¹H-NMR(CDCl₃)δ(ppm): 0.89(3H, t), 1.27-1.36(2H, m), 1.50-1.58(2H, m), 2.54(2H, t), 4.57(2H, s), 5.06(2H, s), 7.07(2H, d), 7.15(2H, d), 7.31-7.36(2H, m), 7.42(1H, d), 7.51(1H, d), 7.74-7.76(2H, m), 8.42(1H, d), 8.61-8.62(1H, m), 8.69-8.70(1H, m)

EXAMPLE B170

1-(4-Butylbenzyl)-7-(4-pyridylmethoxy)isoquinoline

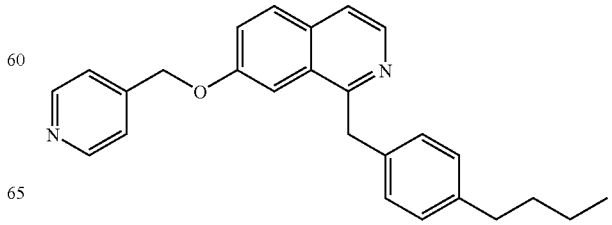

The title compound was obtained in the same manner as in Example B148.

$^1$H-NMR(CDCl$_3$)δ(ppm): 0.89(3H, t), 1.27-1.36(2H, m), 1.50-1.56(2H, m), 2.54(2H, t), 4.53(2H, s), 5.09(2H, s), 7.04 (2H, d), 7.09(2H, d), 7.33-7.39(4H, m), 7.51(1H, d), 7.76(1H, d), 8.41(1H, d), 8.63-8.64(2H, m)

EXAMPLE B171

1-(4-Butylbenzyl)-7-[(2-methoxybenzyl)oxy]isoquinoline

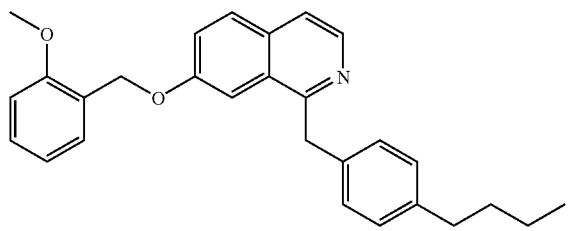

The title compound was obtained in the same manner as in Example B148.

$^1$H-NMR(CDCl$_3$)δ(ppm): 0.89(3H, t), 1.27-1.36(2H, m), 1.50-1.57(2H, m), 2.53(2H, t), 3.82(3H, s), 4.52(2H, s), 5.04 (2H, s), 6.88-6.91(1H, m), 6.99-7.02(2H, m), 7.05(2H, d), 7.14(2H, d), 7.32(1H, t), 7.36(1H, dd), 7.43(1H, d), 7.48(1H, d), 7.72(1H, d), 8.39(1H, d)

EXAMPLE B172

1-(4-Butylbenzyl)-7-[(3-methoxybenzyl)oxy]isoquinoline

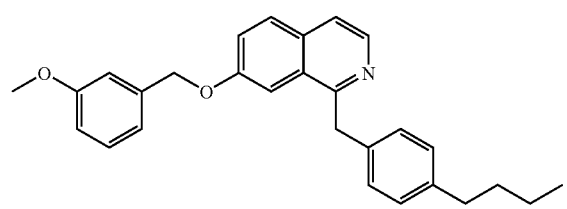

The title compound was obtained in the same manner as in Example B148.

$^1$H-NMR(CDCl$_3$)δ(ppm): 0.89(3H, t), 1.27-1.36(2H, m), 1.50-1.56(2H, m), 2.53(2H, t), 3.90(3H, s), 4.53(2H, s), 5.16 (2H, s), 6.93-6.98(2H, m), 7.03(2H, d), 7.15(2H, d), 7.30-7.35(1H, m), 7.37(1H, dd), 7.41-7.43(1H, m), 7.47(1H, d), 7.51(1H, d), 7.71(1H, d), 8.37(1H, d)

EXAMPLE B173

1-(4-Butylbenzyl)-7-[(4-methoxybenzyl)oxy]isoquinoline

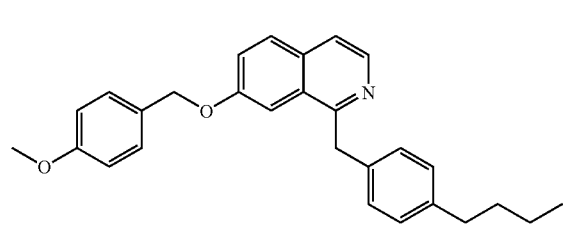

The title compound was obtained in the same manner as in Example B148.

$^1$H-NMR(CDCl$_3$)δ(ppm): 0.89(3H, t), 1.27-1.37(2H, m), 1.51-1.57(2H, m), 2.54(2H, t), 3.83(3H, s), 4.55(2H, s), 4.99 (2H, s), 6.93(2H, d), 7.06(2H, d), 7.15(2H, d), 7.32-7.36(3H, m), 7.44(1H, d), 7.48(1H, d), 7.71(1H, d), 8.38(1H, d)

EXAMPLE B174

7-(1,3-Benzodioxol-5-ylmethoxy)-1-(4-butylbenzyl)isoquinoline

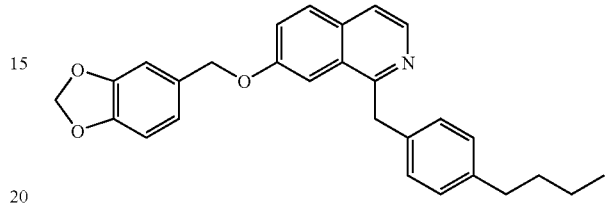

The title compound was obtained in the same manner as in Example B148.

$^1$H-NMR(CDCl$_3$)δ(ppm): 0.89(3H, t), 1.27-1.37(2H, m), 1.51-1.57(2H, m), 2.54(2H, t), 4.55(2H, s), 4.95(2H, s), 5.98 (2H, s), 6.82(1H, d), 6.88(1H, dd), 6.92(1H, d), 7.06(2H, d), 7.15(2H, d), 7.33(1H, dd), 7.42(1H, d), 7.48(1H, d), 7.72(1H, d), 8.39(1H, d)

EXAMPLE B175

1-(4-Butylbenzyl)-7-[(2-nitrobenzyl)oxy]isoquinoline

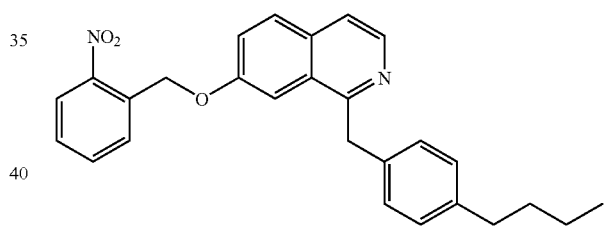

The title compound was obtained in the same manner as in Example B148.

$^1$H-NMR(CDCl$_3$)δ(ppm): 0.87(3H, t), 1.26-1.34(2H, m), 1.48-1.56(2H, m), 2.51(2H, t), 4.53(2H, s), 5.49(2H, s), 7.03 (2H, d), 7.14(2H, d), 7.40(1H, dd), 7.430-7.434(1H, m), 7.45-7.49(1H, m), 7.51(1H, d), 7.64-7.68(1H, m), 7.76(1H, d), 7.85-7.87(1H, m), 8.22-8.24(1H, d), 8.41(1H, d)

EXAMPLE B176

1-(4-Butylbenzyl)-7-[(3-nitrobenzyl)oxy]isoquinoline

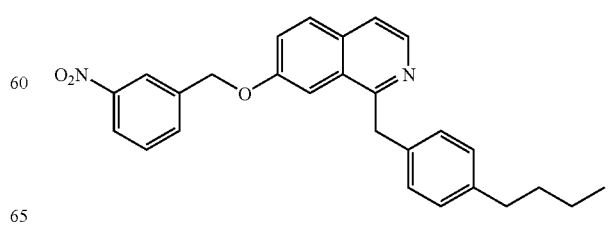

The title compound was obtained in the same manner as in Example B148.

$^1$H-NMR(CDCl$_3$)δ(ppm): 0.89(3H, t), 1.27-1.36(2H, m), 1.50-1.56(2H, m), 2.54(2H, t), 4.55(2H, s), 5.14(2H, s), 7.05 (2H, d), 7.11(2H, d), 7.37-7.40(2H, m), 7.51(1H, d), 7.55-7.59(1H, m), 7.73-7.78(2H, m), 8.19-8.22(1H, m), 8.32-8.33 (1H, m), 8.42(1H, d)

EXAMPLE B177

1-(4-Butylbenzyl)-7-(phenethyloxy)isoquinoline

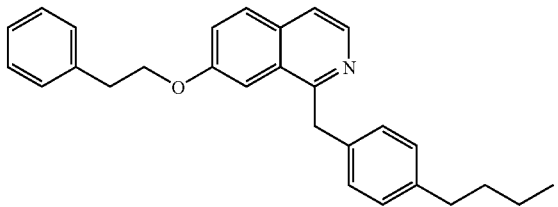

The title compound was obtained in the same manner as in Example B148.

$^1$H-NMR(CDCl$_3$)δ(ppm): 0.89(3H, t), 1.26-1.36(2H, m), 1.49-1.57(2H, m), 2.52(2H, t), 3.10(2H, t), 4.18(2H, t), 4.56 (2H, s), 7.04(2H, d), 7.16(2H, d), 7.26-7.28(4H, m), 7.33-7.35(3H, m), 7.48(1H, d), 7.70(1H, d), 8.38-8.39(1H, m)

EXAMPLE B178

1-(4-Butylbenzyl)-7-(3-phenylpropoxy)isoquinoline

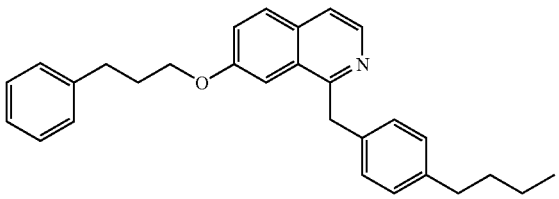

The title compound was obtained in the same manner as in Example B148.

$^1$H-NMR(CDCl$_3$)δ(ppm): 0.89(3H, t), 1.27-1.36(2H, m), 1.49-1.57(2H, m), 2.09-2.15(2H, m), 2.52(2H, t), 2.82(2H, t), 3.97(2H, t), 4.55(2H, s), 7.04(2H, d), 7.16(2H, d), 7.20-7.23 (3H, m), 7.27-7.33(4H, m), 7.48(1H, d), 7.70(1H, d), 8.38 (1H, d)

EXAMPLE B179

1-(4-Butylbenzyl)-7-(2-cyclohexylethoxy)isoquinoline

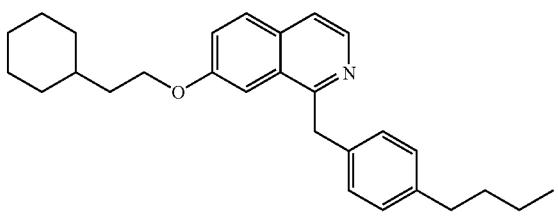

The title compound was obtained in the same manner as in Example B148.

$^1$H-NMR(CDCl$_3$)δ(ppm): 0.89(3H, t), 0.94-1.02(2H, m), 1.17-1.36(4H, m), 1.36-1.57(4H, m), 1.65-1.76(7H, m), 2.53 (2H, t), 3.98(2H, t), 4.58(2H, s), 7.06(2H, d), 7.19(2H, d), 7.25-7.28(1H, m), 7.33(1H, d), 7.47(1H, d), 7.69(1H, d), 8.37(1H, d)

EXAMPLE B180

6-Benzoyl-5,6-dihydro[1,3]dioxolo[4,5-g]isoquinoline-5-carbonitrile

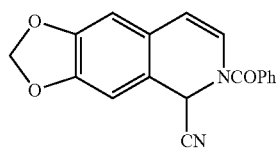

The title compound was obtained by treating [1,3]dioxolo [4,5-g]isoquinoline in the same manner as in Example B140.

$^1$H-NMR(CDCl$_3$)δ(ppm): 5.94-5.96(1H, m), 6.03(1H, d), 6.04(1H, d), 6.47-6.54(2H, m), 6.70(1H, s), 6.83(1H, s), 7.45-7.49(2H, m), 7.54-7.62(3H, m)

EXAMPLE B181

5-(4-Butylbenzyl) [1,3]dioxolo[4,5-g]isoquinoline

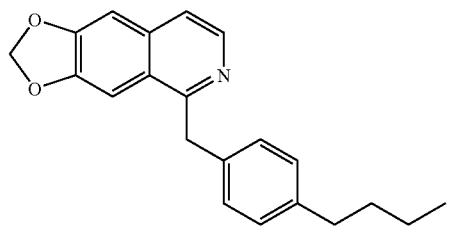

The title compound was obtained by treating the compound of Example B180 and the compound of Example B1 in the same manner as in Example B2.

$^1$H-NMR(CDCl$_3$)δ(ppm): 0.90(3H, t), 1.28-1.37(2H, m), 1.51-1.57(2H, m), 2.54(2H, t), 4.50(2H, s), 6.05(2H, s), 7.05-7.07(3H, m), 7.16(2H, d), 7.38(7.40(2H, m), 8.35(1H, d)

EXAMPLE B182

2-Benzoyl-6-bromo-1,2-dihydro-1-isoquinolinecarbonitrile

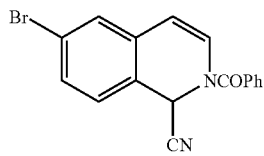

The title compound was obtained by treating 6-bromoisoquinoline, which was synthesized according to J. Am. Chem. Soc., 183 (1942), in the same manner as in Example B140.

¹H-NMR(CDCl₃)δ(ppm): 6.01(1H, d), 6.53(1H, brs), 6.70 (1H, brd), 7.24(1H, d), 7.33(1H, d), 7.47-7.51(3H, m), 7.56 (3H, m)

EXAMPLE B183

6-Bromo-1-(4-butylbenzyl)isoquinoline

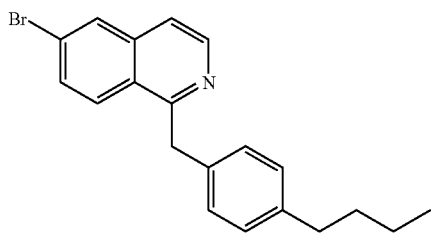

The title compound was obtained by treating the compound of Example B182 and the compound of Example B1 in the same manner as in Example B2.

¹H-NMR(CDCl₃)δ(ppm): 0.89(3H, t), 1.27-1.36(2H, m), 1.50-1.58(2H, m), 2.53(2H, t), 4.60(2H, s), 7.06(2H, d), 7.15 (2H, d), 7.46(1H, d), 7.59(1H, q), 7.98(1H, d), 8.02(1H, d), 8.51(1H, d)

EXAMPLE B184

A mixture of 2-benzoyl-5-bromo-1,2-dihydro-1-isoquinoline-carbonitrile and 2-benzoyl-7-bromo-1,2-dihydro-1-isoquinoline-carbonitrile

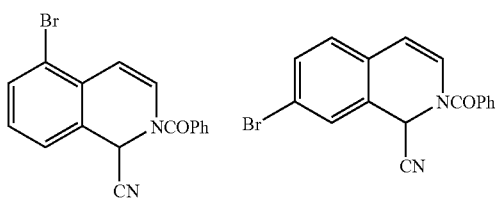

The title compounds were obtained by treating 5-or 7-bromoisoquinoline, which was synthesized according to J. Am. Chem. Soc., 61, 183 (1939), in the same manner as in Example B140. The obtained compounds were used in the following reaction without separation and purification.

EXAMPLE B185

7-Bromo-1-(4-butylbenzyl)isoquinoline

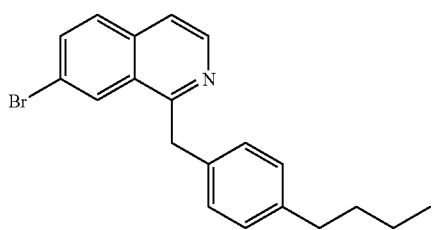

The title compound was obtained by treating the compound of Example B184 and the compound of Example B1 in the same manner as in Example B2.

¹H-NMR(CDCl₃)δ(ppm): 0.90(3H, t), 1.28-1.37(2H, m), 1.51-1.58(2H, m), 2.55(2H, t), 4.58(2H, s), 7.09(2H, d), 7.18 (2H, d), 7.51-7.53(1H, m), 7.69-7.70(2H, m), 8.33-8.34(1H, m), 8.52(1H, d)

EXAMPLE B186

5-Benzoyl-4,5-dihydrothieno[3,2-c]pyridine-4-carbonitrile

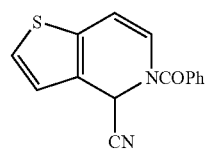

The title compound was obtained by treating thieno[3,2-c]pyridine, synthesized according to J. Heterocycl. Chem., 30, 183 (1993), in the same manner as in Example B140.

¹H-NMR(CDCl₃)δ(ppm): 6.05(1H, d), 6.57(1H, brd), 6.66 (1H, s), 7.07(1H, d), 7.32(1H, d), 7.46-7.50(2H, m), 7.54-7.62(3H, m)

EXAMPLE B187

4-(4-Butylbenzyl)thieno[3,2-c]pyridine

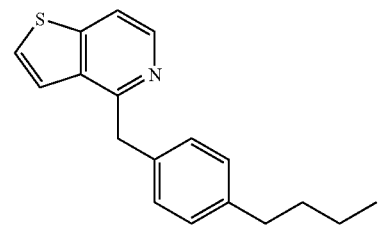

The title compound was obtained by treating the compound of Example B186 and the compound of Example B1 in the same manner as in Example B2.

¹H-NMR(CDCl₃)δ(ppm): 0.90(3H, t), 1.27-1.37(2H, m), 1.51-1.59(2H, m), 2.54(2H, t), 4.47(2H, s), 7.07(2H, d), 7.19 (2H, d), 7.42(1H, d), 7.47(1H, dd), 7.68(1H, d), 8.41(1H, d)

EXAMPLE B188

4-(4-Methoxybenzyl)thieno[3,2-c]pyridine

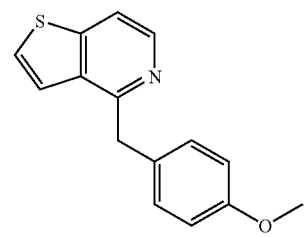

The title compound was obtained by treating the compound of Example B186 and 4-methoxybenzyl chloride in the same manner as in Example B2.

$^1$H-NMR(CDCl$_3$)δ(ppm): 3.75(3H, s), 4.44(2H, s), 6.79-6.82(2H, m), 7.19-7.22(2H, m), 7.43(1H, d), 7.46(1H, dd), 7.68(1H, d), 8.41(1H, d)

EXAMPLE B189

4-(Thieno[3,2-c]pyridin-4-ylmethyl)phenyl trifluoromethane-sulfonate

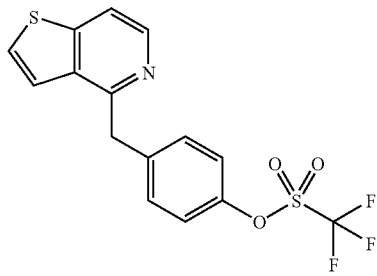

A solution of boron tribromide in methylene chloride (1.0 M, 10 ml, 10 mmol) was added dropwise to a solution of the compound of Example B188 (510 mg, 2.0 mmol) in methylene chloride (10 ml) cooled to 0° C., and this reaction mixture was stirred at that temperature for 1.5 hours. The reaction mixture was made weakly alkaline by addition of a saturated aqueous sodium hydrogencarbonate solution, extracted with ethyl acetate, dried over anhydrous magnesium sulfate, and then concentrated under reduced pressure. The obtained residue was dissolved in pyridine, and the resulting solution was cooled to 0° C. After trifluoromethanesulfonic anhydride (0.34 ml, 2.1 mmol) was added dropwise thereto, the mixture was stirred at that temperature for 2 hours, poured on ice, extracted with ethyl acetate, dried over anhydrous magnesium sulfate, and then concentrated under reduced pressure. The residue was purified by silica gel chromatography to give the title compound (312 mg).

$^1$H-NMR(CDCl$_3$)δ(ppm): 4.52(2H, s), 7.16-7.18(2H, m), 7.36(2H, m), 7.43-7.44(1H, m), 7.49(1H, d), 7.73(1H, d), 8.42(1H, d)

EXAMPLE B190

4-(4-Bromobenzyl)thieno[3,2-c]pyridine

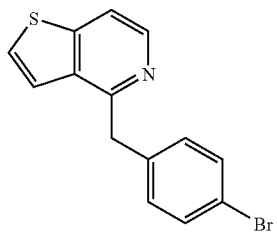

The title compound was obtained by treating the compound of Example B186 and the compound of Example B31 in the same manner as in Example B2.

$^1$H-NMR(CDCl$_3$)δ(ppm): 4.45(2H, s), 7.14-7.16(2H, m), 7.37-7.39(2H, m), 7.41-7.43(1H, m), 7.45(1H, d), 7.71(1H, d), 8.41(1H, d)

EXAMPLE B191

4-(4-Bromo-2-fluorobenzyl)thieno[3,2-c]pyridine

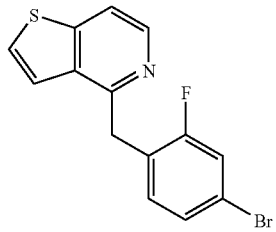

The title compound was obtained by treating the compound of Example B186 and 4-bromo-2-fluorobenzyl bromide in the same manner as in Example B2.

$^1$H-NMR(CDCl$_3$)δ(ppm): 4.46(2H, s), 7.11(1H, t), 7.15-7.18(1H, m), 7.22-7.25(1H, m), 7.47(1H, d), 7.49(1H, d), 7.71(1H, d), 8.41(1H, d)

EXAMPLE B192

4-{4-[4-(Tetrahydro-2H-2-pyranyloxy)-1-butynyl]benzyl}thieno[3,2-c]pyridine

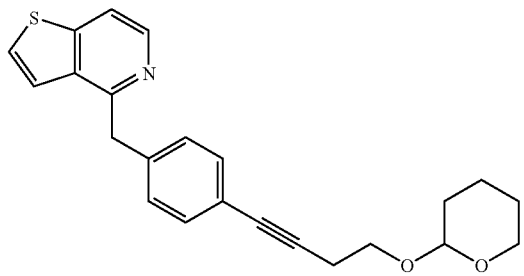

The title compound was obtained by treating the compound of Example B189 and 2-(3-butynyloxy)tetrahydro-2H-pyran in the same manner as in Example B42.

$^1$H-NMR(CDCl$_3$)δ(ppm): 1.40-1.90(6H, m), 2.69(2H, t), 3.45-3.65(2H, m), 3.78-3.95(2H, m), 4.48(2H, s), 4.66-4.69 (1H, m), 7.18(2H, d), 7.27(2H, d), 7.41(1H, d), 7.44(1H, d), 7.70(1H, d), 8.41(1H, d).

EXAMPLE B193

4-[4-(Thieno[3,2-c]pyridin-4-ylmethyl)phenyl]-3-butyn-1-ol

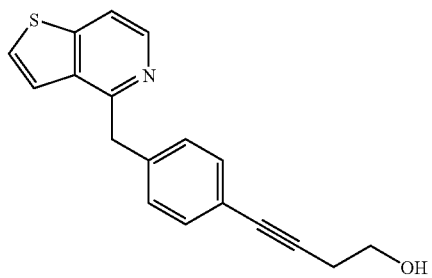

The title compound was obtained by treating the compound of Example B192 in the same manner as in Example B47.

$^1$H-NMR(CDCl$_3$)δ(ppm): 2.67(2H, t), 3.79(2H, t), 4.50 (2H, s), 7.20(2H, d), 7.32(2H, d), 7.41(1H, d), 7.44(1H, d), 7.71(1H, d), 8.42(1H, d).

The proton of the hydroxyl group was not observed in the NMR spectrum.

EXAMPLE B194

6-Benzoyl-6,7-dihydrothieno[2,3-c]pyridine-7-carbonitrile

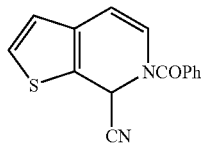

The title compound was obtained by treating thieno[2,3-c]pyridine, which was synthesized according to J. Heterocycl. Chem., 30, 183 (1993), in the same manner as in Example B140.

$^1$H-NMR(CDCl$_3$)δ(ppm): 6.07(1H, d), 6.56(1H, brd), 6.75 (1H, s), 6.97(1H, d), 7.37(1H, d), 7.46-7.51(2H, m), 7.54-7.64(3H, m)

EXAMPLE B195

7-(4-Butylbenzyl)thieno[2,3-c]pyridine

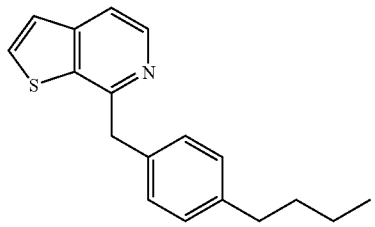

The title compound was obtained by treating the compound of Example B194 and the compound of Example B1 in the same manner as in Example B2.

$^1$H-NMR(CDCl$_3$)δ(ppm): 0.90(3H, t), 1.28-1.37(2H, m), 1.51-1.59(2H, m), 2.55(2H, t), 4.40(2H, s), 7.09(2H, d), 7.28 (2H, d), 7.34(1H, d), 7.57(1H, d), 7.62(1H, d), 8.47(1H, d)

EXAMPLE B196

7-(4-Methoxybenzyl)thieno[2,3-c]pyridine

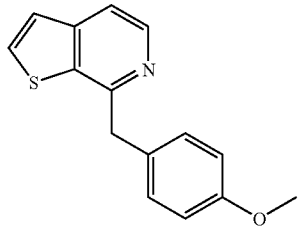

The title compound was obtained by treating the compound of Example B194 and 4-methoxybenzyl chloride in the same manner as in Example B2.

$^1$H-NMR(CDCl$_3$)δ(ppm): 3.76(3H, s), 4.38(2H, s), 6.81-6.83(2H, m), 7.28-7.30(2H, m), 7.35(1H, d), 7.57(1H, d), 7.62(1H, d), 8.47(1H, d)

EXAMPLE B197

4-(Thieno[2,3-c]pyridin-7-ylmethyl)phenyl trifluoromethane-sulfonate

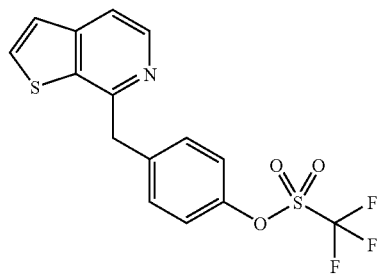

The title compound was obtained by treating the compound of Example B196 in the same manner as in Example B189.

$^1$H-NMR(CDCl$_3$)δ(ppm): 4.44(2H, s), 7.17-7.19(2H, m), 7.38-7.40(1H, m), 7.44-7.46(2H, m), 7.61(1H, d), 7.65-7.67 (1H, m), 8.47-8.49(1H, m)

EXAMPLE B198

7-(4-Bromobenzyl)thieno[2,3-c]pyridine

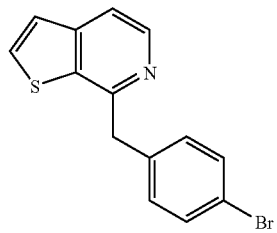

The title compound was obtained by treating the compound of Example B194 and the compound of Example B31 in the same manner as in Example B2.

$^1$H-NMR(CDCl$_3$)δ(ppm): 4.37(2H, s), 7.23-7.25(2H, m), 7.37(1H, d), 7.39-7.41(2H, m), 7.59(1H, d), 7.63-7.65(1H, m), 8.47(1H, d)

EXAMPLE B199

7-(4-Bromo-2-fluorobenzyl)thieno[2,3-c]pyridine

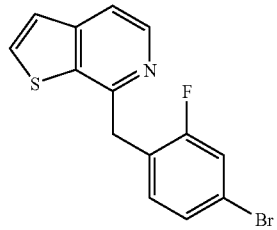

The title compound was obtained by treating the compound of Example B194 and 4-bromo-2-fluorobenzyl bromide in the same manner as in Example B2.

¹H-NMR(CDCl₃)δ(ppm): 4.40-4.41(2H, m), 7.12-7.20 (2H, m), 7.23-7.26(1H, m), 7.37-7.39(1H, m), 7.59-7.62(1H, m), 7.65-7.67(1H, m), 8.45-8.47(1H, m)

EXAMPLE B200

7-{4-[4-(Tetrahydro-2H-2-pyranyloxy)-1-butynyl]benzyl}thieno[2,3-c]pyridine

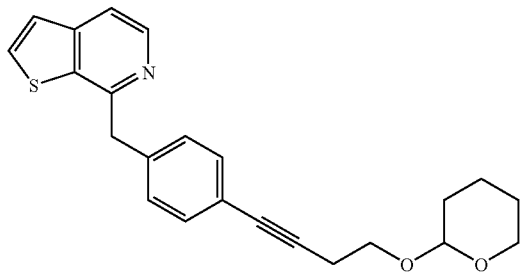

The title compound was obtained by treating the compound of Example B197 and 2-(3-butynyloxy)tetrahydro-2H-pyran in the same manner as in Example B42.
¹H-NMR(CDCl₃)δ(ppm): 1.50-1.90(6H, m), 2.69(2H, t), 3.49-3.54(1H, m), 3.58-3.65(1H, m), 3.85-3.95(2H, m), 4.41 (2H, s), 4.68(1H, t), 7.26-7.31(4H, m), 7.36(1H, d), 7.58(1H, d), 7.63(1H, d), 8.47(1H, d).

EXAMPLE B201

4-[4-(Thieno[2,3-c]pyridin-7-ylmethyl)phenyl]-3-butyn-1-ol

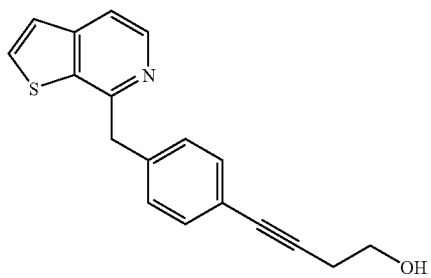

The title compound was obtained by treating the compound of Example B200 in the same manner as in Example B47.
¹H-NMR(CDCl₃)δ(ppm): 1.99(1H, brs), 2.67(2H, t), 3.79 (2H, t), 4.42(2H, s), 7.27-7.34(4H, m), 7.36(1H, d), 7.59(1H, d), 7.64(1H, d), 8.47(1H, d).

EXAMPLE B202

2-Chloro-3-(methoxymethoxy)pyridine

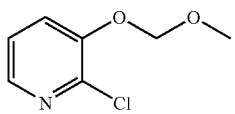

Sodium hydride (66%, 633 mg, 17.4 mmol) was added to an ice-cooled solution of 2-chloro-3-hydroxypyridine (2.05 g, 15.8 mmol) in tetrahydrofuran (30 ml) under nitrogen atmosphere, and this reaction mixture was stirred at that temperature for 15 minutes. Chloromethyl methyl ether (1.32 ml, 17.4 mmol) was added, and the resulting reaction mixture was stirred at that temperature for 30 minutes, then at room temperature for another 2 hours. After water was added, the reaction mixture was extracted with ethyl acetate, washed with saturated brine, and then concentrated under reduced pressure. The residue was purified by silica gel column chromatography to give the title compound (2.44 g).
¹H-NMR(CDCl₃)δ(ppm): 3.53(3H, s), 5.28(2H, s), 7.19 (1H, dd), 7.49(1H, dd), 8.06(1H, dd)

EXAMPLE B203

2-Chloro-4-iodo-3-(methoxymethoxy)pyridine

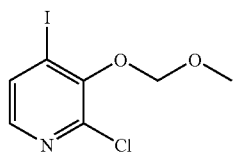

A solution of the compound of Example B202 (1.40 g, 8.06 mmol) in diethyl ether (8 ml) was added dropwise to a solution of 1.51 M t-butyllithium-n-pentane solution (8.01 ml, 12.1 mmol) in diethyl ether (15 ml) cooled to −78° C. under nitrogen atmosphere, and the reaction mixture was stirred at that temperature for 15 minutes. After iodine (3.07 g, 12.1 mmol) was added, the reaction mixture was gradually warmed to room temperature. An aqueous sodium thiosulfate solution was further added, and the diethyl ether layer was separated, washed with saturated brine, and then concentrated under reduced pressure. The residue was purified by silica gel column chromatography to give the title compound (356 mg).
¹H-NMR(CDCl₃)δ(ppm): 3.73(3H, s), 5.22(2H, s), 7.69 (1H, d), 7.80(1H, d)

EXAMPLE B204

7-Chlorofuro[2,3-c]pyridine

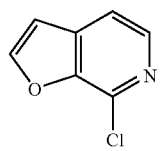

Trimethylsilylacetylene (28.3 μl, 0.201 mmol) and triethylamine (59.8 □l, 0.429 mmol) were added to a solution of the compound of Example B203 (36.6 mg, 0.143 mmol), tetrakis (triphenylphosphine)palladium (16.5 mg, 0.0143 mmol), and copper(I) iodide (2.7 mg, 0.014 mmol) in dimethylformamide (1.5 ml), and this mixture was stirred at 50° C. for 4 hours. After allowing the mixture to cool to room temperature, water was added thereto, and the resulting mixture was extracted with ethyl acetate, washed with saturated brine, and then concentrated under reduced pressure. The residue was dissolved in methanol (5 ml), potassium carbonate (100 mg, 0.724 mmol) was added thereto, and the resulting mixture was stirred at room temperature for 1 hour. After water was added, the mixture was extracted with diethyl ether, washed with saturated brine, and then concentrated under reduced pressure. The residue was purified by silica gel column chromatography to give the title compound (5.5 mg).

$^1$H-NMR(CDCl$_3$)δ(ppm): 6.89(1H, d), 7.51(1H, d), 7.83 (1H, d), 8.21(1H, d)

EXAMPLE B205

4-Butylbenzylmagnesium chloride

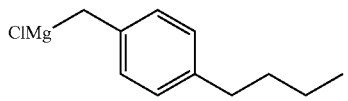

A mixed solution of the compound of Example B1 (1.04 g, 5.69 mmol), magnesium (761 mg, 31.3 mmol), and a catalytic amount of 1,2-dibromoethane in diethyl ether (11 ml) was initiated by heating under reflux. After the heat source was removed, a solution of the compound of Example B 1(4.16 g, 22.8 mmol) in diethyl ether (60 ml) was added dropwise to the reaction mixture at a rate that maintains gentle reflux, and the mixture was heated under reflux for 30 minutes. The mixture was then allowed to cool to room temperature to give the title compound as a 0.4 M solution in diethyl ether. This solution was used in the following reaction as it is.

EXAMPLE B206

7-(4-Butylbenzyl)furo[2,3-c]pyridine

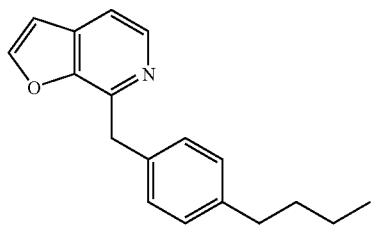

The compound of Example B205 (300 μl, 0.1 mmol) was added to a solution of the compound of Example B204 (5.0 mg, 0.033 mmol) and [1,1'-bis(diphenylphosphino)ferrocene]dichloronickel(II) (4.5 mg, 0.0065 mmol) in tetrahydrofuran (1 ml), and the mixture was stirred at 50° C. for 1 hour. After allowing the mixture to cool to room temperature, ethyl acetate was added thereto. The resulting mixture was washed with a saturated aqueous ammonium chloride solution and saturated brine, then concentrated under reduced pressure. The residue was purified by NH-silica gel column chromatography to give the title compound (2.9 mg).

$^1$H-NMR(CDCl$_3$)δ(ppm): 0.89(3H, t), 1.29-1.35(2H, m), 1.50-1.58(2H, m), 2.54(2H, t), 4.40(2H, s), 6.78(1H, d), 7.08 (2H, d), 7.30(2H, d), 7.40(1H, d), 7.72(1H, d), 8.34(1H, d)

EXAMPLE B207

7-(4-Butylbenzyl)-1H-pyrrolo[2,3-c]pyridine

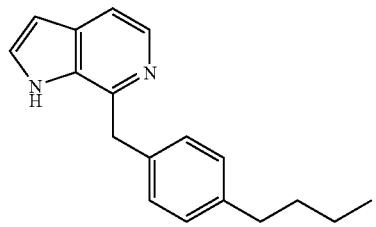

The compound of Example B205 (800 μl, 0.3 mmol) was added to a solution of 1-chloropyrrolopyridine (19.4 mg, 0.127 mmol), which was synthesized from 2-chloro-3-aminopyridine according to the method of H07-165,708A, and dichloro(diphenylphosphinopropane)nickel (6.9 mg, 0.013 mmol) in tetrahydrofuran (1 ml) under ice-cooling, and the mixture was stirred while heating under reflux for 4 hours. After allowing the mixture to cool to room temperature, ethyl acetate was added thereto. The resulting mixture was washed with a saturated aqueous ammonium chloride solution and saturated brine, then concentrated under reduced pressure. The residue was purified by silica gel column chromatography to give the title compound (7.1 mg).

$^1$H-NMR(CDCl$_3$)δ(ppm): 0.91(3H, t), 1.31-1.37(2H, m), 1.55-1.59(2H, m), 2.58(2H, t), 4.44(2H, s), 6.50(1H, d), 7.12 (2H, d), 7.18(1H, d), 7.22(2H, d), 7.45(1H, d), 8.21(1H, d)

The NH proton was not observed in the NMR spectrum.

EXAMPLE B208

4-(4-Butylbenzyl)-1-imidazo[4,5-c]pyridine

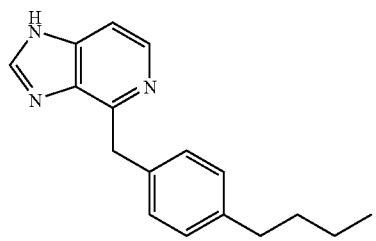

The compound of Example B205 (3.45 ml, 1.38 mmol) was added to a solution of 1-chloroimidazopyridine (88.6 mg, 0.577 mmol), which was synthesized from 4-amino-2-chloropyridine according to the method described in J. Heterocycl. Chem., 2, 196 (1965), and dichloro(diphenylphosphinopropane)nickel (31.3 mg, 0.0577 mmol) in tetrahydrofuran (2 ml), and the mixture was stirred while heating under reflux for 2 hours. After allowing the mixture to cool to room temperature, ethyl acetate was added thereto. The resulting mixture was filtered through silica gel and concentrated under reduced pressure. The residue was purified by silica gel column chromatography to give the title compound (64.2 mg).

¹H-NMR(CDCl₃)δ(ppm): 0.86(3H, t), 1.23-1.32(2H, m), 1.44-1.52(2H, m), 2.47(2H, t), 4.56(2H, s), 7.02(2H, d), 7.19 (2H, d), 7.34(1H, d), 8.00(1H, s), 8.25-8.27(1H, m)

The NH proton was not observed in the NMR spectrum.

EXAMPLE B209

4-Bromo-1-isoquinolinyl

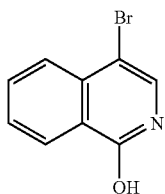

Bromine (1.78 ml, 34.5 mmol) was added to an ice-cooled solution of 1-hydroxyisoquinoline (5.01 g, 34.5 mmol) in acetic acid (50 ml), and this reaction mixture was stirred at room temperature for 2 hours. Water, ethyl acetate, and tetrahydrofuran were added, and the resulting reaction mixture was filtered through filter paper. The organic layer was washed with saturated brine and concentrated under reduced pressure. The residue was recrystallized from ethyl acetate and hexane to give the title compound (6.19 g).

¹H-NMR(DMSO-d6)δ(ppm): 7.56(1H, s), 7.59-7.63(1H, m), 7.76-7.78(1H, m), 7.84-7.89(1H, m), 8.23-8.26(1H, m), 11.59(1H, br s)

EXAMPLE B210

1,4-Dibromoisoquinoline

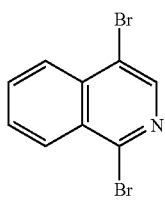

A mixed solution of the compound of Example B209 (1.40 g, 8.06 mmol) and phosphorus tribromide (6 ml) was stirred at 150° C. for 1 hour, and then heated under reflux for another 1 hour. The reaction mixture was allowed to cool to room temperature, poured on ice, then warmed to room temperature. Ethyl acetate was added, and the resulting mixture was washed with saturated brine and concentrated under reduced pressure. The residue was purified by silica gel column chromatography to give the title compound (845 mg).

¹H-NMR(CDCl₃)δ(ppm): 7.76-7.80(1H, m), 7.86-7.90 (1H, m), 8.19(1H, d), 8.31-8.34(1H, m), 8.48(1H, s)

EXAMPLE B211

4-Bromo-1-(4-butylbenzyl)isoquinoline

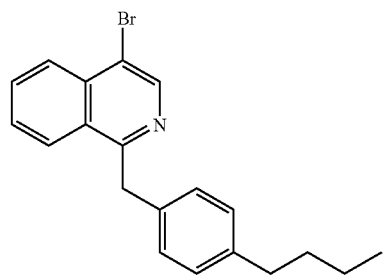

The compound of Example B205 (2.5 ml, 1 mmol) was added to a solution of the compound of Example B210 (200 mg, 0.697 mmol) and [1,1'-bis(diphenylphosphino)ferrocene]dichloronickel(II) (75.6 mg, 0.139 mmol) in tetrahydrofuran (2 ml), and the mixture was stirred at room temperature for 30 minutes. After ethyl acetate was added, the resulting mixture was washed successively with a saturated aqueous ammonium chloride solution, a saturated aqueous sodium hydrogencarbonate solution, and saturated brine, then concentrated under reduced pressure. The residue was purified by silica gel column chromatography to give the title compound (98 mg).

¹H-NMR(CDCl₃)δ(ppm): 0.89(3H, t), 1.29-1.34(2H, m), 1.51-1.60(2H, m), 2.53(2H, t), 4.59(2H, s), 7.06(2H, d), 7.16 (2H, d), 7.57-7.61(1H, m), 7.73-7.77(1H, m), 8.15-8.19(2H, m), 8.69(1H, s)

EXAMPLE B212

1-(4-Butylbenzyl)-5,6,7,8-tetrahydroisoquinoline

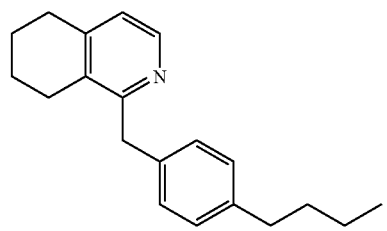

The compound of Example B211 (13.0 mg, 0.0367 mmol) was dissolved in a mixed solution of ethyl acetate and methanol (1:1, 1 ml), 10% palladium-carbon (containing 50% water, 13 mg) was added, and the mixture was stirred at room temperature under hydrogen atmosphere at atmospheric pressure for 12 hours. After purging the reaction system with nitrogen, the catalyst was removed by filtration through celite. The obtained filtrate was concentrated under reduced pressure to give the title compound (8.8 mg).

¹H-NMR(CDCl₃)δ(ppm): 0.90(3H, t), 1.28-1.38(2H, m), 1.52-1.59(2H, m), 1.74-1.82(4H, m), 2.55(2H, t), 2.66(2H, t), 2.81(2H, t), 4.26(2H, s), 7.07-7.15(5H, m), 8.32(1H, d)

EXAMPLE B213

1-[2-(Phenyl)benzyl]isoquinoline

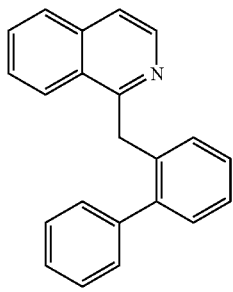

The title compound was obtained by treating 2-phenylbenzyl bromide instead of n-butylbenzyl chloride in the same manner as in Example B2.
$^1$H-NMR(CDCl$_3$)δ(ppm): 4.62(2H, s), 7.05(1H, d), 7.16(1H, dd), 7.22-7.50(8H, m), 7.52(1H, d), 7.58(1H, dd), 7.65(1H, d), 7.76(1H, d), 8.47(1H, d).

EXAMPLE B214

1-[4-Fluoro-2-(trifluoromethyl)benzyl]isoquinoline

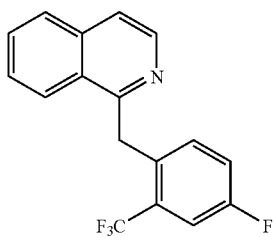

The title compound was obtained by treating 4-fluoro-2-(trifluoromethyl)benzyl methanesulfonate instead of n-butylbenzyl chloride in the same manner as in Example B2.
$^1$H-NMR(CDCl$_3$)δ(ppm): 4.83(2H, s), 6.87(1H, dd), 7.01(1H, ddd), 7.43(1H, dd), 7.54(1H, dd), 7.61(1H, d), 7.67(1H, dd), 7.85(1H, d), 7.96(1H, d), 8.49(1H, d).

EXAMPLE B215

1,3-Benzodioxoyl-4-yl-(1-isoquinolyl)methanol

The title compound was obtained by treating-2,3-methylenedioxybenzaldehyde in the same manner as in Example B82.
$^1$H-NMR(CDCl$_3$)δ(ppm): 5.97-5.99(1H, m), 6.09(1H, brs), 6.20-6.40(1H, m), 6.54-6.60(2H, m), 6.65-6.70(2H, m), 7.52(1H, dd), 7.63(1H, d), 7.64(1H, dd), 7.84(1H, d), 8.04(1H, d), 8.53(1H, d).

EXAMPLE B216

1,3-Benzodioxoyl-4-yl-(1-isoquinolyl)methyl acetate

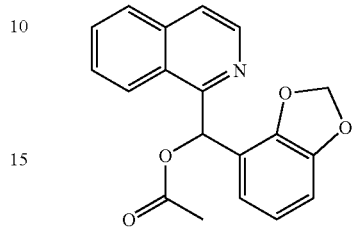

The title compound was obtained by treating the compound of Example B215 in the same manner as in Example B38.
$^1$H-NMR(CDCl$_3$)δ(ppm): 2.23(3H, s), 5.98-6.02(2H, m), 6.74-6.79(1H, m), 6.90-6.93(1H, m), 7.15-7.19(1H, m), 7.23-7.28(1H, m), 7.58(1H, dd), 7.60(1H, d), 7.66(1H, dd), 7.83(1H, d), 8.28(1H, d), 8.57(1H, d).

EXAMPLE B217

1-(1,3-Benzodioxoyl-4-ylmethyl)isoquinoline

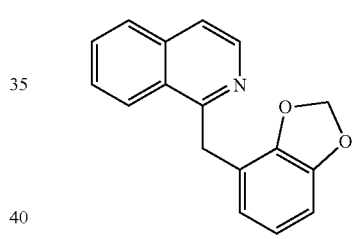

The title compound was obtained by treating the compound of Example B216 in the same manner as in Example B39.
$^1$H-NMR(CDCl$_3$)δ(ppm): 4.62(2H, s), 6.02(2H, s), 6.64-6.70(3H, m), 7.57(1H, dd), 7.58(1H, d), 7.66(1H, dd), 7.83(1H, d), 8.23(1H, d), 8.50(1H, d).

EXAMPLE B218

1-(1-Naphthylmethyl)isoquinoline

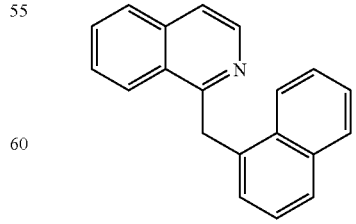

The title compound was obtained by treating 1-(chloromethyl)naphthalene instead of n-butylbenzyl chloride in the same manner as in Example B2.

¹H-NMR(CDCl₃)δ(ppm): 5.13(2H, s), 6.96(1H, d), 7.29 (1H, d), 7.45-7.67(5H, m), 7.72(1H, d), 7.84-7.90(2H, m), 8.08(1H, d), 8.26(1H, d), 8.52(1H, d).

EXAMPLE B219

3-Bromophenylbutyrate

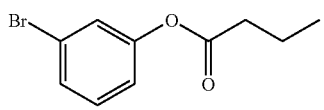

n-Butyryl chloride (7.25 ml) was added to an ice-cooled solution of 3-bromophenol (10.0 g) in pyridine (50 ml), and this reaction mixture was stirred at that temperature for 3 hours, then at room temperature for another 3.5 hours. After ice was added, the reaction mixture was extracted with ethyl acetate, washed with 1 N hydrochloric acid and water, dried over anhydrous magnesium sulfate, and then concentrated under reduced pressure. The residue was purified by silica gel column chromatography to give the title compound (12.77 g).
¹H-NMR(CDCl3)δ(ppm): 1.04(3H, t), 1.72-1.82(2H, m), 2.54(2H, t), 7.04(1H, dd), 7.22-7.29(2H, m), 7.36(1H, d).

EXAMPLE B220

1-(4-Bromo-2-hydroxyphenyl)-1-butanone

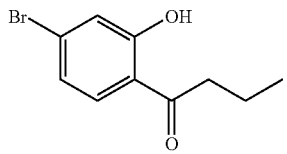

Aluminum chloride (10.51 g) was added to a solution of the compound of Example B219 (12.77 g) in chlorobenzene (70 ml) under nitrogen atmosphere, and this reaction mixture was stirred while heating under reflux for 9 hours. After the reaction mixture was cooled to room temperature, ice was added thereto. The resulting mixture was extracted with ethyl acetate, washed with water, dried over anhydrous magnesium sulfate, and then concentrated under reduced pressure. The compound thus obtained was used in the following reaction without further purification.
¹H-NMR(CDCl3)δ(ppm): 0.91(3H, t), 1.53-1.65(2H, m), 3.00(2H, t), 7.02(1H, dd), 7.19(1H, d), 7.78(1H, d), 12.50 (1H, s).

EXAMPLE B221

1-(4-Bromo-2-methoxyphenyl)-1-butanone

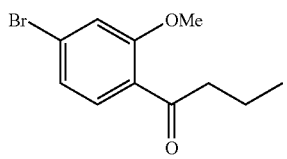

Potassium carbonate (9.07 g) and methyl iodide (3.92 ml) were added to a solution of the compound of Example B220 (13.30 g) in acetone (75 ml), and this reaction mixture was stirred while heating under reflux for 4 hours. The reaction mixture was filtered through celite, ether was added to remove insoluble material by filtration, and the filtrate was concentrated under reduced pressure. The residue was purified by silica gel column chromatography to give the title compound (9.52 g).
¹H-NMR(CDCl3)δ(ppm): 0.95(3H, t), 1.64-1.74(2H, m), 2.91(2H, t), 3.90(3H, s), 7.10(1H, d), 7.14(1H, dd), 7.54(1H, d).

EXAMPLE B222

4-Bromo-1-butyl-2-methoxybenzene

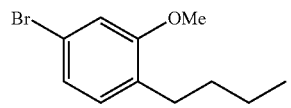

The title compound was obtained by treating the compound of Example B221 in the same manner as in Example B3.
¹H-NMR(CDCl3)δ(ppm): 0.92(3H, t), 1.29-1.39(2H, m), 1.48-1.56(2H, m), 2.54(2H, t), 3.81(3H, s), 6.95(1H, s), 6.96-7.02(2H, m).

EXAMPLE B223

(4-Butyl-3-methoxyphenyl)(1-isoquinolyl)ketone

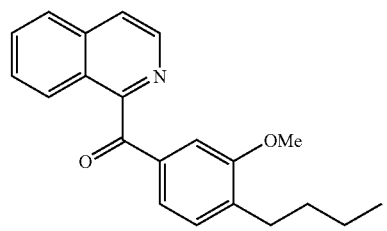

A mixture containing the title compound was obtained by treating the compound of Example B222 in the same manner as in Example B36.
This mixture was used in the following reaction without separation and purification.

EXAMPLE B224

(4-Butyl-3-methoxyphenyl)(1-isoquinolyl)methanol

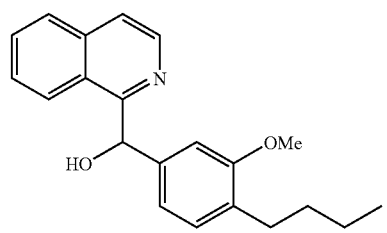

A mixture containing the title compound was obtained by treating the compound of Example B223 in the same manner as in Example B37.

This mixture was used in the following reaction without separation and purification.

EXAMPLE B225

(4-Butyl-3-methoxyphenyl)(1-isoquinolyl)methyl acetate

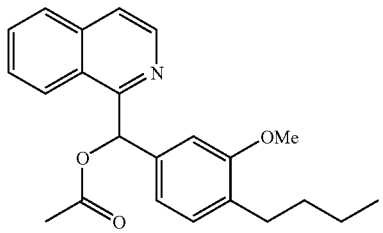

The title compound was obtained by treating the compound of Example B224 in the same manner as in Example B38.

$^1$H-NMR(CDCl3)δ(ppm): 0.90(3H, t), 1.24-1.38(2H, m), 1.46-1.60(2H, m), 2.24(3H, s), 2.54(2H, t), 3.76(3H, s), 6.97(1H, s), 6.98(1H, d), 7.06(1H, d), 7.53-7.67(4H, m), 7.83(1H, d), 8.26(1H, d), 8.58(1H, d).

EXAMPLE B226

1-(4-Butyl-3-methoxybenzyl)isoquinoline

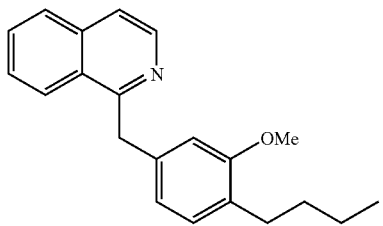

The title compound was obtained by treating the compound of Example B225 in the same manner as in Example B39.

$^1$H-NMR(CDCl3)δ(ppm): 0.89(3H, t), 1.27-1.38(2H, t), 1.45-1.54(2H, t), 2.52(2H, t), 3.72(3H, s), 4.63(2H, s), 6.78(1H, d), 6.79(1H, s), 6.99(1H, d), 7.53(1H, dd), 7.55(1H, d), 7.64(1H, dd), 7.80(1H, d), 8.19(1H, d), 8.49(1H, d).

EXAMPLE B227

2-Butyl-5-(1-isoquinolylomethyl)phenol

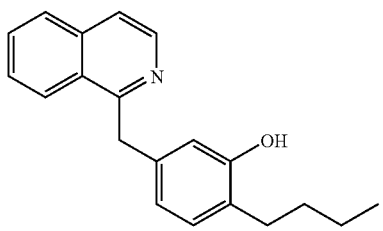

The title compound was obtained by treating the compound of Example B226 in the same manner as in Example B40.

$^1$H-NMR(CDCl3)δ(ppm): 0.91(3H, t), 1.30-1.40(2H, m), 1.52-1.65(2H, m), 2.55(2H, t), 4.55(2H, s), 6.46(1H, brs), 6.85(1H, d), 7.03(1H, d), 7.32-7.40(1H, m), 7.55(1H, dd), 7.68(1H, dd), 7.81(1H, d), 7.94-8.05(1H, m), 8.14(1H, d).

The proton of the phenolic hydroxyl group was not observed in the NMR spectrum.

EXAMPLE B228

2-Bromo-3-(methoxymethoxy)pyridine

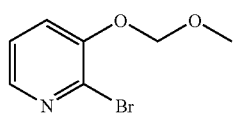

The title compound was synthesized in the same manner as in Example B202 by using 2-bromo-3-hydroxypyridine.

$^1$H-NMR(CDCl$_3$)δ(ppm): 3.53(3H, s), 5.29(2H, s), 7.19-7.23(1H, m), 7.42-7.45(1H, m), 8.04-8.06(1H, m)

EXAMPLE B229

2-(4-Butylbenzyl)-3-(methoxymethoxy)pyridine

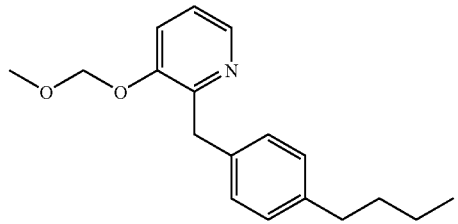

The compound of Example B205 (7 ml, 3 mmol) was added to an ice-cooled mixed solution of the compound of Example B228 (524 mg, 2.40 mmol) and dichloro(diphenylphosphinopropane)nickel (65.0 mg, 0.120 mmol) in tetrahydrofuran (10 ml), and the mixture was stirred while heating under reflux for 5 hours. After allowing the mixture to cool to room temperature, ethyl acetate was added. The resulting mixture was washed successively with a saturated aqueous ammonium chloride solution, a saturated aqueous sodium hydrogencarbonate solution, and saturated brine, then concentrated under reduced pressure. The residue was filtered through NH-silica gel. After concentrating under reduced pressure, the residue was dissolved in methanol (15 ml), triethylamine (500 μl, 3.59 mmol) and 10% palladium-carbon (containing 50% water, 50 mg) were added, and the resulting mixture was stirred at room temperature under hydrogen atmosphere at atmospheric pressure for 3 hours. After purging the reaction system with nitrogen, the catalyst was removed by filtration through celite, and the filtrate was concentrated under reduced pressure. The residue was purified by silica gel column chromatography to give the title compound (280 mg).

¹H-NMR(CDCl₃)δ(ppm): 0.89(3H, t), 1.28-1.34(2H, m), 1.52-1.58(2H, m), 2.53(2H, t), 3.33(3H, s), 4.16(2H, s), 5.16 (2H, s), 7.04-7.10(3H, m), 7.20(2H, d), 7.33-7.35(1H, m), 8.19-8.20(1H, m)

EXAMPLE B230

2-(4-Butylbenzyl)-3-pyridinol

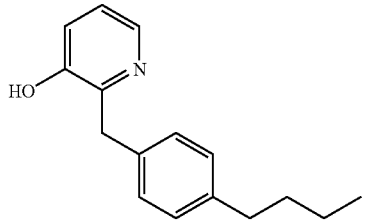

Trifluoroacetic acid (1 ml) was added to a solution of the compound of Example B229 (256 mg, 0.849 mmol) in methylene chloride (5 ml), and this reaction mixture was stirred at room temperature overnight. After a saturated aqueous sodium hydrogencarbonate solution and ethyl acetate were added, the reaction mixture was washed with saturated brine and concentrated under reduced pressure. The residue was purified by silica gel column chromatography to give the title compound (182 mg).

¹H-NMR(CDCl₃)δ(ppm): 0.90(3H, t), 1.28-1.37(2H, m), 1.51-1.58(2H, m), 2.54(2H, t), 4.20(2H, s), 7.02-7.08(4H, m), 7.22(2H, d), 8.08-8.09(1H, m)

The proton of the phenolic hydroxyl group was not observed in the NMR spectrum.

EXAMPLE B231

2-(4-Butylbenzyl)-3-methoxypyridine

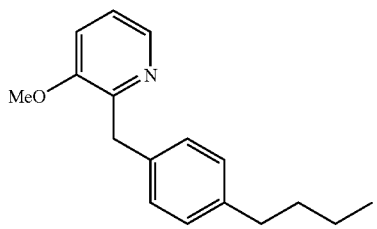

Potassium carbonate (33.0 mg, 0.239 mmol) and methyl iodide (14.9 µl, 0.239 mmol) were added to a solution of the compound of Example B230 (19.2 mg, 0.0796 mmol) in acetone (1 ml), and this reaction mixture was stirred at room temperature for 3 hours. After ethyl acetate was added, the reaction mixture was washed with saturated brine and concentrated under reduced pressure. The residue was purified by silica gel column chromatography to give the title compound (1.47 mg).

¹H-NMR(CDCl₃)δ(ppm): 0.90(3H, t), 1.32-1.34(2H, m), 1.53-1.57(2H, m), 2.54(2H, t), 3.82(3H, s), 4.14(2H, s), 7.06 (2H, d), 7.10-7.11(2H, m), 7.21(2H, d), 8.12-8.14(1H, m)

EXAMPLE B232

2-(4-Butylbenzyl)-3-chloropyridine

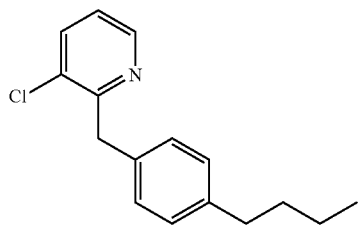

The compound of Example B205 (12 ml, 5 mmol) was added to an ice-cooled mixed solution of 2,3-dichloropyridine (525 mg, 3.55 mmol) and dichloro(diphenylphosphinopropane)nickel (96.2 mg, 0.178 mmol) in tetrahydrofuran (4 ml), and this reaction mixture was stirred at room temperature for 1 hour. After ethyl acetate was added, the reaction mixture was washed successively with a saturated aqueous ammonium chloride solution, a saturated aqueous sodium hydrogencarbonate solution, and saturated brine, and then concentrated under reduced pressure. The residue was purified by silica gel column chromatography to give the title compound (199 mg).

¹H-NMR(CDCl₃)δ(ppm): 0.91(3H, t), 1.29-1.38(2H, m), 1.52-1.60(2H, m), 2.56(2H, t), 4.28(2H, s), 7.08-7.13(3H, m), 7.21(2H, d), 7.64(1H, dd), 8.46(1H, dd)

EXAMPLE B233

2-(4-Butylbenzyl)-3-ethylpyridine

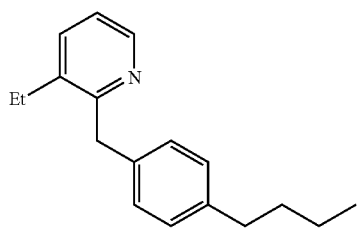

Ethylmagnesium chloride (0.97 M, 102 µl, 0.993 mmol) was added to a mixed solution of the compound of Example B232 (12.9 mg, 0.0496 mmol) and dichloro(diphenylphosphinoferrocene)nickel (3.4 mg, 0.0050 mmol) in tetrahydrofuran (1 ml). The reaction mixture was stirred at 50° C. for 1 hour, then heated under reflux for another 2 hours. After allowing the reaction mixture to reach room temperature, ethyl acetate was added thereto. The reaction mixture was washed with a saturated aqueous ammonium chloride solution and saturated brine, then concentrated under reduced pressure. The residue was purified by silica gel column chromatography to give the title compound (3.29 mg).

¹H-NMR(CDCl₃)δ(ppm): 0.90-0.93(6H, m), 1.30-1.37 (2H, m), 1.54-1.59(2H, m), 2.55-2.59(4H, m), 4.12(2H, s), 7.05-7.18(5H, m), 7.55-7.59(1H, m), 8.53-8.55(1H, m)

EXAMPLE B234 tert-Butyl N-(2-bromo-3-pyridyl)carbamate

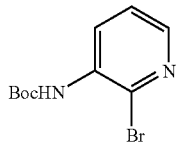

N-bromosuccinimide (7.51 g, 42.2 mmol) was added to an ice-cooled mixed solution of 3-aminopyridine (3.97 g, 42.2 mmol) in dimethylformamide (25 ml), and this reaction mixture was stirred at that temperature for 30 minutes. After ethyl acetate was added, the reaction mixture was washed with saturated brine and concentrated under reduced pressure. A solution of the residue in methylene chloride (20 ml) was cooled on ice, then triethylamine (3.74 ml, 26.8 mmol), a catalytic amount of dimethylaminopyridine, and di-t-butyl dicarbonate (3.08 ml, 13.4 mmol) were added to the solution, and the mixture was stirred at room temperature overnight. After concentration under reduced pressure, the residue was purified by silica gel column chromatography to give the title compound (344 mg).

¹H-NMR(CDCl₃)δ(ppm): 1.55(9H, s), 7.03(1H, brs), 7.25 (1H, dd), 8.03(1H, dd), 8.46(1H, d)

EXAMPLE B235

2-Bromo-3-(N-t-butoxycarbonyl-N-methyl)aminopyridine

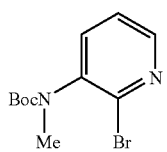

Methyl iodide (157 μl, 2.52 mmol) and 66% sodium hydride (91.6 mg, 2.52 mmol) were added to an ice-cooled solution of the compound of Example B234 (344 mg, 1.26 mmol) in dimethylformamide (5 ml), and this reaction mixture was stirred at that temperature for 40 minutes. After ethyl acetate was added, the reaction mixture was washed with saturated brine and filtered through silica gel. The organic layer was concentrated under reduced pressure to give the title compound (356 mg).

¹H-NMR(CDCl₃)δ(ppm): 1.36(9H, s), 3.17(3H, s), 7.30 (1H, dd), 7.55(1H, d), 8.30(1H, dd)

EXAMPLE B236

N-[2-(4-Butylbenzyl)-3-pyridyl]-N-methylamine

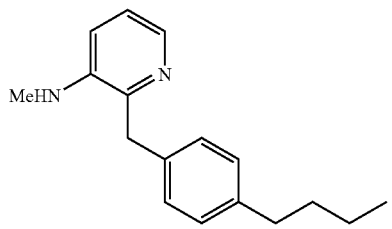

To a methylene chloride solution (2 ml) of a compound, which was obtained by introduction of a 4-butylbenzyl group to the compound of Example B235 (62.8 mg, 0.219 mmol) in the same manner as in Example B211, trifluoroacetic acid (2 ml) was added at room temperature. The mixture was stirred at room temperature for 1 hour, and then added dropwise to an aqueous solution of sodium hydrogencarbonate. After ethyl acetate was added, the mixture was washed with saturated brine and concentrated under reduced pressure. The residue was purified by silica gel column chromatography to give the title compound (29.7 mg).

¹H-NMR(CDCl₃)δ(ppm): 0.91(3H, t), 1.29-1.38(2H, m), 1.53-1.60(2H, m), 2.56(2H, t), 2.72(3H, s), 3.63(1H, br s), 4.09(2H, s), 6.86(1H, d), 7.08-7.12(5H, m), 7.98(1H, dd)

EXAMPLE B237

N-[2-(4-Butylbenzyl)-3-pyridyl]-N,N-dimethylamine

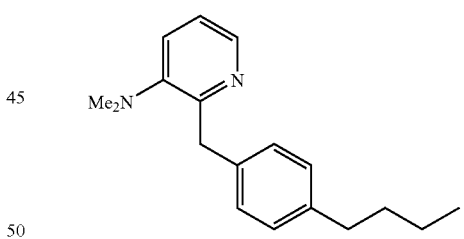

Acetic acid (12.1 μl, 0.211 mmol), 37% formalin (15.8 μl, 0.211 mmol), and sodium triacetoxyborohydride (44.7 mg, 0.211 mmol) were added to an ice-cooled solution of the compound of Example B236 (26.8 mg, 0.105 mmol) in methylene chloride (2 ml), and the mixture was stirred at room temperature for 30 minutes. After ethyl acetate was added, the mixture was washed with a saturated aqueous sodium hydrogencarbonate solution and saturated brine and concentrated under reduced pressure. The residue was purified by silica gel column chromatography to give the title compound (23.3 mg)

¹H-NMR(CDCl₃)δ(ppm): 0.91(3H, t), 1.30-1.36(2H, m), 1.52-1.59(2H, m), 2.55(2H, t), 2.67(6H, s), 4.24(2H, s), 7.06 (2H, d), 7.10(1H, dd), 7.18(2H, d), 7.40(1H, dd), 8.27(1H, dd)

EXAMPLE B238

2-(4-Butylbenzyl)-4-methoxypyridine

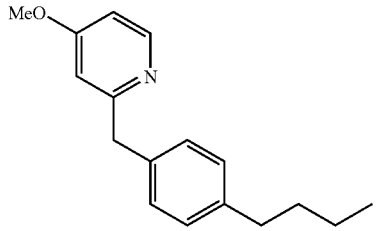

The title compound was obtained in the same manner as in Example B211 using 2-chloro-4-methoxypyridine.
$^1$H-NMR(CDCl$_3$)δ(ppm): 0.91(3H, t), 1.31-1.37(2H, m), 1.53-1.59(2H, m), 2.57(2H, t), 3.78(3H, s), 4.06(2H, s), 6.61-6.65(2H, m), 7.11(2H, d), 7.17(2H, d), 8.36(1H, d)

EXAMPLE B239

2-(4-Butylbenzyl)-4-chloropyridine

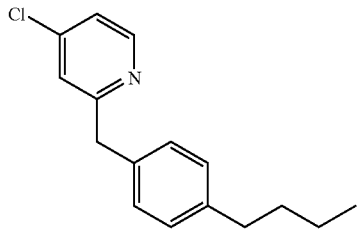

Phosphorus oxychloride (57.0 μl, 0.612 mmol) was added to an ice-cooled solution of the compound of Example B238 (52.0 mg, 0.204 mmol) in dimethylformamide (1 ml), and this reaction mixture was stirred at 100° C. for 8 hours. The reaction mixture was allowed to cool, poured on ice, and warmed to room temperature. After ethyl acetate was added, the mixture was washed with a saturated aqueous sodium hydrogencarbonate solution and saturated brine, then concentrated under reduced pressure. The residue was purified by silica gel column chromatography to give the title compound (2.29 mg).
$^1$H-NMR(CDCl$_3$)δ(ppm): 0.92(3H, t), 1.31-1.38(2H, m), 1.53-1.61(2H, m), 2.59(2H, t), 4.10(2H, s), 7.12-0.18(6H, m), 8.44(1H, d)

EXAMPLE B240

2-Chloro-3-methoxypyridine

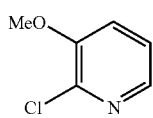

The title compound was obtained in the same manner as in Example B231 using 2-chloro-3-hydroxypyridine.
$^1$H-NMR(CDCl$_3$)δ(ppm): 3.93(3H, s), 7.21-7.22(2H, m), 7.99-8.01(1H, m)

EXAMPLE B241

2-Chloro-3,4-dimethoxypyridine

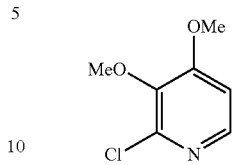

A solution of diisopropylamine (84.0 μl, 0.599 mmol) and the compound of Example B240 (860 mg, 5.99 mmol) in tetrahydrofuran (4 ml) was added to a solution of 1.06 M phenyllithium cyclopentane-diethyl ether solution in tetrahydrofuran (11 ml) cooled to −78° C. under nitrogen atmosphere. This reaction mixture was stirred at −40° C. for 1 hour, then at −18° C. for another 20 minutes. The reaction mixture was cooled again to −78° C., trimethoxyborate (2.04 ml, 18.0 mmol) was added dropwise thereto, and the resulting mixture was stirred at 0° C. for 20 minutes. At that temperature, aqueous ammonia (29%, 30 ml), ammonium chloride (4.5 g,), and an aqueous hydrogen peroxide solution (30%, 12 ml) were added in this order, and the mixture was stirred at room temperature for 2 hours. Saturated sodium thiosulfate, acetic acid and ethyl acetate were added, and the mixture was washed with saturated brine. The ethyl acetate layer obtained upon filtration through silica gel was concentrated under reduced pressure. The resulting residue was treated in the same manner as in Example B231 to obtain the title compound (31 0.3 mg).
$^1$H-NMR(CDCl$_3$)δ(ppm): 3.89(3H, s), 3.94(3H, s), 6.82(1H, d), 8.05(1H, d)

EXAMPLE B242

2-(4-Butylbenzyl)-3,4-dimethoxypyridine

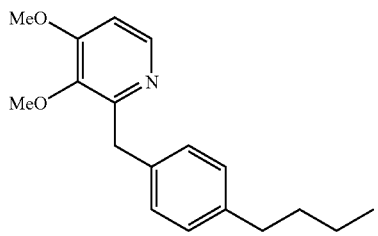

The title compound was obtained in the same manner as in Example B206 using the compound of Example B241.
$^1$H-NMR(CDCl$_3$)δ(ppm): 0.90(3H, t), 1.26-1.35(2H, m), 1.53-1.57(2H, m), 2.54(2H, t), 3.70(3H, s), 3.89(3H, s), 4.12(2H, s), 6.72(1H, d), 7.06(2H, d), 7.21(2H, d), 8.20(1H, d)

EXAMPLE B243

2,4-Di-(4-butylbenzyl)-3-methoxypyridine

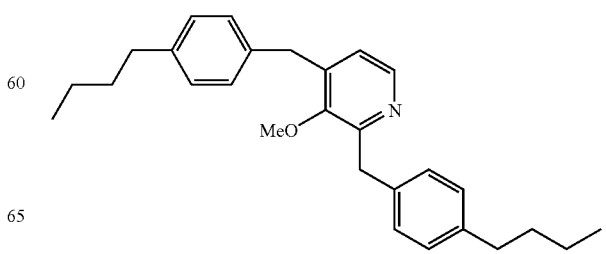

A solution of the compound of Example B240 (436 mg, 3.04 mmol) in diethyl ether (2 ml) was added to a solution of 1.43 M t-butyllithium n-pentane solution (2.76 ml, 3.95 mmol) in diethyl ether (5 ml) cooled to −78° C. under nitrogen atmosphere, and this reaction mixture was stirred at that temperature for 30 minutes. A solution of tetramethylethylenediamine (688 μl, 4.56 mmol) and hexachloroethane (719 mg, 3.04 mmol) in diethyl ether (3 ml) was further added and the reaction mixture was stirred at that temperature for 1 hour. After warming gradually to room temperature, ethyl acetate was added, and the mixture was washed with saturated brine. The ethyl acetate layer obtained upon filtration through silica gel was concentrated under reduced pressure. The resulting residue was treated in the same manner as in Example B206 to obtain the title compound (10.1 mg).

$^1$H-NMR(CDCl$_3$)δ(ppm): 0.89-0.94(6H, m), 1.31-1.37 (4H, m), 1.52-1.62(4H, m), 2.53-2.59(4H, m), 3.74(3H, s), 4.07(2H, s), 4.13(2H, s), 6.84(1H, d), 6.98(1H, d), 7.04-7.22 (8H, m)

EXAMPLE B244

2-(4-Bromo-2-fluorobenzyl)-3-(methoxymethoxy) pyridine

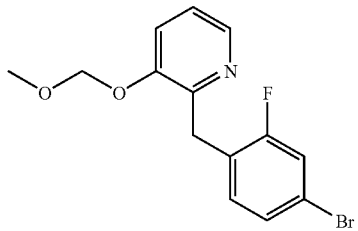

A solution of the compound of Example B228 (422 mg, 1.94 mmol) in tetrahydrofuran (3 ml) was added to a solution of 2.47 M n-butyllithium n-hexane solution (862 μl, 2.13 mmol) in tetrahydrofuran (3 ml) cooled to −78° C. under nitrogen atmosphere, and this reaction mixture was stirred at that temperature for 1 hour. After copper(I) bromide (139 mg, 0.968 mmol) was added, the reaction mixture was stirred at 0° C. for 1 hour and cooled again to −78° C. Next, 4-bromo-2-fluorobenzyl bromide (259 mg, 0.968 mmol) was added, and the resulting mixture was stirred at 0° C. for 1 hour. Tetramethylethylenediamine (584 μl, 3.88 mmol) was further added, and the resulting reaction mixture was stirred at that temperature for 1 hour. After diethyl ether and an aqueous ammonia solution were added to the reaction mixture, the organic layer was washed with saturated brine and concentrated under reduced pressure. The residue was purified by silica gel column chromatography to give the title compound (81.0 mg).

$^1$H-NMR(CDCl$_3$)δ(ppm): 3.38(3H, s), 4.17(2H, s), 5.18 (2H, s), 7.04(1H, t), 7.11-7.22(3H, m), 7.38(1H, dd), 8.19 (1H, dd)

EXAMPLE B245

2-(4-Bromo-2-fluorobenzyl)-3-pyridinol

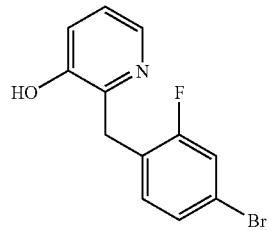

Trifluoroacetic acid (1 ml) was added to the compound of Example B244 (134 mg, 0.411 mmol) in methylene chloride (4 ml), and this reaction mixture was stirred at room temperature overnight. After neutralizing the mixture with saturated aqueous sodium hydrogencarbonate, ethyl acetate was added. The ethyl acetate layer was washed with saturated brine and concentrated under reduced pressure. The residue was purified by silica gel column chromatography to give the title compound (97.5 mg).

$^1$H-NMR(CDCl$_3$)δ(ppm): 4.17(2H, s), 7.10-7.24(5H, m), 8.15(1H, t)

The proton of the phenolic hydroxyl group was not observed in the NMR spectrum.

EXAMPLE B246

2-(4-Bromo-2-fluorobenzyl)-3-methoxypyridine

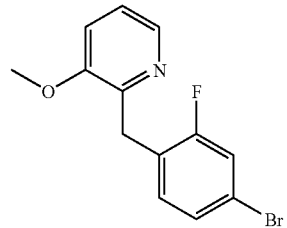

Potassium carbonate (38.7 mg, 0.280 mmol) and methyl iodide (10.5 μl, 168 mmol) were added to a solution of the compound of Example B245 (15.8 mg, 0.0560 mmol) in dimethylformamide (1 ml), and this reaction mixture was stirred at room temperature for 2 hours. After ethyl acetate was added, the reaction mixture was washed with saturated brine and concentrated under reduced pressure. The residue was purified by silica gel column chromatography to give the title compound (14.0 mg).

$^1$H-NMR(CDCl$_3$)δ(ppm): 3.82(3H, s), 4.15(2H, s), 7.03 (1H, t), 7.12-7.22(4H, m), 8.13(1H, dd)

The following compounds of Example B were synthesized in the same manner as in Example B246, and purification was performed by LC-MS [eluent: an acetonitrile solution containing 0.1% trifluoroacetic acid: an aqueous solution containing 0.1% trifluoroacetic acid=1:99 to 100:0/20-minute cycle, flow rate: 20 ml/minute, column: YMC Combiprep ODS-AM, 20 mm Φ×50 mm (long)].

EXAMPLE B247

2-(4-Bromo-2-fluorobenzyl)-3-ethoxypyridine

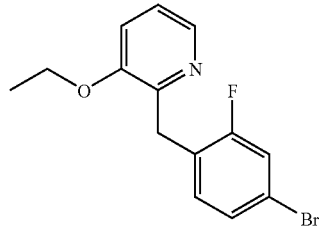

MS m/z (ESI: MH+): 310.0

EXAMPLE B248

2-(4-Bromo-2-fluorobenzyl)-3-propoxypyridine

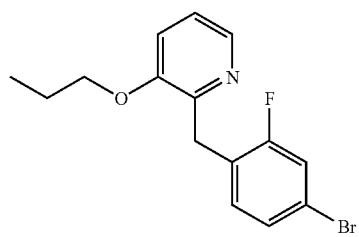

MS m/z (ESI: MH+): 324.0

EXAMPLE B249

2-(4-Bromo-2-fluorobenzyl)-3-butoxypyridine

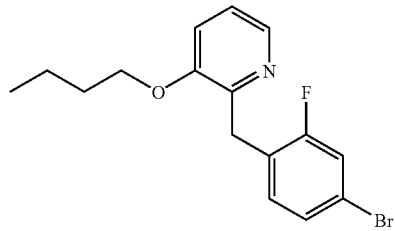

MS m/z (ESI: MH+): 338.1

EXAMPLE B250

2-(4-Bromo-2-fluorobenzyl)-3-(pentyloxy)pyridine

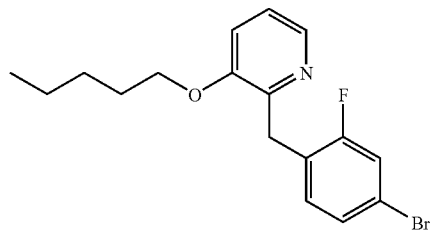

MS m/z (ESI: MH+): 352.1

EXAMPLE B251

2-(4-Bromo-2-fluorobenzyl)-3-(hexyloxy)pyridine

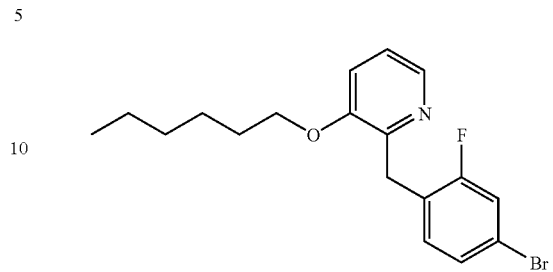

MS m/z (ESI: MH+): 366.0

EXAMPLE B252

2-(4-Bromo-2-fluorobenzyl)-3-(2-fluoroethoxy)pyridine

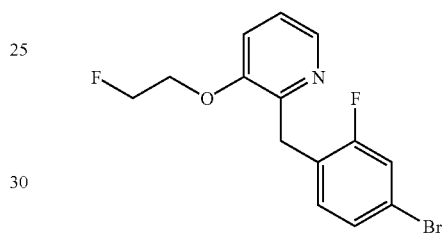

MS m/z (ESI: MH+): 328.0

EXAMPLE B253

2-(4-Bromo-2-fluorobenzyl)-3-(3-fluoropropoxy)pyridine

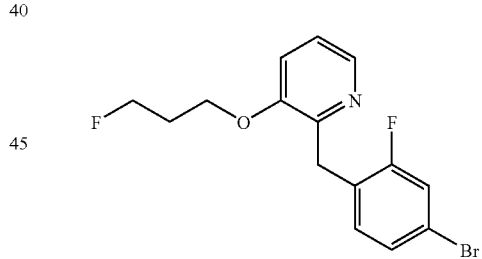

MS m/z (ESI: MH+): 342.0

EXAMPLE B254

2-(4-Bromo-2-fluorobenzyl)-3-isopropoxypyridine

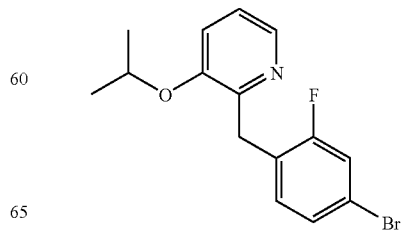

MS m/z (ESI: MH+): 324.0

EXAMPLE B255

2-(4-Bromo-2-fluorobenzyl)-3-(2,2,2-trifluoroethoxy)pyridine

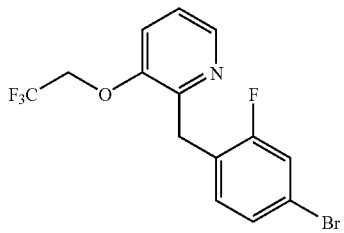

MS m/z (ESI: MH⁺): 364.0

EXAMPLE B256

2-(4-Bromo-2-fluorobenzyl)-3-(3,3,3-trifluoropropoxy)pyridine

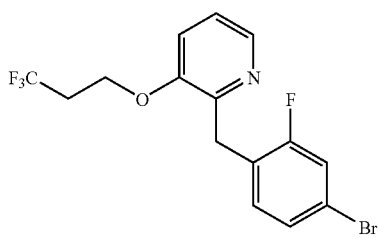

MS m/z (ESI: MH⁺): 378.0

EXAMPLE B257

Compounds were evaluated using the *S. cerevisiae* reporter system of Example A2. The lowest concentration at which cephalosporinase activity in the cell wall fraction became 50% or less compared to that obtained where the compound was not treated, was defined to be the IC50 value. Effects of the representative compounds are shown in Table 1.

TABLE 1

| Compound | IC50 (µg/ml) |
| --- | --- |
| 1-(4-butylbenzyl)isoquinoline (Example B2) | 0.39 |
| N1-{3-[4-(1-isoquinolylmethyl)phenyl]-2-propynyl} acetamide (Example B60) | 6.25 |
| N1-(3-[4-(1-isoquinolylmethyl)phenyl]propyl}-N1-methylacetamide (Example B73) | 50 |
| 5-butyl-2-(1-isoquinolylmethyl)phenol (Example B85) | 0.20 |
| 4-(4-butylbenzyl)thieno[3,2-c]pyridine (Example B187) | 0.78 |
| 7-(4-butylbenzyl)thieno[2,3-c]pyridine (Example B195) | 0.39 |
| 2-(4-butylbenzyl)-3-methoxypyridine (Example B231) | 0.78 |
| 2-(4-butylbenzyl)-3,4-dimethoxypyridine (Example B242) | 0.78 |

INDUSTRIAL APPLICABILITY

The present invention revealed genes encoding the proteins participating in the transport process of the GPI-anchored proteins to the cell wall. Furthermore, this invention discloses a method of screening for compounds that inhibit the activity of these proteins, and also discloses representative compounds having the inhibitory activity.

Using novel compounds, the present invention showed that antifungal agents having a novel mechanism of inhibiting the transport process of the GPI-anchored proteins to the cell wall can be provided.

---

What is claimed is:

1. An isolated DNA that encodes a GWT1 protein having an activity of transporting a glycosylphosphatidylinositol (GPI)-anchored protein in the cell wall of a fungus, wherein the DNA is selected from the group consisting of:
   (a) a DNA encoding a GWT1 protein comprising the amino acid sequence of SEQ ID NO:40, and
   (b) a DNA comprising the nucleotide sequence of SEQ ID NO:39.

2. A vector into which the DNA of claim 1 has been inserted.

3. A transformant transformed with the DNA of claim 1, or a vector into which the DNA of claim 1 has been inserted.

4. The transformant of claim 3, wherein the transformant is a fungus.

5. A method for producing a protein encoded by the DNA of claim 1, which comprises the steps of culturing the transformant of claim 3, and collecting the expressed protein from the transformant, or from the culture supernatant thereof, wherein the culture supernatant comprises the protein encoded by the DNA of claim 1 and produced by the transformant transformed with the vector comprising the DNA of claim 1.

* * * * *

SEQUENCE LISTING

```
<160> NUMBER OF SEQ ID NOS: 69

<210> SEQ ID NO 1
<211> LENGTH: 1497
<212> TYPE: DNA
<213> ORGANISM: Saccharomyces cerevisiae
<220> FEATURE:
<221> NAME/KEY: CDS
<222> LOCATION: (1)..(1497)
<223> OTHER INFORMATION: GWT1

<400> SEQUENCE: 1 atg gca aca gta cat cag aag aat atg tcg act tta aaa cag aga aaa      48
Met Ala Thr Val His Gln Lys Asn Met Ser Thr Leu Lys Gln Arg Lys
  1               5                  10                  15 gag gac ttt gtg aca ggg ctc aat ggc ggt tct ata aca gaa att aac      96
Glu Asp Phe Val Thr Gly Leu Asn Gly Gly Ser Ile Thr Glu Ile Asn
             20                  25                  30 gca gtg aca tca att gct ttg gta act tac ata tca tgg aac tta ttg     144
Ala Val Thr Ser Ile Ala Leu Val Thr Tyr Ile Ser Trp Asn Leu Leu
         35                  40                  45 aaa aat tcc aac ctt atg cct cct ggc att tcc agc gtg caa tac ata     192
Lys Asn Ser Asn Leu Met Pro Pro Gly Ile Ser Ser Val Gln Tyr Ile
     50                  55                  60
```

```
att gat ttt gca ttg aac tgg gtt gct ttg ctt cta tct att act att      240
Ile Asp Phe Ala Leu Asn Trp Val Ala Leu Leu Leu Ser Ile Thr Ile
 65                  70                  75                  80 tat gct agt gaa cca tac ctt cta aac acg cta ata ctg tta cct tgt      288
Tyr Ala Ser Glu Pro Tyr Leu Leu Asn Thr Leu Ile Leu Leu Pro Cys
             85                  90                  95 ttg ctc gca ttc ata tat gga aaa ttt act agc tcg agt aaa cct tct      336
Leu Leu Ala Phe Ile Tyr Gly Lys Phe Thr Ser Ser Ser Lys Pro Ser
                100                 105                 110 aat cca ata tac aat aaa aaa aaa atg att aca cag cgg ttc caa cta      384
Asn Pro Ile Tyr Asn Lys Lys Lys Met Ile Thr Gln Arg Phe Gln Leu
            115                 120                 125 gaa aaa aag ccg tat att act gcg tat cgt ggt ggg atg ctt att ctg      432
Glu Lys Lys Pro Tyr Ile Thr Ala Tyr Arg Gly Gly Met Leu Ile Leu
130                 135                 140 act gct att gcc atc ttg gct gta gat ttt cca att ttc cca agg agg      480
Thr Ala Ile Ala Ile Leu Ala Val Asp Phe Pro Ile Phe Pro Arg Arg
145                 150                 155                 160 ttt gcc aag gtg gaa act tgg ggg aca tcc ctg atg gat ctt ggt gta      528
Phe Ala Lys Val Glu Thr Trp Gly Thr Ser Leu Met Asp Leu Gly Val
                165                 170                 175 gga tca ttc gtt ttc agt aac ggt att gtt tct tct agg gca ctg ttg      576
Gly Ser Phe Val Phe Ser Asn Gly Ile Val Ser Ser Arg Ala Leu Leu
                180                 185                 190 aaa aac cta agc ttg aag agt aaa ccc agc ttc tta aaa aat gca ttt      624
Lys Asn Leu Ser Leu Lys Ser Lys Pro Ser Phe Leu Lys Asn Ala Phe
            195                 200                 205 aat gcc tta aaa tca gga gga act cta ttg ttc cta gga ttg ctg agg      672
Asn Ala Leu Lys Ser Gly Gly Thr Leu Leu Phe Leu Gly Leu Leu Arg
210                 215                 220 ttg ttt ttt gta aaa aat ttg gaa tat caa gaa cat gtc aca gaa tat      720
Leu Phe Phe Val Lys Asn Leu Glu Tyr Gln Glu His Val Thr Glu Tyr
225                 230                 235                 240 ggg gtt cat tgg aat ttt ttt atc acc cta tca ttg ttg cca ctt gta      768
Gly Val His Trp Asn Phe Phe Ile Thr Leu Ser Leu Leu Pro Leu Val
                245                 250                 255 ttg acc ttt att gat ccc gtc aca aga atg gtt cca cgc tgc tca att      816
Leu Thr Phe Ile Asp Pro Val Thr Arg Met Val Pro Arg Cys Ser Ile
                260                 265                 270 gca ata ttc att tca tgc att tat gaa tgg cta ctt tta aag gac gat      864
Ala Ile Phe Ile Ser Cys Ile Tyr Glu Trp Leu Leu Leu Lys Asp Asp
            275                 280                 285 cgc act tta aac ttt tta att ttg gct gat aga aat tgt ttc ttc agt      912
Arg Thr Leu Asn Phe Leu Ile Leu Ala Asp Arg Asn Cys Phe Phe Ser
290                 295                 300 gct aat aga gaa ggc atc ttc tca ttt cta ggt tat tgc tcg att ttt      960
Ala Asn Arg Glu Gly Ile Phe Ser Phe Leu Gly Tyr Cys Ser Ile Phe
305                 310                 315                 320 ctt tgg ggc caa aac acg gga ttt tac ttg ttg gga aat aaa cca act     1008
Leu Trp Gly Gln Asn Thr Gly Phe Tyr Leu Leu Gly Asn Lys Pro Thr
                325                 330                 335 tta aac aat ctt tat aag cct tct acg caa gac gta gtt gca gca tca     1056
Leu Asn Asn Leu Tyr Lys Pro Ser Thr Gln Asp Val Val Ala Ala Ser
            340                 345                 350 aag aag tct tcg act tgg gac tat tgg act tca gta acc cca tta agt     1104
Lys Lys Ser Ser Thr Trp Asp Tyr Trp Thr Ser Val Thr Pro Leu Ser
355                 360                 365 ggc ctc tgt ata tgg agt aca att ttt ctt gtt atc agc cag ttg gtt     1152
Gly Leu Cys Ile Trp Ser Thr Ile Phe Leu Val Ile Ser Gln Leu Val
370                 375                 380
```

```
ttt caa tac cat cct tat agt gtt tca aga agg ttt gct aac tta cca   1200
Phe Gln Tyr His Pro Tyr Ser Val Ser Arg Arg Phe Ala Asn Leu Pro
385                 390                 395                 400 tat act ttg tgg gtc att act tat aat tta cta ttt ttg act ggg tac   1248
Tyr Thr Leu Trp Val Ile Thr Tyr Asn Leu Leu Phe Leu Thr Gly Tyr
                405                 410                 415 tgc ttg act gac aaa att ttc ggt aat tct tcg gaa tat tat aaa gtt   1296
Cys Leu Thr Asp Lys Ile Phe Gly Asn Ser Ser Glu Tyr Tyr Lys Val
                420                 425                 430 gcc gaa tgc ttg gaa tca atc aac tcc aat ggg ttg ttt tta ttt ttg   1344
Ala Glu Cys Leu Glu Ser Ile Asn Ser Asn Gly Leu Phe Leu Phe Leu
                435                 440                 445 ttg gca aat gtc tct act ggt tta gtc aat atg tct atg gtc acg ata   1392
Leu Ala Asn Val Ser Thr Gly Leu Val Asn Met Ser Met Val Thr Ile
450                 455                 460 gat tct tca ccc tta aaa tca ttc ctg gtt ttg ttg gca tac tgc tca   1440
Asp Ser Ser Pro Leu Lys Ser Phe Leu Val Leu Leu Ala Tyr Cys Ser
465                 470                 475                 480 ttc ata gct gtc ata tcg gtt ttc ttg tat aga aaa aga ata ttc att   1488
Phe Ile Ala Val Ile Ser Val Phe Leu Tyr Arg Lys Arg Ile Phe Ile
                485                 490                 495 aag cta taa                                                       1497
Lys Leu

<210> SEQ ID NO 2
<211> LENGTH: 498
<212> TYPE: PRT
<213> ORGANISM: Saccharomyces cerevisiae
<220> FEATURE:
<223> OTHER INFORMATION: GWT1

<400> SEQUENCE: 2

Met Ala Thr Val His Gln Lys Asn Met Ser Thr Leu Lys Gln Arg Lys
1               5                   10                  15

Glu Asp Phe Val Thr Gly Leu Asn Gly Gly Ser Ile Thr Glu Ile Asn
                20                  25                  30

Ala Val Thr Ser Ile Ala Leu Val Thr Tyr Ile Ser Trp Asn Leu Leu
            35                  40                  45

Lys Asn Ser Asn Leu Met Pro Pro Gly Ile Ser Ser Val Gln Tyr Ile
        50                  55                  60

Ile Asp Phe Ala Leu Asn Trp Val Ala Leu Leu Ser Ile Thr Ile
65                  70                  75                  80

Tyr Ala Ser Glu Pro Tyr Leu Leu Asn Thr Leu Ile Leu Leu Pro Cys
                85                  90                  95

Leu Leu Ala Phe Ile Tyr Gly Lys Phe Thr Ser Ser Ser Lys Pro Ser
                100                 105                 110

Asn Pro Ile Tyr Asn Lys Lys Met Ile Thr Gln Arg Phe Gln Leu
        115                 120                 125

Glu Lys Lys Pro Tyr Ile Thr Ala Tyr Arg Gly Gly Met Leu Ile Leu
    130                 135                 140

Thr Ala Ile Ala Ile Leu Ala Val Asp Phe Pro Ile Phe Pro Arg Arg
145                 150                 155                 160

Phe Ala Lys Val Glu Thr Trp Gly Thr Ser Leu Met Asp Leu Gly Val
                165                 170                 175

Gly Ser Phe Val Phe Ser Asn Gly Ile Val Ser Ser Arg Ala Leu Leu
                180                 185                 190

Lys Asn Leu Ser Leu Lys Ser Lys Pro Ser Phe Leu Lys Asn Ala Phe
        195                 200                 205
```

```
Asn Ala Leu Lys Ser Gly Gly Thr Leu Leu Phe Leu Gly Leu Leu Arg
        210                 215                 220

Leu Phe Phe Val Lys Asn Leu Glu Tyr Gln Glu His Val Thr Glu Tyr
225                 230                 235                 240

Gly Val His Trp Asn Phe Phe Ile Thr Leu Ser Leu Leu Pro Leu Val
                    245                 250                 255

Leu Thr Phe Ile Asp Pro Val Thr Arg Met Val Pro Arg Cys Ser Ile
                260                 265                 270

Ala Ile Phe Ile Ser Cys Ile Tyr Glu Trp Leu Leu Leu Lys Asp Asp
                275                 280                 285

Arg Thr Leu Asn Phe Leu Ile Leu Ala Asp Arg Asn Cys Phe Ser
        290                 295                 300

Ala Asn Arg Glu Gly Ile Phe Ser Phe Leu Gly Tyr Cys Ser Ile Phe
305                 310                 315                 320

Leu Trp Gly Gln Asn Thr Gly Phe Tyr Leu Leu Gly Asn Lys Pro Thr
                    325                 330                 335

Leu Asn Asn Leu Tyr Lys Pro Ser Thr Gln Asp Val Val Ala Ala Ser
                340                 345                 350

Lys Lys Ser Ser Thr Trp Asp Tyr Trp Thr Ser Val Thr Pro Leu Ser
        355                 360                 365

Gly Leu Cys Ile Trp Ser Thr Ile Phe Leu Val Ile Ser Gln Leu Val
        370                 375                 380

Phe Gln Tyr His Pro Tyr Ser Val Ser Arg Arg Phe Ala Asn Leu Pro
385                 390                 395                 400

Tyr Thr Leu Trp Val Ile Thr Tyr Asn Leu Leu Phe Leu Thr Gly Tyr
                    405                 410                 415

Cys Leu Thr Asp Lys Ile Phe Gly Asn Ser Ser Glu Tyr Tyr Lys Val
                420                 425                 430

Ala Glu Cys Leu Glu Ser Ile Asn Ser Asn Gly Leu Phe Leu Phe Leu
            435                 440                 445

Leu Ala Asn Val Ser Thr Gly Leu Val Asn Met Ser Met Val Thr Ile
        450                 455                 460

Asp Ser Ser Pro Leu Lys Ser Phe Leu Val Leu Leu Ala Tyr Cys Ser
465                 470                 475                 480

Phe Ile Ala Val Ile Ser Val Phe Leu Tyr Arg Lys Arg Ile Phe Ile
                    485                 490                 495

Lys Leu

<210> SEQ ID NO 3
<211> LENGTH: 1458
<212> TYPE: DNA
<213> ORGANISM: Candida albicans
<220> FEATURE:
<221> NAME/KEY: CDS
<222> LOCATION: (1)..(1458)
<223> OTHER INFORMATION: CaGWT1

<400> SEQUENCE: 3 atg tca tcg tct tta aaa caa ttg aaa gaa caa ttt gtc tca gat ttg      48
Met Ser Ser Ser Leu Lys Gln Leu Lys Glu Gln Phe Val Ser Asp Leu
1               5                   10                  15 act ggt ggc aca att gaa gaa att tat gct gta acc agt ata gca tta      96
Thr Gly Gly Thr Ile Glu Glu Ile Tyr Ala Val Thr Ser Ile Ala Leu
                20                  25                  30 tca tct tat ttg tcc ttt aga ttg ttg aaa aag tct ctt ggt gat tta     144
Ser Ser Tyr Leu Ser Phe Arg Leu Leu Lys Lys Ser Leu Gly Asp Leu
            35                  40                  45
```

```
                                        -continued
gct ttg att tac gac tac att ctt aat gtg ttg aca att cta gca tcc       192
Ala Leu Ile Tyr Asp Tyr Ile Leu Asn Val Leu Thr Ile Leu Ala Ser
 50                  55                  60 att act gtt tat agc aac agc cct tct tat ttg cat tat ttt att gtt       240
Ile Thr Val Tyr Ser Asn Ser Pro Ser Tyr Leu His Tyr Phe Ile Val
 65                  70                  75                  80 att cca tca tta gtt ata tat cta gtg aat tac cat gtt gag aaa cca       288
Ile Pro Ser Leu Val Ile Tyr Leu Val Asn Tyr His Val Glu Lys Pro
                 85                  90                  95 tct tca ccc cat aga caa aat gat aca aaa gaa gat aaa tcg gac gaa       336
Ser Ser Pro His Arg Gln Asn Asp Thr Lys Glu Asp Lys Ser Asp Glu
            100                 105                 110 cta ttg ccg aga aaa caa ttt ata aca gcc tat cgt tct caa atg ttg       384
Leu Leu Pro Arg Lys Gln Phe Ile Thr Ala Tyr Arg Ser Gln Met Leu
        115                 120                 125 ata att act aat cta gct ata tta gct gtt gat ttt cct att ttc cca       432
Ile Ile Thr Asn Leu Ala Ile Leu Ala Val Asp Phe Pro Ile Phe Pro
    130                 135                 140 aga aga ttt gcc aaa gtg gaa aca tgg ggc acg tca atg atg gat tta       480
Arg Arg Phe Ala Lys Val Glu Thr Trp Gly Thr Ser Met Met Asp Leu
145                 150                 155                 160 gga gtt ggg tcg ttt gtg ttc tcc atg ggg ttg gct aat tct cga caa       528
Gly Val Gly Ser Phe Val Phe Ser Met Gly Leu Ala Asn Ser Arg Gln
                165                 170                 175 ttg atc aag aac cac acc gac aac tac aaa ttt agt tgg aag agt tat       576
Leu Ile Lys Asn His Thr Asp Asn Tyr Lys Phe Ser Trp Lys Ser Tyr
            180                 185                 190 ttg aaa aca atc aag cag aac ttt atc aag tca gtg cct ata ctt gtt       624
Leu Lys Thr Ile Lys Gln Asn Phe Ile Lys Ser Val Pro Ile Leu Val
        195                 200                 205 tta gga gct att cgt ttt gtt agt gtt aag caa ttg gac tat cag gaa       672
Leu Gly Ala Ile Arg Phe Val Ser Val Lys Gln Leu Asp Tyr Gln Glu
    210                 215                 220 cac gaa aca gag tat gga atc cat tgg aat ttt ttc ttc aca tta ggg       720
His Glu Thr Glu Tyr Gly Ile His Trp Asn Phe Phe Phe Thr Leu Gly
225                 230                 235                 240 ttc ttg cca att gta ttg gga ata tta gac ccg gtg ttg aat ttg gtt       768
Phe Leu Pro Ile Val Leu Gly Ile Leu Asp Pro Val Leu Asn Leu Val
                245                 250                 255 cca cgc ttc ata ata gga att ggt atc tca att gct tat gag gta gcg       816
Pro Arg Phe Ile Ile Gly Ile Gly Ile Ser Ile Ala Tyr Glu Val Ala
            260                 265                 270 ttg aat aag act ggt ttg ttg aag ttc att ttg agc agc gaa aac aga       864
Leu Asn Lys Thr Gly Leu Leu Lys Phe Ile Leu Ser Ser Glu Asn Arg
        275                 280                 285 ctt gaa tct ctc atc acc atg aat aaa gaa ggt att ttt tcg ttt att       912
Leu Glu Ser Leu Ile Thr Met Asn Lys Glu Gly Ile Phe Ser Phe Ile
    290                 295                 300 gga tat ctt tgt att ttt ata att ggt cag tct ttt ggg tca ttt gtt       960
Gly Tyr Leu Cys Ile Phe Ile Ile Gly Gln Ser Phe Gly Ser Phe Val
305                 310                 315                 320 tta aca ggc tac aaa aca aag aac aac tta ata acc att agc aaa att      1008
Leu Thr Gly Tyr Lys Thr Lys Asn Asn Leu Ile Thr Ile Ser Lys Ile
                325                 330                 335 cgt att tca aaa aaa caa cac aag aaa gag ctg ctg ctg ttt ttc tca      1056
Arg Ile Ser Lys Lys Gln His Lys Lys Glu Leu Leu Leu Phe Phe Ser
            340                 345                 350 gtc gcc act act cag gga tta tat ttg gca tgt atc ttc tat cac tta      1104
Val Ala Thr Thr Gln Gly Leu Tyr Leu Ala Cys Ile Phe Tyr His Leu
        355                 360                 365
```

```
gct ttc agt ttg ttc atc agc aac tta tca ttc ttg caa cca att tca    1152
Ala Phe Ser Leu Phe Ile Ser Asn Leu Ser Phe Leu Gln Pro Ile Ser
370                 375                 380 aga cga ttg gcc aat ttc ccc tac gtc atg tgg gtc gtt tcg tac aat    1200
Arg Arg Leu Ala Asn Phe Pro Tyr Val Met Trp Val Val Ser Tyr Asn
385                 390                 395                 400 gct acg ttt tta tta tgt tat gac tta att gaa aaa ttt atc ccg ggg    1248
Ala Thr Phe Leu Leu Cys Tyr Asp Leu Ile Glu Lys Phe Ile Pro Gly
            405                 410                 415 aac ctt act tct act gta ttg gac tct att aat aac aat ggt tta ttt    1296
Asn Leu Thr Ser Thr Val Leu Asp Ser Ile Asn Asn Asn Gly Leu Phe
            420                 425                 430 atc ttc ttg gtc agc aat tta tta aca ggg ttt att aac atg tcc atc    1344
Ile Phe Leu Val Ser Asn Leu Leu Thr Gly Phe Ile Asn Met Ser Ile
            435                 440                 445 aac act ttg gaa act agc aat aaa atg gca gtg att atc ttg att ggc    1392
Asn Thr Leu Glu Thr Ser Asn Lys Met Ala Val Ile Leu Ile Gly
450                 455                 460 tat agt ctt act tgg aca ttg ctc gcc tta tat ttg gat aag agg aag    1440
Tyr Ser Leu Thr Trp Thr Leu Leu Ala Leu Tyr Leu Asp Lys Arg Lys
465                 470                 475                 480 atc tac atc aag ctt tag                                            1458
Ile Tyr Ile Lys Leu
            485

<210> SEQ ID NO 4
<211> LENGTH: 485
<212> TYPE: PRT
<213> ORGANISM: Candida albicans
<220> FEATURE:
<223> OTHER INFORMATION: CaGWT1

<400> SEQUENCE: 4

Met Ser Ser Ser Leu Lys Gln Leu Lys Glu Gln Phe Val Ser Asp Leu
1               5                   10                  15

Thr Gly Gly Thr Ile Glu Glu Ile Tyr Ala Val Thr Ser Ile Ala Leu
            20                  25                  30

Ser Ser Tyr Leu Ser Phe Arg Leu Leu Lys Lys Ser Leu Gly Asp Leu
        35                  40                  45

Ala Leu Ile Tyr Asp Tyr Ile Leu Asn Val Leu Thr Ile Leu Ala Ser
    50                  55                  60

Ile Thr Val Tyr Ser Asn Ser Pro Ser Tyr Leu His Tyr Phe Ile Val
65                  70                  75                  80

Ile Pro Ser Leu Val Ile Tyr Leu Val Asn Tyr His Val Glu Lys Pro
                85                  90                  95

Ser Ser Pro His Arg Gln Asn Asp Thr Lys Glu Asp Lys Ser Asp Glu
            100                 105                 110

Leu Leu Pro Arg Lys Gln Phe Ile Thr Ala Tyr Arg Ser Gln Met Leu
        115                 120                 125

Ile Ile Thr Asn Leu Ala Ile Leu Ala Val Asp Phe Pro Ile Phe Pro
    130                 135                 140

Arg Arg Phe Ala Lys Val Glu Thr Trp Gly Thr Ser Met Met Asp Leu
145                 150                 155                 160

Gly Val Gly Ser Phe Val Phe Ser Met Gly Leu Ala Asn Ser Arg Gln
                165                 170                 175

Leu Ile Lys Asn His Thr Asp Asn Tyr Lys Phe Ser Trp Lys Ser Tyr
            180                 185                 190

Leu Lys Thr Ile Lys Gln Asn Phe Ile Lys Ser Val Pro Ile Leu Val
        195                 200                 205
```

Leu Gly Ala Ile Arg Phe Val Ser Val Lys Gln Leu Asp Tyr Gln Glu
    210             215                 220

His Glu Thr Glu Tyr Gly Ile His Trp Asn Phe Phe Thr Leu Gly
225             230                 235                 240

Phe Leu Pro Ile Val Leu Gly Ile Leu Asp Pro Val Leu Asn Leu Val
                245                 250                 255

Pro Arg Phe Ile Ile Gly Ile Gly Ile Ser Ile Ala Tyr Glu Val Ala
            260                 265                 270

Leu Asn Lys Thr Gly Leu Leu Lys Phe Ile Leu Ser Ser Glu Asn Arg
        275                 280                 285

Leu Glu Ser Leu Ile Thr Met Asn Lys Glu Gly Ile Phe Ser Phe Ile
    290                 295                 300

Gly Tyr Leu Cys Ile Phe Ile Ile Gly Gln Ser Phe Gly Ser Phe Val
305             310                 315                 320

Leu Thr Gly Tyr Lys Thr Lys Asn Asn Leu Ile Thr Ile Ser Lys Ile
                325                 330                 335

Arg Ile Ser Lys Lys Gln His Lys Lys Glu Leu Leu Leu Phe Phe Ser
            340                 345                 350

Val Ala Thr Thr Gln Gly Leu Tyr Leu Ala Cys Ile Phe Tyr His Leu
        355                 360                 365

Ala Phe Ser Leu Phe Ile Ser Asn Leu Ser Phe Leu Gln Pro Ile Ser
    370                 375                 380

Arg Arg Leu Ala Asn Phe Pro Tyr Val Met Trp Val Ser Tyr Asn
385             390                 395                 400

Ala Thr Phe Leu Leu Cys Tyr Asp Leu Ile Glu Lys Phe Ile Pro Gly
                405                 410                 415

Asn Leu Thr Ser Thr Val Leu Asp Ser Ile Asn Asn Gly Leu Phe
            420                 425                 430

Ile Phe Leu Val Ser Asn Leu Leu Thr Gly Phe Ile Asn Met Ser Ile
        435                 440                 445

Asn Thr Leu Glu Thr Ser Asn Lys Met Ala Val Ile Leu Ile Gly
    450                 455                 460

Tyr Ser Leu Thr Trp Thr Leu Leu Ala Leu Tyr Leu Asp Lys Arg Lys
465             470                 475                 480

Ile Tyr Ile Lys Leu
            485

<210> SEQ ID NO 5
<211> LENGTH: 1458
<212> TYPE: DNA
<213> ORGANISM: Candida albicans
<220> FEATURE:
<221> NAME/KEY: CDS
<222> LOCATION: (1)..(1458)
<223> OTHER INFORMATION: CaGWT1

<400> SEQUENCE: 5 atg tca tcg tct tta aaa caa ttg aaa gaa caa ttt gtc tca gat ttg    48
Met Ser Ser Ser Leu Lys Gln Leu Lys Glu Gln Phe Val Ser Asp Leu
1               5                   10                  15 act ggt ggc aca att gaa gaa att tat gct gta acc agt ata gca tta    96
Thr Gly Gly Thr Ile Glu Glu Ile Tyr Ala Val Thr Ser Ile Ala Leu
            20                  25                  30 tca tct tat ttg tcc ttt aga ttg ttg aaa aag tct ctt ggt gat tta   144
Ser Ser Tyr Leu Ser Phe Arg Leu Leu Lys Lys Ser Leu Gly Asp Leu
        35                  40                  45

```
gct ttg att tac gac tac att ctt aat gtg ttg aca att cta gca tcc    192
Ala Leu Ile Tyr Asp Tyr Ile Leu Asn Val Leu Thr Ile Leu Ala Ser
    50              55                  60 att act gtt tat agc aac agc cct tct tat ttg cat tat ttt att gtt    240
Ile Thr Val Tyr Ser Asn Ser Pro Ser Tyr Leu His Tyr Phe Ile Val
65              70                  75                  80 att cca tca tta gtt ata tat cta gtg aat tac cat gtt gag aaa cca    288
Ile Pro Ser Leu Val Ile Tyr Leu Val Asn Tyr His Val Glu Lys Pro
                85                  90                  95 tct tca ccc cat aga caa aat gat aca aaa gaa gat aaa tcg gac gaa    336
Ser Ser Pro His Arg Gln Asn Asp Thr Lys Glu Asp Lys Ser Asp Glu
            100                 105                 110 cta ttg ccg aga aaa caa ttt ata aca gcc tat cgt tct caa atg ttg    384
Leu Leu Pro Arg Lys Gln Phe Ile Thr Ala Tyr Arg Ser Gln Met Leu
        115                 120                 125 ata att act aat cta gct ata tta gct gtt gat ttt cct att ttc cca    432
Ile Ile Thr Asn Leu Ala Ile Leu Ala Val Asp Phe Pro Ile Phe Pro
    130                 135                 140 aga aga ttt gcc aaa gtg gaa aca tgg ggc acg tca atg atg gat tta    480
Arg Arg Phe Ala Lys Val Glu Thr Trp Gly Thr Ser Met Met Asp Leu
145                 150                 155                 160 gga gtt ggg tcg ttt gtg ttc tcc atg ggg ttg gct aat tct cga caa    528
Gly Val Gly Ser Phe Val Phe Ser Met Gly Leu Ala Asn Ser Arg Gln
                165                 170                 175 ttg atc aag aac cac acc gac aat tac aaa ttt agt tgg aag agt tat    576
Leu Ile Lys Asn His Thr Asp Asn Tyr Lys Phe Ser Trp Lys Ser Tyr
            180                 185                 190 ttg aaa aca atc aag cag aac ttt atc aag tca gtg cct ata ctt gtt    624
Leu Lys Thr Ile Lys Gln Asn Phe Ile Lys Ser Val Pro Ile Leu Val
        195                 200                 205 tta gga gct att cgt ttt gtt agt gtt aag caa ttg gac tat cag gaa    672
Leu Gly Ala Ile Arg Phe Val Ser Val Lys Gln Leu Asp Tyr Gln Glu
    210                 215                 220 cac gaa aca gag tat gga atc cat tgg aat ttt ttc ttc aca tta ggg    720
His Glu Thr Glu Tyr Gly Ile His Trp Asn Phe Phe Phe Thr Leu Gly
225                 230                 235                 240 ttc ttg cca att gta ttg gga ata tta gac ccg gtg ttg aat ttg gtt    768
Phe Leu Pro Ile Val Leu Gly Ile Leu Asp Pro Val Leu Asn Leu Val
                245                 250                 255 cca cgc ttc ata ata gga att ggt atc tca att ggt tat gag gta gcg    816
Pro Arg Phe Ile Ile Gly Ile Gly Ile Ser Ile Gly Tyr Glu Val Ala
            260                 265                 270 ttg aat aag act ggt ttg ttg aag ttc att ttg agc agc gaa aac aga    864
Leu Asn Lys Thr Gly Leu Leu Lys Phe Ile Leu Ser Ser Glu Asn Arg
        275                 280                 285 ctt gaa tct ctc atc gcc atg aat aaa gaa ggt att ttt tcg ttt att    912
Leu Glu Ser Leu Ile Ala Met Asn Lys Glu Gly Ile Phe Ser Phe Ile
    290                 295                 300 gga tat ctt tgt att ttt ata att ggt cag tct ttt ggg tca ttt gtt    960
Gly Tyr Leu Cys Ile Phe Ile Ile Gly Gln Ser Phe Gly Ser Phe Val
305                 310                 315                 320 tta aca ggc tac aaa aca aag aac aac tta ata acc att agc aaa att   1008
Leu Thr Gly Tyr Lys Thr Lys Asn Asn Leu Ile Thr Ile Ser Lys Ile
                325                 330                 335 cgt att tca aaa aaa caa cac aag aaa gag ctg ctg ctg ttt ttc tca   1056
Arg Ile Ser Lys Lys Gln His Lys Lys Glu Leu Leu Leu Phe Phe Ser
            340                 345                 350 gtc gcc act act cag gga tta tat ttg gca tgt atc ttc tat cac tta   1104
Val Ala Thr Thr Gln Gly Leu Tyr Leu Ala Cys Ile Phe Tyr His Leu
        355                 360                 365
```

```
gct ttc agt ttg ttc atc agc aac tta tca ttc ttg caa cca att tca    1152
Ala Phe Ser Leu Phe Ile Ser Asn Leu Ser Phe Leu Gln Pro Ile Ser
370                 375                 380 aga cga ttg gcc aat ttc ccc tac gtc atg tgg gtc gtt tcg tac aat    1200
Arg Arg Leu Ala Asn Phe Pro Tyr Val Met Trp Val Val Ser Tyr Asn
385                 390                 395                 400 gct acg ttt tta tta tgt tat gac tta att gaa aaa ttt atc ccg ggg    1248
Ala Thr Phe Leu Leu Cys Tyr Asp Leu Ile Glu Lys Phe Ile Pro Gly
                405                 410                 415 aac ctt act tct act gta ttg gac tct att aat aac aat ggt tta ttt    1296
Asn Leu Thr Ser Thr Val Leu Asp Ser Ile Asn Asn Asn Gly Leu Phe
            420                 425                 430 atc ttc ttg gtc agc aat tta tta aca ggg ttt att aac atg tcc atc    1344
Ile Phe Leu Val Ser Asn Leu Leu Thr Gly Phe Ile Asn Met Ser Ile
        435                 440                 445 aac act ttg gaa act agc aat aaa atg gca gtg att atc ttg att ggc    1392
Asn Thr Leu Glu Thr Ser Asn Lys Met Ala Val Ile Ile Leu Ile Gly
    450                 455                 460 tat agt ctt act tgg aca ttg ctc gcc tta tat ttg gat aag agg aag    1440
Tyr Ser Leu Thr Trp Thr Leu Leu Ala Leu Tyr Leu Asp Lys Arg Lys
465                 470                 475                 480 atc tac atc aag ctt tag                                            1458
Ile Tyr Ile Lys Leu
                485

<210> SEQ ID NO 6
<211> LENGTH: 485
<212> TYPE: PRT
<213> ORGANISM: Candida albicans
<220> FEATURE:
<223> OTHER INFORMATION: CaGWT1

<400> SEQUENCE: 6

Met Ser Ser Ser Leu Lys Gln Leu Lys Glu Gln Phe Val Ser Asp Leu
1               5                   10                  15

Thr Gly Gly Thr Ile Glu Glu Ile Tyr Ala Val Thr Ser Ile Ala Leu
            20                  25                  30

Ser Ser Tyr Leu Ser Phe Arg Leu Leu Lys Lys Ser Leu Gly Asp Leu
        35                  40                  45

Ala Leu Ile Tyr Asp Tyr Ile Leu Asn Val Leu Thr Ile Leu Ala Ser
    50                  55                  60

Ile Thr Val Tyr Ser Asn Ser Pro Ser Tyr Leu His Tyr Phe Ile Val
65                  70                  75                  80

Ile Pro Ser Leu Val Ile Tyr Leu Val Asn Tyr His Val Glu Lys Pro
                85                  90                  95

Ser Ser Pro His Arg Gln Asn Asp Thr Lys Glu Asp Lys Ser Asp Glu
            100                 105                 110

Leu Leu Pro Arg Lys Gln Phe Ile Thr Ala Tyr Arg Ser Gln Met Leu
        115                 120                 125

Ile Ile Thr Asn Leu Ala Ile Leu Ala Val Asp Phe Pro Ile Phe Pro
    130                 135                 140

Arg Arg Phe Ala Lys Val Glu Thr Trp Gly Thr Ser Met Met Asp Leu
145                 150                 155                 160

Gly Val Gly Ser Phe Val Phe Ser Met Gly Leu Ala Asn Ser Arg Gln
                165                 170                 175

Leu Ile Lys Asn His Thr Asp Asn Tyr Lys Phe Ser Trp Lys Ser Tyr
            180                 185                 190

Leu Lys Thr Ile Lys Gln Asn Phe Ile Lys Ser Val Pro Ile Leu Val
        195                 200                 205
```

```
Leu Gly Ala Ile Arg Phe Val Ser Val Lys Gln Leu Asp Tyr Gln Glu
            210                 215                 220

His Glu Thr Glu Tyr Gly Ile His Trp Asn Phe Phe Thr Leu Gly
225                 230                 235                 240

Phe Leu Pro Ile Val Leu Gly Ile Leu Asp Pro Val Leu Asn Leu Val
                245                 250                 255

Pro Arg Phe Ile Ile Gly Ile Gly Ile Ser Ile Gly Tyr Glu Val Ala
                260                 265                 270

Leu Asn Lys Thr Gly Leu Leu Lys Phe Ile Leu Ser Ser Glu Asn Arg
            275                 280                 285

Leu Glu Ser Leu Ile Ala Met Asn Lys Glu Gly Ile Phe Ser Phe Ile
        290                 295                 300

Gly Tyr Leu Cys Ile Phe Ile Ile Gly Gln Ser Phe Gly Ser Phe Val
305                 310                 315                 320

Leu Thr Gly Tyr Lys Thr Lys Asn Asn Leu Ile Thr Ile Ser Lys Ile
                325                 330                 335

Arg Ile Ser Lys Lys Gln His Lys Lys Glu Leu Leu Leu Phe Phe Ser
            340                 345                 350

Val Ala Thr Thr Gln Gly Leu Tyr Leu Ala Cys Ile Phe Tyr His Leu
        355                 360                 365

Ala Phe Ser Leu Phe Ile Ser Asn Leu Ser Phe Leu Gln Pro Ile Ser
370                 375                 380

Arg Arg Leu Ala Asn Phe Pro Tyr Val Met Trp Val Val Ser Tyr Asn
385                 390                 395                 400

Ala Thr Phe Leu Leu Cys Tyr Asp Leu Ile Glu Lys Phe Ile Pro Gly
                405                 410                 415

Asn Leu Thr Ser Thr Val Leu Asp Ser Ile Asn Asn Asn Gly Leu Phe
            420                 425                 430

Ile Phe Leu Val Ser Asn Leu Leu Thr Gly Phe Ile Asn Met Ser Ile
        435                 440                 445

Asn Thr Leu Glu Thr Ser Asn Lys Met Ala Val Ile Ile Leu Ile Gly
        450                 455                 460

Tyr Ser Leu Thr Trp Thr Leu Leu Ala Leu Tyr Leu Asp Lys Arg Lys
465                 470                 475                 480

Ile Tyr Ile Lys Leu
                485

<210> SEQ ID NO 7
<211> LENGTH: 1458
<212> TYPE: DNA
<213> ORGANISM: Candida albicans
<220> FEATURE:
<223> OTHER INFORMATION: homologue of S. cerevisiae GWT1

<400> SEQUENCE: 7
atgtcatcgt ctttaaaaca attgaaagaa caatttgtct cagatttgac tggtggcaca      60
attgaagaaa tttatgctgt aaccagtata gcattatcat cttatttgtc ctttagattg     120
ttgaaaaagt ctcttggtga tttagctttg atttacgact acattcttaa tgtgttgaca     180
attctagcat ccattactgt ttatagcaac agcccttctt atttgcatta ttttattgtt     240
attccatcat tagttatata tctagtgaat taccatgttg agaaaccatc ttcaccccat     300
agacaaaatg atacaaaaga agataaatcg gacgaactat tgccgagaaa acaatttata     360
acagcctatc gttctcaaat gttgataatt actaatctag ctatattagc tgttgatttt     420
cctattttcc caagaagatt tgccaaagtg gaaacatggg gcacgtcaat gatggattta     480
```

-continued

```
ggggttgggt cgtttgtgtt ctccatgggg ttggctaatt ctcgacaatt gatcaagaac    540
cacaccgaca actacaaatt tagttggaag agttatttga aaacaatcaa gcagaacttt    600
atcaagtcag tgcctatact tgttttagga gctattcgtt ttgttagtgt taagcaattg    660
gactatcagg aacacgaaac agagtatgga atccattgga attttttctt cacattaggg    720
ttcttgccaa ttgtattggg aatattagac ccggtgttga atttggttcc acgcttcata    780
ataggaattg gtatctcaat tggttatgag gtagcgttga ataagactgg tttgttgaag    840
ttcattttga gcagcgaaaa cagacttgaa tctctcatcg ccatgaataa agaaggtatt    900
ttttcgttta ttggatatct ttgtatttt ataattggtc agtcttttgg gtcatttgtt    960
ttaacaggct acaaaacaaa gaacaactta ataaccatta gcaaaattcg tatttcaaaa   1020
aaacaacaca agaaagagct gctgctgttt ttctcagtcg ccactactca gggattatat   1080
ttggcatgta tcttctatca cttagctttc agtttgttca tcagcaactt atcattcttg   1140
caaccaattt caagacgatt ggccaatttc ccctacgtca tgtgggtcgt ttcgtacaat   1200
gctacgtttt tattatgtta tgacttaatt gaaaaattta tcccggggaa ccttacttct   1260
actgtattgg attctattaa taacaatggt ttatttatct tcttggtcag caatttatta   1320
acagggttta ttaacatgtc catcaacact ttggaaacta gcaataaaat ggcagtgatt   1380
atcttgattg gctatagtct tacttggaca ttgctcgcct tatatttgga taagaggaag   1440
atctacatca agctttag                                                 1458
```

```
<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
gcagtcgact cgatgaggtc tttgctaatc ttg                                 33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 9
gcagaattcg acaccacaac cttgaacgta ttg                                 33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 10
cccgaattca ctgacggtca aatccaagct act                                 33

<210> SEQ ID NO 11
<211> LENGTH: 32
<212> TYPE: DNA
<213> ORGANISM: Artificial Sequence
```

```
<220> FEATURE:
<223> OTHER INFORMATION: Description of Artificial Sequence:
      oligonucleotide primer

<400> SEQUENCE: 11
ggaagctttt ataacaacat agcggcagca gc                                      32

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 12
cccgcggccg cttgatagta agcttgcttg ggccgcatca tgtaattag                    49

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
cccggtacca aattaaagcc ttcgagcctc cca                                     33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
cccggatcct gtttgcagca tgagacttgc ata                                     33

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
cccgcggccg cccccttccaa ttcgaaaacc ttccccagag cagcc                       45

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
ggttcgaagc cgcaaaaaca gaacaacaaa tt                                      32

<210> SEQ ID NO 17
<211> LENGTH: 32
<212> TYPE: DNA
<213> ORGANISM: Artificial Sequence
```

```
<220> FEATURE:
<223> OTHER INFORMATION: Description of Artificial Sequence:
      oligonucleotide primer

<400> SEQUENCE: 17
ggtctagatt gcagtttttc aagaatgcgc ca                                32

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
gggtctagaa ctgacggtca aatccaagct act                               33

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
ggaagctttt ataacaacat agcggcagca gc                                32

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:
      Candida albicans Als1p synthetic peptide

<400> SEQUENCE: 20

Cys Phe Thr Ala Gly Thr Asn Thr Val Thr Phe Asn Asp Gly Asp Lys
 1               5                  10                  15

Asp Ile

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 21
aaactgttca ctgaacaacc aaatctc                                      27

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 22
caactgtacc atttgttaga catcact                                      27
```

-continued

```
<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 23
aaacagctgg gatcgcaata agaagacacg                                        30

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 24
aaacagctga tggaaatgtg gatggtgtg                                         29

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 25
atggcaacag tacatcagga gaatatgtcg actttaaaac cggatccccg tcgtttaaac       60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 26
ttatagctta atgaatattc tttttctata caagaaaacc gaattcgagc tcgtttaaac       60

<210> SEQ ID NO 27
<211> LENGTH: 1380
<212> TYPE: DNA
<213> ORGANISM: Schizosaccharomyces pombe
<220> FEATURE:
<221> NAME/KEY: CDS
<222> LOCATION: (1)..(1380)
<223> OTHER INFORMATION: homologue of S. cerevisiae GWT1

<400> SEQUENCE: 27 atg tca tac aaa ttg gaa aaa gaa gca ttt gtc tca aac ctg acg ggt         48
Met Ser Tyr Lys Leu Glu Lys Glu Ala Phe Val Ser Asn Leu Thr Gly
1               5                   10                  15 tca agt tcc att gag aca tgt ggc ttg tta tta ata gga att gct tgc         96
Ser Ser Ser Ile Glu Thr Cys Gly Leu Leu Leu Ile Gly Ile Ala Cys
            20                  25                  30 aac gtt ttg tgg gta aac atg act gcg aga aac atc tta ccc aaa ggg        144
Asn Val Leu Trp Val Asn Met Thr Ala Arg Asn Ile Leu Pro Lys Gly
        35                  40                  45 aat ctt ggg ttt ctt gtt gag ttt ttc atc ttt tgc tta att cca tta        192
Asn Leu Gly Phe Leu Val Glu Phe Phe Ile Phe Cys Leu Ile Pro Leu
    50                  55                  60
```

-continued

| | |
|---|---|
| ttt gtc att tac gtt tca tcg aaa gtt ggc gtt ttc act ctt tgc ata<br>Phe Val Ile Tyr Val Ser Ser Lys Val Gly Val Phe Thr Leu Cys Ile<br>65                       70                       75                     80 | 240 |
| gcc tct ttt ttg cct tcc ttc gtc ctt cat gtt ata agt cca att aat<br>Ala Ser Phe Leu Pro Ser Phe Val Leu His Val Ile Ser Pro Ile Asn<br>                  85                       90                       95 | 288 |
| tgg gat gtg ctg aga aga aaa cct ggt tgt tgt ctt act aaa aaa aat<br>Trp Asp Val Leu Arg Arg Lys Pro Gly Cys Cys Leu Thr Lys Lys Asn<br>           100                     105                   110 | 336 |
| gaa aat act ttt gat cga cga att gct gga gtc aca ttt tat cgt tct<br>Glu Asn Thr Phe Asp Arg Arg Ile Ala Gly Val Thr Phe Tyr Arg Ser<br>        115                     120                     125 | 384 |
| caa atg atg ttg gtt act gtc act tgc atc ctg gcc gtt gac ttt acc<br>Gln Met Met Leu Val Thr Val Thr Cys Ile Leu Ala Val Asp Phe Thr<br>130                       135                       140 | 432 |
| ctt ttc ccg agg aga tat gcc aaa gtt gaa acc tgg gga aca tca ctg<br>Leu Phe Pro Arg Arg Tyr Ala Lys Val Glu Thr Trp Gly Thr Ser Leu<br>145                       150                     155                     160 | 480 |
| atg gat ctt ggt gtt gga tct ttc atg ttt tct tca ggt act gtg gct<br>Met Asp Leu Gly Val Gly Ser Phe Met Phe Ser Ser Gly Thr Val Ala<br>                  165                     170                     175 | 528 |
| gga cgg aaa aat gac att aaa aaa cca aat gcg ttt aaa aat gta ttg<br>Gly Arg Lys Asn Asp Ile Lys Lys Pro Asn Ala Phe Lys Asn Val Leu<br>                     180                     185                     190 | 576 |
| tgg aat tct ttc atc ctt ttg att tta gga ttt gcg cgc atg ttt tta<br>Trp Asn Ser Phe Ile Leu Leu Ile Leu Gly Phe Ala Arg Met Phe Leu<br>              195                     200                     205 | 624 |
| acg aaa agc atc aat tac caa gaa cat gta agc gaa tat ggc atg cat<br>Thr Lys Ser Ile Asn Tyr Gln Glu His Val Ser Glu Tyr Gly Met His<br>210                       215                       220 | 672 |
| tgg aac ttt ttt ttc acc cta ggt ttc atg gct ctt ggc gta ttt ttt<br>Trp Asn Phe Phe Phe Thr Leu Gly Phe Met Ala Leu Gly Val Phe Phe<br>225                       230                     235                     240 | 720 |
| ttt cgt cgt tct tta aaa aaa gtc tcc tat ttt aat tta gca acc ttc<br>Phe Arg Arg Ser Leu Lys Lys Val Ser Tyr Phe Asn Leu Ala Thr Phe<br>                       245                     250                     255 | 768 |
| att act ctt ctt cat cat tgt ttg ctt gtt tta acc cct ttc caa aaa<br>Ile Thr Leu Leu His His Cys Leu Leu Val Leu Thr Pro Phe Gln Lys<br>                  260                     265                     270 | 816 |
| tgg gca cta tcc gcc ccc aga aca aat att ttg gct cag aat aga gag<br>Trp Ala Leu Ser Ala Pro Arg Thr Asn Ile Leu Ala Gln Asn Arg Glu<br>                  275                     280                     285 | 864 |
| ggt att gct tct ctt ccc gga tac att gct att tac ttt tat gga atg<br>Gly Ile Ala Ser Leu Pro Gly Tyr Ile Ala Ile Tyr Phe Tyr Gly Met<br>290                       295                     300 | 912 |
| tat acc ggt agt gta gtt ttg gct gat cga cct cta atg tat act aga<br>Tyr Thr Gly Ser Val Val Leu Ala Asp Arg Pro Leu Met Tyr Thr Arg<br>305                       310                     315                     320 | 960 |
| gct gag tcg tgg aag cgc ttt caa cgt cta tta ttc ccg cta tgc att<br>Ala Glu Ser Trp Lys Arg Phe Gln Arg Leu Leu Phe Pro Leu Cys Ile<br>                  325                     330                     335 | 1008 |
| ttg tta gtg ttg tat ctt gtg tct aac ttt ttg tca gtt ggt gtt tct<br>Leu Leu Val Leu Tyr Leu Val Ser Asn Phe Leu Ser Val Gly Val Ser<br>                  340                     345                     350 | 1056 |
| cgc cga ctt gct aat acg cct tat gtt gcg aat gtt gcc ttt atc aat<br>Arg Arg Leu Ala Asn Thr Pro Tyr Val Ala Asn Val Ala Phe Ile Asn<br>                     355                     360                     365 | 1104 |
| atg ttt ttt ctt act ata tac ata ctt att gat gcc tat tta ttc cca<br>Met Phe Phe Leu Thr Ile Tyr Ile Leu Ile Asp Ala Tyr Leu Phe Pro<br>370                       375                     380 | 1152 |

```
tct tct gtg cca tat gga agt cgc gtc ccc aaa ctg ctt gaa gat gcc    1200
Ser Ser Val Pro Tyr Gly Ser Arg Val Pro Lys Leu Leu Glu Asp Ala
385                 390                 395                 400 aat aat aat ggc ttg ttg gtg ttt ttg att gct aac gtt tta aca gga    1248
Asn Asn Asn Gly Leu Leu Val Phe Leu Ile Ala Asn Val Leu Thr Gly
                405                 410                 415 gta gtt aat tta tcg ttc gac acc ctt cat tct agc aat gca aaa ggc    1296
Val Val Asn Leu Ser Phe Asp Thr Leu His Ser Ser Asn Ala Lys Gly
420                 425                 430 ttg aca atc atg act atg tat ctt ttt att att tgc tat atg gca cat    1344
Leu Thr Ile Met Thr Met Tyr Leu Phe Ile Ile Cys Tyr Met Ala His
            435                 440                 445 tgg ctt gct caa cac gga att cgt ttt cgc ctt tag                    1380
Trp Leu Ala Gln His Gly Ile Arg Phe Arg Leu
450                 455                 460

<210> SEQ ID NO 28
<211> LENGTH: 459
<212> TYPE: PRT
<213> ORGANISM: Schizosaccharomyces pombe
<220> FEATURE:
<223> OTHER INFORMATION: homologue of S. cerevisiae GWT1

<400> SEQUENCE: 28

Met Ser Tyr Lys Leu Glu Lys Glu Ala Phe Val Ser Asn Leu Thr Gly
1               5                   10                  15

Ser Ser Ser Ile Glu Thr Cys Gly Leu Leu Ile Gly Ile Ala Cys
                20                  25                  30

Asn Val Leu Trp Val Asn Met Thr Ala Arg Asn Ile Leu Pro Lys Gly
            35                  40                  45

Asn Leu Gly Phe Leu Val Glu Phe Phe Ile Phe Cys Leu Ile Pro Leu
        50                  55                  60

Phe Val Ile Tyr Val Ser Ser Lys Val Gly Val Phe Thr Leu Cys Ile
65                  70                  75                  80

Ala Ser Phe Leu Pro Ser Phe Val Leu His Val Ile Ser Pro Ile Asn
                85                  90                  95

Trp Asp Val Leu Arg Arg Lys Pro Gly Cys Cys Leu Thr Lys Lys Asn
            100                 105                 110

Glu Asn Thr Phe Asp Arg Arg Ile Ala Gly Val Thr Phe Tyr Arg Ser
        115                 120                 125

Gln Met Met Leu Val Thr Val Thr Cys Ile Leu Ala Val Asp Phe Thr
130                 135                 140

Leu Phe Pro Arg Arg Tyr Ala Lys Val Glu Thr Trp Gly Thr Ser Leu
145                 150                 155                 160

Met Asp Leu Gly Val Gly Ser Phe Met Phe Ser Ser Gly Thr Val Ala
                165                 170                 175

Gly Arg Lys Asn Asp Ile Lys Lys Pro Asn Ala Phe Lys Asn Val Leu
            180                 185                 190

Trp Asn Ser Phe Ile Leu Leu Ile Leu Gly Phe Ala Arg Met Phe Leu
        195                 200                 205

Thr Lys Ser Ile Asn Tyr Gln Glu His Val Ser Glu Tyr Gly Met His
210                 215                 220

Trp Asn Phe Phe Thr Leu Gly Phe Met Ala Leu Gly Val Phe Phe
225                 230                 235                 240

Phe Arg Arg Ser Leu Lys Lys Val Ser Tyr Phe Asn Leu Ala Thr Phe
                245                 250                 255

Ile Thr Leu Leu His His Cys Leu Leu Val Leu Thr Pro Phe Gln Lys
            260                 265                 270
```

-continued

```
Trp Ala Leu Ser Ala Pro Arg Thr Asn Ile Leu Ala Gln Asn Arg Glu
        275                 280                 285

Gly Ile Ala Ser Leu Pro Gly Tyr Ile Ala Ile Tyr Phe Tyr Gly Met
    290                 295                 300

Tyr Thr Gly Ser Val Val Leu Ala Asp Arg Pro Leu Met Tyr Thr Arg
305                 310                 315                 320

Ala Glu Ser Trp Lys Arg Phe Gln Arg Leu Leu Phe Pro Leu Cys Ile
                325                 330                 335

Leu Leu Val Leu Tyr Leu Val Ser Asn Phe Leu Ser Val Gly Val Ser
            340                 345                 350

Arg Arg Leu Ala Asn Thr Pro Tyr Val Ala Asn Val Ala Phe Ile Asn
        355                 360                 365

Met Phe Phe Leu Thr Ile Tyr Ile Leu Ile Asp Ala Tyr Leu Phe Pro
    370                 375                 380

Ser Ser Val Pro Tyr Gly Ser Arg Val Pro Lys Leu Leu Glu Asp Ala
385                 390                 395                 400

Asn Asn Asn Gly Leu Leu Val Phe Leu Ile Ala Asn Val Leu Thr Gly
                405                 410                 415

Val Val Asn Leu Ser Phe Asp Thr Leu His Ser Ser Asn Ala Lys Gly
            420                 425                 430

Leu Thr Ile Met Thr Met Tyr Leu Phe Ile Ile Cys Tyr Met Ala His
        435                 440                 445

Trp Leu Ala Gln His Gly Ile Arg Phe Arg Leu
    450                 455

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence:primer based
      on presumed DNA encoding GWT1 highly conserved region
<220> FEATURE:
<221> NAME/KEY: modified_base
<222> LOCATION: (1)..(35)
<223> OTHER INFORMATION: n = g, a, c or t

<400> SEQUENCE: 29
gcnaargtng aracntgggg nacnwsnytn atgga                              35

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence:primer based
      on presumed DNA encoding GWT1 highly conserved region
<220> FEATURE:
<221> NAME/KEY: modified_base
<222> LOCATION: (1)..(38)
<223> OTHER INFORMATION: n = g, a, c or t

<400> SEQUENCE: 30
ttccartgna ynccrtaytc ngtnacrtgy tcytgrta                           38

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence:primer based
      on presumed DNA encoding GWT1 highly conserved region
```

```
<220> FEATURE:
<221> NAME/KEY: modified_base
<222> LOCATION: (1)..(32)
<223> OTHER INFORMATION: n = g, a, c or t

<400> SEQUENCE: 31
gtraaraara arttccartg naynccrtay tc                                    32

<210> SEQ ID NO 32
<211> LENGTH: 188
<212> TYPE: DNA
<213> ORGANISM: Aspergillus fumigatus
<220> FEATURE:
<223> OTHER INFORMATION: fragment having homology to S. cerevisiae GWT1

<400> SEQUENCE: 32
atggatctgg gcgttggatc gtttgtctttt tcgggcggag tagtatccgc tcgctcacta    60
ctcaagagca ggaccaatgg ctctaaaagg ttgcctcttg ccaagaggtt gattgcgtcg   120
acgcgacact ctattcctct gctcgtcctc ggcctgattc ggctatacag cgtcaaaggc   180
ttggacta                                                             188

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:PCR
      amplification primer based on amplified fragment

<400> SEQUENCE: 33
ggagtagtat ccgctcgctc acta                                             24

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer based on amplified fragment

<400> SEQUENCE: 34
gtccaagcct ttgacgctgt atagc                                            25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer outside gene insertion site
      of library

<400> SEQUENCE: 35
gggatgtgct gcaaggcgat taagt                                            25

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer outside gene insertion site
      of library

<400> SEQUENCE: 36
tttatgcttc cggctcgtat gttgtg                                           26
```

-continued

```
<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:primer
      corresponding to sequence upstream of initiation
      codon

<400> SEQUENCE: 37
aaaggtgcaa atcccgcggc attga                                       25

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence:primer
      corresponding to sequence downstream of stop codon

<400> SEQUENCE: 38
agttcactat atatcttcaa cacaccac                                    28

<210> SEQ ID NO 39
<211> LENGTH: 1576
<212> TYPE: DNA
<213> ORGANISM: Aspergillus fumigatus
<220> FEATURE:
<223> OTHER INFORMATION: amplified fragment of homologue of S.
      cerevisiae GWT1 from cDNA library
<220> FEATURE:
<221> NAME/KEY: CDS
<222> LOCATION: (31)..(1536)
<223> OTHER INFORMATION: homologue of S. cerevisiae GWT1

<400> SEQUENCE: 39
aaggtgcaaa tcccgcggca ttgagtcaag atg gat cca gat tat aaa gct cgc    54
                                    Met Asp Pro Asp Tyr Lys Ala Arg
                                    1               5 aaa gag gcc ttt gtc tca ggt ctt gca gga gga agc atc ctg gaa atc   102
Lys Glu Ala Phe Val Ser Gly Leu Ala Gly Gly Ser Ile Leu Glu Ile
        10                  15                  20 aac gcc gtc acc ttg gtt gct tcg gta tcc gtt ttt ctg tgg tca att   150
Asn Ala Val Thr Leu Val Ala Ser Val Ser Val Phe Leu Trp Ser Ile
 25                  30                  35                  40 cta caa tct cgc cta tcc ttt ttc aca ccc tac agc gcc gct gcc ctt   198
Leu Gln Ser Arg Leu Ser Phe Phe Thr Pro Tyr Ser Ala Ala Ala Leu
                 45                  50                  55 ctc gtt gat ttc ctg ctc aat gta cta gct atc ttg ttc gca acc act   246
Leu Val Asp Phe Leu Leu Asn Val Leu Ala Ile Leu Phe Ala Thr Thr
             60                  65                  70 tta tac tct tcg gcg cct ctt ctt ctc aat ctc ctt cta ata tct ccc   294
Leu Tyr Ser Ser Ala Pro Leu Leu Leu Asn Leu Leu Leu Ile Ser Pro
         75                  80                  85 gct ctg ctg ata ctc ctc tct acg aaa cgt cct cgg acc ccc gtc aaa   342
Ala Leu Leu Ile Leu Leu Ser Thr Lys Arg Pro Arg Thr Pro Val Lys
     90                  95                 100 gcg aaa cct cct cgc cag tcc gct aga gct ggg aaa gat gac tcg aaa   390
Ala Lys Pro Pro Arg Gln Ser Ala Arg Ala Gly Lys Asp Asp Ser Lys
105                 110                 115                 120 cat gcg aca gcc ttg cca gag tct cta ccc att cat cca ttt ctc acg   438
His Ala Thr Ala Leu Pro Glu Ser Leu Pro Ile His Pro Phe Leu Thr
                125                 130                 135 aca tat cgc gcc gcc atg atg gtt atc acg tgc atc gct atc ttg gct   486
Thr Tyr Arg Ala Ala Met Met Val Ile Thr Cys Ile Ala Ile Leu Ala
            140                 145                 150
```

```
                                                              -continued gtg gat ttt cgc att ttt cct cgc cga ttc gcc aag gta gaa aac tgg      534
Val Asp Phe Arg Ile Phe Pro Arg Arg Phe Ala Lys Val Glu Asn Trp
        155                 160                 165 ggt aca tca ctc atg gat ctg ggc gtt gga tcg ttt gtc ttt tcg ggc      582
Gly Thr Ser Leu Met Asp Leu Gly Val Gly Ser Phe Val Phe Ser Gly
    170                 175                 180 gga gta gta tcc gct cgc tca cta ctc aag agc agg acc aat ggc tct      630
Gly Val Val Ser Ala Arg Ser Leu Leu Lys Ser Arg Thr Asn Gly Ser
185                 190                 195                 200 aaa agg ttg cct ctt gcc aag agg ttg att gcg tcg acg cga cac tct      678
Lys Arg Leu Pro Leu Ala Lys Arg Leu Ile Ala Ser Thr Arg His Ser
                205                 210                 215 att cct ctg ctc gtc ctc ggc ctg att cgg cta tac agc gtc aaa ggc      726
Ile Pro Leu Leu Val Leu Gly Leu Ile Arg Leu Tyr Ser Val Lys Gly
        220                 225                 230 ttg gac tat gcg gag cac gtc acc gag tac ggc gta cat tgg aac ttc      774
Leu Asp Tyr Ala Glu His Val Thr Glu Tyr Gly Val His Trp Asn Phe
    235                 240                 245 ttc ttt aca ttg ggt ctt ttg cct ccg ttc gtg gag gtc ttc gac gcc      822
Phe Phe Thr Leu Gly Leu Leu Pro Pro Phe Val Glu Val Phe Asp Ala
250                 255                 260 ttg gct acg atc att ccg tca tac gag gtt ctc tcc gtg ggg atc gcc      870
Leu Ala Thr Ile Ile Pro Ser Tyr Glu Val Leu Ser Val Gly Ile Ala
265                 270                 275                 280 gtc ttg tat caa gtt gcc cta gag tca aca gac ttg aaa agc tac atc      918
Val Leu Tyr Gln Val Ala Leu Glu Ser Thr Asp Leu Lys Ser Tyr Ile
                285                 290                 295 ctc gtc tcc cct cgt ggg cca agc tta ctg tcc aag aat cgt gaa ggc      966
Leu Val Ser Pro Arg Gly Pro Ser Leu Leu Ser Lys Asn Arg Glu Gly
        300                 305                 310 gtc ttc tcc ttc tca ggt tat ctc gcg att ttt ctt gct ggt cgt gcg     1014
Val Phe Ser Phe Ser Gly Tyr Leu Ala Ile Phe Leu Ala Gly Arg Ala
    315                 320                 325 atc ggc att cgg ata atc cct cgc gga act tct ttc tca aga agc cca     1062
Ile Gly Ile Arg Ile Ile Pro Arg Gly Thr Ser Phe Ser Arg Ser Pro
330                 335                 340 gaa cag gcc agg aga cgg gtc ctg atc agc ctt ggc gtg caa gcg tta     1110
Glu Gln Ala Arg Arg Arg Val Leu Ile Ser Leu Gly Val Gln Ala Leu
345                 350                 355                 360 gtg tgg acc act ctt ttt gtg ttg aac tcc act tat gcg atg gga tac     1158
Val Trp Thr Thr Leu Phe Val Leu Asn Ser Thr Tyr Ala Met Gly Tyr
                365                 370                 375 gga gct aat atc cct gtc tcc cgc cgc ctc gct aac atg ccc tat gtc     1206
Gly Ala Asn Ile Pro Val Ser Arg Arg Leu Ala Asn Met Pro Tyr Val
        380                 385                 390 ctt tgg gtt tcg gcg ttc aac acc gcg caa ctg ttt gtg ttc tgc ctg     1254
Leu Trp Val Ser Ala Phe Asn Thr Ala Gln Leu Phe Val Phe Cys Leu
    395                 400                 405 atc gaa aca ctc tgc ttt cct gca gtt cat cgg aca acg act caa gag     1302
Ile Glu Thr Leu Cys Phe Pro Ala Val His Arg Thr Thr Thr Gln Glu
410                 415                 420 agc gaa tct gag cga gtc gat ttt gct acg agc cga atc atg tcg gcc     1350
Ser Glu Ser Glu Arg Val Asp Phe Ala Thr Ser Arg Ile Met Ser Ala
425                 430                 435                 440 ttc aat aag aac agt ctc gcg atc ttt ctt ttg gcc aat ctt ctg act     1398
Phe Asn Lys Asn Ser Leu Ala Ile Phe Leu Leu Ala Asn Leu Leu Thr
                445                 450                 455 gga gct gtg aat ctg agc atc tcc aca att gat gct aat aca gcg cag     1446
Gly Ala Val Asn Leu Ser Ile Ser Thr Ile Asp Ala Asn Thr Ala Gln
        460                 465                 470
```

```
gcc atc gct gtt ctc att gga tat tca tcc att atc aca ggg gtt gct    1494
Ala Ile Ala Val Leu Ile Gly Tyr Ser Ser Ile Ile Thr Gly Val Ala
475                 480                 485 cta gca ttg cat cat gcc aat atc aaa gta ctt cct ttc tag            1536
Leu Ala Leu His His Ala Asn Ile Lys Val Leu Pro Phe
490                 495                 500 ggtatttacg agcaattggt ggtgtgttga agatatatag                        1576
```

<210> SEQ ID NO 40
<211> LENGTH: 501
<212> TYPE: PRT
<213> ORGANISM: Aspergillus fumigatus
<220> FEATURE:
<223> OTHER INFORMATION: homologue of S. cerevisiae GWT1

<400> SEQUENCE: 40

```
Met Asp Pro Asp Tyr Lys Ala Arg Lys Glu Ala Phe Val Ser Gly Leu
1               5                   10                  15

Ala Gly Gly Ser Ile Leu Glu Ile Asn Ala Val Thr Leu Val Ala Ser
                20                  25                  30

Val Ser Val Phe Leu Trp Ser Ile Leu Gln Ser Arg Leu Ser Phe Phe
            35                  40                  45

Thr Pro Tyr Ser Ala Ala Leu Leu Val Asp Phe Leu Leu Asn Val
    50                  55                  60

Leu Ala Ile Leu Phe Ala Thr Thr Leu Tyr Ser Ser Ala Pro Leu Leu
65                  70                  75                  80

Leu Asn Leu Leu Leu Ile Ser Pro Ala Leu Leu Ile Leu Leu Ser Thr
                85                  90                  95

Lys Arg Pro Arg Thr Pro Val Lys Ala Lys Pro Pro Arg Gln Ser Ala
            100                 105                 110

Arg Ala Gly Lys Asp Asp Ser Lys His Ala Thr Ala Leu Pro Glu Ser
        115                 120                 125

Leu Pro Ile His Pro Phe Leu Thr Thr Tyr Arg Ala Ala Met Met Val
    130                 135                 140

Ile Thr Cys Ile Ala Ile Leu Ala Val Asp Phe Arg Ile Phe Pro Arg
145                 150                 155                 160

Arg Phe Ala Lys Val Glu Asn Trp Gly Thr Ser Leu Met Asp Leu Gly
                165                 170                 175

Val Gly Ser Phe Val Phe Ser Gly Val Val Ser Ala Arg Ser Leu
            180                 185                 190

Leu Lys Ser Arg Thr Asn Gly Ser Lys Arg Leu Pro Leu Ala Lys Arg
        195                 200                 205

Leu Ile Ala Ser Thr Arg His Ser Ile Pro Leu Leu Val Leu Gly Leu
    210                 215                 220

Ile Arg Leu Tyr Ser Val Lys Gly Leu Asp Tyr Ala Glu His Val Thr
225                 230                 235                 240

Glu Tyr Gly Val His Trp Asn Phe Phe Thr Leu Gly Leu Leu Pro
                245                 250                 255

Pro Phe Val Glu Val Phe Asp Ala Leu Ala Thr Ile Ile Pro Ser Tyr
            260                 265                 270

Glu Val Leu Ser Val Gly Ile Ala Val Leu Tyr Gln Val Ala Leu Glu
        275                 280                 285

Ser Thr Asp Leu Lys Ser Tyr Ile Leu Val Ser Pro Arg Gly Pro Ser
    290                 295                 300

Leu Leu Ser Lys Asn Arg Glu Gly Val Phe Ser Phe Ser Gly Tyr Leu
305                 310                 315                 320
```

```
                        -continued

Ala Ile Phe Leu Ala Gly Arg Ala Gly Ile Arg Ile Ile Pro Arg
                325                 330                 335

Gly Thr Ser Phe Ser Arg Ser Pro Glu Gln Ala Arg Arg Val Leu
                340                 345                 350

Ile Ser Leu Gly Val Gln Ala Leu Val Trp Thr Thr Leu Phe Val Leu
                355                 360                 365

Asn Ser Thr Tyr Ala Met Gly Tyr Gly Ala Asn Ile Pro Val Ser Arg
                370                 375             380

Arg Leu Ala Asn Met Pro Tyr Val Leu Trp Val Ser Ala Phe Asn Thr
385                 390                 395                 400

Ala Gln Leu Phe Val Phe Cys Leu Ile Glu Thr Leu Cys Phe Pro Ala
                405                 410                 415

Val His Arg Thr Thr Thr Gln Glu Ser Glu Ser Glu Arg Val Asp Phe
                420                 425                 430

Ala Thr Ser Arg Ile Met Ser Ala Phe Asn Lys Asn Ser Leu Ala Ile
                435                 440                 445

Phe Leu Leu Ala Asn Leu Leu Thr Gly Ala Val Asn Leu Ser Ile Ser
                450                 455                 460

Thr Ile Asp Ala Asn Thr Ala Gln Ala Ile Ala Val Leu Ile Gly Tyr
465                 470                 475                 480

Ser Ser Ile Ile Thr Gly Val Ala Leu Ala Leu His His Ala Asn Ile
                485                 490                 495

Lys Val Leu Pro Phe
                500

<210> SEQ ID NO 41
<211> LENGTH: 1648
<212> TYPE: DNA
<213> ORGANISM: Aspergillus fumigatus
<220> FEATURE:
<223> OTHER INFORMATION: cloned homologue of S. cerevisiae GWT1 from
      genomic library
<220> FEATURE:
<221> NAME/KEY: CDS
<222> LOCATION: join(26..121, 199..1608)
<223> OTHER INFORMATION: homologue of S. cerevisiae GWT1
<220> FEATURE:
<221> NAME/KEY: exon
<222> LOCATION: (26)..(121)
<220> FEATURE:
<221> NAME/KEY: intron
<222> LOCATION: (122)..(198)
<220> FEATURE:
<221> NAME/KEY: exon
<222> LOCATION: (199)..(1608)

<400> SEQUENCE: 41
gcaaatcccg cggcattgag tcaag atg gat cca gat tat aaa gct cgc aaa        52
                           Met Asp Pro Asp Tyr Lys Ala Arg Lys
                            1               5 gag gcc ttt gtc tca ggt ctt gca gga gga agc atc ctg gaa atc aac       100
Glu Ala Phe Val Ser Gly Leu Ala Gly Gly Ser Ile Leu Glu Ile Asn
 10              15                  20                  25 gcc gtc acc ttg gtt gct tcg gttcgtgtta ctatcttatt gtggctactt         151
Ala Val Thr Leu Val Ala Ser
                30 cgcctacatt gtttctcgac taaccgagtc tctttgcgat caatcag gta tcc gtt       207
                                                   Val Ser Val
                                                               35 ttt ctg tgg tca att cta caa tct cgc cta tcc ttt ttc aca ccc tac       255
Phe Leu Trp Ser Ile Leu Gln Ser Arg Leu Ser Phe Phe Thr Pro Tyr
             40                  45                  50
```

```
agc gcc gct gcc ctt ctc gtt gat ttc ctg ctc aat gta cta gct atc        303
Ser Ala Ala Ala Leu Leu Val Asp Phe Leu Leu Asn Val Leu Ala Ile
             55                  60                  65 ttg ttc gca acc act tta tac tct tcg gcg cct ctt ctt ctc aat ctc        351
Leu Phe Ala Thr Thr Leu Tyr Ser Ser Ala Pro Leu Leu Leu Asn Leu
         70                  75                  80 ctt cta ata tct ccc gct ctg ctg ata ctc ctc tct acg aaa cgt cct        399
Leu Leu Ile Ser Pro Ala Leu Leu Ile Leu Leu Ser Thr Lys Arg Pro
     85                  90                  95 cgg acc ccc gtc aaa gcg aaa cct cct cgc cag tcc gct aga gct ggg        447
Arg Thr Pro Val Lys Ala Lys Pro Pro Arg Gln Ser Ala Arg Ala Gly
100                 105                 110                 115 aaa gat gac tcg aaa cat gcg aca gcc ttg cca gag tct cta ccc att        495
Lys Asp Asp Ser Lys His Ala Thr Ala Leu Pro Glu Ser Leu Pro Ile
                120                 125                 130 cat cca ttt ctc acg aca tat cgc gcc gcc atg atg gtt atc acg tgc        543
His Pro Phe Leu Thr Thr Tyr Arg Ala Ala Met Met Val Ile Thr Cys
            135                 140                 145 atc gct atc ttg gct gtg gat ttt cgc att ttt cct cgc cga ttc gcc        591
Ile Ala Ile Leu Ala Val Asp Phe Arg Ile Phe Pro Arg Arg Phe Ala
        150                 155                 160 aag gta gaa aac tgg ggt aca tca ctc atg gat ctg ggc gtt gga tcg        639
Lys Val Glu Asn Trp Gly Thr Ser Leu Met Asp Leu Gly Val Gly Ser
    165                 170                 175 ttt gtc ttt tcg gga gga gta gta tcc gct cgc tca cta ctc aag agc        687
Phe Val Phe Ser Gly Gly Val Val Ser Ala Arg Ser Leu Leu Lys Ser
180                 185                 190                 195 agg acc aat ggc tct aaa agg ttg cct ctt gcc aag agg ttg att gcg        735
Arg Thr Asn Gly Ser Lys Arg Leu Pro Leu Ala Lys Arg Leu Ile Ala
                200                 205                 210 tcg acg cga cac tct att cct ctg ctc gtc ctc ggc ctg att cgg cta        783
Ser Thr Arg His Ser Ile Pro Leu Leu Val Leu Gly Leu Ile Arg Leu
            215                 220                 225 tac agc gtc aaa ggc ttg gac tat gcg gag cac gtc acc gag tac ggc        831
Tyr Ser Val Lys Gly Leu Asp Tyr Ala Glu His Val Thr Glu Tyr Gly
        230                 235                 240 gta cat tgg aac ttc ttc ttt aca ttg ggt ctt ttg cct ccg ttc gtg        879
Val His Trp Asn Phe Phe Phe Thr Leu Gly Leu Leu Pro Pro Phe Val
    245                 250                 255 gag gtc ttc gac gcc ttg gct acg atc att ccg tca tac gag gtt ctc        927
Glu Val Phe Asp Ala Leu Ala Thr Ile Ile Pro Ser Tyr Glu Val Leu
260                 265                 270                 275 tcc gtg ggg atc gcc gtc ttg tat caa gtt gcc cta gag tca aca gac        975
Ser Val Gly Ile Ala Val Leu Tyr Gln Val Ala Leu Glu Ser Thr Asp
                280                 285                 290 ttg aaa agc tac atc ctc gtc tcc cct cgt ggg cca agc tta ctg tcc       1023
Leu Lys Ser Tyr Ile Leu Val Ser Pro Arg Gly Pro Ser Leu Leu Ser
            295                 300                 305 aag aat cgt gaa ggc gtc ttc tcc ttc tca ggt tat ctc gcg att ttt       1071
Lys Asn Arg Glu Gly Val Phe Ser Phe Ser Gly Tyr Leu Ala Ile Phe
        310                 315                 320 ctt gct ggt cgt gcg atc ggc att cgg ata atc cct cgc gga act tct       1119
Leu Ala Gly Arg Ala Ile Gly Ile Arg Ile Ile Pro Arg Gly Thr Ser
    325                 330                 335 ttc tca aga agc cca gaa cag gcc agg aga cgg gtc ctg atc agc ctt       1167
Phe Ser Arg Ser Pro Glu Gln Ala Arg Arg Arg Val Leu Ile Ser Leu
340                 345                 350                 355 ggc gtg caa gcg tta gtg tgg acc act ctt ttt gtg ttg aac tcc act       1215
Gly Val Gln Ala Leu Val Trp Thr Thr Leu Phe Val Leu Asn Ser Thr
                360                 365                 370
```

```
tat gcg atg gga tac gga gct aat atc cct gtc tcc cgc cgc ctc gct    1263
Tyr Ala Met Gly Tyr Gly Ala Asn Ile Pro Val Ser Arg Arg Leu Ala
            375                 380                 385 aac atg ccc tat gtc ctt tgg gtt tcg gcg ttc aac acc gcg caa ctg    1311
Asn Met Pro Tyr Val Leu Trp Val Ser Ala Phe Asn Thr Ala Gln Leu
        390                 395                 400 ttt gtg ttc tgc ctg atc gaa aca ctc tgc ttt cct gca gtt cat cgg    1359
Phe Val Phe Cys Leu Ile Glu Thr Leu Cys Phe Pro Ala Val His Arg
    405                 410                 415 aca acg act caa gag agc gaa tct gag cga gtc gat ttt gct acg agc    1407
Thr Thr Thr Gln Glu Ser Glu Ser Glu Arg Val Asp Phe Ala Thr Ser
420                 425                 430                 435 cga atc atg tcg gcc ttc aat aag aac agt ctc gcg atc ttt ctt ttg    1455
Arg Ile Met Ser Ala Phe Asn Lys Asn Ser Leu Ala Ile Phe Leu Leu
                440                 445                 450 gcc aat ctt ctg act gga gct gtg aat ctg agc atc tcc aca att gat    1503
Ala Asn Leu Leu Thr Gly Ala Val Asn Leu Ser Ile Ser Thr Ile Asp
            455                 460                 465 gct aat aca gcg cag gcc atc gct gtt ctc att gga tat tca tcc att    1551
Ala Asn Thr Ala Gln Ala Ile Ala Val Leu Ile Gly Tyr Ser Ser Ile
        470                 475                 480 atc aca ggg gtt gct cta gca ttg cat cat gcc aat atc aaa gta ctt    1599
Ile Thr Gly Val Ala Leu Ala Leu His His Ala Asn Ile Lys Val Leu
    485                 490                 495 cct ttc tag ggtatttacg agcaattggt ggtgtgttga agatatatag            1648
Pro Phe
500

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 42
gccataataa gctaccgaat tgcaatg                                       27

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 43
cattaacacc cccattgaca accacg                                        26

<210> SEQ ID NO 44
<211> LENGTH: 1869
<212> TYPE: DNA
<213> ORGANISM: Cryptococcus neoformans
<220> FEATURE:
<223> OTHER INFORMATION: amplified fragment showing homology to S.
      cerevisiae GWT1

<400> SEQUENCE: 44
ggggattaca agtcggccaa agaggccttt gtctcggata acccaggtgc ttctatctgg    60
agtatcaacg ctgtcagcct ggtcgcactg gtatgtagct cgttctccga ggggttctgt   120
catttggaga cgcttattaa ttgggatcgc aggcgacata tgctctctgg atcgccttat   180
cgccgtacat ccgtcatgga ctcctgaaca actacctgat ctgtgttctt ccctattat    240
```

```
tcggggtgac catcttctca acttcgcctc tcgtatttac ctcttttttg tccattattt    300
ccctcgcttt catcacgaaa tcccaaaaat gcttcaaatc tgtcagttcg cccgaaaagc    360
caaaaggcca atggctagac gaatcagact ccgatgagga accagcggaa cctgcttctg    420
cagctggatc tgcagcagtc tcaccagtaa agcttctacc ttcccaagtg gcgttcgctt    480
cgggatccct attatctccc gatccgacaa catcccccat gtcgccaagt agttcttcag    540
cttcaggaca tgaagaccct ttggggatta tgggcgttaa cagacggagg tcgctattag    600
aaggagtttc gcttgatgtt ccgtcacata tcgactccaa ggtcagaata tctcctgttc    660
cctacttgag gctcaaaaag tctagggcaa cgaaggcgca atgggtgaaa gaaagggaa     720 gattaccatt tttgacagtg taccgagcgc acatgatgct catgactgtt atctgcatct    780
tggcggtaga ttttgaagtg tttcctagat ggcagggcaa gtgcgaagat tttggtacta    840
gtctggtaag ctttccttca gccatggtcc agtgctcacc gctctacttg ccgtagatgg    900
acgtgggtgt cgggtcattc gtcttttccc tcggtctcgt ctccacaaaa tctctttctc    960
ctccacctcc aactcctacg ccctcctcgc ccgctctcaa ctctcacatc attcccctca    1020
ccccgtcccc gttcacttcc atcctcatct cgctccgaaa atccatcccc atcctcgtcc    1080
tcggctttat acggttgatt atggtcaagg gatctgatta tcctgagcat gtgacggagt    1140
acggcgtgca ctggaatttc ttcttcaccc tcgcattggt tcctgtgctc gccgtgggca    1200
ttcgaccatt gacgcagtgg cttcgctgga gtgtgcttgg ggtaatcatc tctttgctgc    1260
atcagctgtg gttaacatat tatctccaat ccatcgtctt ctcattcggc cggtcaggta    1320
tctttctagc aaacaaggaa ggcttctcct ctcttcctgg ttatcttttcc atattttga    1380 tcggcttgtc tattggagat catgttttaa ggctcagttt accaccaaga agagagaggg   1440
tcgtgtcaga acaaatgaa gagcatgagc agagtcattt tgagagaaaa aaattggatt    1500
tgattatgga gttgattgga tatagcttag gctggtgggc actcttagga ggctggatt     1560 gggccggcgg ggaggtatcc aggcgtttag taagtggaca tctttggtaa tattgtacct   1620
atactaatcc ctgcataaag gccaacgctc cttatgtatt tgggtagcg gcatacaata    1680 ccaccttctct cctcggctac ctcctcctta cccacattat tccatctccc acctcttccc  1740
aaacatcacc atcgatctta gtgcctccct tgctcgacgc tatgaataaa acggtctcg    1800 cgatattttt ggcggccaac ttgcttacag gactggtgaa tgtgagcatg aagacaatgt   1860
atgcgccgg                                                           1869
```

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 45
gtaaaggaag gcgctagaaa agatatg                                        27

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence:PCR
      amplification primer -continued

```
<400> SEQUENCE: 46
ctcatcggag tctgattcgt ctagcc                                          26

<210> SEQ ID NO 47
<211> LENGTH: 470
<212> TYPE: DNA
<213> ORGANISM: Cryptococcus neoformans
<220> FEATURE:
<223> OTHER INFORMATION: amplified fragment ovelapping SEQ ID NO:44

<400> SEQUENCE: 47
gaaggcgcta aaaagatat ggtcttgtca tagcattaaa tccccgccat aataagctac      60
tgaattgcaa tggggatta caagtcggcc aaagaggcct ttgtctcgga tacccaggt     120 gcttctatct ggagtatcaa cgctgtcagc ctggtcgcac tggtatgtag ctcgttctcc    180
gaggggttct gtcatttgga gacgcttatt aattgggatc gcaggcgaca tatgctctct    240
ggatcgcctt atcgccgtac atccgtcatg gactcctgaa caactacctg atctgtgttc    300
ttcccctatt attcggggtg accatcttct caacttcgcc tctcgtattt acctcttttt    360
tgtccattat ttccctcgct ttcatcacga aatcccaaaa atgcttcaaa tctgtcagtt    420
cgcccgaaaa gccaaaaggc caatggctag acgaatcaga ctccgatgag              470

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence:3'-RACE
      adaptor-primer

<400> SEQUENCE: 48
gcccacgcgt cgactagtac tttttttttt tttttt                               37

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 49
catcttggcg gtagattttg aagtgttcc                                       29

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:PCR
      amplification primer

<400> SEQUENCE: 50
ggccacgcgt cgactagtac                                                 20

<210> SEQ ID NO 51
<211> LENGTH: 1136
<212> TYPE: DNA
<213> ORGANISM: Cryptococcus neoformans
<220> FEATURE:
<223> OTHER INFORMATION: amplified fragment showing homology to S.
      cerevisiae GWT1
```

<400> SEQUENCE: 51

```
gcggtagatt ttgaagtgtt ccctagatgg cagggcaagt gcgaagattt tggtactagt     60
ctgatggacg tgggtgtcgg gtcattcgtc ttttccctcg gtctcgtctc cacaaaatct    120
ctttctcctc cacctccaac tcctacgccc tcctcgcccg ctctcaactc tcacatcatt    180
cccctcaccc cgtccccgtt cacttccatc ctcatctcgc tccgaaaatc catccccatc    240
ctcgtcctcg gctttatacg gttgattatg gtcaagggat ctgattatcc tgagcatgtg    300
acggagtacg gcgtgcactg gaatttcttc ttcaccctcg cattggttcc tgtgctcgcc    360
gtgggcattc gaccattgac gcagtggctt cgctggagtg tgcttggggt aatcatctct    420
ttgctgcatc agctgtggtt aacatattat ctccaatcca tcgtcttctc attcggccgg    480
tcaggtatct ttctagcaaa caaggaaggc ttctcctctc ttcctggtta tctttccata    540
ttttttgatcg gcttgtctat tggagatcat gttttaaggc tcagtttacc accaagaaga    600
gagagggtcg tgtcagaaac aaatgaagag catgagcaga gtcattttga gagaaaaaaa    660
ttggatttga ttatggagtt gattggatat agcttaggct ggtgggcact cttaggaggc    720
tggatttggg ccggcgggga ggtatccagg cgtttagcca acgctcctta tgtattttgg    780
gtagcggcat acaataccac ctttctcctc ggctacctcc tccttaccca cattattcca    840
tctcccacct cttcccaaac atcaccatcg atcttagtgc ctcccttgct cgacgctatg    900
aataaaaacg gtctcgcgat atttttggcg gccaacttgc ttacaggact ggtgaatgtg    960
agcatgaaga caatgtatgc gccggcgtgg ttgtcaatgg gggtgttaat gttgtatacc   1020
ttgacaatca gttgtgtagg gtggatactg aaaggacgga ggatcaagat atagttaaag   1080
tgtttaccat gcaggatact gagtatctcg gttcaaaaaa aaaaaaaaaa aaaaaa       1136
```

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence:PCR amplification primer

<400> SEQUENCE: 52

```
gtcttgtcat agcattaaat ccccgcc                                          27
```

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence:PCR amplification primer

<400> SEQUENCE: 53

```
gaaccgagat actcagtatc ctgcatgg                                         28
```

<210> SEQ ID NO 54
<211> LENGTH: 2045
<212> TYPE: DNA
<213> ORGANISM: Cryptococcus neoformans
<220> FEATURE:
<223> OTHER INFORMATION: full length homologue of S. cerevisiae GWT1
<220> FEATURE:
<221> NAME/KEY: CDS
<222> LOCATION: join(44..136, 199..891, 943..1635, 1687..2004)
<223> OTHER INFORMATION: homologue of S. cerevisiae GWT1
<220> FEATURE:
<221> NAME/KEY: exon
<222> LOCATION: (44)..(136)

```
<220> FEATURE:
<221> NAME/KEY: intron
<222> LOCATION: (137)..(198)
<220> FEATURE:
<221> NAME/KEY: exon
<222> LOCATION: (199)..(891)
<220> FEATURE:
<221> NAME/KEY: intron
<222> LOCATION: (892)..(942)
<220> FEATURE:
<221> NAME/KEY: exon
<222> LOCATION: (943)..(1635)
<220> FEATURE:
<221> NAME/KEY: intron
<222> LOCATION: (1636)..(1686)
<220> FEATURE:
<221> NAME/KEY: exon
<222> LOCATION: (1687)..(2004)

<400> SEQUENCE: 54
gtcatagcat taaatccccg ccataataag ctactgaatt gca atg ggg gat tac      55
                                              Met Gly Asp Tyr
                                                1 aag tcg gcc aaa gag gcc ttt gtc tcg gat aac cca ggt gct tct atc     103
Lys Ser Ala Lys Glu Ala Phe Val Ser Asp Asn Pro Gly Ala Ser Ile
  5              10                  15                  20 tgg agt atc aac gct gtc agc ctg gtc gca ctg gtatgtagct cgttctccga   156
Trp Ser Ile Asn Ala Val Ser Leu Val Ala Leu
             25                  30 ggggttctgt catttggaga cgcttattaa ttgggatcgc ag gcg aca tat gct       210
                                                Ala Thr Tyr Ala
                                                          35 ctc tgg atc gcc tta tcg ccg tac atc cgt cat gga ctc ctg aac aac     258
Leu Trp Ile Ala Leu Ser Pro Tyr Ile Arg His Gly Leu Leu Asn Asn
         40                  45                  50 tac ctg atc tgt gtt ctt ccc cta tta ttc ggg gtg acc atc ttc tca     306
Tyr Leu Ile Cys Val Leu Pro Leu Leu Phe Gly Val Thr Ile Phe Ser
 55                  60                  65 act tcg cct ctc gta ttt acc tct ttt ttg tcc att att tcc ctc gct     354
Thr Ser Pro Leu Val Phe Thr Ser Phe Leu Ser Ile Ile Ser Leu Ala
     70                  75                  80 ttc atc acg aaa tcc caa aaa tgc ttc aaa tct gtc agt tcg ccc gaa     402
Phe Ile Thr Lys Ser Gln Lys Cys Phe Lys Ser Val Ser Ser Pro Glu
 85                  90                  95 aag cca aaa ggc caa tgg cta gac gaa tca gac tcc gat gag gaa cca     450
Lys Pro Lys Gly Gln Trp Leu Asp Glu Ser Asp Ser Asp Glu Glu Pro
100                 105                 110                 115 gcg gaa cct gct tct gca gct gga tct gca gca gtc tca cca gta aag     498
Ala Glu Pro Ala Ser Ala Ala Gly Ser Ala Ala Val Ser Pro Val Lys
                120                 125                 130 ctt cta cct tcc caa gtg gcg ttc gct tcg gga tcc cta tta tct ccc     546
Leu Leu Pro Ser Gln Val Ala Phe Ala Ser Gly Ser Leu Leu Ser Pro
            135                 140                 145 gat ccg aca aca tcc ccc atg tcg cca agt agt tct tca gct tca gga     594
Asp Pro Thr Thr Ser Pro Met Ser Pro Ser Ser Ser Ser Ala Ser Gly
        150                 155                 160 cat gaa gac cct ttg ggg att atg ggc gtt aac aga cgg agg tcg cta     642
His Glu Asp Pro Leu Gly Ile Met Gly Val Asn Arg Arg Arg Ser Leu
165                 170                 175 tta gaa gga gtt tcg ctt gat gtt ccg tca cat atc gac tcc aag gtc     690
Leu Glu Gly Val Ser Leu Asp Val Pro Ser His Ile Asp Ser Lys Val
180                 185                 190                 195 aga ata tct cct gtt ccc tac ttg agg ctc aaa aag tct agg gca acg     738
Arg Ile Ser Pro Val Pro Tyr Leu Arg Leu Lys Lys Ser Arg Ala Thr
                200                 205                 210
```

```
aag gcg caa tgg gtg aaa gaa aag gga aga tta cca ttt ttg aca gtg      786
Lys Ala Gln Trp Val Lys Glu Lys Gly Arg Leu Pro Phe Leu Thr Val
            215                 220                 225 tac cga gcg cac atg atg ctc atg act gtt atc tgc atc ttg gcg gta      834
Tyr Arg Ala His Met Met Leu Met Thr Val Ile Cys Ile Leu Ala Val
            230                 235                 240 gat ttt gaa gtg ttt cct aga tgg cag ggc aag tgc gaa gat ttt ggt      882
Asp Phe Glu Val Phe Pro Arg Trp Gln Gly Lys Cys Glu Asp Phe Gly
            245                 250                 255 act agt ctg gtaagctttc cttcagccat ggtccagtgc tcaccgctct              931
Thr Ser Leu
260 acttgccgta g atg gac gtg ggt gtc ggg tca ttc gtc ttt tcc ctc ggt     981
            Met Asp Val Gly Val Gly Ser Phe Val Phe Ser Leu Gly
                            265                 270                 275 ctc gtc tcc aca aaa tct ctt tct cct cca cct cca act cct acg ccc     1029
Leu Val Ser Thr Lys Ser Leu Ser Pro Pro Pro Pro Thr Pro Thr Pro
                280                 285                 290 tcc tcg ccc gct ctc aac tct cac atc att ccc ctc acc ccg tcc ccg     1077
Ser Ser Pro Ala Leu Asn Ser His Ile Ile Pro Leu Thr Pro Ser Pro
                295                 300                 305 ttc act tcc atc ctc atc tcg ctc cga aaa tcc atc ccc atc ctc gtc     1125
Phe Thr Ser Ile Leu Ile Ser Leu Arg Lys Ser Ile Pro Ile Leu Val
                310                 315                 320 ctc ggc ttt ata cgg ttg att atg gtc aag gga tct gat tat cct gag     1173
Leu Gly Phe Ile Arg Leu Ile Met Val Lys Gly Ser Asp Tyr Pro Glu
                325                 330                 335 cat gtg acg gag tac ggc gtg cac tgg aat ttc ttc acc ctc gca         1221
His Val Thr Glu Tyr Gly Val His Trp Asn Phe Phe Thr Leu Ala
340                 345                 350                 355 ttg gtt cct gtg ctc gcc gtg ggc att cga cca ttg acg cag tgg ctt     1269
Leu Val Pro Val Leu Ala Val Gly Ile Arg Pro Leu Thr Gln Trp Leu
                360                 365                 370 cgc tgg agt gtg ctt ggg gta atc atc tct ttg ctg cat cag ctg tgg     1317
Arg Trp Ser Val Leu Gly Val Ile Ile Ser Leu Leu His Gln Leu Trp
                375                 380                 385 tta aca tat tat ctc caa tcc atc gtc ttc tca ttc ggc cgg tca ggt     1365
Leu Thr Tyr Tyr Leu Gln Ser Ile Val Phe Ser Phe Gly Arg Ser Gly
                390                 395                 400 atc ttt cta gca aac aag gaa ggc ttc tcc tct ctt cct ggt tat ctt     1413
Ile Phe Leu Ala Asn Lys Glu Gly Phe Ser Ser Leu Pro Gly Tyr Leu
                405                 410                 415 tcc ata ttt ttg atc ggc ttg tct att gga gat cat gtt tta agg ctc     1461
Ser Ile Phe Leu Ile Gly Leu Ser Ile Gly Asp His Val Leu Arg Leu
420                 425                 430                 435 agt tta cca cca aga aga gag agg gtc gtg tca gaa aca aat gaa gag     1509
Ser Leu Pro Pro Arg Arg Glu Arg Val Val Ser Glu Thr Asn Glu Glu
                440                 445                 450 cat gag cag agt cat ttt gag aga aaa aaa ttg gat ttg att atg gag     1557
His Glu Gln Ser His Phe Glu Arg Lys Lys Leu Asp Leu Ile Met Glu
                455                 460                 465 ttg att gga tat agc tta ggc tgg tgg gca ctc tta gga ggc tgg att     1605
Leu Ile Gly Tyr Ser Leu Gly Trp Trp Ala Leu Leu Gly Gly Trp Ile
                470                 475                 480 tgg gcc ggc ggg gag gta tcc agg cgt tta gtaagtggac atctttggta       1655
Trp Ala Gly Gly Glu Val Ser Arg Arg Leu
485                 490 atattgtacc tatactaatc cctgcataaa g gcc aac gct cct tat gta ttt      1707
                                  Ala Asn Ala Pro Tyr Val Phe
                                  495                 500
```

```
tgg gta gcg gca tac aat acc acc ttt ctc ctc ggc tac ctc ctc ctt   1755
Trp Val Ala Ala Tyr Asn Thr Thr Phe Leu Leu Gly Tyr Leu Leu Leu
                505                 510                 515 acc cac att att cca tct ccc acc tct tcc caa aca tca cca tcg atc   1803
Thr His Ile Ile Pro Ser Pro Thr Ser Ser Gln Thr Ser Pro Ser Ile
                520                 525                 530 tta gtg cct ccc ttg ctc gac gct atg aat aaa aac ggt ctc gcg ata   1851
Leu Val Pro Pro Leu Leu Asp Ala Met Asn Lys Asn Gly Leu Ala Ile
                535                 540                 545 ttt ttg gcg gcc aac ttg ctt aca gga ctg gtg aat gtg agc atg aag   1899
Phe Leu Ala Ala Asn Leu Leu Thr Gly Leu Val Asn Val Ser Met Lys
                550                 555                 560 aca atg tat gcg ccg gcg tgg ttg tca atg ggg gtg tta atg ttg tat   1947
Thr Met Tyr Ala Pro Ala Trp Leu Ser Met Gly Val Leu Met Leu Tyr
565                 570                 575                 580 acc ttg aca atc agt tgt gta ggg tgg ata ctg aaa gga cgg agg atc   1995
Thr Leu Thr Ile Ser Cys Val Gly Trp Ile Leu Lys Gly Arg Arg Ile
                585                 590                 595 aag ata tag ttaaagtgtt taccatgcag gatactgagt atctcggttc a         2045
Lys Ile

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence:PCR
      amplification primer predicted to be junction
      between exons

<400> SEQUENCE: 55
cagcctggtc gcactggcga cat                                         23

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence:PCR
      amplification primer predicted to be junction
      between exons

<400> SEQUENCE: 56
cataaggagc gttggctaaa cgcct                                       25

<210> SEQ ID NO 57
<211> LENGTH: 1418
<212> TYPE: DNA
<213> ORGANISM: Cryptococcus neoformans
<220> FEATURE:
<223> OTHER INFORMATION: amplified fragment showing homology to S.
      cerevisiae GWT1

<400> SEQUENCE: 57
cagcctggtc gcactggcga catatgctct ctggatcgcc ttatcgccgt acatccgtca   60
tggactcctg aacaactacc tgatctgtgt tcttcccta ttattcgggg tgaccatctt   120
ctcaacttcg cctctcgtat ttacctcttt tttgtccatt atttccctcg ctttcatcac   180
gaaatcccaa aaatgcttca aatctgtcag ttcgcccgaa aagccaaaag gccaatggct   240
agacgaatca gactccgatg aggaaccagc ggaacctgct tctgcagctg gatctgcagc   300 agtctccacca gtaagcttc taccttccca agtggcgttc gcttcgggat ccctattatc   360
tcccgatccg acaacatccc ccatgtcgcc aagtagttct tcagcttcag gacatgaaga   420
```

-continued

```
ccctttgggg attatgggcg ttaacagacg gaggtcgcta ttagaaggag tttcgcttga        480
tgttccgtca catatcgact ccaaggtcag aatatctcct gttccctact tgaggctcaa        540
aaagtctagg gcaacgaagg cgcaatgggt gaaagaaaag ggaagattac cattttttgac       600 agtgtaccga gcgcacatga tgctcatgac tgttatctgc atcttggcgg tagatttttga      660 agtgttttcct agatggcagg gcaagtgcga agattttggt actagtctga tggacgtggg       720
tgtcgggtca ttcgtctttt ccctcggtct cgtctccaca aaatctcttt ctcctccacc        780
tccaactcct acgccctcct cgcccgctct caactctcac atcattcccc tcaccccgtc        840
cccgttcact tccatcctca tctcgctccg aaaatccatc cccatcctcg tcctcggctt        900
tatacggttg attatggtca agggatctga ttatcctgag catgtgacgg agtacggcgt        960
gcactggaat tcttcttca ccctcgcatt ggttcctgtg ctcgccgtgg gcattcgacc        1020
attgacgcag tggcttcgct ggagtgtgct tggggtaatc atctctttgc tgcatcagct      1080
gtggttaaca tattatctcc aatccatcgt cttctcattc ggccggtcag gtatctttct      1140
agcaaacaag gaaggcttct cctctcttcc tggttatctt tccatatttt tgatcggctt      1200
gtctattgga gatcatgttt taaggctcag tttaccacca agaagagaga gggtcgtgtc      1260
agaaacaaat gaagagcatg agcagagtca ttttgagaga aaaaaattgg atttgattat      1320
ggagttgatt ggatatagct taggctggtg ggcactctta ggaggctgga tttgggccgg      1380
cggggaggta tccaggcgtt tagccaacgc tccttatg                              1418
```

<210> SEQ ID NO 58
<211> LENGTH: 1797
<212> TYPE: DNA
<213> ORGANISM: Cryptococcus neoformans
<220> FEATURE:
<221> NAME/KEY: CDS
<222> LOCATION: (1)..(1797)
<223> OTHER INFORMATION: homologue of S. cerevisiae GWT1

<400> SEQUENCE: 58

```
atg ggg gat tac aag tcg gcc aaa gag gcc ttt gtc tcg gat aac cca        48
Met Gly Asp Tyr Lys Ser Ala Lys Glu Ala Phe Val Ser Asp Asn Pro
 1               5                  10                  15 ggt gct tct atc tgg agt atc aac gct gtc agc ctg gtc gca ctg gcg        96
Gly Ala Ser Ile Trp Ser Ile Asn Ala Val Ser Leu Val Ala Leu Ala
             20                  25                  30 aca tat gct ctc tgg atc gcc tta tcg ccg tac atc cgt cat gga ctc       144
Thr Tyr Ala Leu Trp Ile Ala Leu Ser Pro Tyr Ile Arg His Gly Leu
         35                  40                  45 ctg aac aac tac ctg atc tgt gtt ctt ccc cta tta ttc ggg gtg acc       192
Leu Asn Asn Tyr Leu Ile Cys Val Leu Pro Leu Leu Phe Gly Val Thr
     50                  55                  60 atc ttc tca act tcg cct ctc gta ttt acc tct ttt ttg tcc att att       240
Ile Phe Ser Thr Ser Pro Leu Val Phe Thr Ser Phe Leu Ser Ile Ile
 65                  70                  75                  80 tcc ctc gct ttc atc acg aaa tcc caa aaa tgc ttc aaa tct gtc agt       288
Ser Leu Ala Phe Ile Thr Lys Ser Gln Lys Cys Phe Lys Ser Val Ser
                 85                  90                  95 tcg ccc gaa aag cca aaa ggc caa tgg cta gac gaa tca gac tcc gat       336
Ser Pro Glu Lys Pro Lys Gly Gln Trp Leu Asp Glu Ser Asp Ser Asp
            100                 105                 110 gag gaa cca gcg gaa cct gct tct gca gct gga tct gca gca gtc tca       384
Glu Glu Pro Ala Glu Pro Ala Ser Ala Ala Gly Ser Ala Ala Val Ser
        115                 120                 125
```

```
cca gta aag ctt cta cct tcc caa gtg gcg ttc gct tcg gga tcc cta      432
Pro Val Lys Leu Leu Pro Ser Gln Val Ala Phe Ala Ser Gly Ser Leu
    130                 135                 140 tta tct ccc gat ccg aca aca tcc ccc atg tcg cca agt agt tct tca      480
Leu Ser Pro Asp Pro Thr Thr Ser Pro Met Ser Pro Ser Ser Ser Ser
145                 150                 155                 160 gct tca gga cat gaa gac cct ttg ggg att atg ggc gtt aac aga cgg      528
Ala Ser Gly His Glu Asp Pro Leu Gly Ile Met Gly Val Asn Arg Arg
                165                 170                 175 agg tcg cta tta gaa gga gtt tcg ctt gat gtt ccg tca cat atc gac      576
Arg Ser Leu Leu Glu Gly Val Ser Leu Asp Val Pro Ser His Ile Asp
        180                 185                 190 tcc aag gtc aga ata tct cct gtt ccc tac ttg agg ctc aaa aag tct      624
Ser Lys Val Arg Ile Ser Pro Val Pro Tyr Leu Arg Leu Lys Lys Ser
            195                 200                 205 agg gca acg aag gcg caa tgg gtg aaa gaa aag gga aga tta cca ttt      672
Arg Ala Thr Lys Ala Gln Trp Val Lys Glu Lys Gly Arg Leu Pro Phe
    210                 215                 220 ttg aca gtg tac cga gcg cac atg atg ctc atg act gtt atc tgc atc      720
Leu Thr Val Tyr Arg Ala His Met Met Leu Met Thr Val Ile Cys Ile
225                 230                 235                 240 ttg gcg gta gat ttt gaa gtg ttt cct aga tgg cag ggc aag tgc gaa      768
Leu Ala Val Asp Phe Glu Val Phe Pro Arg Trp Gln Gly Lys Cys Glu
                245                 250                 255 gat ttt ggt act agt ctg atg gac gtg ggt gtc ggg tca ttc gtc ttt      816
Asp Phe Gly Thr Ser Leu Met Asp Val Gly Val Gly Ser Phe Val Phe
        260                 265                 270 tcc ctc ggt ctc gtc tcc aca aaa tct ctt tct cct cca cct cca act      864
Ser Leu Gly Leu Val Ser Thr Lys Ser Leu Ser Pro Pro Pro Pro Thr
            275                 280                 285 cct acg ccc tcc tcg ccc gct ctc aac tct cac atc att ccc ctc acc      912
Pro Thr Pro Ser Ser Pro Ala Leu Asn Ser His Ile Ile Pro Leu Thr
    290                 295                 300 ccg tcc ccg ttc act tcc atc ctc atc tcg ctc cga aaa tcc atc ccc      960
Pro Ser Pro Phe Thr Ser Ile Leu Ile Ser Leu Arg Lys Ser Ile Pro
305                 310                 315                 320 atc ctc gtc ctc ggc ttt ata cgg ttg att atg gtc aag gga tct gat     1008
Ile Leu Val Leu Gly Phe Ile Arg Leu Ile Met Val Lys Gly Ser Asp
                325                 330                 335 tat cct gag cat gtg acg gag tac ggc gtg cac tgg aat ttc ttc ttc     1056
Tyr Pro Glu His Val Thr Glu Tyr Gly Val His Trp Asn Phe Phe Phe
        340                 345                 350 acc ctc gca ttg gtt cct gtg ctc gcc gtg ggc att cga cca ttg acg     1104
Thr Leu Ala Leu Val Pro Val Leu Ala Val Gly Ile Arg Pro Leu Thr
            355                 360                 365 cag tgg ctt cgc tgg agt gtg ctt ggg gta atc atc tct ttg ctg cat     1152
Gln Trp Leu Arg Trp Ser Val Leu Gly Val Ile Ile Ser Leu Leu His
    370                 375                 380 cag ctg tgg tta aca tat tat ctc caa tcc atc gtc ttc tca ttc ggc     1200
Gln Leu Trp Leu Thr Tyr Tyr Leu Gln Ser Ile Val Phe Ser Phe Gly
385                 390                 395                 400 cgg tca ggt atc ttt cta gca aac aag gaa ggc ttc tcc tct ctt cct     1248
Arg Ser Gly Ile Phe Leu Ala Asn Lys Glu Gly Phe Ser Ser Leu Pro
                405                 410                 415 ggt tat ctt tcc ata ttt ttg atc ggc ttg tct att gga gat cat gtt     1296
Gly Tyr Leu Ser Ile Phe Leu Ile Gly Leu Ser Ile Gly Asp His Val
        420                 425                 430 tta agg ctc agt tta cca cca aga aga gag agg gtc gtg tca gaa aca     1344
Leu Arg Leu Ser Leu Pro Pro Arg Arg Glu Arg Val Val Ser Glu Thr
            435                 440                 445
```

```
                                                       -continued aat gaa gag cat gag cag agt cat ttt gag aga aaa aaa ttg gat ttg      1392
Asn Glu Glu His Glu Gln Ser His Phe Glu Arg Lys Lys Leu Asp Leu
    450                 455                 460 att atg gag ttg att gga tat agc tta ggc tgg tgg gca ctc tta gga      1440
Ile Met Glu Leu Ile Gly Tyr Ser Leu Gly Trp Trp Ala Leu Leu Gly
465                 470                 475                 480 ggc tgg att tgg gcc ggc ggg gag gta tcc agg cgt tta gcc aac gct      1488
Gly Trp Ile Trp Ala Gly Gly Glu Val Ser Arg Arg Leu Ala Asn Ala
                485                 490                 495 cct tat gta ttt tgg gta gcg gca tac aat acc acc ttt ctc ctc ggc      1536
Pro Tyr Val Phe Trp Val Ala Ala Tyr Asn Thr Thr Phe Leu Leu Gly
            500                 505                 510 tac ctc ctc ctt acc cac att att cca tct ccc acc tct tcc caa aca      1584
Tyr Leu Leu Leu Thr His Ile Ile Pro Ser Pro Thr Ser Ser Gln Thr
        515                 520                 525 tca cca tcg atc tta gtg cct ccc ttg ctc gac gct atg aat aaa aac      1632
Ser Pro Ser Ile Leu Val Pro Pro Leu Leu Asp Ala Met Asn Lys Asn
    530                 535                 540 ggt ctc gcg ata ttt ttg gcg gcc aac ttg ctt aca gga ctg gtg aat      1680
Gly Leu Ala Ile Phe Leu Ala Ala Asn Leu Leu Thr Gly Leu Val Asn
545                 550                 555                 560 gtg agc atg aag aca atg tat gcg ccg gcg tgg ttg tca atg ggg gtg      1728
Val Ser Met Lys Thr Met Tyr Ala Pro Ala Trp Leu Ser Met Gly Val
                565                 570                 575 tta atg ttg tat acc ttg aca atc agt tgt gta ggg tgg ata ctg aaa      1776
Leu Met Leu Tyr Thr Leu Thr Ile Ser Cys Val Gly Trp Ile Leu Lys
            580                 585                 590 gga cgg agg atc aag ata tag                                          1797
Gly Arg Arg Ile Lys Ile
        595

<210> SEQ ID NO 59
<211> LENGTH: 598
<212> TYPE: PRT
<213> ORGANISM: Cryptococcus neoformans
<220> FEATURE:
<223> OTHER INFORMATION: homologue of S. cerevisiae GWT1

<400> SEQUENCE: 59

Met Gly Asp Tyr Lys Ser Ala Lys Glu Ala Phe Val Ser Asp Asn Pro
1               5                   10                  15

Gly Ala Ser Ile Trp Ser Ile Asn Ala Val Ser Leu Val Ala Leu Ala
            20                  25                  30

Thr Tyr Ala Leu Trp Ile Ala Leu Ser Pro Tyr Ile Arg His Gly Leu
        35                  40                  45

Leu Asn Asn Tyr Leu Ile Cys Val Leu Pro Leu Leu Phe Gly Val Thr
    50                  55                  60

Ile Phe Ser Thr Ser Pro Leu Val Phe Thr Ser Phe Leu Ser Ile Ile
65                  70                  75                  80

Ser Leu Ala Phe Ile Thr Lys Ser Gln Lys Cys Phe Lys Ser Val Ser
                85                  90                  95

Ser Pro Glu Lys Pro Lys Gly Gln Trp Leu Asp Glu Ser Asp Ser Asp
            100                 105                 110

Glu Glu Pro Ala Glu Pro Ala Ser Ala Ala Gly Ser Ala Ala Val Ser
        115                 120                 125

Pro Val Lys Leu Leu Pro Ser Gln Val Ala Phe Ala Ser Gly Ser Leu
    130                 135                 140

Leu Ser Pro Asp Pro Thr Thr Ser Pro Met Ser Pro Ser Ser Ser Ser
145                 150                 155                 160
```

```
Ala Ser Gly His Glu Asp Pro Leu Gly Ile Met Gly Val Asn Arg Arg
            165                 170                 175

Arg Ser Leu Leu Glu Gly Val Ser Leu Asp Val Pro Ser His Ile Asp
            180                 185                 190

Ser Lys Val Arg Ile Ser Pro Val Pro Tyr Leu Arg Leu Lys Lys Ser
            195                 200                 205

Arg Ala Thr Lys Ala Gln Trp Val Lys Glu Lys Gly Arg Leu Pro Phe
            210                 215                 220

Leu Thr Val Tyr Arg Ala His Met Met Leu Met Thr Val Ile Cys Ile
225                 230                 235                 240

Leu Ala Val Asp Phe Glu Val Phe Pro Arg Trp Gln Gly Lys Cys Glu
            245                 250                 255

Asp Phe Gly Thr Ser Leu Met Asp Val Gly Val Gly Ser Phe Val Phe
            260                 265                 270

Ser Leu Gly Leu Val Ser Thr Lys Ser Leu Ser Pro Pro Pro Pro Thr
            275                 280                 285

Pro Thr Pro Ser Ser Pro Ala Leu Asn Ser His Ile Ile Pro Leu Thr
            290                 295                 300

Pro Ser Pro Phe Thr Ser Ile Leu Ile Ser Leu Arg Lys Ser Ile Pro
305                 310                 315                 320

Ile Leu Val Leu Gly Phe Ile Arg Leu Ile Met Val Lys Gly Ser Asp
            325                 330                 335

Tyr Pro Glu His Val Thr Glu Tyr Gly Val His Trp Asn Phe Phe Phe
            340                 345                 350

Thr Leu Ala Leu Val Pro Val Leu Ala Val Gly Ile Arg Pro Leu Thr
            355                 360                 365

Gln Trp Leu Arg Trp Ser Val Leu Gly Val Ile Ile Ser Leu Leu His
            370                 375                 380

Gln Leu Trp Leu Thr Tyr Tyr Leu Gln Ser Ile Val Phe Ser Phe Gly
385                 390                 395                 400

Arg Ser Gly Ile Phe Leu Ala Asn Lys Glu Gly Phe Ser Ser Leu Pro
            405                 410                 415

Gly Tyr Leu Ser Ile Phe Leu Ile Gly Leu Ser Ile Gly Asp His Val
            420                 425                 430

Leu Arg Leu Ser Leu Pro Pro Arg Arg Glu Arg Val Val Ser Glu Thr
435                 440                 445

Asn Glu Glu His Glu Gln Ser His Phe Glu Arg Lys Lys Leu Asp Leu
            450                 455                 460

Ile Met Glu Leu Ile Gly Tyr Ser Leu Gly Trp Trp Ala Leu Leu Gly
465                 470                 475                 480

Gly Trp Ile Trp Ala Gly Gly Glu Val Ser Arg Arg Leu Ala Asn Ala
            485                 490                 495

Pro Tyr Val Phe Trp Val Ala Ala Tyr Asn Thr Thr Phe Leu Leu Gly
            500                 505                 510

Tyr Leu Leu Leu Thr His Ile Ile Pro Ser Pro Thr Ser Ser Gln Thr
            515                 520                 525

Ser Pro Ser Ile Leu Val Pro Pro Leu Leu Asp Ala Met Asn Lys Asn
            530                 535                 540

Gly Leu Ala Ile Phe Leu Ala Ala Asn Leu Leu Thr Gly Leu Val Asn
545                 550                 555                 560

Val Ser Met Lys Thr Met Tyr Ala Pro Ala Trp Leu Ser Met Gly Val
            565                 570                 575
```

```
Leu Met Leu Tyr Thr Leu Thr Ile Ser Cys Val Gly Trp Ile Leu Lys
        580                 585                 590

Gly Arg Arg Ile Lys Ile
        595
```

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence:R1 and R5
      mutant GWT1 gene primer

<400> SEQUENCE: 60
aaagaattca tggcaacagt acatcagaag                                    30

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:R1 and R5
      mutant GWT1 gene primer

<400> SEQUENCE: 61
gggcactgtt gaaaaaccta                                               20

<210> SEQ ID NO 62
<211> LENGTH: 1428
<212> TYPE: DNA
<213> ORGANISM: Saccharomyces cerevisiae
<220> FEATURE:
<221> NAME/KEY: promoter
<222> LOCATION: (1)..(1428)
<223> OTHER INFORMATION: GWT1 promoter region

<400> SEQUENCE: 62
gttgttcaaa atgggggtaa aattgagacg tcttacttga gcggcattta cgatcattct    60
tattacatca ttccaagtaa taaagctctt gactccttca atgatttacc tgagattata   120
gatgataatg atggtatagt tacagaattt ttcattgaac gctgcttgta ttatcaaaaa   180
ttactacacc caatagattt atggtcaaaa cccttcctca gcacaataga gtttcaagtt   240
tcgtcttctt caaagttatt gcatcatgaa ttttcttctt cccctttttct gaatgttact   300 atcactggat tctctggcgt agagctgtta catctgacta aagtattaaa tcttctaaaa   360
ccaatgggca tcaattatgt agaataccte aataaatcca ctgacattct gctaatcaac   420
ttagcagctt tacccagtat cccgaaaacc catccgttat ggtcgaatga atttagcgat   480
ctttttactc agtttttgcat taataacaat aatgatgatc ctggtgataa taacagaaaa   540
gattttcaaa ataattcaat cttgagaaat tcgatgaaaa ggaaaattga atatatcaag   600
aaattccact ccataccggt agttactcca gcatttattt ttaaattatt gtccgctgca   660
tctggagaaa ataatgaaat cttttttaaac aatatcaagt ggtgtattat ctgcccaaga   720
ggacacaagg acgattttaa atgtaagata aaaaaaccat actataccag cattagttca   780
gaaaaaaagt accaaacaa tgatccaaaa atcgacaaaa ctattctttt gaaaagaaac   840
aattcctcat tatcggagca ctctatgaaa gataccaaaa acgaattatt gcagaaaatt   900
agagaaactg attctggaag aaaaaagcgt agtgtctcat cgagtatcat ggatgttct   960 tcagagagac aaatgccgga tacgaaaagg atcaagttgg agtcactgcc aaaaaatttc  1020
gttcctaaac aaattaaacg aaccacgagt tggggcacaa taatgtcaga aatgtgcct  1080

-continued

```
acagagcagc cgactgcaat ttctaatcca gaagagatcc caagaactga ggaagtttca   1140
catactcaag ttacctatgg ctccattcaa gataagaaac gtactgcctc tttagaaaaa   1200
cctatgagac gacagacaag aaatcagaca aaggaattag attcttgaaa tgtagtccgt   1260
aattttataa gatattcatt tacatacgcc atctacagca ttattcaaat ctactcatct   1320
atatgtatta ccgttttgta tgataatact ttccatgaca tgctcgcgtg aaaaaacagc   1380
atgagaaaaa gaggatcgca ataagaagac acgtaaatat ctaaataa                1428
```

<210> SEQ ID NO 63
<211> LENGTH: 133
<212> TYPE: DNA
<213> ORGANISM: Saccharomyces cerevisiae
<220> FEATURE:
<221> NAME/KEY: terminator
<222> LOCATION: (1)..(133)
<223> OTHER INFORMATION: GWT1 terminator region

<400> SEQUENCE: 63

```
taacacacca tccacatttc catgtagttc gtatacaaac cctaccagta aaataaaatt   60
aactcctatg tgctttaaat aaaaattata aaccgcctcc aatagttgac gtagtcaggc   120
atgaaagtgc tac                                                       133
```

<210> SEQ ID NO 64
<211> LENGTH: 31
<212> TYPE: PRT
<213> ORGANISM: Saccharomyces cerevisiae
<220> FEATURE:
<223> OTHER INFORMATION: highly conserved GWT1 F-domain

<400> SEQUENCE: 64

```
Ile Leu Ala Val Asp Phe Pro Ile Phe Pro Arg Arg Phe Ala Lys Val
 1               5                  10                  15

Glu Thr Trp Gly Thr Ser Leu Met Asp Leu Gly Val Gly Ser Phe
            20                  25                  30
```

<210> SEQ ID NO 65
<211> LENGTH: 31
<212> TYPE: PRT
<213> ORGANISM: Candida albicans
<220> FEATURE:
<223> OTHER INFORMATION: highly conserved GWT1 F-domain

<400> SEQUENCE: 65

```
Ile Leu Ala Val Asp Phe Pro Ile Phe Pro Arg Arg Phe Ala Lys Val
 1               5                  10                  15

Glu Thr Trp Gly Thr Ser Met Met Asp Leu Gly Val Gly Ser Phe
            20                  25                  30
```

<210> SEQ ID NO 66
<211> LENGTH: 31
<212> TYPE: PRT
<213> ORGANISM: Schizosaccharomyces pombe
<220> FEATURE:
<223> OTHER INFORMATION: highly conserved GWT1 F-domain

<400> SEQUENCE: 66

```
Ile Leu Ala Val Asp Phe Thr Leu Phe Pro Arg Arg Tyr Ala Lys Val
 1               5                  10                  15

Glu Thr Trp Gly Thr Ser Leu Met Asp Leu Gly Val Gly Ser Phe
            20                  25                  30
```

```
<210> SEQ ID NO 67
<211> LENGTH: 17
<212> TYPE: PRT
<213> ORGANISM: Saccharomyces cerevisiae
<220> FEATURE:
<223> OTHER INFORMATION: highly conserved GWT1 R-domain

<400> SEQUENCE: 67

Tyr Gln Glu His Val Thr Glu Tyr Gly Val His Trp Asn Phe Phe Ile
  1               5                  10                  15

Thr

<210> SEQ ID NO 68
<211> LENGTH: 17
<212> TYPE: PRT
<213> ORGANISM: Candida albicans
<220> FEATURE:
<223> OTHER INFORMATION: highly conserved GWT1 R-domain

<400> SEQUENCE: 68

Tyr Gln Glu His Glu Thr Glu Tyr Gly Ile His Trp Asn Phe Phe Phe
  1               5                  10                  15

Thr

<210> SEQ ID NO 69
<211> LENGTH: 17
<212> TYPE: PRT
<213> ORGANISM: Schizosaccharomyces pombe
<220> FEATURE:
<223> OTHER INFORMATION: highly conserved GWT1 R-domain

<400> SEQUENCE: 69

Tyr Gln Glu His Val Ser Glu Tyr Gly Met His Trp Asn Phe Phe Phe
  1               5                  10                  15

Thr
```